(12) United States Patent
Kojima et al.

(10) Patent No.: US 10,123,994 B2
(45) Date of Patent: Nov. 13, 2018

(54) HETEROCYCLIC DERIVATIVE HAVING AMPK-ACTIVATING ACTIVITY

(71) Applicant: SHIONOGI & CO., LTD., Osaka-shi (JP)

(72) Inventors: Eiichi Kojima, Toyonaka (JP); Yu Hinata, Toyonaka (JP); Toshihiro Wada, Toyonaka (JP)

(73) Assignee: SHIONOGI & CO., LTD., Osaka-shi (JP)

( * ) Notice: Subject to any disclaimer, the term of this patent is extended or adjusted under 35 U.S.C. 154(b) by 0 days.

(21) Appl. No.: 15/522,504

(22) PCT Filed: Oct. 27, 2015

(86) PCT No.: PCT/JP2015/080162
§ 371 (c)(1),
(2) Date: Apr. 27, 2017

(87) PCT Pub. No.: WO2016/068099
PCT Pub. Date: May 6, 2016

(65) Prior Publication Data
US 2017/0333398 A1 Nov. 23, 2017

(30) Foreign Application Priority Data

Oct. 28, 2014 (JP) ................. 2014-218860
Apr. 20, 2015 (JP) ................. 2015-085522

(51) Int. Cl.
| | | |
|---|---|---|
| A61K 31/4188 | (2006.01) |
| C07D 419/14 | (2006.01) |
| A61K 31/382 | (2006.01) |
| A61K 31/34 | (2006.01) |
| A61K 31/5375 | (2006.01) |
| A61K 31/415 | (2006.01) |

(52) U.S. Cl.
CPC ........ *A61K 31/4188* (2013.01); *C07D 419/14* (2013.01); *A61K 31/34* (2013.01); *A61K 31/382* (2013.01); *A61K 31/415* (2013.01); *A61K 31/5375* (2013.01)

(58) Field of Classification Search
CPC .. A61K 31/4188; A61K 31/382; A61K 31/34; A61K 31/5375; A61K 31/415; C07D 419/14
See application file for complete search history.

(56) References Cited

U.S. PATENT DOCUMENTS

| | | |
|---|---|---|
| 2009/0176760 A1 | 7/2009 | Yanagisawa et al. |
| 2010/0081643 A1 | 4/2010 | Bookser et al. |
| 2010/0280012 A1 | 11/2010 | Lee |
| 2011/0195964 A1 | 8/2011 | Dang et al. |
| 2013/0184240 A1 | 7/2013 | Tonogaki et al. |
| 2014/0194420 A1 | 7/2014 | Kojima et al. |
| 2015/0203450 A1 | 7/2015 | Tamura et al. |
| 2015/0266869 A1 | 9/2015 | Ohnuki et al. |

FOREIGN PATENT DOCUMENTS

| | | |
|---|---|---|
| EP | 2 617 722 A1 | 7/2013 |
| JP | 5-339224 A | 12/1993 |
| JP | 2012-167027 A | 9/2012 |
| WO | 2005/082905 A1 | 9/2005 |
| WO | 2006/017214 A2 | 2/2006 |
| WO | 2008/096829 A1 | 8/2008 |
| WO | 2009/100130 A1 | 8/2009 |
| WO | 2010/036613 A1 | 4/2010 |
| WO | 2010/047982 A1 | 4/2010 |
| WO | 2010/051176 A1 | 5/2010 |
| WO | 2010/051206 A1 | 5/2010 |

(Continued)

OTHER PUBLICATIONS

CAS Registry No. 1071669-39-0; Benzenesulfonamide, N-[2-[(aminocarbonyl)oxy]-1H-benzimidazol-6-yl-; American Chemical Society, 2017, 1 page.
G.W. Vainer, et al., "PF-4708671 Activates AMPK Independently of p70S6K1 Inhibition," PLOS ONE, Sep. 2014, vol. 9, Issue 9, 5 pages.
J. Charton, et al., "Synthesis and biological evaluation of benzimidazole derivatives as potent AMP-activated protein kinase activators," Bioorganic & Medicinal Chemistry, vol. 14, 2006, pp. 4490-4518.
B. B. Zhang, et al., "AMPK: An Emerging Drug Target for Diabetes and the Metabolic Syndrome," Cell Metabolism, vol. 9, May 6, 2009, pp. 407-416.
International Search Report dated Dec. 15, 2015 in PCT/JP2015/080162 filed Oct. 27, 2015.

*Primary Examiner* — Alexander R Pagano
*Assistant Examiner* — Ebenezer O Sackey
(74) *Attorney, Agent, or Firm* — Oblon, McClelland, Maier & Neustadt, L.L.P.

(57) ABSTRACT

A compound of formula:

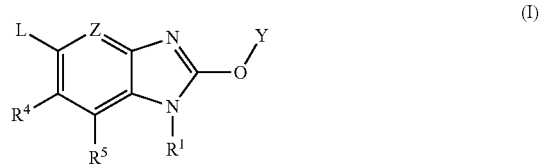

or its pharmaceutically acceptable salt. L is $NR^2R^3$, $SR^7$, $SO_2R^8$, alkyl, or alkenyl; $R^2$ is hydrogen, alkyl, alkenyl, or alkynyl; $R^3$ is hydrogen, alkyl, alkenyl, alkynyl; $R^7$ is hydrogen, alkyl, alkenyl, or alkynyl; $R^8$ is hydrogen, alkyl, alkenyl, or alkynyl, provided that $R^8$ is not unsubstituted methyl or trifluoromethyl; Y is alkyl, alkenyl, alkynyl, aryl, provided that Y is not unsubstituted methyl or unsubstituted ethyl; Z is $-CR^6=$, or $-N=$; $R^1$ is hydrogen, or alkyl; $R^4$, $R^5$ and $R^6$ are each independently hydrogen, halogen, hydroxy, cyano, nitro, carboxy, alkyl, alkenyl, or alkynyl.

23 Claims, No Drawings

(56) References Cited

FOREIGN PATENT DOCUMENTS

| | | |
|---|---|---|
| WO | 2010/124648 A1 | 11/2010 |
| WO | 2011/106273 A1 | 9/2011 |
| WO | 2012/033149 A1 | 3/2012 |
| WO | 2012/040499 A2 | 3/2012 |
| WO | 2012/116145 A1 | 8/2012 |
| WO | 2012/147765 A1 | 11/2012 |
| WO | 2013/011932 A1 | 1/2013 |
| WO | 2014/031441 A1 | 2/2014 |
| WO | 2014/031445 A1 | 2/2014 |
| WO | 2014/031465 A1 | 2/2014 |
| WO | 2014/031468 A1 | 2/2014 |
| WO | 2014/031515 A1 | 2/2014 |
| WO | 2014/031517 A1 | 2/2014 |
| WO | 2014/069426 A1 | 5/2014 |
| WO | 2014/133008 A1 | 9/2014 |
| WO | 2014/139388 A1 | 9/2014 |
| WO | 2014/175330 A1 | 10/2014 |
| WO | 2014/199933 A1 | 12/2014 |
| WO | 2015/007669 A1 | 1/2015 |
| WO | 2015/063011 A1 | 5/2015 |
| WO | 2016/023789 A1 | 2/2016 |
| WO | 2016/031842 A1 | 3/2016 |
| WO | 2016/113299 A1 | 7/2016 |
| WO | 2016/113300 A1 | 7/2016 |

HETEROCYCLIC DERIVATIVE HAVING AMPK-ACTIVATING ACTIVITY

FIELD OF THE INVENTION

The present invention relates to a compound which has an activating effect on adenosine monophosphate-activated protein kinase (hereinafter referred to as AMPK) and is useful as a medicine.

BACKGROUND ART

AMPK is a serine-threonine kinase, which is activated by AMP, and has three subunits, α, β and γ. In each subunit, there exist multiple isoforms (α1, α2, β1, β2, γ1, γ2 and γ3).

AMPK is involved in various physiological functions, such as suppression of gluconeogenesis and inhibition of fatty acid synthesis in liver and incorporation of sugars and an increase in fatty acid oxidation in skeletal muscles, as an energy sensor in living organisms, and has attracted attention as a target molecule of a therapeutic agent for diabetes. Therefore, an AMPK activator is expected to be effective in the treatment of diabetes as an insulin resistance improving drug, which has an insulin independent hypoglycemic effect and a lipid improving effect (Non-Patent Document 1).

Patent Documents 1 to 15, and 26 disclose a variety of compounds having an AMPK activating effect. However, heterocyclic derivatives like the compounds of the present invention are not disclosed in any of the documents.

Patent Document 7 discloses the compounds shown below.

[Chemical formula 1]

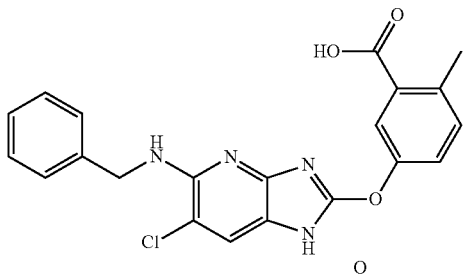

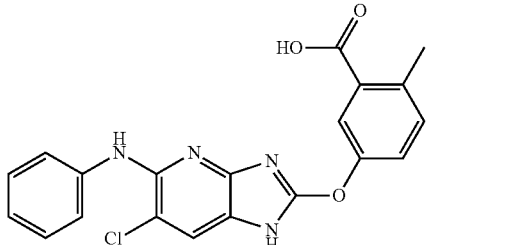

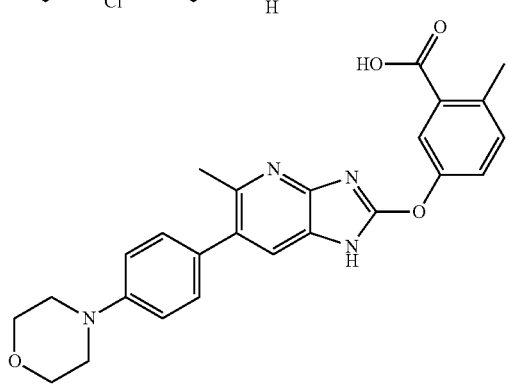

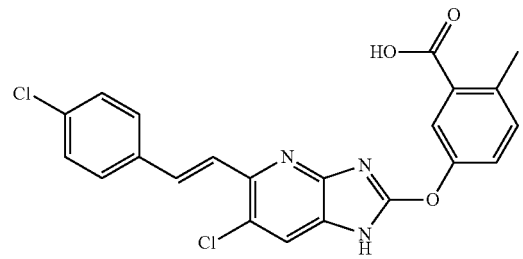

Patent Documents 16 and 17 describe the compounds shown below, as compounds useful for diabetes, but do not provide a description of AMPK activating effects.

[Chemical formula 2]

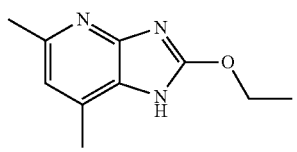

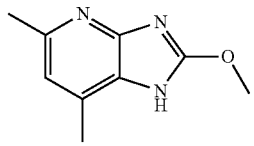

Patent Document 18 describes the compounds shown below, as compounds useful for obesity, but does not provide a description of AMPK activating effects.

[Chemical formula 3]

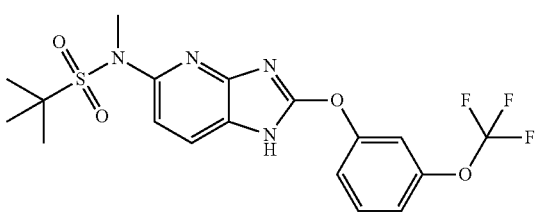

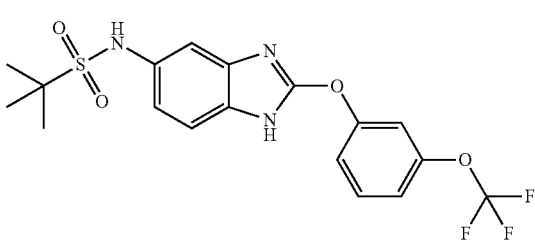

-continued

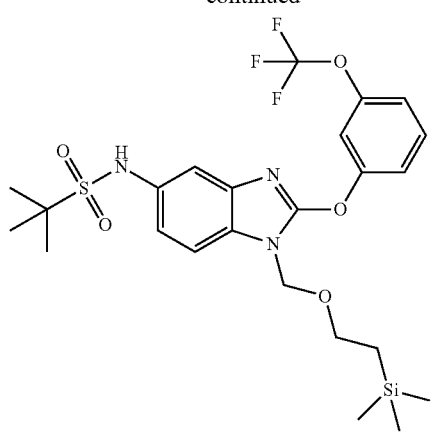

Patent Documents 18 and 19 describe, as compounds useful for obesity, compounds in which unsubstituted ethylsulfonyl is present at position 5 of the benzimidazole ring, such as the compounds shown below, but do not provide a description of AMPK activating effects.

[Chemical formula 4]

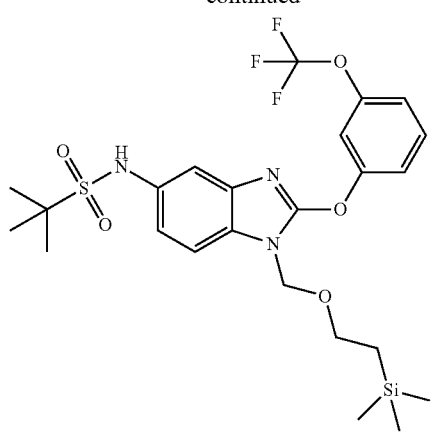

Patent Document 20 describes the compounds shown below, as compounds useful for cancers, but does not provide a description of AMPK activating effects.

[Chemical formula 5]

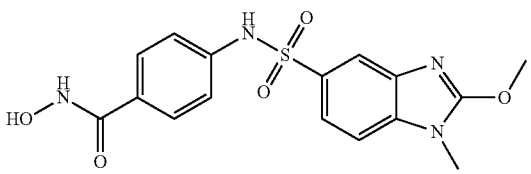

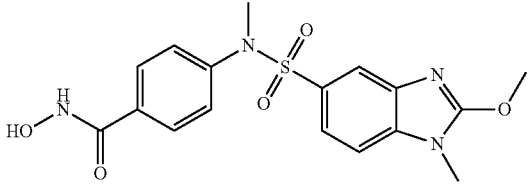

Patent Document 21 describes the compound shown below, as compounds useful for herbicides, but does not provide a description of AMPK activating effects.

[Chemical formula 6]

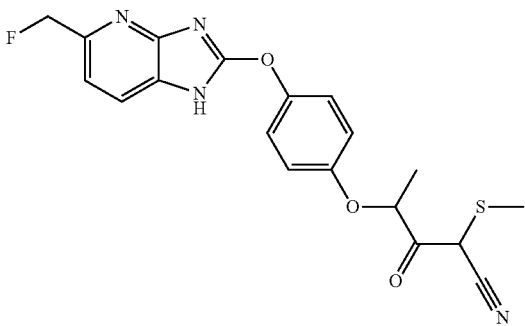

The compound shown below is hit by searching structures on SciFinder (online database), but there is no literature information and the AMPK activating effect of the compound is not described.

[Chemical formula 7]

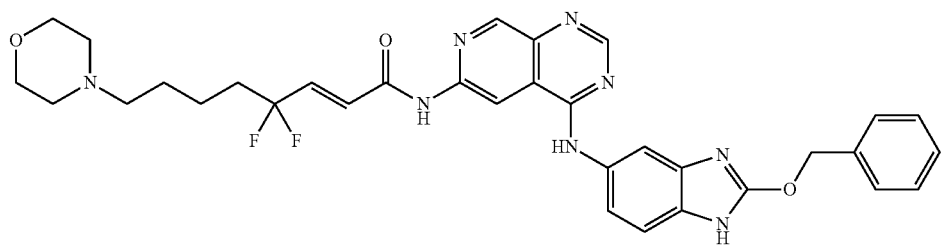

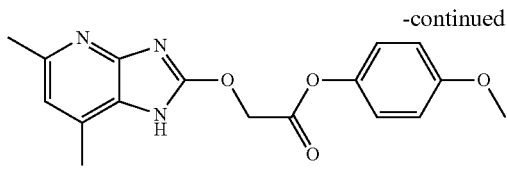

PRIOR ART DOCUMENT

Patent Document

Patent Document 1: WO2010/036613
Patent Document 2: WO2010/047982
Patent Document 3: WO2010/051176
Patent Document 4: WO2010/051206
Patent Document 5: WO2011/106273
Patent Document 6: WO2012/116145
Patent Document 7: WO2012/033149
Patent Document 8: WO2013/011932
Patent Document 9: WO2014/031441
Patent Document 10: WO2014/031445
Patent Document 11: WO2014/031468
Patent Document 12: WO2014/031517
Patent Document 13: WO2014/031465
Patent Document 14: WO2014/031515
Patent Document 15: WO2014/069426
Patent Document 16: WO2008/096829
Patent Document 17: WO2005/082905
Patent Document 18: JP2012-167027 A
Patent Document 19: WO2012/147765
Patent Document 20: WO2006/017214
Patent Document 21: JP05-339224 A
Patent Document 22: WO2015/007669
Patent Document 23: WO2015/063011
Patent Document 24: WO2014/139388
Patent Document 25: WO2014/175330
Patent Document 26: WO2014/133008

Non-Patent Document

Non-Patent Document 1: Cell Metabolism Vol. 9, Issue 5, 407-416, 2009

DISCLOSURE OF INVENTION

Problems to be Solved by the Invention

An object of the present invention is to provide an excellent AMPK activator.

Means for Solving the Problem

As a result of intensive research, the present inventors succeeded in synthesizing an excellent compound having an AMPK activating effect.

The present invention relates to the following.
(1)
A compound represented by the formula (I):

[Chemical formula 8]

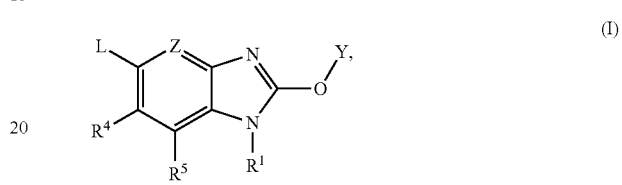

or its pharmaceutically acceptable salt,
wherein
L is $NR^2R^3$, $SR^7$, $SO_2R^8$, substituted or unsubstituted alkyl, or substituted or unsubstituted alkenyl;
$R^2$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl;
$R^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl;
$R^7$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, or substituted or unsubstituted carbamoyl;

R⁸ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, or substituted or unsubstituted amino, provided that R⁸ is not unsubstituted methyl or unsubstituted ethyl;

Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, provided that Y is not unsubstituted methyl or unsubstituted ethyl;

Z is —CR⁶=, or —N=;

R¹ is hydrogen, or substituted or unsubstituted alkyl;

R⁴, R⁵ and R⁶ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

wherein R¹ is hydrogen when Z is —CR⁶= and L is SO₂R⁸;

with the proviso that compounds wherein Y is substituted or unsubstituted aryl, Z is —CR⁶=, L is NR²R³ and one of R² and R³ is substituted or unsubstituted alkylsulfonyl;

compounds wherein Z is —CR⁶= and L is substituted or unsubstituted alkyl, or substituted or unsubstituted alkenyl; and compounds shown below are excluded:

[Chemical formula 9]

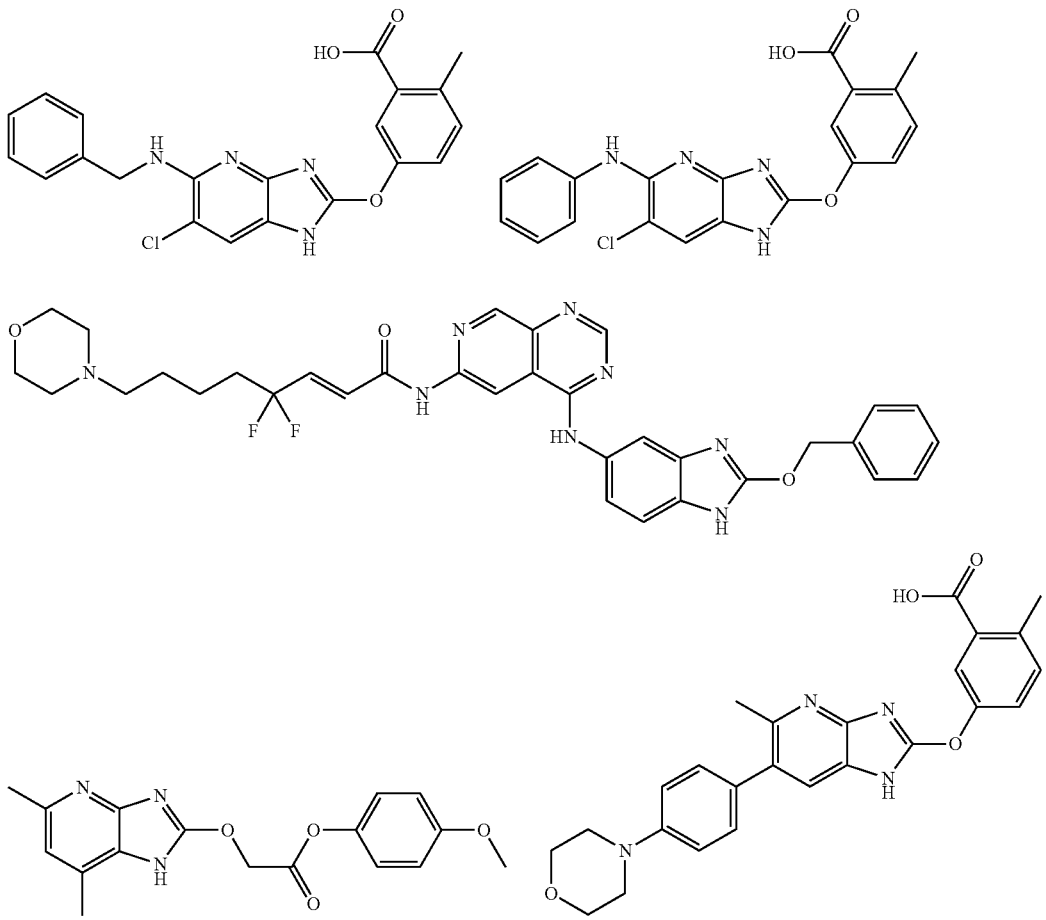

(2)

The compound according to the above (1), or its pharmaceutically acceptable salt, wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl.

(3)

The compound according to the above (1), or its pharmaceutically acceptable salt, wherein Y is substituted or unsubstituted heteroaryl, substituted or unsubstituted cycloalkyl, substituted or unsubstituted cycloalkenyl, or substituted or unsubstituted heterocyclyl.

(4)

The compound according to the above (1), or its pharmaceutically acceptable salt, wherein Y is substituted or unsubstituted heterocyclyl.

(5)

The compound according to the above (4), or its pharmaceutically acceptable salt, wherein Y is substituted or unsubstituted heterocyclyl and the substituted or unsubstituted heterocyclyl is

[Chemical formula 10]

wherein $R^9$ and $R^{10}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

$R^{11}$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino;

m is an integer from 0 to 6.

(6)

The compound according to any one of the above (1) to (5), or its pharmaceutically acceptable salt, wherein Z is —N=.

(7)

The compound according to any one of the above (1) to (5), or its pharmaceutically acceptable salt, wherein Z is —$CR^6$=.

(8)

The compound according to any one of the above (1) to (7), or its pharmaceutically acceptable salt, wherein L is $NR^2R^3$, $SR^7$, or $SO_2R^8$.

(9)

The compound according to any one of the above (1) to (8), or its pharmaceutically acceptable salt, wherein L is $NR^2R^3$.

(10)

The compound according to the above (1), or its pharmaceutically acceptable salt, wherein $R^2$ is hydrogen or substituted or unsubstituted alkyl.

(11)

The compound according to the above (9), or its pharmaceutically acceptable salt, wherein $R^3$ is substituted or unsubstituted alkyl, substituted or unsubstituted cycloalkenyl, or substituted or unsubstituted heterocyclyl.

(12)

The compound according to the above (11), or its pharmaceutically acceptable salt, wherein $R^3$ is substituted alkyl, wherein the substituent of substituted alkyl is one or more substituent(s) selected from substituted or unsubstituted aryl, substituted or unsubstituted heteroaryl, substituted or unsubstituted cycloalkyl, substituted or unsubstituted cycloalkenyl, and/or substituted or unsubstituted heterocyclyl.

(13)

The compound according to the above (11), or its pharmaceutically acceptable salt, wherein $R^3$ is substituted or unsubstituted cycloalkenyl, or substituted or unsubstituted heterocyclyl.

(14)

The compound according to any one of the above (1) to (13), or its pharmaceutically acceptable salt, wherein $R^4$ is hydrogen.

(15)

The compound according to any one of the above (1) to (14), or its pharmaceutically acceptable salt, wherein $R^5$ is hydrogen.

(16)

The compound according to any one of the above (1) to (15), or its pharmaceutically acceptable salt, wherein $R^4$ is hydrogen, halogen, cyano, or substituted or unsubstituted alkyl.

(17)

The compound according to the above (16), or its pharmaceutically acceptable salt, wherein $R^4$ is halogen.

(18)

A pharmaceutical composition having an activating effect on adenosine monophosphate-activated protein kinase, which comprises a compound represented by formula (II):

[Chemical formula 11]

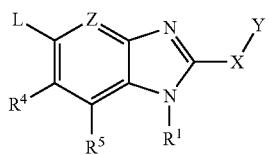

(II)

or its pharmaceutically acceptable salt,
wherein
L is $NR^2R^3$, $SR^7$, $SO_2R^8$, substituted or unsubstituted alkyl, or substituted or unsubstituted alkenyl;
X is single bond, —O—, —S—, —$NR^{12}$—, —C(=O)—, —C(=O)—$NR^{13}$—, —$NR^{14}$C(=O)—, —$NR^{15}$—SO_2—, —SO_2—$NR^{16}$—, or —C(=O)—O—;
$R^{12}$, $R^{13}$, $R^{14}$, $R^{15}$ and $R^{16}$ are each independently hydrogen or substituted or unsubstituted alkyl;
Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, provided that Y is not unsubstituted methyl or unsubstituted ethyl;
Z is —$CR^6$=, or —N=;
$R^1$ is hydrogen, or substituted or unsubstituted alkyl;
$R^2$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl;
$R^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl;
$R^4$, $R^5$ and $R^6$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;
$R^7$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, or substituted or unsubstituted carbamoyl;
$R^8$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, or substituted or unsubstituted amino, provided that $R^8$ is not unsubstituted methyl or unsubstituted ethyl;
with the proviso that
compounds wherein X is —O—, Y is substituted or unsubstituted aryl, Z is —$CR^6$=, L is $NR^2R^3$ and one of $R^2$ and $R^3$ is substituted or unsubstituted alkylsulfonyl; and
compounds shown below are excluded

[Chemical formula 12]

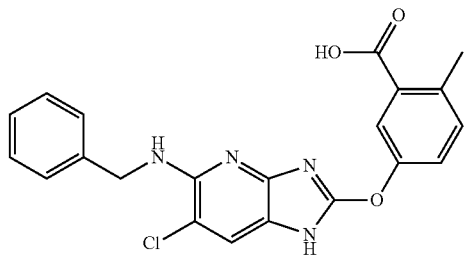

13

-continued

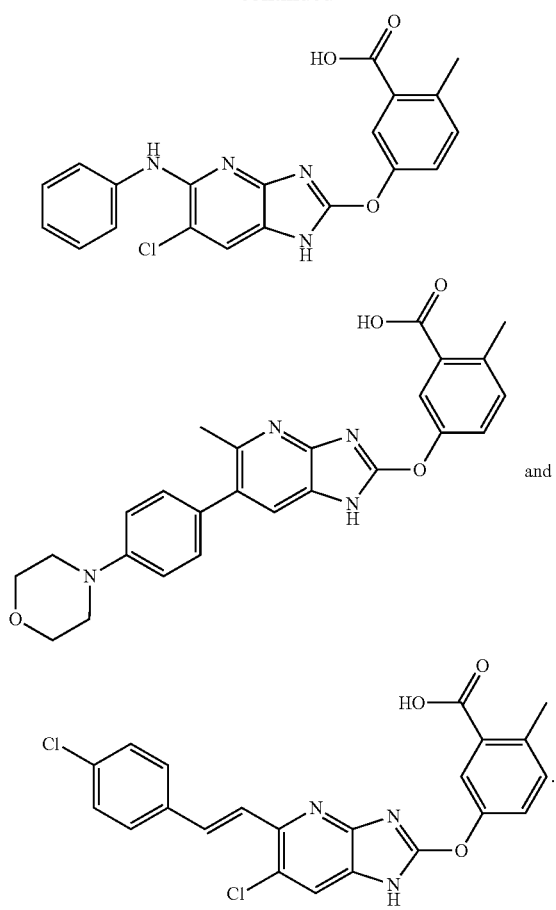

(19)

A pharmaceutical composition comprising the compound according to any one of the above (1) to (17), or its pharmaceutically acceptable salt.

(20)

The pharmaceutical composition according to the above (19), which has an activating effect on adenosine monophosphate-activated protein kinase.

(21)

A method for preventing or treating diabetes, comprising administering the compound according to any one of the above (1) to (18), or its pharmaceutically acceptable salt.

(22)

The compound according to any one of the above (1) to (18), or its pharmaceutically acceptable salt, for the treatment and/or prevention of diabetes.

(23)

A compound selected from compound (I-1-1), (I-1-4), (I-1-6), (I-1-8), (I-1-10), (I-1-11), (I-1-13), (I-1-14), (I-1-15), (I-1-36), (I-1-38), (I-1-39), (I-1-52), (I-1-80), (I-1-109), (I-1-116), (I-1-119), (I-1-126), (I-2-1), (I-2-19), (I-2-22), (I-2-62), (I-2-75), (I-2-91), (I-2-119), (I-2-147), (I-2-153), (I-2-185), (I-2-188), (I-2-192), (I-2-209), (I-2-217), (I-2-220), (I-2-222), (I-2-223), (I-2-228), (I-2-233), (I-2-238), (I-2-239) or (I-2-244), or its pharmaceutically acceptable salt.

14

(24)

A compound represented by the formula (IIIa) or (IIIb):

[Chemical formula 13]

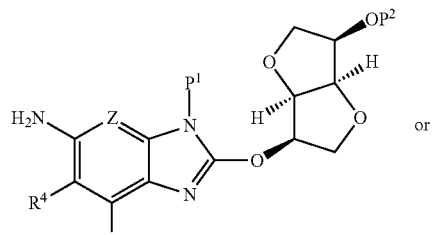

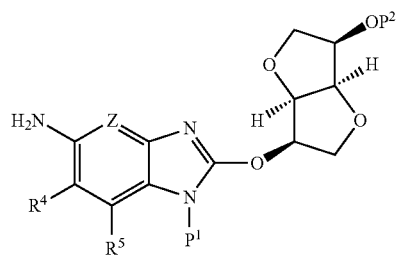

its pharmaceutically acceptable salt,
wherein
Z is $-CR^6=$, or $-N=$;
$P^1$ and $P^2$ are each independently protecting group;
$R^4$, $R^5$ and $R^6$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

(25)

The pharmaceutical composition according to any one of the above (18) to (20), for the treatment and/or prevention of diabetes.

(26)

A pharmaceutical composition for oral administration, comprising a compound represented by the above formula (I) or its pharmaceutically acceptable salt.

(27)

The pharmaceutical composition according to the above (26), which is a tablet, powder, granule, capsule, pill, film, suspension, emulsion, elixir, syrup, lemonade, spirit, aromatic water, extract, decoction or tincture.

(28)

The pharmaceutical composition according to the above (27), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, micro capsule or sustained-release capsule.

(29)

A pharmaceutical composition for parenteral administration, comprising a compound represented by the above formula (I) or its pharmaceutically acceptable salt.

(30)

The pharmaceutical composition according to the above (29), for dermal, subcutaneous, intravenous, intraarterial, intramuscular, intraperitoneal, transmucosal, inhalation, transnasal, ophthalmic, inner ear or vaginal administration.

(31)

The pharmaceutical composition according to the above (29) or (30), which is injection, infusion, eye drop, nose drop, ear drop, aerosol, inhalation, lotion, impregnation, liniment, mouthwash, enema, ointment, plaster, jelly, cream, patch, cataplasm, external powder or suppository.

(32)

A pharmaceutical composition for a pediatric or geriatric patient, comprising a compound represented by the above formula (I) or its pharmaceutically acceptable salt.

(33)

A pharmaceutical composition consisting of a combination of a compound represented by the above formula (T) or its pharmaceutically acceptable salt, and an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor.

(34)

A pharmaceutical composition comprising a compound represented by the above formula (I) or its pharmaceutically acceptable salt, for a combination therapy with an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor, (1A)

A compound represented by formula (I);

[Chemical formula 14]

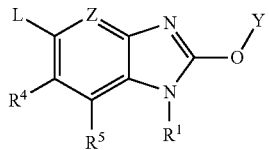

(I)

or its pharmaceutically acceptable salt, wherein
L is $NR^2R^3$, $SR^7$, $SO_2R^8$, or substituted or unsubstituted alkyl;

$R^2$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl;

$R^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl;

$R^7$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, or substituted or unsubstituted carbamoyl;

$R^8$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, or substituted or unsubstituted amino, provided that $R^8$ is not unsubstituted methyl or unsubstituted ethyl;

Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, provided that Y is not unsubstituted methyl or unsubstituted ethyl;

Z is —$CR^6$=, or —N=;

$R^1$ is hydrogen, or substituted or unsubstituted alkyl;

$R^4$, $R^5$ and $R^6$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; wherein $R^1$ is hydrogen when Z is —$CR^6$= and L is $SO_2R^8$;

with the proviso that a compound wherein Y is substituted or unsubstituted aryl, Z is —$CR^6$=, L is $NR^2R^3$, and one of $R^2$ and $R^3$ is substituted or unsubstituted alkylsulfonyl;

a compound wherein Z is —$CR^6$=, and L is substituted or unsubstituted alkyl;

and the compounds shown below are excluded:

[Chemical formula 15]

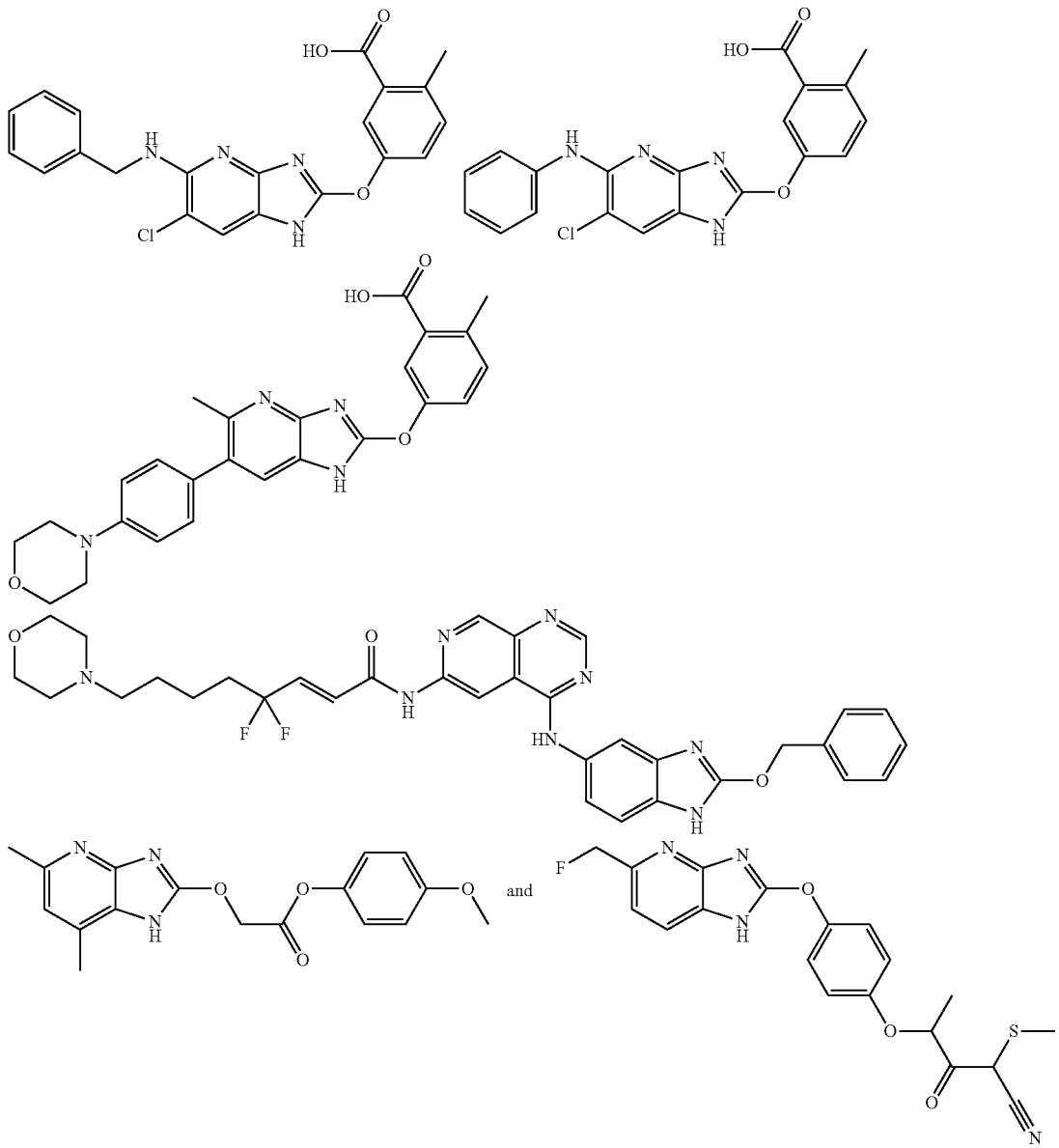

(2A)

The compound according to the above (1A), or its pharmaceutically acceptable salt, wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl.

(3A)
The compound according to the above (1A), or its pharmaceutically acceptable salt, wherein Y is substituted or unsubstituted heteroaryl, substituted or unsubstituted cycloalkyl, substituted or unsubstituted cycloalkenyl, or substituted or unsubstituted heterocyclyl.

(4A)
The compound according to the above (1A), or its pharmaceutically acceptable salt, wherein Y is substituted or unsubstituted heterocyclyl.

(5A)
The compound according to the above (4A), or its pharmaceutically acceptable salt, wherein Y is substituted or unsubstituted heterocyclyl, wherein the substituted or unsubstituted heterocyclyl is

[Chemical formula 16]

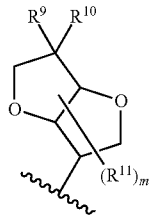

wherein $R^9$ and $R^{10}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; $R^{11}$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; m is an integer from 0 to 6.

(6A)
The compound according to any one of the above (1A) to (5A), or its pharmaceutically acceptable salt, wherein Z is —N=.

(7A)
The compound according to any one of the above (1A) to (5A), or its pharmaceutically acceptable salt, wherein Z is —$CR^6$=.

(8A)
The compound according to any one of the above (1A) to (7A), or its pharmaceutically acceptable salt, wherein L is $NR^2R^3$, $SR^7$, or $SO_2R^8$.

(9A)
The compound according to any one of the above (1A) to (8A), or its pharmaceutically acceptable salt, wherein L is $NR^2R^3$.

(10A)
The compound according to any one of the above (1A) to (9A), or its pharmaceutically acceptable salt, wherein $R^2$ is hydrogen, or substituted or unsubstituted alkyl.

(11A)
The compound according to any one of the above (1A) to (10A), or its pharmaceutically acceptable salt, wherein $R^3$ is substituted or unsubstituted alkyl, substituted or unsubstituted cycloalkenyl, or substituted or unsubstituted heterocyclyl.

(12A)
The compound according to the above (11A), or its pharmaceutically acceptable salt, wherein $R^3$ is substituted alkyl, wherein the substituent of the substituted alkyl is one or more substituent(s) selected from substituted or unsubstituted aryl, substituted or unsubstituted heteroaryl, substituted or unsubstituted cycloalkyl, substituted or unsubstituted cycloalkenyl, and substituted or unsubstituted heterocyclyl.

(13A)
The compound according to any one of the above (1A) to (11A), or its pharmaceutically acceptable salt, wherein $R^3$ is substituted or unsubstituted cycloalkenyl, or substituted or unsubstituted heterocyclyl.

(14A)
The compound according to any one of the above (1A) to (13A), or its pharmaceutically acceptable salt, wherein $R^1$ is hydrogen.

(15A)
The compound according to any one of the above (1A) to (14A), or its pharmaceutically acceptable salt, wherein $R^5$ is hydrogen.

(16A)
The compound according to any one of the above (1A) to (15A), or its pharmaceutically acceptable salt, wherein $R^4$ is hydrogen, halogen, cyano, substituted or unsubstituted alkyl.

(17A)
The compound according to the above (16A), or its pharmaceutically acceptable salt, wherein $R^4$ is halogen.

(18A)
A pharmaceutical composition having an activating effect on adenosine monophosphate-activated protein kinase, which comprises a compound represented by formula (II):

[Chemical formula 17]

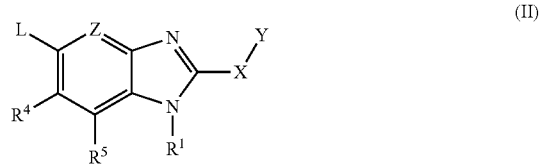

(II)

or its pharmaceutically acceptable salt,
wherein
L is $NR^2R^3$, $SR^7$, $SO_2R^8$, or substituted or unsubstituted alkyl;
X is single bond, —O—, —S—, —$NR^{12}$—, —C(=O)—, —C(=O)$NR^{13}$—, —$NR^{14}$C(=O)—, —$NR^{15}$—$SO_2$—, —$SO_2$—$NR^{16}$—, or —C(=O)—O—;
$R^{12}$, $R^{13}$, $R^{14}$, $R^{15}$ and $R^{16}$ are each independently hydrogen or substituted or unsubstituted alkyl;
Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, provided that Y is not unsubstituted methyl or unsubstituted ethyl; Z is —$CR^6$= or —N=;

R¹ is hydrogen, or substituted or unsubstituted alkyl;

R² is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl;

R³ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl;

R⁴, R⁵ and R⁶ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or unsubstituted amino;

R⁷ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, or substituted or unsubstituted carbamoyl;

R⁸ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, or substituted or unsubstituted amino, provided that R⁸ is not unsubstituted methyl or unsubstituted ethyl;

with the proviso that a compound wherein X is —O—, Y is substituted or unsubstituted aryl, Z is —CR⁶=, L is NR²R³, and one of R² and R³ is substituted or unsubstituted alkylsulfonyl;

and the compounds shown below are excluded:

[Chemical formula 18]

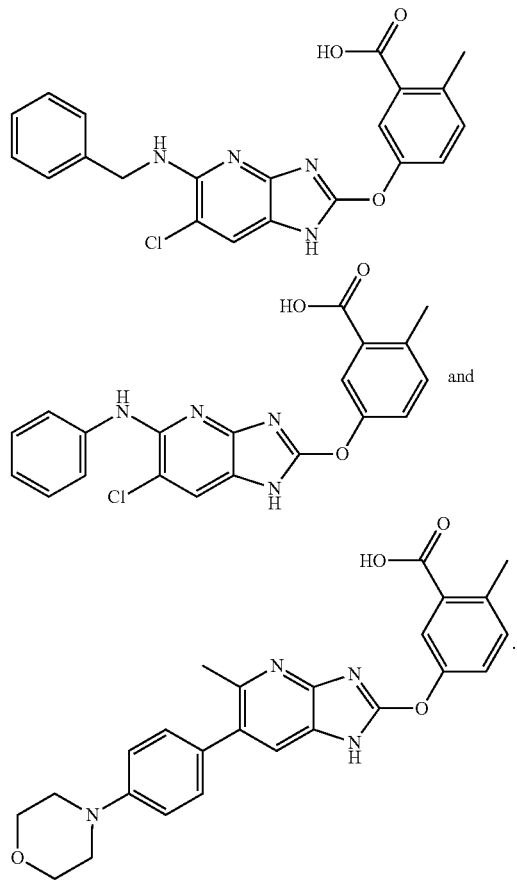

(19A)

A pharmaceutical composition comprising the compound according to any one of the above (1A) to (17A), or its pharmaceutically acceptable salt.

(20A)

The pharmaceutical composition according to the above (19A), which has an activating effect on adenosine monophosphate-activated protein kinase.

(21A)

A compound represented by formula (IIIa) or (IIIb):

[Chemical formula 19]

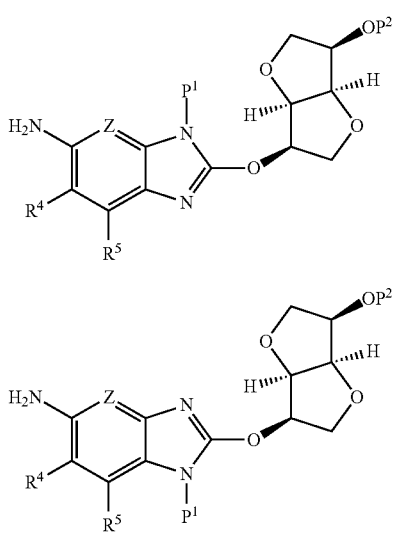

or its pharmaceutically acceptable salt,
wherein
Z is —CR$^6$═, or —N═;
P$^1$ and P$^2$ are each independently a protecting group;
R$^4$, R$^5$ and R$^6$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

(22A)

The pharmaceutical composition according to any one of the above (18A) to (20A), for the treatment and/or prevention of diabetes.

(23A)

A method for preventing or treating diabetes, comprising administering the compound according to any one of the above (1A) to (18A), or its pharmaceutically acceptable salt.

(24A)

The compound according to any one of the above (1A) to (18A), or its pharmaceutically acceptable salt, for the treatment and/or prevention of diabetes.

(25A)

A pharmaceutical composition for oral administration, comprising a compound represented by the above formula (I) or its pharmaceutically acceptable salt.

(26A)

The pharmaceutical composition according to the above (25A), which is a tablet, powder, granule, capsule, pill, film, suspension, emulsion, elixir, syrup, lemonade, spirit, aromatic water, extract, decoction or tincture.

(27A)

The pharmaceutical composition according to the above (26A), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, micro capsule or sustained-release capsule.

(28A)

A pharmaceutical composition for parenteral administration, comprising a compound represented by the above formula (I) or its pharmaceutically acceptable salt.

(29A)

The pharmaceutical composition according to the above (28A), for dermal, subcutaneous, intravenous, intraarterial, intramuscular, intraperitoneal, transmucosal, inhalation, transnasal, ophthalmic, inner ear or vaginal administration.

(30A)

The pharmaceutical composition according to the above (28A) or (29A), which is injection, infusion, eye drop, nose drop, ear drop, aerosol, inhalation, lotion, impregnation, liniment, mouthwash, enema, ointment, plaster, jelly, cream, patch, cataplasm, external powder or suppository.

(31A)

A pharmaceutical composition for a pediatric or geriatric patient, comprising a compound represented by the above formula (I) or its pharmaceutically acceptable salt.

(32A)

A pharmaceutical composition consisting of a combination of a compound represented by the above formula (T) or its pharmaceutically acceptable salt, and an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor.

(33A)

A pharmaceutical composition comprising a compound represented by the above formula (I) or its pharmaceutically acceptable salt, for a combination therapy with an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor, (1B)
A compound represented by formula (I):

[Chemical formula 20]

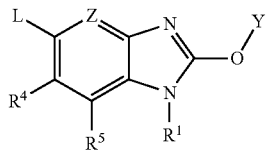

or its pharmaceutically acceptable salt,
wherein
L is $NR^2R^3$, $SR^7$, $SO_2R^8$, substituted or unsubstituted alkyl, or substituted or unsubstituted alkenyl;

$R^2$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl;

$R^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl;

$R^7$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, or substituted or unsubstituted carbamoyl;

$R^8$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, or substituted or unsubstituted amino, provided that $R^8$ is not unsubstituted methyl or unsubstituted ethyl;

Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, provided that Y is not unsubstituted methyl or unsubstituted ethyl;

Z is $-CR^6=$, or $-N=$;

$R^1$ is hydrogen, or substituted or unsubstituted alkyl;

$R^4$, $R^5$ and $R^6$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

wherein $R^1$ is hydrogen when Z is $-CR^6=$ and L is $SO_2R^8$;

with the proviso that a compound wherein Y is substituted or unsubstituted aryl, Z is $-CR^6=$, L is $NR^2R^3$, and one of $R^2$ and $R^3$ is substituted or unsubstituted alkylsulfonyl;

a compound wherein Z is $-CR^6=$, and L is substituted or unsubstituted alkyl, or substituted or unsubstituted alkenyl;

and the compounds shown below are excluded:

[Chemical formula 21]

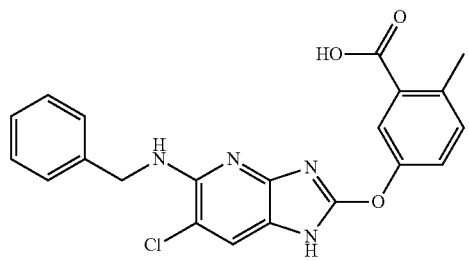 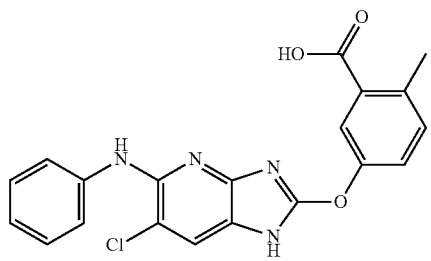

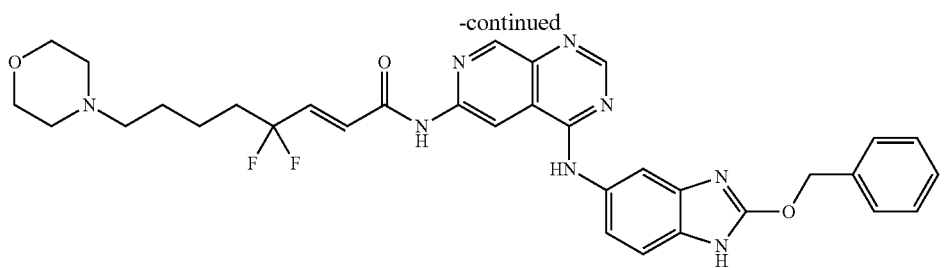

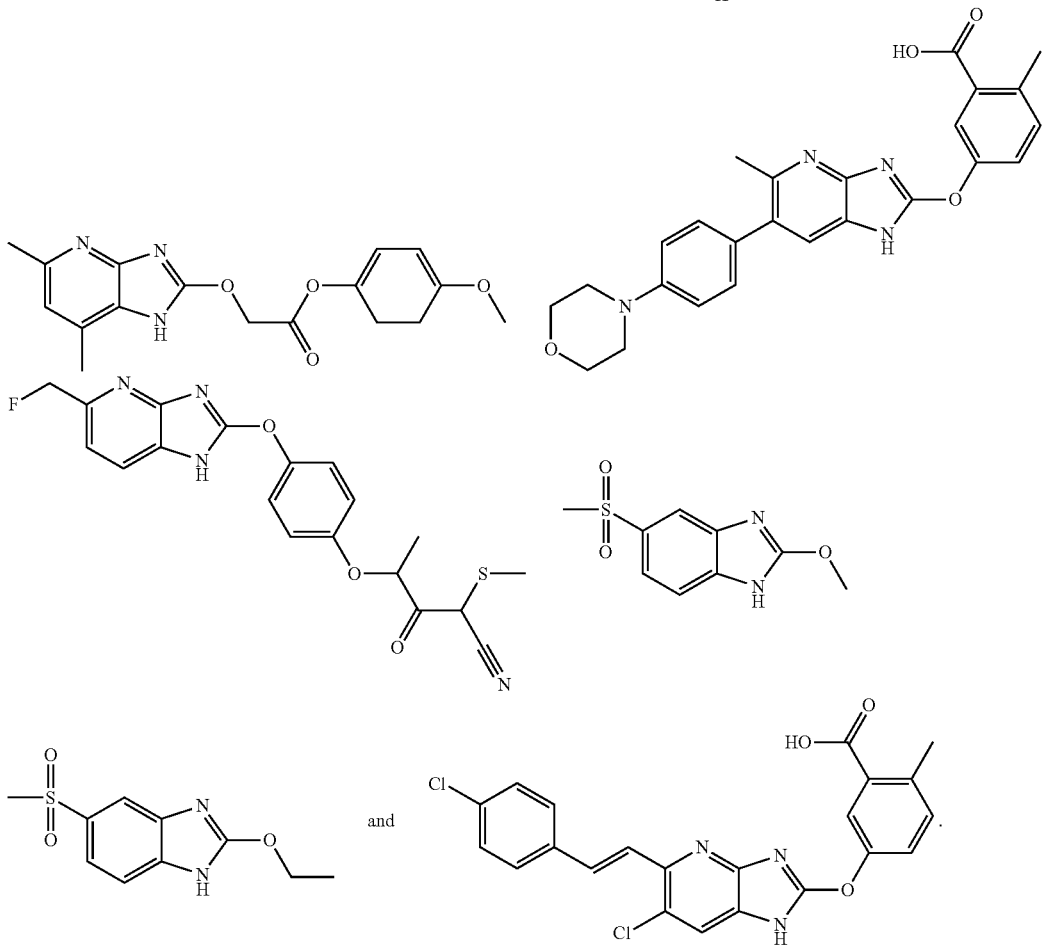

and (2B)

The compound according to the above (1B), or its pharmaceutically acceptable salt, wherein Y is substituted or unsubstituted aryl, substituted or unsubstituted heteroaryl, substituted or unsubstituted cycloalkyl, substituted or unsubstituted cycloalkenyl, or substituted or unsubstituted heterocyclyl.

(3B)

The compound according to the above (1B), or its pharmaceutically acceptable salt, wherein Y is substituted or unsubstituted heteroaryl, substituted or unsubstituted cycloalkyl, substituted or unsubstituted cycloalkenyl, or substituted or unsubstituted heterocyclyl.

(4B)

The compound according to the above (1B), or its pharmaceutically acceptable salt, wherein Y is substituted or unsubstituted heterocyclyl.

(5B)

The compound according to the above (4B), or its pharmaceutically acceptable salt, wherein Y is substituted or unsubstituted heterocyclyl, wherein the substituted or unsubstituted heterocyclyl is

[Chemical formula 22]

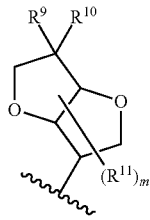

wherein $R^9$ and $R^{10}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; $R^{11}$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; m is an integer from 0 to 6.

(6B)

The compound according to any one of the above (1B) to (5B), or its pharmaceutically acceptable salt, wherein Z is —N=.

(7B)

The compound according to any one of the above (1B) to (5B), or its pharmaceutically acceptable salt, wherein Z is —$CR^6$=.

(8B)

The compound according to any one of the above (1B) to (7B), or its pharmaceutically acceptable salt, wherein L is $NR^2R^3$, $SR^7$, or $SO_2R^8$.

(9B)

The compound according to any one of the above (1B) to (8B), or its pharmaceutically acceptable salt, wherein L is $NR^2R^3$.

(10B)

The compound according to any one of the above (1B) to (9B), or its pharmaceutically acceptable salt, wherein $R^2$ is hydrogen, or substituted or unsubstituted alkyl.

(11B)

The compound according to any one of the above (1B) to (10B), or its pharmaceutically acceptable salt, wherein $R^3$ is substituted or unsubstituted alkyl, substituted or unsubstituted cycloalkenyl, or substituted or unsubstituted heterocyclyl.

(12B)

The compound according to the above (11B), or its pharmaceutically acceptable salt, wherein $R^3$ is substituted alkyl, wherein the substituent of the substituted alkyl is one or more substituent(s) selected from substituted or unsubstituted aryl, substituted or unsubstituted heteroaryl, substituted or unsubstituted cycloalkyl, substituted or unsubstituted cycloalkenyl, and substituted or unsubstituted heterocyclyl.

(13B)

The compound according to any one of the above (1B) to (11B), or its pharmaceutically acceptable salt, wherein $R^3$ is substituted or unsubstituted cycloalkenyl, or substituted or unsubstituted heterocyclyl.

(14B)

The compound according to any one of the above (1B) to (13B), or its pharmaceutically acceptable salt, wherein $R^1$ is hydrogen.

(15B)

The compound according to any one of the above (1B) to (14B), or its pharmaceutically acceptable salt, wherein $R^5$ is hydrogen.

(16B)

The compound according to any one of the above (1B) to (15B), or its pharmaceutically acceptable salt, wherein $R^4$ is hydrogen, halogen, cyano, substituted or unsubstituted alkyl.

(17B)

The compound according to the above (16B), or its pharmaceutically acceptable salt, wherein $R^4$ is halogen.

(18B)

A pharmaceutical composition having an activating effect on adenosine monophosphate-activated protein kinase, which comprises a compound represented by formula (11):

[Chemical formula 23]

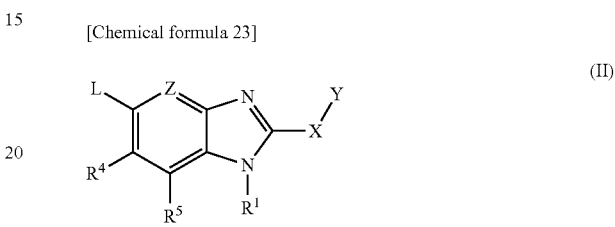

(II)

or its pharmaceutically acceptable salt,
wherein
L is $NR^2R^3$, $SR^7$, $SO_2R^8$, substituted or unsubstituted alkyl, or substituted or unsubstituted alkenyl;
X is single bond, —O—, —S—, —$NR^{12}$—, —C(=O)—, —C(=O)—$NR^{13}$—, —$NR^{14}$C(=O)—, —$NR^{15}$—$SO_2$—, —$SO_2$—$NR^{16}$—, or —C(=O)—O—;
$R^{12}$, $R^{13}$, $R^{14}$, $R^{15}$ and $R^{16}$ are each independently hydrogen or substituted or unsubstituted alkyl;
Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, provided that Y is not unsubstituted methyl or unsubstituted ethyl; Z is —$CR^6$= or —N=;
$R^1$ is hydrogen, or substituted or unsubstituted alkyl;
$R^2$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl;
$R^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkynylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl;

$R^4$, $R^5$ and $R^6$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino;

$R^7$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, or substituted or unsubstituted carbamoyl;

$R^8$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, or substituted or unsubstituted amino, provided that $R^8$ is not unsubstituted methyl or unsubstituted ethyl;

with the proviso that a compound wherein X is —O—, Y is substituted or unsubstituted aryl, Z is —$CR^6$=, L is $NR^2R^3$, and one of $R^2$ and $R^3$ is substituted or unsubstituted alkylsulfonyl;

and the compounds shown below are excluded:

[Chemical formula 24]

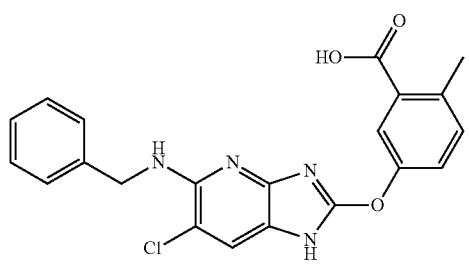

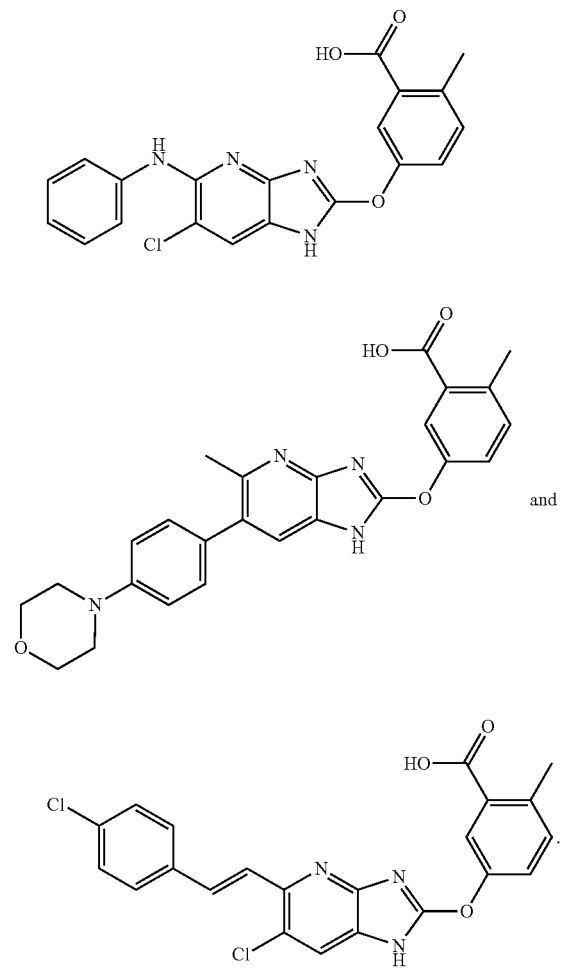

(19B)

A pharmaceutical composition comprising the compound according to any one of the above (1B) to (17B), or its pharmaceutically acceptable salt.

(20B)

The pharmaceutical composition according to the above (19B), which has an activating effect on adenosine monophosphate-activated protein kinase.

(21B)

A compound represented by formula (IIIa) or (IIIb):

[Chemical formula 25]

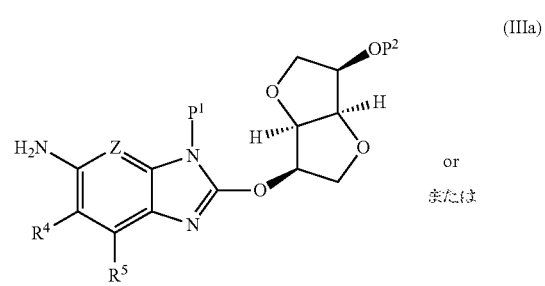

or
または

-continued (IIIb)

or its pharmaceutically acceptable salt,
wherein
Z is —$CR^6$=, or —N=;
$P^4$ and $P^2$ are each independently a protecting group;
$R^4$, $R^5$ and $R^6$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

(22B)

The pharmaceutical composition according to any one of the above (18B) to (20B), for the treatment and/or prevention of diabetes.

(23B)

A method for preventing or treating diabetes, comprising administering the compound according to any one of the above (1B) to (18B), or its pharmaceutically acceptable salt.

(24B)

The compound according to any one of the above (1B) to (18B), or its pharmaceutically acceptable salt, for the treatment and/or prevention of diabetes.

(25B)

A pharmaceutical composition for oral administration, comprising a compound represented by the above formula (I) or its pharmaceutically acceptable salt.

(26B)

The pharmaceutical composition according to the above (25B), which is a tablet, powder, granule, capsule, pill, film, suspension, emulsion, elixir, syrup, lemonade, spirit, aromatic water, extract, decoction or tincture.

(27B)

The pharmaceutical composition according to the above (26B), which is a sugar-coated tablet, film-coated tablet, enteric-coated tablet, sustained-release tablet, troche tablet, sublingual tablet, buccal tablet, chewable tablet, orally disintegrating tablet, dry syrup, soft capsule, micro capsule or sustained-release capsule.

(28B)

A pharmaceutical composition for parenteral administration, comprising a compound represented by the above formula (I) or its pharmaceutically acceptable salt.

(29B)

The pharmaceutical composition according to the above (28B), for dermal, subcutaneous, intravenous, intraarterial, intramuscular, intraperitoneal, transmucosal, inhalation, transnasal, ophthalmic, inner ear or vaginal administration.

(30B)

The pharmaceutical composition according to the above (28B) or (29B), which is injection, infusion, eye drop, nose drop, ear drop, aerosol, inhalation, lotion, impregnation, liniment, mouthwash, enema, ointment, plaster, jelly, cream, patch, cataplasm, external powder or suppository.

(31B)

A pharmaceutical composition for a pediatric or geriatric patient, comprising a compound represented by the above formula (I) or its pharmaceutically acceptable salt.

(32B)

A pharmaceutical composition consisting of a combination of a compound represented by the above formula (T) or its pharmaceutically acceptable salt, and an insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor.

(33B)

A pharmaceutical composition comprising a compound represented by the above formula (I) or its pharmaceutically acceptable salt, for a combination therapy with au insulin secretagogue, a fast-acting insulin secretagogue, a glucose uptake inhibitor, an insulin resistance improving drug, a thiazolidine derivative, an insulin formulation, a peptidyl peptidase IV inhibitor, a GLP-1 receptor agonist, a sodium-dependent glucose transporter 1 inhibitor, or a sodium-dependent glucose transporter 2 inhibitor.

Effect of the Invention

The compound of the present invention has an AMPK activating effect, and thus a pharmaceutical composition comprising a compound of the present invention is very useful as a medicinal product, particularly, a medicine for treating and/or preventing type II diabetes, hyperglycemia, metabolic syndrome, obesity, hypercholesterolemia and/or hypertension. Further, the compound of the present invention is a compound which has usefulness as a medicine. The usefulness as a medicine herein comprises good metabolic stability, slight induction of a drug-metabolizing enzyme, slight inhibition of drug-metabolizing enzymes which metabolize other drugs, high oral absorption, low clearance, a sufficiently long half-life period to express the efficacy of a medicine, a high enzyme activity, a high maximal activation rate, a low protein binding rate, high penetration into target tissue, high solubility, high safety, an insulin resistance improving effect based on an energy consumption increase, the effect of decreasing hemoglobin $A_{1C}$ (HbA1c), the effect of improving fatty liver or the like.

Mode for Carrying Out the Invention

Each term used in this description will be described below. In this description, even when each term is used individually or used with other terms, the term has the same meaning.

"Halogen" includes fluorine, chlorine, bromine, and iodine.

"Alkyl" means a C1 to C10 straight or branched alkyl group, and examples thereof include methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl, and the like. Preferable is a C1 to C6 or C1 to C4 alkyl, and examples thereof include methyl, ethyl, n-propyl, isopropyl, n-butyl, isobutyl, sec-butyl, tert-butyl, n-pentyl, isopentyl, neopentyl, n-hexyl, and isohexyl.

"Alkenyl" means a C2 to C8 straight or branched alkenyl having one or more double bond(s) in the above "alkyl", and examples thereof include vinyl, 1-propenyl, 2-propenyl, 1-butenyl, 2-butenyl, 3-butenyl, 1,3-butadienyl, 3-methyl-2-butenyl, and the like.

"Alkynyl" means a C2 to C8 straight or branched alkynyl having one or more triple bond(s) in the above "alkyl", and examples thereof include ethynyl, propynyl, butynyl, and the like. Furthermore, an "alkynyl" may have a double bond.

"Cycloalkyl" means a C3 to C15 cyclic saturated hydrocarbon group, and examples thereof include cyclopropyl, cyclobutyl, cyclopentyl, cyclohexyl, cycloheptyl, cyclooctyl, a bridged cyclic hydrocarbon group, a Spiro hydrocarbon group, and the like. Preferable is cyclopropyl, cyclobutyl, cyclopentyl, cyclohexyl, or a bridged cyclic hydrocarbon group.

A "bridged cyclic hydrocarbon group" includes a group which is derived by removing one hydrogen from a C5 to C8 aliphatic cycle which consists of two or more rings that share two or more atoms. Specific examples include bicyclo[2.1.0]pentyl, bicyclo[2.2.1]heptyl, bicyclo[2.2.2]octyl, bicyclo[3.2.1]octyl, tricyclo[2.2.1.0]heptyl, or the like.

A "Spiro hydrocarbon group" includes a group which is derived by removing one hydrogen from a cycle which consists of two hydrocarbon rings that share one carbon atom. Specific examples include spiro[3.4]octyl, or the like.

"Cycloalkenyl" means a C3 to C10 cyclic unsaturated aliphatic hydrocarbon group, and examples thereof include cyclopropenyl (e.g.: 1-cyclopropenyl), cyclobutenyl (e.g.: 1-cyclobutenyl), cyclopentenyl (e.g.: 1-cyclopenten-1-yl, 2-cyclopenten-1-yl, 3-cyclopenten-1-yl), cyclohexenyl (e.g.: 1-cyclohexen-1-yl, 2-cyclohexen-1-yl, 3-cyclohexen-1-yl), cycloheptenyl (e.g.: 1-cycloheptenyl), cyclooctenyl (e.g.: 1-cyclooctenyl), and the like. Preferable is cyclopropenyl, cyclobutenyl, cyclopentenyl, cyclohexenyl. Cycloalkenyls also include a bridged cyclic hydrocarbon group and a Spiro hydrocarbon group which both have an unsaturated bond in the ring. Cycloalkenyls also include a cyclic group in which a cycloalkene or benzene ring is condensed to an above-described cycloalkyl. For example, cycloalkenyls include the groups shown below:

[Chemical formula 26]

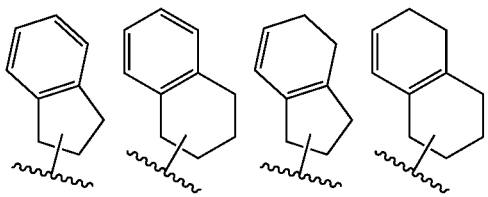

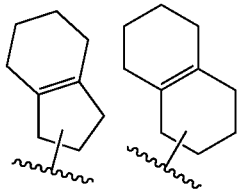

"Aryl" means a monocyclic aromatic hydrocarbon group (e.g.: phenyl) and a polycyclic aromatic hydrocarbon group (e.g.: 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, etc.). Preferable is phenyl or naphthyl (1-naphthyl, 2-naphthyl).

"Heteroaryl" means a monocyclic aromatic heterocyclic group and a fused aromatic heterocyclic group.

A "monocyclic aromatic heterocyclic group" means a group which is derived from a 5 to 8-membered aromatic ring which has one or more same or different heteroatoms optionally selected from oxygen, sulfur, and nitrogen atoms in the ring, which group may have a bond at any substitutable position.

A "fused aromatic heterocyclic group" means a group in which a 5 to 8-membered aromatic ring which has one or more same or different heteroatoms optionally selected from oxygen, sulfur, and nitrogen atoms in the ring is fused with one to four 5 to 8-membered aromatic carbocyclic rings or another 5 to 8-membered aromatic hetero ring, which group may have a bond at any substitutable position.

Examples of a "heteroaryl" include furyl (e.g.: 2-furyl, 3-furyl), thienyl (e.g.: 2-thienyl, 3-thienyl), pyrrolyl (e.g.: 1-pyrrolyl, 2-pyrrolyl, 3-pyrrolyl), imidazolyl (e.g.: 1-imidazolyl, 2-imidazolyl, 4-imidazolyl), pyrazolyl (e.g.: 1-pyrazolyl, 3-pyrazolyl, 4-pyrazolyl), triazolyl (e.g.: 1,2,4-triazol-1-yl, 1,2,4-triazol-3-yl, 1,2,4-triazol-4-yl), tetrazolyl (e.g.: 1-tetrazolyl, 2-tetrazolyl, 5-tetrazolyl), oxazolyl (e.g.: 2-oxazolyl, 4-oxazolyl, 5-oxazolyl), isoxazolyl (e.g.: 3-isoxazolyl, 4-isoxazolyl, 5-isoxazolyl), thiazolyl (e.g.: 2-thiazolyl, 4-thiazolyl, 5-thiazolyl), thiadiazolyl, isothiazolyl (e.g.: 3-isothiazolyl, 4-isothiazolyl, 5-isothiazolyl), pyridyl (e.g.: 2-pyridyl, 3-pyridyl, 4-pyridyl), pyridazinyl (e.g.: 3-pyridazinyl 4-pyridazinyl), pyrimidinyl (e.g.: 2-pyrimidinyl, 4-pyrimidinyl, 5-pyrimidinyl), furazanyl (e.g.: 3-furazanyl), pyrazinyl (e.g.: 2-pyrazinyl), oxadiazolyl (e.g.: 1,3,4-oxadiazol-2-yl), benzofuryl (e.g.: 2-benzo[b]furyl, 3-benzo[b]furyl, 4-benzo[b]furyl, 5-benzo[b]furyl, 6-benzo[b]furyl, 7-benzo[b]furyl), benzothienyl (e.g.: 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g.: 1-benzimidazolyl, 2-benzimidazolyl, 4-benzimidazolyl, 5-benzimidazolyl), benzopyrazolyl, dibenzofuryl, benzoxazolyl, benzothiazolyl, quinoxalinyl (e.g.: 2-quinoxalinyl, 5-quinoxalinyl, 6-quinoxalinyl), cinnolinyl (e.g.: 3-cinnolinyl, 4-cinnolinyl, 5-cinnolinyl, 6-cinnolinyl, 7-cinnolinyl, 8 cinnolinyl), quinazolinyl (e.g.: 2-quinazolinyl, 4-quinazolinyl, 5-quinazolinyl, 6-quinazolinyl, 7-quinazolinyl, 8-quinazolinyl), quinolyl (e.g.: 2-quinolyl, 3-quinolyl, 4-quinolyl, 5-quinolyl, 6-quinolyl, 7-quinolyl, 8-quinolyl), phthalazinyl (e.g.: 1-phthalazinyl, 5-phthalazinyl, 6-phthalazinyl), isoquinolyl (e.g.: 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g.: 2-pteridinyl, 4-pteridinyl, 6-pteridinyl, 7-pteridinyl), carbazolyl, phenanthridinyl, acridinyl (e.g.: 1-acridinyl, 2-acridinyl, 3-acridinyl, 4-acridinyl, 9-acridinyl), indolyl (e.g.: 1-indolyl, 2-indolyl, 3-indolyl, 4-indolyl, 5-indolyl, 6-indolyl, 7-indolyl), isoindolyl, phenazinyl (e.g.: 1-phenazinyl, 2-phenazinyl), phenothiazinyl (e.g.: 1-phenothiazinyl, 2-phenothiazinyl, 3-phenothiazinyl, 4-phenothiazinyl), or the like.

"Heterocyclyl" means a non-aromatic heterocyclic group, which may have a bond at any substitutable position of a ring which has at least one or more nitrogen, oxygen, or sulfur atoms in the ring, or a ring in which such ring is fused with a cycloalkane (preferably 5 to 6-membered), a benzene ring and/or a ring which has at least one or more nitrogen, oxygen, or sulfur atoms in the ring. A "non-aromatic heterocyclic group" can be saturated or unsaturated as long as it is non-aromatic. Preferable is a 5- to 10-membered ring. Examples include 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperazinyl, 2-piperazinyl, 2-morpholinyl, 3-morpholinyl, morpholino, tetrahydropyranyl, tetrahydrofuranyl, 1,2,3,4-tetrahydroisoquinolinyl, 1,2,3,4-tetrahydroquinolinyl, 1,3-dihydro-2H-isoindol-5-yl, the following group, or the like

[Chemical formula 27]

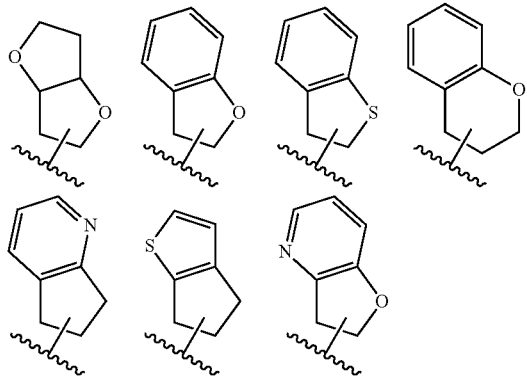

Further, examples of a "heterocyclyl" group also include a bridged group or a Spiro ring forming group shown below.

[Chemical formula 28]

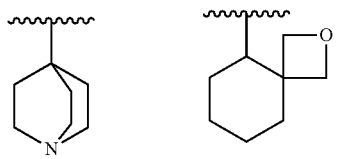

"Acyl" means formyl, substituted or unsubstituted alkylcarbonyl, substituted or unsubstituted alkenylcarbonyl, substituted or unsubstituted cycloalkylcarbonyl, substituted or unsubstituted cycloalkenylcarbonyl, substituted or unsubstituted arylcarbonyl, substituted or unsubstituted heteroarylcarbonyl or substituted or unsubstituted heterocyclylcarbonyl. The alkyl part of "alkylcarbonyl", the alkenyl part of "alkenylcarbonyl", the cycloalkyl part of "cycloalkylcarbonyl", the cycloalkenyl part of "cycloalkenylcarbonyl", the aryl part of "arylcarbonyl", the heteroaryl part of "heteroarylcarbonyl", and the heterocyclyl part of "heterocyclylcarbonyl" mean the above "alkyl", the above "alkenyl", the above "cycloalkyl", the above "cycloalkenyl", the above "aryl", the above "heteroaryl" and the above "heterocyclyl", respectively.

The alkyl parts of "alkyloxy", "alkylthio", and "alkylsulfonyl" mean the above "alkyl".

The alkenyl part of "alkenylsulfonyl" means the above "alkenyl".

The alkynyl part of "alkynylsulfonyl" means the above "alkynyl".

The aryl parts of "aryloxy", "arylthio", and "arylsulfonyl" mean the above "aryl".

The heteroaryl parts of "heteroaryloxy", "heteroarylthio", and "heteroarylsulfonyl" mean the above "heteroaryl".

The cycloalkyl parts of "cycloalkyloxy", "cycloalkylthio", and "cycloalkylsulfonyl" mean the above "cycloalkyl".

The cycloalkenyl parts of "cycloalkenyloxy", "cycloalkenylthio", and "cycloalkenylsulfonyl" mean the above "cycloalkenyl".

The heterocyclyl parts of "heterocyclyloxy", "heterocyclylthio", and "heterocyclylsulfonyl" mean the above "heterocyclyl".

Examples of substituents of a "substituted alkyl", a "substituted alkenyl", a "substituted alkynyl", a "substituted aryl", a "substituted heteroaryl", a "substituted cycloalkyl", a "substituted cycloalkenyl", a "substituted heterocyclyl", a "substituted acyl", a "substituted alkylsulfonyl", a "substituted alkenylsulfonyl", a "substituted alkynylsulfonyl", a "substituted arylsulfonyl", a "substituted heteroarylsulfonyl", a "substituted cycloalkylsulfonyl", a "substituted cycloalkenylsulfonyl", a "substituted heterocyclylsulfonyl", a "substituted alkyloxy", a "substituted aryloxy", a "substituted heteroaryloxy", a "substituted cycloalkyloxy", a "substituted cycloalkenyloxy", a "substituted heterocyclyloxy", a "substituted alkylthio", a "substituted arylthio", a "substituted heteroarylthio", a "substituted cycloalkylthio", a "substituted cycloalkenylthio", a "substituted heterocyclylthio" include groups selected from the group consisting of
halogen; hydroxy; carboxy; nitro; cyano;
substituted or unsubstituted alkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, substituted or unsubstituted amino (when substituted, substituents include alkylsulfonyl, alkyl, or alkylcarbonyl), aryloxy, alkylsulfonyl, acylamino, or alkyloxycarbonyl; e.g., methyl, ethyl, isopropyl, tert-butyl, or $CF_3$);
substituted or unsubstituted alkenyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino, or alkyloxy; e.g., vinyl);
substituted or unsubstituted alkynyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino, or alkyloxy; e.g., ethynyl);
substituted or unsubstituted aryl (when substituted, substituents include halogen, hydroxy, carboxy, nitro, cyano, substituted or unsubstituted alkyl (when substituted, substituents include halogen, hydroxy, heterocyclyl, heterocyclylcarbonyl, substituted or unsubstituted amino (when substituted, substituents include alkyl)), substituted or unsubstituted alkenyl (when substituted, substituents include hydroxy, alkyloxy, amino, or carboxy), substituted or unsubstituted alkynyl (when substituted, substituents include hydroxy, substituted or unsubstituted amino (when substituted, substituents include alkyl), alkyloxy, or carboxy), aryl, cycloalkyl, substituted or unsubstituted cycloalkyloxy (when substituted, substituents include halogen), substituted or unsubstituted cycloalkenyl (when substituted, substituents include carboxy), substituted or unsubstituted heteroaryl (when substituted, substituents include alkyl, oxo, or heterocyclylalkyl), substituted or unsubstituted heterocyclyl (when substituted, substituents include alkyl, alkylsulfonyl, cycloalkylcarbonyl, or oxo), substituted or unsubstituted heterocyclyloxy (when substituted, substituents include oxo, alkyl, alkylcarbonyl, or alkyloxycarbonyl), substituted or unsubstituted carbamoyl (when substituted, substituents include alkyl), sulfamoyl, amino, alkylcarbonylamino, substituted or unsubstituted alkyloxy (when substituted, substituents include halogen, hydroxy, cycloalkyl, substituted or unsubstituted alkyloxy (when substituted, substituents include alkyloxy, halogen, or $CF_3$), substituted or unsubstituted heterocyclyl (when substituted, substituents include halogen, alkyl, alkylsulfonyl, acyl, hydroxyalkyl, alkyloxycarbonyl, or oxo), substituted or unsubstituted heteroaryl (when substituted, substituents include alkyl), alkylamino, alkylsulfonyl, alkylsulfonylamino, oxo, alkylcarbonyl, alkylcarbonylamino, carbamoyl, carbamoylamino, carboxy, or cyano), alkylsulfonyl, alkyloxycarbonyl, $SF_5$, —N=S(=O)$R^S R^{S'}$, —$R^{2f}$—N=S(=O)$R^S R^{S'}$, —C(=O)—N=S(=O)$R^S R^{S'}$, —S(=O)($R^S$)(=N—$R^N$), —$R^{2f}$—S(=O)($R^S$)(=N—$R^N$), —N=S(=N—$R^{N'}$)$R^S R^{S'}$, —S($R^S$)(=N—$R^N$)$_2$, —O—C(=O)—N($R^N$)$R^{N'}$, —N($R^N$)—C(=O)—O—$R^O$, or —O—C(=O)—O$R^O$; e.g., phenyl, or naphthyl);

substituted or unsubstituted cycloalkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino, $SF_5$, —N=S(=O)$R^S R^{S'}$, —$R^{2f}$—N=S(=O)$R^S R^{S'}$, —C(=O)—N=S(=O)$R^S R^{S'}$, —S(=O)($R^S$)(=N—$R^N$), —$R^{2f}$—S(=O)($R^S$)(=N—$R^N$), —N=S(=N—$R^{N'}$)$R^S R^{S'}$, —S($R^S$)(=N—$R^N$)$_2$, —O—C(=O)—N($R^N$)$R^{N'}$, —N($R^N$)—C(=O)—O—$R^O$, or —O—C(=O)—O$R^O$; e.g., cyclopropyl, or cyclobutyl);

substituted or unsubstituted cycloalkenyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino, $SF_5$, —N=S(=O)$R^S R^{S'}$, —$R^{2f}$—N=S(=O)$R^S R^{S'}$, —C(=O)—N=S(=O)$R^S R^{S'}$, —S(=O)($R^S$)(=N—$R^N$), —$R^{2f}$—S(=O)($R^S$)(=N—$R^N$), —N=S(=N—$R^{N'}$)$R^S R^{S'}$, —S($R^S$)(=N—$R^N$)$_2$, —O—C(=O)—N($R^N$)$R^{N'}$, —N($R^N$)—C(=O)—O—$R^O$, or —O—C(=O)—O$R^O$; e.g., cyclopropenyl);

substituted or unsubstituted heteroaryl (when substituted, substituents include halogen, hydroxy, carboxy, nitro, cyano, substituted or unsubstituted alkyl (when substituted, substituents include hydroxy, alkyl, substituted or unsubstituted alkyloxy (when substituted, substituents include alkyloxy), aryl, carbamoyl, or alkylsulfonylamino), alkenyl, alkynyl, aryl, cycloalkyl, cycloalkylalkyl, cycloalkenyl, heteroaryl, heteroarylalkyl, heterocyclyl, heterocyclyloxy, heterocyclylalkyl, heterocyclylalkylcarbamoyl, sulfamoyl, amino, alkylamino, alkyloxy, alkyloxycarbonyl, or hydroxyalkyl), substituted or unsubstituted heterocyclyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino; e.g., morpholinyl, piperidyl, pyrrolidinyl, $SF_5$, —N=S(=O)$R^S R^{S'}$, —$R^{2f}$—N=S(=O)$R^S R^{S'}$, —C(=O)—N=S(=O)$R^S R^{S'}$, —S(=O)($R^S$)(=N—$R^N$), —$R^{2f}$—S(=O)($R^S$)(=N—$R^N$), —N=S(=N—$R^{N'}$)$R^S R^{S'}$, —S($R^S$)(=N—$R^N$)$_2$, —O—C(=O)—N($R^N$)$R^{N'}$, —N($R^N$)—C(=O)—O—$R^O$, or —O—C(=O)—O$R^O$;

substituted or unsubstituted alkyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, substituted or unsubstituted amino (when substituted, substituents include alkyl), alkyloxy, alkylsulfonylamino, alkylsulfonyl, —N=S(=O)$R^S R^{S'}$, —$R^{2f}$—N=S(=O)$R^S R^{S'}$, —C(=O)—N=S(=O)$R^S R^{S'}$, —S(=O)($R^S$)(=N—$R^N$), —$R^{2f}$—S(=O)($R^S$)(=N—$R^N$), —N=S(=N—$R^{N'}$)$R^S R^{S'}$, —S($R^S$)(=N—$R^N$)$_2$, —O—C(=O)—N($R^N$)$R^{N'}$, —N($R^N$)—C(=O)—O—$R^O$, or —O—C(=O)—O$R^O$; e.g., methoxy, or ethoxy);

substituted or unsubstituted alkenyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., vinyloxy, or aryloxy);

substituted or unsubstituted aryloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., phenyloxy);

substituted or unsubstituted cycloalkyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkenyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heteroaryloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, amino, or alkylcarbonyl);

substituted or unsubstituted arylalkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., benzyl);

substituted or unsubstituted amino (e.g., alkylamino (e.g., methylamino, ethylamino, or dimethylamino), arylamino, cycloalkylamino, cycloalkenylamino, heteroarylamino, heterocyclylamino, acylamino (e.g., acetylamino, or benzoylamino), arylalkylamino (e.g., benzylamino, or tritylamino), hydroxyamino, alkyloxycarbonylamino, carbamoylamino, alkylsulfonylamino, arylsulfonylamino, cycloalkylsulfonylamino, cycloalkenylsulfonylamino, heteroarylsulfonylamino, or heterocyclylsulfonylamino);

substituted or unsubstituted carbamoyl (when substituted, substituents include halogen, hydroxy, carboxy, nitro, cyano, substituted or unsubstituted alkyl (when substituted, substituents include heterocyclyl), alkenyl, alkynyl, aryl, cycloalkyl, cycloalkenyl, heteroaryl, or heterocyclyl; e.g., alkylcarbamoyl (e.g., methylcarbamoyl, ethylcarbamoyl, dimethylcarbamoyl, phenylethylcarbamoyl, dimethylaminoethylcarbamoyl, isopropylcarbamoyl, or hydroxyethylcarbamoyl), alkylsulfonylcarbamoyl, heteroarylalkylcarbamoyl, or alkyloxycarbamoyl);

substituted or unsubstituted carbamoyloxy (when substituted, substituents include halogen, hydroxy, carboxy, nitro, cyano, alkyl, alkenyl, alkynyl, aryl, cycloalkyl, cycloalkenyl, heteroaryl, or heterocyclyl);

substituted or unsubstituted acyl (when substituted, substituents include halogen, hydroxy, hydroxyalkyl, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., alkylcarbonyl, arylcarbonyl, cycloalkylcarbonyl, cycloalkenylcarbonyl, heteroarylcarbonyl, heterocyclylcarbonyl, formyl, or acetyl);

substituted or unsubstituted alkylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., methanesulfonyl, or ethanesulfonyl);

substituted or unsubstituted arylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkenylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heteroarylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted alkylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted arylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkenylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heteroarylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclylthio (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted sulfamoyl (when substituted, substituents include halogen, hydroxy, carboxy, nitro, cyano, alkyl, alkenyl, alkynyl, aryl, cycloalkyl, cycloalkenyl, heteroaryl, or heterocyclyl);

substituted or unsubstituted alkyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., methoxycarbonyl, ethoxycarbonyl, or tert-butoxycarbonyl);

substituted or unsubstituted aryloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkenyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heteroaryloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted alkylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted arylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkenylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heteroarylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclylsulfinyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino); nitroso;

azido;

isocyano; isocyanato; thiocyanato; isothiocyanato; mercapto; formyloxy; haloformyl; oxalo; thioformyl; thiocarboxy; dithiocarboxy; thiocarbamoyl; sulfino; sulfo; sulfoamino; hydrazino; ureido; amidino; guanidino; phthalimido; oxo; $SF_5$, $-N=S(=O)R^S R^{S'}$, $-R^{2f}-N=S(=O)R^S R^{S'}$, $-C(=O)-N=S(=O)R^S R^{S'}$, $-S(=O)(R^S)(=N-R^N)$, $-R^{2f}-S(=O)(R^S)(=N-R^N)$, $-S(R^S)(=N-R^N)_2$, $-O-C(=O)-N(R^N)R^{N'}$, $-N(R^N)-C(=O)-O-R^O$, or $-O-C(=O)-OR^O$.

The above substituted groups can be substituted with one to four of these substituents.

Preferred examples of substituents of a "substituted carbamoyl", a "substituted sulfamoyl", or a "substituted amino" include substituted or unsubstituted alkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., methyl, ethyl, isopropyl, tert-butyl, or $CF_3$);

substituted or unsubstituted alkenyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., vinyl);

substituted or unsubstituted aryl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., phenyl, or naphthyl);

substituted or unsubstituted cycloalkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., cyclopropyl, or cyclobutyl);

substituted or unsubstituted cycloalkenyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., cyclopropenyl);

substituted or unsubstituted heteroaryl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted arylalkyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted alkyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., methoxy, or ethoxy);

substituted or unsubstituted aryloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., phenyloxy);

substituted or unsubstituted cycloalkyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkenyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heteroaryloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclyloxy (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted acyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted alkyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., methoxycarbonyl, ethoxycarbonyl, or tert-butoxycarbonyl);

substituted or unsubstituted aryloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkenyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heteroaryloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclyloxycarbonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted sulfamoyl (when substituted, substituents include halogen, hydroxy, carboxy, nitro, cyano, alkyl, alkenyl, alkynyl, aryl, cycloalkyl, cycloalkenyl, heteroaryl, or heterocyclyl);

substituted or unsubstituted alkylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino; e.g., methanesulfonyl, or ethanesulfonyl);

substituted or unsubstituted arylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heteroarylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted cycloalkenylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted heterocyclylsulfonyl (when substituted, substituents include halogen, hydroxy, carboxy, nitro, cyano, alkyl, alkenyl, alkynyl, aryl, cycloalkyl, cycloalkenyl, heteroaryl, heterocyclyl, carbamoyl, sulfamoyl, or amino);

substituted or unsubstituted carbamoyl (when substituted, substituents include halogen, hydroxy, carboxy, nitro, cyano, alkyl, alkenyl, alkynyl, aryl, cycloalkyl, cycloalkenyl, heteroaryl, or heterocyclyl);

halogen, hydroxy, carboxy, nitro, cyano, alkylsulfinyl, cycloalkylsulfinyl, cycloalkenylsulfinyl, arylsulfinyl, heteroarylsulfinyl, heterocyclylsulfinyl, amino, $SF_5$, $-N=S(=O)R^SR^{S'}$, $-R^{2f}-N=S(=O)R^SR^{S'}$, $-C(=O)-N=S(=O)R^SR^{S'}$, $-S(=O)(R^S)(=N-R^N)$, $-R^{2f}-S(=O)(R^S)(=N-R^N)$, $-N=S(=N-R^N)R^SR^{S'}$, $-S(R^S)(=N-R^N)_2$, $-O-C(=O)-N(R^N)R^{N'}$, $-N(R^N)-C(=O)-O-R^O$, or $-O-C(=O)-OR^O$.

The alkyl parts of "alkylamino", "arylalkylamino", "alkyloxycarbonylamino", "alkylsulfonylamino", "alkylcarbamoyl", "alkylsulfonylcarbamoyl", "heteroarylalkylcarbamoyl", "alkyloxycarbamoyl", "alkyloxycarbonyl" and "arylalkyl" mean the above-described "alkyl".

The alkenyl part of "alkenyloxy" means the above-described "alkenyl".

The aryl parts of "arylalkyl", "arylamino", "arylalkylamino", "arylsulfonylamino", "aryloxycarbonyl", and "arylsulfinyl" mean the above-described "aryl".

The heteroaryl parts of "heteroarylamino", "heteroarylsulfonylamino", "heteroarylalkylcarbamoyl", "heteroaryloxycarbonyl", and "heteroarylsulfinyl" mean the above-described "heteroaryl".

The cycloalkyl parts of "cycloalkylamino", "cycloalkylsulfonylamino", "cycloalkyloxycarbonyl", and "cycloalkylsulfinyl" mean the above-described "cycloalkyl".

The cycloalkenyl parts of "cycloalkenylamino", "cycloalkenylsulfonylamino", "cycloalkenyloxycarbonyl", and "cycloalkenylsulfinyl" mean the above-described "cycloalkenyl".

The heterocyclyl parts of "heterocyclylamino", "heterocyclylsulfonylamino", "heterocyclyloxycarbonyl", and "heterocyclylsulfinyl" mean the above-described "heterocyclyl".

Among the compounds of the present invention, compounds in the following embodiments are preferred.

L is $NR^2R^3$, $SR^7$, $SO_2R^8$, or substituted or unsubstituted alkyl.

Preferably, L is $NR^2R^3$, $SR^7$, or $SO_2R^8$.

Further preferably, L is $NR^2R^3$.

$R^2$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl.

Preferably, $R^2$ is hydrogen, substituted or unsubstituted alkyl, substituted or unsubstituted cycloalkenyl, or substituted or unsubstituted heterocyclyl.

Further preferably, $R^2$ is hydrogen.

$R^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl.

Preferably, $R^3$ is substituted or unsubstituted alkyl, substituted or unsubstituted cycloalkenyl, or substituted or unsubstituted heterocyclyl.

$R^7$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, or substituted or unsubstituted carbamoyl.

Preferably, $R^7$ is substituted or unsubstituted alkyl, substituted or unsubstituted cycloalkenyl, or substituted or unsubstituted heterocyclyl.

$R^8$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, or substituted or unsubstituted amino, provided that $R^8$ is not unsubstituted methyl or unsubstituted ethyl.

Preferably, $R^8$ is substituted or unsubstituted alkyl, substituted or unsubstituted cycloalkenyl, or substituted or unsubstituted heterocyclyl.

Y is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl, provided that Y is not unsubstituted methyl or unsubstituted ethyl.

Preferably, Y is substituted or unsubstituted aryl, substituted or unsubstituted heteroaryl, substituted or unsubstituted cycloalkyl, substituted or unsubstituted cycloalkenyl, or substituted or unsubstituted heterocyclyl.

Further preferably, Y is substituted or unsubstituted heteroaryl, substituted or unsubstituted cycloalkyl, substituted or unsubstituted cycloalkenyl, or substituted or unsubstituted heterocyclyl.

Further preferably, Y is substituted or unsubstituted heterocyclyl.

Particularly preferably, Y is

[Chemical formula 29]

$R^9$ and $R^{10}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Preferably, one of $R^9$ and $R^{10}$ is hydroxy, and the other is hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

Further preferably, one of $R^9$ and $R^{10}$ is hydroxy, and the other is hydrogen, or substituted or unsubstituted alkyl.

Particularly preferably, one of $R^9$ and $R^{10}$ is hydroxy, and the other is hydrogen.

$R^{11}$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino.

m is an integer from 0 to 6. Preferably, m is 0 or 1. Further preferably, m is 0.

Z is —$CR^6$= or —N=.

Preferably, Z is —N=.

$R^1$ is hydrogen, or substituted or unsubstituted alkyl.

Preferably, $R^1$ is hydrogen.

$R^4$, $R^5$ and $R^6$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

Preferably, $R^4$ is hydrogen, halogen, cyano, or substituted or unsubstituted alkyl.

Further preferably, $R^4$ is halogen.

Preferably, $R^5$ is hydrogen, halogen, cyano, or substituted or unsubstituted alkyl.

Further preferably, $R^5$ is hydrogen.

Preferably, $R^6$ is hydrogen, halogen, cyano, or substituted or unsubstituted alkyl.

Further preferably, $R^6$ is hydrogen or halogen.

Particularly preferably, $R^6$ is hydrogen.

X is single bond, —O—, —S—, —$NR^{12}$—, —C(=O)—, —C(=O)$NR^{13}$—, —$NR^{14}$C(=O)—, —$SO_2$—, —$NR^{15}$—$SO_2$—, —$SO_2$—$NR^{16}$—, or —C(=O)—O—.

Preferably, X is single bond, —O—, —S—, —$NR^{12}$—, or —$SO_2$—.

Further preferably, X is —O—.

$R^{12}$ is hydrogen, or substituted or unsubstituted alkyl.
$R^{13}$ is hydrogen, or substituted or unsubstituted alkyl.
$R^{14}$ is hydrogen, or substituted or unsubstituted alkyl.
$R^{15}$ is hydrogen, or substituted or unsubstituted alkyl.
$R^{16}$ is hydrogen, or substituted or unsubstituted alkyl.

$P^1$ and $P^2$ are each independently a protecting group. Preferably, $P^1$ and $P^2$ are each independently a benzyl-derived protecting group (a benzyl group, a para-methoxybenzyl group, etc.), an acyl-derived protecting group (an acetyl group, a benzoyl group, etc.), an alkyl-derived protecting group (SEM (trimethylsilylethoxymethyl), THP (tetrahydropyran), etc.), a silyl-derived protecting group (TBS (tert-butyldimethylsilyl), TBDPS (tert-butyldiphenylsilyl), etc.), or the like.

$R^S$ and $R^{S'}$ are each independently substituted or unsubstituted alkyl, substituted or unsubstituted cycloalkyl, substituted or unsubstituted heterocyclyl, substituted or unsubstituted aryl, or substituted or unsubstituted heteroaryl. $R^S$ and $R^{S'}$ bound to the same sulfur atom may form a substituted or unsubstituted ring together with the sulfur atom.

Preferably, $R^S$ and $R^{S'}$ are each independently substituted or unsubstituted alkyl.

The ring, which is formed by $R^S$ and $R^{S'}$ which are bound to the same sulfur atom, together with the sulfur atom, means a 3- to 15-membered saturated or unsaturated hetero ring that may contain one to four oxygen, nitrogen, and/or sulfur atom(s) in the ring, other than the sulfur atom. Preferred is a non aromatic ring, and such non aromatic ring may be further cross-linked by a C1 to C4 alkyl chain, and may be fused with cycloalkane (preferably 5 to 6-membered) and a benzene ring. Examples of such a ring include

[Chemical formula 30]

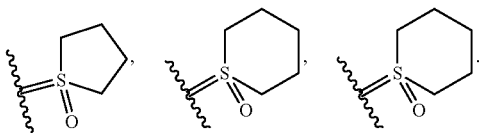

$R^{2f}$ is substituted or unsubstituted alkylene.

$R^N$ is each independently hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl, or substituted or unsubstituted carbamoyl.

In the case of —S($R^S$)(=N—$R^N$)$_2$, $R^N$ together with the adjacent nitrogen atom may form a substituted or unsubstituted ring.

Preferably, $R^N$ is hydrogen, substituted or unsubstituted alkyl, or substituted or unsubstituted carbamoyl.

In the case of —S($R^S$)(=N—$R^N$)$_2$, examples of a ring which $R^N$ together with the adjacent nitrogen atom forms include

[Chemical formula 31]

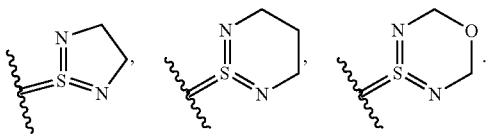

$R^{N'}$ is hydrogen, cyano, substituted or unsubstituted alkyl, substituted or unsubstituted alkylcarbonyl, substituted or unsubstituted alkyloxycarbonyl, substituted or unsubstituted cycloalkyl, substituted or unsubstituted cycloalkylcarbonyl, substituted or unsubstituted heterocyclyl, substituted or unsubstituted heterocyclylcarbonyl, substituted or unsubstituted aryl, substituted or unsubstituted arylcarbonyl, substituted or unsubstituted heteroaryl, substituted or unsubstituted heteroarylcarbonyl or substituted or unsubstituted carbamoyl. Preferably, $R^{N'}$ is hydrogen, cyano, substituted or unsubstituted alkyl, substituted or unsubstituted cycloalkyl, substituted or unsubstituted aryl, or substituted or unsubstituted heteroaryl.

$R^O$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocyclyl.

Preferred combinations of substituents of a compound represented by formula (I) include the following 1) to 6):

1) a compound wherein L is $NR^2R^3$, $R^2$ is hydrogen, $R^3$ is substituted or unsubstituted alkyl, Y is substituted or unsubstituted heterocyclyl, Z is —N=, $R^1$ is hydrogen, $R^4$ is halogen, and $R^5$ is hydrogen;

2) a compound wherein L is $NR^2R^3$, $R^2$ is hydrogen, $R^3$ is substituted or unsubstituted cycloalkenyl, Y is substituted or unsubstituted heterocyclyl, Z is —N=, $R^1$ is hydrogen, $R^4$ is halogen, and $R^5$ is hydrogen;

3) a compound wherein L is $NR^2R^3$, $R^2$ is hydrogen, $R^3$ is substituted or unsubstituted heterocyclyl, Y is substituted or unsubstituted heterocyclyl, Z is —N=, $R^1$ is hydrogen, $R^4$ is halogen, and $R^5$ is hydrogen;

4) a compound wherein L is $NR^2R^3$, $R^2$ is hydrogen, $R^3$ is substituted or unsubstituted acyl, Y is substituted or unsubstituted heterocyclyl, Z is —N=, $R^1$ is hydrogen, $R^4$ is halogen, and $R^5$ is hydrogen;

5) a compound wherein L is $SR^7$, $R^7$ is substituted or unsubstituted alkyl, Y is substituted or unsubstituted heterocyclyl, Z is —N=, is hydrogen, $R^4$ is halogen, and $R^5$ is hydrogen;

6) a compound wherein L is $SO_2R^8$, $R^8$ is substituted or unsubstituted alkyl, Y is substituted or unsubstituted heterocyclyl, Z is —N=, is hydrogen, $R^4$ is halogen, and $R^5$ is hydrogen.

One or more hydrogen, carbon or other atoms of the compounds of formula (I), formula (II), formula (IIIa), and formula (IIIb) of the present invention can be replaced by an isotope of the hydrogen, carbon or other atoms.

For example, compounds of formula (I) include all radiolabeled forms of compounds of formula (I). Such "radioactive labeling," "radiolabeled forms", and the like of compounds of formula (I) are encompassed by the present invention and useful as a research and/or diagnostic tool in metabolism pharmacokinetic studies and in binding assays. Examples of isotopes that can be incorporated into a compound of formula (I) of the present invention include isotopes of hydrogen, carbon, nitrogen, oxygen, phosphorus, sulfur, fluorine, and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Radiolabeled compounds of the present invention can be prepared by methods well-known in the art. For example, tritium-labeled compounds of formula (I) can be prepared by introducing tritium into the particular compound of formula (I), for example, by catalytic dehalogenation with tritium. This method may include reacting a suitably halogen-substituted precursor of a compound of formula (I) with tritium gas in the presence of a suitable catalyst such as Pd/C, in the presence or absence of a base. Other suitable methods for preparing tritiated compounds can be found in Isotopes in the Physical and Biomedical Sciences, Vol. 1, Labeled Compounds (Part A), Chapter 6 (1987). $^{14}C$-labeled compounds can be prepared by employing starting materials having a $^{14}C$ carbon.

As a pharmaceutically acceptable salt of the present compound, the following salts can be included.

As a basic salt, examples include alkali metal salts such as sodium salts or potassium salts; alkaline earth metal salts such as calcium salts or strontium salts; metal salts such as beryllium salts, or magnesium salts; transition metal salts such as zinc salts; ammonium salts; aliphatic amine salts such as trimethylamine salts, triethylamine salts, dicyclohexylamine salts, ethanolamine salts, diethanolamine salts, triethanolamine salts, procaine salts, meglumine salts, diethanolamine salts or ethylenediamine salts; aralkylamine salts such as N,N-dibenzylethylenediamine salts or benethamine salts; heterocyclic aromatic amine salts such as pyridine salts, picoline salts, quinoline salts, or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts, or tetrabutylammonium salts; basic amino acids salt such as arginine salts or lysine salts, or the like.

As an acidic salt, examples include inorganic acid salts such as hydrochloride, sulfate, nitrate, phosphate, carbonate, hydrogencarbonate, or perchlorate; organic acid salts such as acetate, propionate, lactate, maleate, fumarate, tartrate, malate, citrate or ascorbate; sulfonate salts such as methanesulfonate, isethionate, benzenesulfonate or p-toluenesulfonate; acidic amino acid salts such as aspartate or glutamate, or the like.

Compounds represented by formula (I) and formula (II) of the present invention or their pharmaceutically acceptable salts may form a solvate (e.g., hydrate, etc.), a cocrystal, and/or a crystal polymorph, and the present invention also contains such various types of solvate, cocrystal, and crystal polymorph. In a "solvate", any number of solvent molecules (e.g., water molecule, etc.) may be coordinated with a compound represented by formula (I). When left in the atmosphere, a compound represented by formula (I) or its pharmaceutically acceptable salt may absorb water, and a case where adsorbed water is attached thereto or a case where hydrate is formed may arise. In addition, by recrystallization of a compound represented by formula (I) or its pharmaceutically acceptable salt, a crystal polymorph thereof can be formed. A "cocrystal" means that a compound represented by formula (I) or a salt thereof and a counter molecule are present in the same crystal lattice, and can be formed with any number of counter molecules.

Compounds represented by formula (I) and formula (II) of the present invention or their pharmaceutically acceptable salts can form prodrugs, and the present invention also contains such various types of prodrug. The prodrugs are a derivative of the compound of the present invention, which has a chemically or metabolically decomposable group, and a compound which is changed into the compound of the present invention, which is pharmaceutically active, by solvolysis or in vivo under physiological conditions. The prodrugs contain a compound which is converted into a compound represented by formula (I) or formula (II) by enzymatic oxidation, reduction, hydrolysis and the like in living organisms under physiological conditions; a compound which is converted into a compound represented by formula (I) or formula (II) by hydrolysis by e.g., gastric acid; and the like. A method for selecting and a method for producing a proper prodrug derivative are described in e.g., Design of Prodrugs, Elsevier, Amsterdam 1985. Prodrugs can have activity in themselves.

When a compound represented by formula (I) or its pharmaceutically acceptable salt has a hydroxyl group, prodrugs such as an acyloxy derivative and a sulfonyloxy derivative are exemplified, which derivatives are produced, for example, by a reaction of a compound having a hydroxyl group and a proper acyl halide, a proper acid anhydride, a proper sulfonyl chloride, a proper sulfonyl anhydride and a mixed anhydride, or a reaction using a condensing agent. Examples thereof include $CH_3COO-$, $C_2H_5COO-$, tert-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3O$-$PhSO_3-$, $PhSO_3-$ and p-$CH_3PhSO_3-$.

The term "activating" means that the compound of the present invention activates the function of AMPK.

The term "pharmaceutically acceptable" means preventively or therapeutically harmless.

A general method for producing the compound of the present invention will be illustrated below. For extraction, purification and the like, treatments which are carried out in common experiments in organic chemistry may be carried out.

A compound represented by formula (I-1) can be synthesized as follows.

[Chemical formula 32]

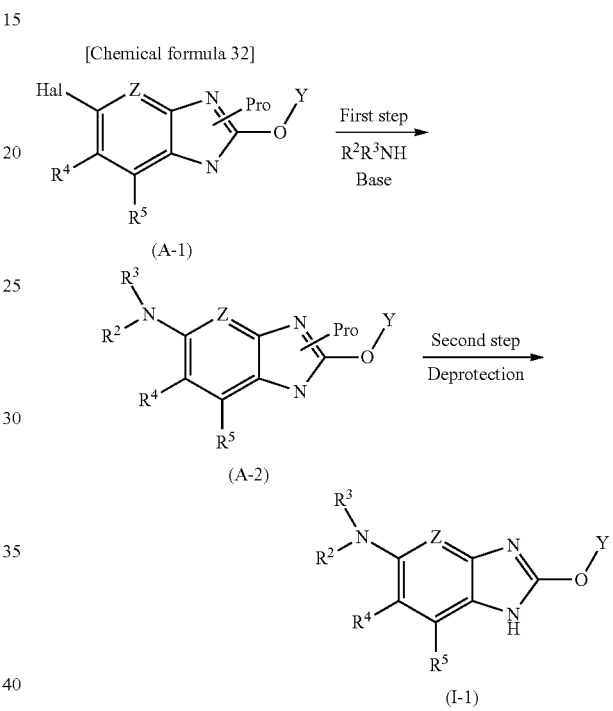

wherein, each symbol has the same meaning as above, and as a compound represented by formula (A-1), a known compound can be used, or a compound which is derived from a known compound by a conventional method can be used. "Hal" means a halogen, and Pro means a protecting group. Pro is a benzyl group, a para-methoxybenzyl group, an acetyl group, a benzoyl group, SEM (trimethylsilylethoxymethyl), THP (tetrahydropyran), TBS (tert-butyldimethylsilyl), TBDPS (tert-butyldiphenylsilyl), or the like.

First Step

The first step is a step in which a compound represented by formula (A-2) is produced from a compound represented by formula (A-1).

As a reaction solvent, examples include N,N-dimethylformamide, dimethyl sulfoxide, aromatic hydrocarbons (e.g., toluene, benzene, xylene, etc.), saturated hydrocarbons (e.g., cyclohexane, hexane, etc.), halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.), esters (e.g., methyl acetate, ethyl acetate, etc.), ketones (e.g., acetone, methyl ethyl ketone, etc.), nitriles (e.g., acetonitrile, etc.), alcohols (e.g., methanol, ethanol, t-butanol, etc.), water, a mixed solvent thereof, or the like.

Preferably, aromatic hydrocarbons (e.g., toluene, benzene, xylene, etc.), N,N-dimethylformamide, ethers (e.g., tetrahydrofuran, diethyl ether, dioxane, 1,2-dimethoxyethane, etc.), or the like can be used.

As a base, examples include metal hydrides (e.g., sodium hydride, etc.), metal hydroxides (e.g., sodium hydroxide, potassium hydroxide, lithium hydroxide, barium hydroxide, etc.), metal carbonates (e.g., sodium carbonate, calcium carbonate, cesium carbonate, etc.), metal alkoxides (e.g., sodium methoxide, sodium ethoxide, potassium t-butoxide, etc.), sodium hydrogencarbonate, metal sodium, metal amides, organic amines (e.g., triethylamine, diisopropylethylamine, DBU, 2,6-lutidine, etc.), pyridine, alkyllithiums (n-BuLi, sec-BuLi, tert-BuLi), or the like.

As a base, preferable examples include metal carbonates (e.g., sodium carbonate, calcium carbonate, cesium carbonate, etc.), metal alkoxides (e.g., sodium methoxide, sodium ethoxide, potassium t-butoxide, etc.), or the like.

The reaction may be carried out in the presence of a palladium catalyst (e.g., Pd(PPh$_3$)$_4$, PdCl$_2$, Pd(OAc)$_2$, Pd(dba)$_2$, Pd$_2$(dba)$_3$, etc.) and a phosphine ligand (e.g., PPh$_3$, BINAP, Ruphos, etc.).

The reaction can be carried out at 50 to 120° C. for 0.5 to 24 hours.

When using microwave, the reaction can be carried out at 80 to 200° C. for 5 minutes to 3 hours.

Examples of a compound represented by formula: R$^2$R$^3$NH include benzylamine, aniline, and others.

Second Step

The second step is a step in which the compound represented by formula (A-2) is deprotected to produce a compound represented by formula (I-1).

As a reaction solvent, solvents described for the first step can be used. Preferably, halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.), alcohols (e.g., methanol, ethanol, t-butanol, etc.), or water, and a mixed solvent thereof, and the like can be used.

The reaction can be carried out in the presence of hydrochloric acid, PPTS (pyridinium p-toluenesulfonate), TFA (trifluoroacetic acid), TBAF (tetrabutylammonium fluoride), or the like, at 0 to 100° C. for 0.5 to 24 hours.

Among compounds represented by formula (I), a compound wherein R$^1$ is substituted or unsubstituted alkyl can be synthesized, for example, from a compound represented by formula (I-1) by an alkylation reaction using sodium hydride and an alkyl halide.

A compound represented by formula (I-2) can be synthesized as follows.

[Chemical formula 33]

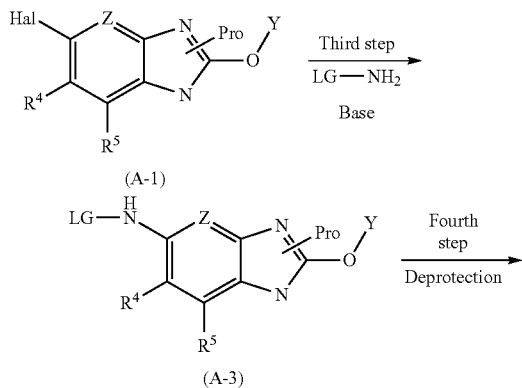

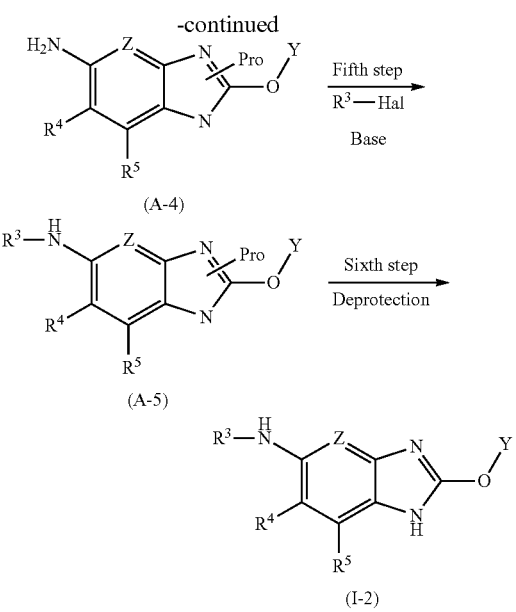

wherein, each symbol has the same meaning as above, and as a compound represented by formula (A-1), a known compound can be used, or a compound which is derived from a known compound by a conventional method can be used. "Hal" means a halogen, Pro means a protecting group, and LG means a leaving group. Pro is a benzyl group, a para-methoxybenzyl group, an acetyl group, a benzoyl group, SEM (trimethylsilylethoxymethyl), THP (tetrahydropyran), TBS (tert-butyldimethylsilyl), TBDPS (tert-butyldiphenylsilyl), or the like. LG is para-methoxybenzylamine, or the like.

Third Step

The third step is a step in which a compound represented by formula (A-3) is produced from a compound represented by formula (A-1).

As a reaction solvent, solvents described for the first step can be used. Preferably, aromatic hydrocarbons (e.g., toluene, benzene, xylene, etc.), N,N-dimethylformamide, ethers (e.g., tetrahydrofuran, diethyl ether, dioxane, 1,2-dimethoxyethane, etc.), or the like can be used.

As a base, examples include metal hydrides (e.g., sodium hydride, etc.), metal hydroxides (e.g., sodium hydroxide, potassium hydroxide, lithium hydroxide, barium hydroxide, etc.), metal carbonates (e.g., sodium carbonate, calcium carbonate, cesium carbonate, etc.), metal alkoxides (e.g., sodium methoxide, sodium ethoxide, potassium t-butoxide, etc.), sodium hydrogencarbonate, metal sodium, metal amides, organic amines (e.g., triethylamine, diisopropylethylamine, DBU, 2,6-lutidine, etc.), pyridine, alkyllithiums (n-BuLi, sec-BuLi, tert-BuLi), or the like.

As a base, preferable examples include metal carbonates (e.g., sodium carbonate, calcium carbonate, cesium carbonate, etc.), metal alkoxides (e.g., sodium methoxide, sodium ethoxide, potassium t-butoxide, etc.), or the like.

The reaction may be carried out in the presence of a palladium catalyst (e.g., Pd(PPh$_3$)$_4$, PdCl$_2$, Pd(OAc)$_2$, Pd(dba)$_2$, Pd$_2$(dba)$_3$, etc.) and a phosphine ligand (e.g., PPh$_3$, BINAP, Ruphos, etc.).

The reaction can be carried out at 50 to 120° C. for 0.5 to 24 hours. When using microwave, the reaction can be carried out at 80 to 200° C. for 5 minutes to 3 hours.

Examples of a compound represented by formula: LG-NH$_2$ include para-methoxybenzylamine and others.

Fourth Step

The fourth step is a step in which the compound represented by formula (A-3) is deprotected to produce a compound represented by formula (A-4).

As a reaction solvent, solvents described for the first step can be used. Preferably, N,N-dimethylformamide, halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.), alcohols (e.g., methanol, ethanol, t-butanol, etc.), or water, and a mixed solvent thereof, and the like can be used.

The reaction can be carried out in the presence of hydrochloric acid, PPTS (pyridinium p-toluenesulfonate), TFA (trifluoroacetic acid), or the like, at 0 to 100° C. for 0.5 to 24 hours.

Fifth Step

The fifth step is a step in which a compound represented by formula (A-5) is produced from the compound represented by formula (A-4).

As a reaction solvent, solvents described for the first step can be used. Preferably, N,N-dimethylformamide, halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.), esters (e.g., methyl acetate, ethyl acetate, etc.), nitriles (e.g., acetonitrile, etc.), water, or the like can be used.

As a base, bases described for the first step can be used. Preferably, metal hydrides (e.g., sodium hydride, etc.), metal hydroxides (e.g., sodium hydroxide, potassium hydroxide, lithium hydroxide, barium hydroxide, etc.), metal carbonates (e.g., sodium carbonate, calcium carbonate, cesium carbonate, etc.), metal alkoxides (e.g., sodium methoxide, sodium ethoxide, potassium t-butoxide, etc.), sodium hydrogencarbonate, metal sodium, metal amides, organic amines (e.g., triethylamine, diisopropylethylamine, DBU, 2,6-lutidine, etc.), pyridine, alkyllithiums (n-BuLi, sec-BuLi, tert-BuLi), or the like can be used.

The reaction can be carried out at 0 to 200° C. for 0.5 to 24 hours.

Examples of a compound represented by formula: R$^3$-Hal include benzyl bromide, and others.

Sixth Step

The sixth step is a step in which the compound represented by formula (A-5) is deprotected to produce a compound represented by formula (I-2).

The reaction can be carried out in a similar way as in the second step.

A compound represented by formula (I-3) can be synthesized as follows.

[Chemical formula 34]

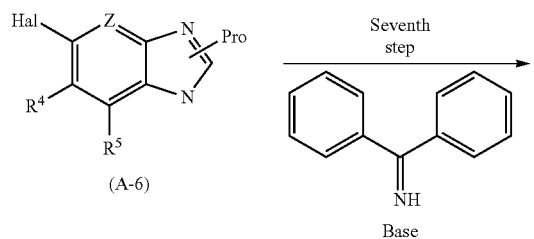

(A-6)

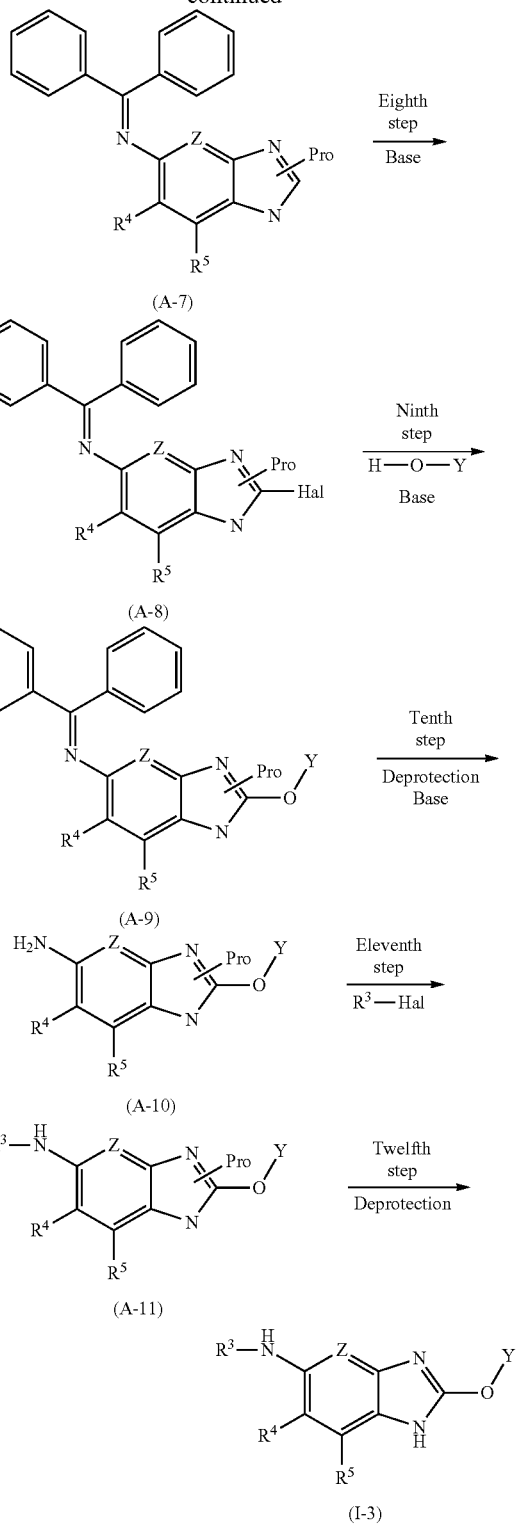

wherein, each symbol has the same meaning as above, and as a compound represented by formula (A-6), a known compound can be used and a compound which is derived from a known compound by a conventional method can be used. "Hal" means a halogen, and Pro means a protecting group. Pro is a benzyl group, a para-methoxybenzyl group, an acetyl group, a benzoyl group, SEM (trimethylsilylethoxymethyl), THP (tetrahydropyran), TBS (tert-butyldimethylsilyl), TBDPS (tert-butyldiphenylsilyl), or the like.

Seventh Step

The seventh step is a step in which a compound represented by formula (A-7) is produced from a compound represented by formula (A-6).

As a reaction solvent, solvents described for the first step can be used. Preferably, aromatic hydrocarbons (e.g., toluene, benzene, xylene, etc.), N,N-dimethylformamide, ethers (e.g., tetrahydrofuran, diethyl ether, dioxane, 1,2-dimethoxyethane, etc.), or the like can be used.

As a base, bases described for the first step can be used. As a base, preferable examples include metal carbonates (e.g., sodium carbonate, calcium carbonate, cesium carbonate, etc.), metal alkoxides (e.g., sodium methoxide, sodium ethoxide, potassium t-butoxide, etc.), or the like.

The reaction may be carried out in the presence of a palladium catalyst (e.g., $Pd(PPh_3)_4$, $PdCl_2$, $Pd(OAc)_2$, $Pd(dba)_2$, $Pd_2(dba)_3$, etc.) and a phosphine ligand (e.g., $PPh_3$, BINAP, Ruphos, dppf, etc.).

The reaction can be carried out at 50 to 120° C. for 0.5 to 24 hours. When using microwave, the reaction can be carried out at 80 to 200° C. for 5 minutes to 3 hours.

Eighth Step

The eighth step is a step in which the compound represented by formula (A-7) is halogenated to produce a compound represented by formula (A-8).

As a reaction solvent, solvents described for the first step can be used. Preferably, N,N-dimethylformamide, halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.) or nitriles (e.g., acetonitrile, etc.) can be used. Further preferably, alcohols (e.g., methanol, ethanol, t-butanol, etc.) can be used.

As a base, bases described for the first step can be used. Preferably, metal hydrides (e.g., sodium hydride, etc.), metal amides (e.g., lithium hexamethyldisilazide, etc.), alkyllithiums (n-BuLi, sec-BuLi, tert-BuLi), or the like can be used.

The reaction can be carried out at −78 to 50° C. for 0.5 to 24 hours.

As a halogenating agent, $I_2$, $Br_2$, NIS (N-iodosuccinimide), NBS (N-bromosuccinimide), NCS (N-chlorosuccinimide), $CCl_3$—$CCl_3$ (hexachloroethane), or the like can be used.

Ninth Step

The ninth step is a step in which the compound represented by formula (A-8) and a compound represented by formula: H—O—Y are reacted to produce a compound represented by formula (A-9).

As the compound represented by formula: H—O—Y, examples include phenol, methanol, ethanol, or the like.

As a reaction solvent, solvents described for the first step can be used. Preferably, N,N-dimethylformamide, dimethyl sulfoxide, ethers (e.g., tetrahydrofuran, diethyl ether, dioxane, 1,2-dimethoxyethane, etc.), nitriles (e.g., acetonitrile, etc.), or the like can be used.

As a base, bases described for the first step can be used. Preferably, metal hydrides (e.g., sodium hydride, etc.), metal carbonates (e.g., sodium carbonate, calcium carbonate, cesium carbonate, etc.), metal amides, organic amines (e.g., triethylamine, diisopropylethylamine, DBU, 2,6-lutidine, etc.), pyridine, alkyllithiums (n-BuLi, sec-BuLi, tert-BuLi), or the like can be used.

Further preferably, metal hydrides (e.g., sodium hydride, etc.) or metal carbonates (e.g., sodium carbonate, calcium carbonate, cesium carbonate, etc.) can be used.

The reaction can be carried out at 0 to 100° C. for 0.5 to 12 hours.

(When Hal is Bromine or Iodine)

The reaction can be carried out using conditions for a reaction which is known as the Ullmann reaction.

As a reaction solvent, solvents described for the first step can be used. Preferably, N,N-dimethylformamide, dimethyl sulfoxide, ethers (e.g., tetrahydrofuran, diethyl ether, dioxane, 1,2-dimethoxyethane, etc.), nitriles (e.g., acetonitrile, etc.), or the like can be used.

As a base, bases described for the first step can be used. Preferably, metal hydrides (e.g., sodium hydride, etc.), metal carbonates (e.g., sodium carbonate, calcium carbonate, cesium carbonate, etc.), metal amides, organic amines (e.g., triethylamine, diisopropylethylamine, DBU, 2,6-lutidine, etc.), pyridine, alkyllithiums (n-BuLi, sec-BuLi, tert-BuLi), or the like can be used.

Further preferably, metal carbonates (e.g., sodium carbonate, calcium carbonate, cesium carbonate, etc.) can be used.

As a catalyst, copper iodide can be used.

The reaction can be carried out at from room temperature to 100° C. for 0.5 to 12 hours.

Tenth Step

The tenth step is a step in which the compound represented by formula (A-9) is deprotected to produce a compound represented by formula (A-10).

As a reaction solvent, solvents described for the first step can be used. Preferably, N,N-dimethylformamide, halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.), esters (e.g., methyl acetate, ethyl acetate, etc.), nitriles (e.g., acetonitrile, etc.), alcohols (e.g., methanol, ethanol, t-butanol, etc.), or water, and a mixed solvent thereof, or the like can be used.

As a base, bases described for the first step can be used. As a base, examples include metal hydrides (e.g., sodium hydride, etc.), metal hydroxides (e.g., sodium hydroxide, potassium hydroxide, lithium hydroxide, barium hydroxide, etc.), metal carbonates (e.g., sodium carbonate, calcium carbonate, cesium carbonate, etc.), metal alkoxides (e.g., sodium methoxide, sodium ethoxide, potassium t-butoxide, etc.), sodium hydrogencarbonate, metal sodium, metal amides, organic amines (e.g., triethylamine, diisopropylethylamine, DBU, 2,6-lutidine, etc.), pyridine, alkyllithiums (n-BuLi, sec-BuLi, tert-BuLi), hydroxylamine, or the like.

The reaction can be carried out at 0 to 200° C. for 0.5 to 24 hours.

Eleventh Step

The eleventh step is a step in which a compound represented by formula (A-11) is produced from the compound represented by formula (A-10).

The reaction can be carried out in a similar way as in the fifth step.

Twelfth Step

The twelfth step is a step in which the compound represented by formula (A-11) is deprotected to produce a compound represented by formula (I-3).

The reaction can be carried out in a similar way as in the second step.

A compound represented by formula (I-4) can be synthesized as follows.

[Chemical formula 35]

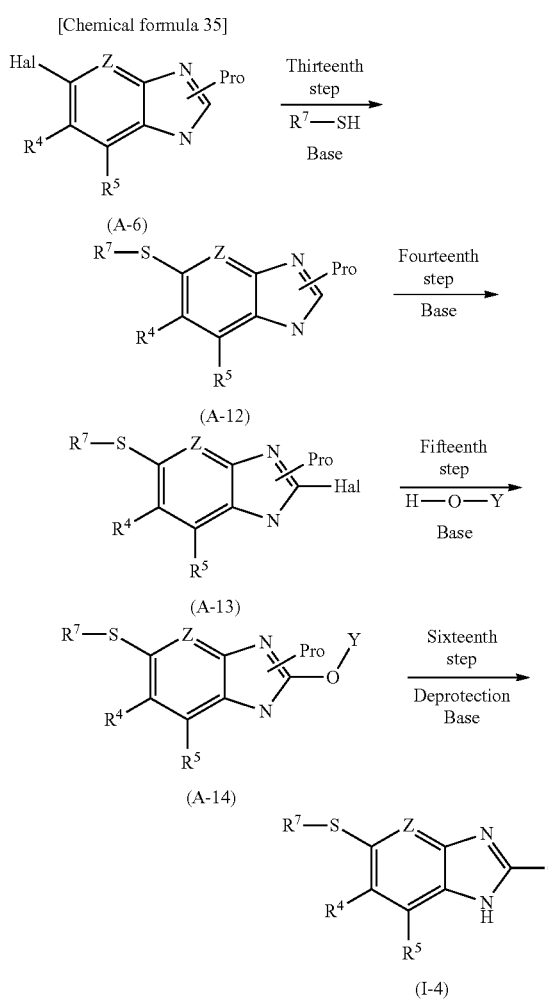

wherein, each symbol has the same meaning as above, and as a compound represented by formula (A-6), a known compound can be used and a compound which is derived from a known compound by a conventional method can be used. "Hal" means a halogen, and Pro means a protecting group. Pro is a benzyl group, a para-methoxybenzyl group, an acetyl group, a benzoyl group, SEM (trimethylsilylethoxymethyl), THP (tetrahydropyran), TBS (tert-butyldimethylsilyl), TBDPS (tert-butyldiphenylsilyl), etc.), or the like.

Thirteenth Step

The thirteenth step is a step in which a compound represented by formula (A-12) is produced from a compound represented by formula (A-6).

As a reaction solvent, solvents described for the first step can be used. Preferably, N,N-dimethylformamide, halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.) or esters (e.g., methyl acetate, ethyl acetate, etc.), nitriles (e.g., acetonitrile, etc.), or the like can be used.

As a base, bases described for the first step can be used. Preferably, metal hydrides (e.g., sodium hydride, etc.), metal hydroxides (e.g., sodium hydroxide, potassium hydroxide, lithium hydroxide, barium hydroxide, etc.), metal carbonates (e.g., sodium carbonate, calcium carbonate, cesium carbonate, etc.), metal alkoxides (e.g., sodium methoxide, sodium ethoxide, potassium t-butoxide, etc.), sodium hydrogencarbonate, metal sodium, metal amides, organic amines (e.g., triethylamine, diisopropylethylamine, DBU, 2,6-lutidine, etc.), pyridine, or the like can be used.

The reaction can be carried out at 0 to 200° C. for 0.5 to 24 hours.

Examples of a compound represented by formula: $R^7$-SH include benzyl mercaptan, and others.

Fourteenth Step

The fourteenth step is a step in which the compound represented by formula (A-12) is halogenated to produce a compound represented by formula (A-13).

The reaction can be carried out in a similar way as in the eighth step.

Fifteenth Step

The fifteenth step is a step in which the compound represented by formula (A-13) and a compound represented by formula: H—O—Y are reacted to produce a compound represented by formula (A-14).

The reaction can be carried out in a similar way as in the ninth step.

Sixteenth Step

The sixteenth step is a step in which the compound represented by formula (A-14) is deprotected to produce a compound represented by formula (I-4).

The reaction can be carried out in a similar way as in the second step.

A compound represented by formula (I-5) can be synthesized as follows.

[Chemical formula 36]

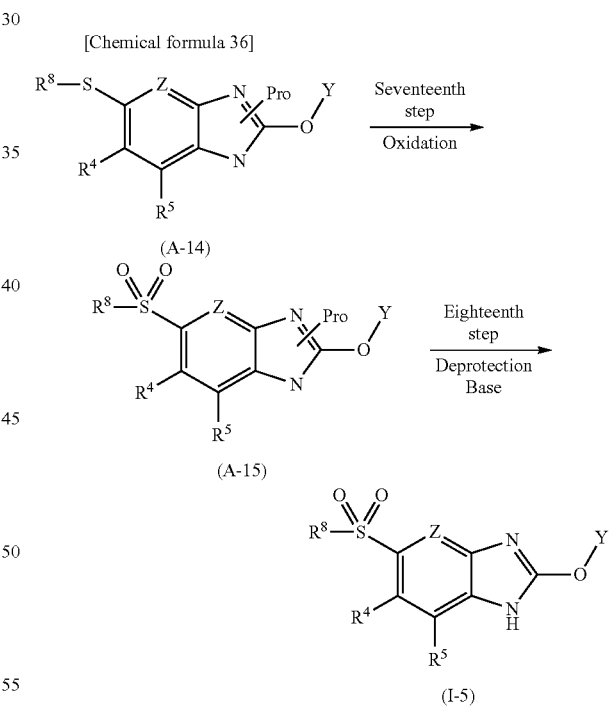

wherein each symbol has the same meaning as above, "Hal" means a halogen, and Pro means a protecting group. Pro is a benzyl group, a para-methoxybenzyl group, an acetyl group, a benzoyl group, SEM (trimethylsilylethoxymethyl), THP (tetrahydropyran), TBS (tert-butyldimethylsilyl), TBDPS (tert-butyldiphenylsilyl), or the like.

Seventeenth Step

The seventeenth step is a step in which a compound represented by formula (A-14) is oxidized to produce a compound represented by formula (A-15).

As a reaction solvent, solvents described for the first step can be used. Preferably, N,N-dimethylformamide, halogenated hydrocarbons (e.g., dichloromethane, chloroform, 1,2-dichloroethane, etc.), ethers (e.g., tetrahydrofuran, diethyl ether, dioxane, 1,2-dimethoxyethane, etc.), esters (e.g., methyl acetate, ethyl acetate, etc.), nitriles (e.g., acetonitrile, etc.), alcohols (e.g., methanol, ethanol, t-butanol, etc.), or the like can be used.

Examples of an oxidizing agent include hydrogen peroxide, mCPBA (m-chloroperoxybenzoic acid), and the like.

The reaction can be carried out at 0 to 200° C. for 0.5 to 24 hours.

Eighteenth Step

The eighteenth step is a step in which the compound represented by formula (A-15) is deprotected to produce a compound represented by formula (I-5).

The reaction can be carried out in a similar way as in the second step.

Among compounds represented by formula (II), a compound wherein X is —O—, —S—, or —$NR^{12}$— can be synthesized as follows.

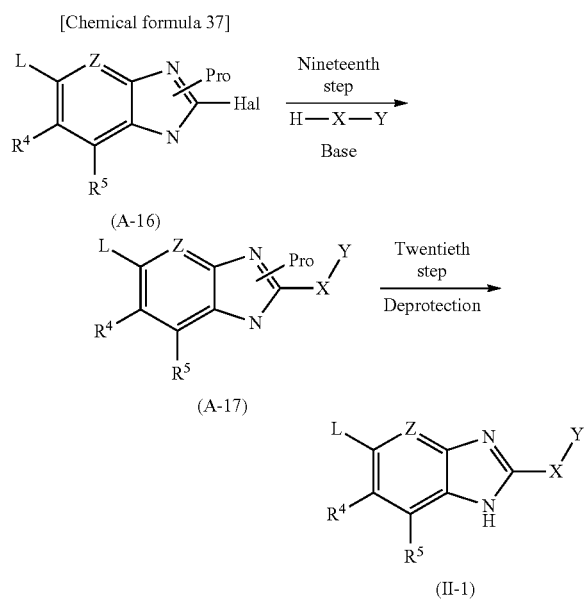

[Chemical formula 37]

(A-16)

(A-17)

(II-1)

wherein each symbol has the same meaning as above. "Hal" means a halogen, and Pro means a protecting group. Pro is a benzyl group, a para-methoxybenzyl group, an acetyl group, a benzoyl group, SEM (trimethylsilylethoxymethyl), THP (tetrahydropyran), TBS (tert-butyldimethylsilyl), TBDPS (tert-butyldiphenylsilyl), or the like.

Nineteenth Step

The nineteenth step is a step in which a compound represented by formula (A-16) and a compound represented by formula: H—X—Y are reacted to produce a compound represented by formula (A-17).

When X is —O—, examples of a compound represented by formula: H—O—Y include phenol, methanol, ethanol, or the like.

When X is —S—, examples of a compound represented by formula: H-S-Y include methanethiol, ethanethiol, or the like.

When X is —$NR^{12}$—, examples of a compound represented by formula: H—$NR^{12}$—Y include methylamine, ethylamine, or the like.

The reaction can be carried out in a similar way as in the ninth step.

Twentieth Step

The twentieth step is a step in which the compound represented by formula (A-17) is deprotected to produce a compound represented by formula (II-1).

The reaction can be carried out in a similar way as in the second step.

The substituents $R^4$, $R^5$, and $R^6$ can be introduced in any step of the above-described first to twentieth steps.

A compound represented by formula (II-2) can be synthesized as follows.

[Chemical formula 38]

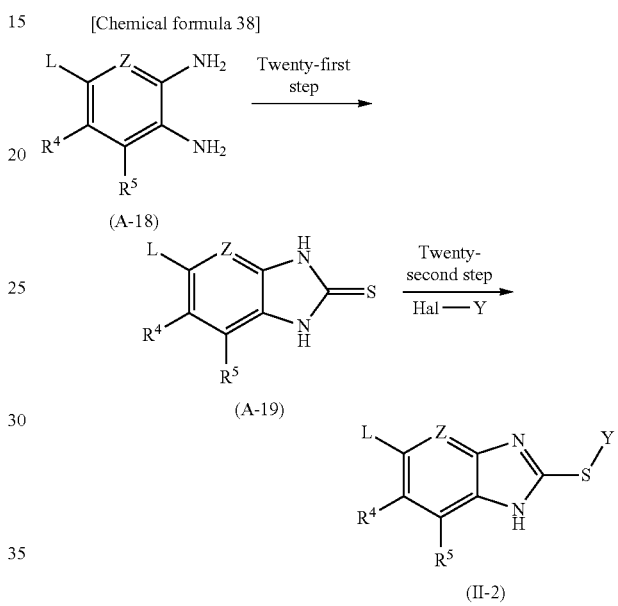

(A-18)

(A-19)

(II-2)

wherein, each symbol has the same meaning as above, and as a compound represented by formula (A-18), a known compound can be used, or a compound which is derived from a known compound by a conventional method can be used. "Hal" means a halogen.

Twenty-First Step

The twenty-first step is a step in which a compound represented by formula (A-18) and thiocarbonyldiimidazole or carbon disulfide ($CS_2$) are reacted to produce a compound represented by formula (A-19).

As a reaction solvent, solvents described for the first step can be used. Preferably, N,N-dimethylformamide, halogenated hydrocarbons (e.g., dichloromethane, chloroform, 1,2-dichloroethane, etc.), nitriles (e.g., acetonitrile, etc.), water, or the like can be used.

When carbon disulfide ($CS_2$) is used, it is preferable to use a base.

As a base, bases described for the first step can be used. Preferably, examples include metal hydrides (e.g., sodium hydride, etc.), metal hydroxides (e.g., sodium hydroxide, potassium hydroxide, lithium hydroxide, barium hydroxide, etc.), or the like.

The reaction can be carried out at from room temperature to 150° C. for 0.5 to 12 hours.

When using microwave, the reaction can be carried out at 80 to 200° C. for 5 minutes to 1 hour.

Twenty-Second Step

The twenty-second step is a step in which the compound represented by formula (A-19) and a compound represented by formula: Hal-Y are reacted to produce a compound represented by formula (II-2).

As a reaction solvent, solvents described for the first step can be used. Preferably, N,N-dimethylformamide, dimethyl sulfoxide, ethers (e.g., tetrahydrofuran, diethyl ether, dioxane, 1,2-dimethoxyethane, etc.), nitriles (e.g., acetonitrile, etc.), alcohols (e.g., methanol, ethanol, t-butanol, etc.), or the like can be used.

As a base, bases described for the first step can be used. Preferably, examples include metal hydrides (e.g., sodium hydride, etc.), metal hydroxides (e.g., sodium hydroxide, potassium hydroxide, lithium hydroxide, barium hydroxide, etc.), metal carbonates (e.g., sodium carbonate, calcium carbonate, cesium carbonate, etc.), or the like.

The reaction can be carried out at 0 to 150° C. for 0.5 to 12 hours.

When using microwave, the reaction can be carried out at 80 to 200° C. for 5 minutes to 1 hour.

A compound represented by formula (IIIa-1) can be synthesized as follows.

[Chemical formula 39]

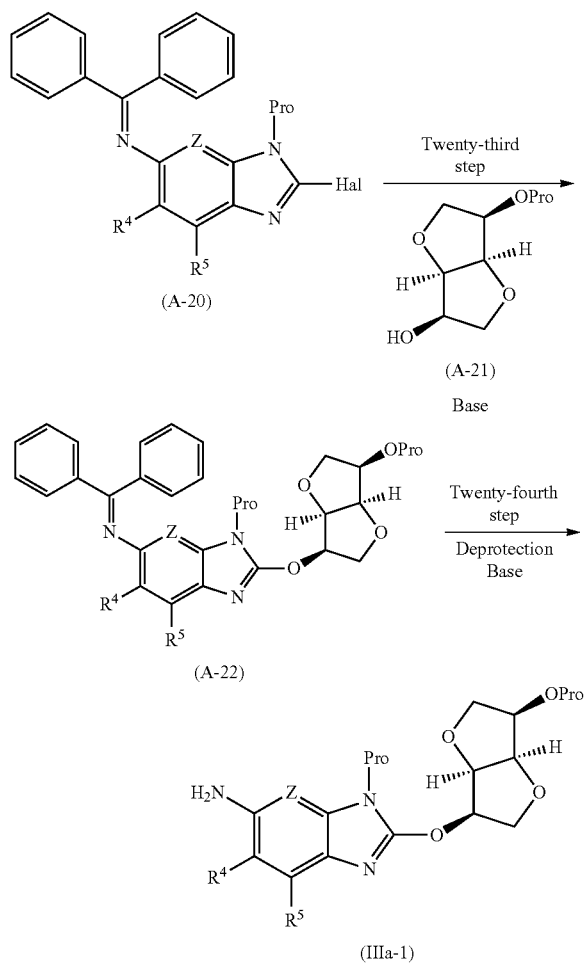

wherein each symbol has the same meaning as above. "Hal" means a halogen, and Pro means a protecting group. Pro is a benzyl group, a para-methoxybenzyl group, an acetyl group, a benzoyl group, SEM (trimethylsilylethoxymethyl), THP (tetrahydropyran), TBS (tert-butyldimethylsilyl), TBDPS (tert-butyldiphenylsilyl), or the like.

Twenty-Third Step

The twenty-third step is a step in which a compound represented by formula (A-20) and a compound represented by formula (A-21) are reacted to produce a compound represented by formula (A-22).

The reaction can be carried out in a similar way as in the ninth step.

Twenty-Fourth Step

The twenty-fourth step is a step in which the compound represented by formula (A-22) is deprotected to produce a compound represented by formula (IIIa-1).

The reaction can be carried out in a similar way as in the tenth step.

Various types of substituent on compounds of the present invention can be introduced by reference to (1) Alan R. Katriszly et al., Comprehensive Heterocyclic Chemistry, (2) Alan R. Katriszly et al., Comprehensive Heterocyclic Chemistry II, (3) RODD'S CHEMISTRY OF CARBON COMPOUNDS VOLUME IV HETEROCYCLIC COMPOUNDS, and the like.

A compound of the present invention has an excellent AMPK activating effect. Therefore, the compound can be used for the treatment or prevention of diseases associated with AMPK, particularly diseases such as type I diabetes, type II diabetes, hyperglycemia, metabolic syndrome, obesity, hypercholesterolemia, and/or hypertension. Particularly, the compound is useful in the treatment or prevention of type II diabetes, hyperglycemia, metabolic syndrome, or obesity.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, inner ear or vaginal administration, and the like.

In the case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may be prepared according to the usual method and administered. The tablets can be sugar-coated tablets, film-coated tablets, enteric-coating tablets, sustained-release tablets, troche tablets, sublingual tablets, buccal tablets, chewable tablets or orally disintegrating tablets. Powders and granules can be dry syrups. Capsules can be soft capsules, micro capsules or sustained-release capsules.

In the case of parenteral administration, any forms, which are usually used, such as injections, drips, external preparations (e.g., ophthalmic drops, nasal drops, ear drops, aerosols, inhalations, lotion, infusion, liniment, mouthwash, enema, ointment, plaster, jelly, cream, patch, cataplasm, external powder, suppository or the like) and the like can be preferably administered. Injections can be emulsions whose type is O/W, W/O, O/W/O, W/O/W or the like.

The pharmaceutical composition may be manufactured by mixing an effective amount of the compound of the present invention with various pharmaceutical additives suitable for formulation, such as excipients, binders, disintegrants, lubricants and the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although the dosage of a pharmaceutical composition of the present invention should be determined in consideration of the patient's age and body weight, the type and degree of diseases, the administration route and the like, a usual oral dosage is 0.05 to 100 and preferably 0.1 to 10 mg/kg/day. For parenteral administration, although the dosage highly varies with administration routes, a usual dosage is 0.005 to 10 and preferably 0.01 to 1 mg/kg/day. The dosage may be administered in one to several divisions per day.

A compound of the present invention can be used in combination with an insulin secretagogue (e.g., a sulfonylurea (SU) drug), a fast-acting insulin secretagogue (e.g., a phenylalanine derivative), a glucose uptake inhibitor (e.g., an α-glucosidase inhibitor (α-GI drug)), an insulin resistance improving drug (e.g., a biguanide drug (BG drug), a thiazolidine derivative (TZD drug)), an insulin formulation, a peptidyl peptidase IV (DPP-IV) inhibitor, a GLP-1 receptor agonist, a sodium-dependent glucose transporter 1 (SGLT1) inhibitor, a sodium-dependent glucose transporter 2 (SGLT 2) inhibitor and the like (hereinafter, abbreviated as concomitant drugs) for the purpose of an increase in the effect of the compound, a decrease in a dose of the compound or the like. In this case, the time when a compound of the present invention and a concomitant drug are administered is not restricted, and they can be administered to a subject of administration simultaneously or at intervals. Further, a compound of the present invention and a concomitant drug can be administered as two kinds of formulation comprising each active ingredient and as a single formulation comprising both active ingredients.

The dose of a concomitant drug can be suitably selected on the basis of a dosage which is clinically used. In addition, the mixing ratio of a compound of the present invention and a concomitant drug can be suitably selected depending on a subject of administration, an administration route, a target disease, symptoms, combination and the like. When a subject of administration is a human, for example, 0.01 to 100 parts by weight of a concomitant drug can be used per part by weight of a compound of the present invention.

The present invention is described in more detail below with reference to Examples, which are not intended to limit the scope of the present invention.

NMR spectrum data of the compounds and intermediates thereof of the present invention are shown. NMR analysis in each example was performed at 400 MHz using deuterated chloroform (CDCl$_3$) or dimethyl sulfoxide (d6-DMSO).

LC/MS was measured under the following conditions.
(Method A)
Column: ACQUITY UPLC BEH C18 (1.7 μm, i.d. 2.1×50 mm) (Waters)
Flow rate: 0.8 mL/min
UV detection wavelength: 254 nm
Mobile phase: [A] 0.1% formic acid-containing aqueous solution, [B] 0.1% formic acid-containing acetonitrile solution
Gradient: a linear gradient of the solvent [B] from 5 to 100% was carried out for 3.5 minutes and the solvent [B] at 100% was maintained for 0.5 minutes.
(Method B)
Column: Shim-pack XR-ODS (2.2 mm, i.d. 50×3.0 mm) (Shimadzu)
Flow rate: 1.6 mL/min
UV detection wavelength: 254 nm
Mobile phase: [A] 0.1% formic acid-containing aqueous solution, [B] 0.1% formic acid-containing acetonitrile solution
Gradient: a linear gradient of the solvent [B] from 10 to 100% was carried out for 3 minutes and the solvent [B] at 100% was maintained for 0.5 minutes.
(Method C)
Column: ACQUITY UPLC BEH C18 (1.7 μm, i.d. 2.1×50 mm) (Waters)
Flow rate: 0.55 mL/min
UV detection wavelength: 254 nm
Mobile phase: [A] 0.1% formic acid-containing aqueous solution, [B] 0.1% formic acid-containing acetonitrile solution
Gradient: a linear gradient of the solvent [B] from 5 to 100% was carried out for 3 minutes and the solvent [B] at 100% was maintained for 0.5 minutes.

The meaning of each term in Examples is as follows.
Ruphos: 2-dicyclohexylphosphino-2',6'-diisopropoxybiphenyl
Pd$_2$(dba)$_3$: tris(dibenzylideneacetone)dipalladium
NaOt-Bu: sodium tert-butoxide
TBAF: tetrabutylammonium fluoride
THF: tetrahydrofuran
Pd(OAc)$_2$: palladium(II) acetate
BINAP: 2,2'-bis(diphenylphosphino)-1,1'-binaphthyl
TFA: trifluoroacetic acid
DMF: N,N-dimethylformamide
CPBA: chloroperoxybenzoic acid
PPTS: pyridinium p-toluenesulfonate
SEM: trimethylsilylethoxymethyl
TBS: tert-butyldimethylsilyl
THP: tetrahydropyran
LAH: lithium aluminum hydride

EXAMPLE 1

[Chemical formula 40]

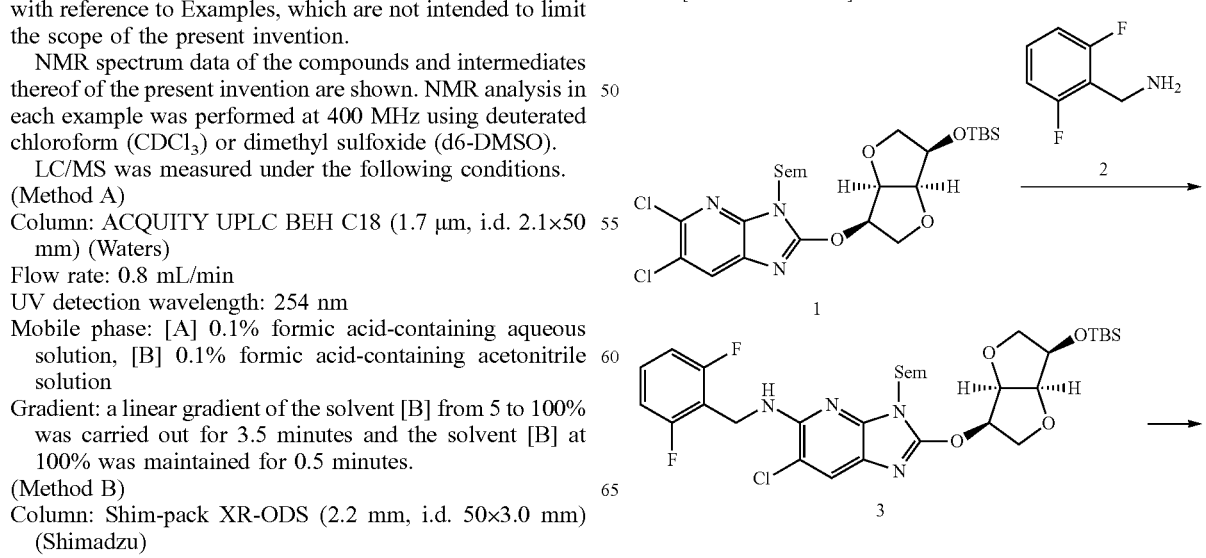

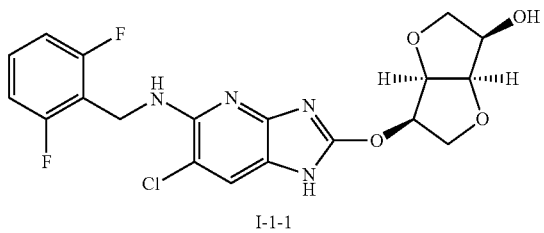

I-1-1

To a solution of Compound 1 (500 mg, 0.867 mmol) and Compound 2 (161 mg, 1.13 mmol) in toluene (10 mL) were successively added Ruphos (40.5 mg, 0.087 mmol), Pd$_2$(dba)$_3$ (39.7 mg, 0.043 mmol), and NaOt-Bu (167 mg, 1.73 mmol) at room temperature, and the reaction mixture was stirred under microwave irradiation at 120° C. for 10 minutes. The reaction mixture was purified by silica gel column chromatography to obtain Compound 3 (274 mg, 0.400 mmol, 46%) as a colorless oil. Compound 3; Retention time=3.30 min, Mass(M+H)=683.35, Method=C To Compound 3 (274 mg, 0.400 mmol) was added a solution of TRAF in THF (1 M solution, 6.00 mL, 6.00 mmol), and the reaction mixture was stirred at 80° C. for 6 hours. The reaction mixture was purified by silica gel column chromatography and then solidified with hexane/ethyl acetate to obtain Compound I-1-1 (81.4 mg, 0.186 mmol, 46%) as a white solid.

Compound I-1-1; $^1$H-NMR (DMSO-D$_6$) δ: 3.39-3.42 (m, 1H), 3.76-3.81 (m, 2H), 4.09-4.12 (m, 2H), 4.34 (t, J=4.9 Hz, 1H), 4.63 (d, J=5.5 Hz, 2H), 4.77 (t, J=4.9 Hz, 1H), 4.95 (d, J=6.8 Hz, 1H), 5.32-5.34 (m, 1H), 6.10 (s, 1H), 7.02-7.08 (m, 2H), 7.31-7.39 (m, 1H), 7.62 (s, 1H).

EXAMPLE 2

[Chemical formula 41]

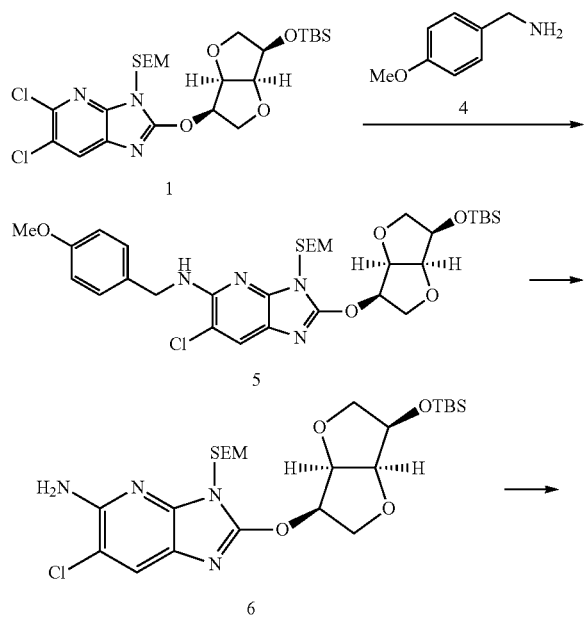

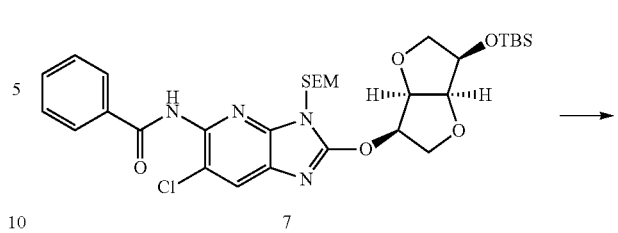

I-1-2

To a solution of Compound 1 (500 mg, 0.867 mmol) and Compound 4 (155 mg, 1.13 mmol) in toluene (10 mL) were successively added Ruphos (40.5 mg, 0.087 mmol), Pd$_2$(dba)$_3$ (39.7 mg, 0.043 mmol), and NaOt-Bu (167 mg, 1.73 mmol) at room temperature, and the reaction mixture was stirred under microwave irradiation at 120° C. for 10 minutes. The reaction mixture was purified by silica gel column chromatography to obtain Compound 5 (274 mg, 0.404 mmol, 47%) as a yellow oil.

Compound 5; Retention time=3.26 min, Mass(M+H)=677.45, Method=C

To a solution of Compound 5 (245 mg, 0.362 mmol) in dichloromethane (1.2 mL) was added trifluoroacetic acid (1.2 mL, 15.8 mmol), and the reaction mixture was stirred at 0° C. for 1 hour. Under ice cooling, the reaction mixture was quenched with a saturated aqueous solution of sodium hydrogencarbonate, and then extracted with ethyl acetate. The solvent was removed under reduced pressure, and the obtained crude product (196 mg), containing Compound 6, was used directly in the next reaction.

To a solution of the crude product (196 mg) in THF (1.6 mL) were added pyridine (0.069 mL, 0.857 mmol) and benzoyl chloride (0.066 mL, 0.571 mmol), and the mixture was stirred at 50° C. for 5 hours. A crude product (86.7 mg), containing Compound 7, was obtained and used directly in the next reaction.

To the crude product (86.7 mg) was added a solution of TBAF in THF (1 M solution, 1.97 mL, 1.97 mmol), and the reaction mixture was stirred at 80° C. for 4 hours. The reaction mixture was purified by silica gel column chromatography and then solidified with hexane/ethyl acetate to obtain Compound I-1-2 (20.7 mg, 0.050 mmol, 14% in 3 steps) as a white solid.

Compound I-1-2; $^1$H-NMR (DMSO-D$_6$) δ: 3.77-3.78 (m, 1H), 3.90-3.91 (m, 1H), 4.10-4.12 (m, 2H), 4.35 (s, 1H), 4.82 (s, 1H), 5.01-5.02 (m, 1H), 5.44-5.46 (m, 1H), 7.52-7.54 (m, 2H), 7.59-7.60 (m, 1H), 7.94-7.97 (m, 3H), 10.51 (s, 1H).

EXAMPLE 3

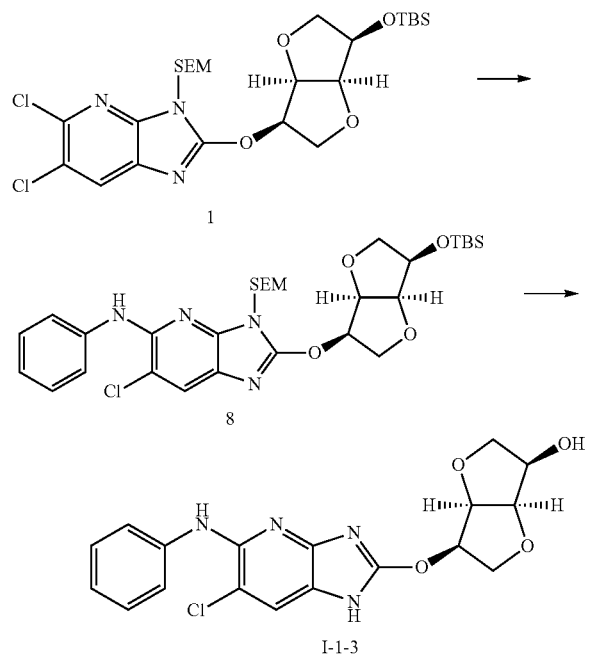

Toluene (1 mL) was added to a mixture of Compound 1 (50 mg, 0.087 mmol), Pd(OAc)$_2$ (1.947 mg, 0.00867 mmol), BINAP (5.40 mg, 0.00867 mmol), K$_2$CO$_3$ (41.9 mg, 0.303 mmol), and aniline (9.50 μL, 0.104 mmol), and the reaction mixture was stirred under microwave irradiation at 150° C. for 30 minutes. Water was added to the reaction mixture, which was then extracted with ethyl acetate. The solvent was removed under reduced pressure. The obtained residue was purified by silica gel column chromatography to obtain Compound 8 (36 mg, 0.057 mmol, 66%) as a colorless oil.

Compound 8; $^1$H-NMR (CDCl$_3$) δ: −0.09 (9H, s), 0.13 (6H, d, J=6.8 Hz), 0.89-0.96 (2H, m), 0.92 (9H, s), 3.61-3.72 (3H, m), 3.84 (1H, t, J=7.7 Hz), 4.07-4.20 (2H, m), 4.30 (1H, dd, J=12.7, 7.4 Hz), 4.41 (1H, t, J=4.3 Hz), 4.92 (1H, t, J=4.9 Hz), 5.45 (2H, s), 5.45-5.51 (1H, m), 6.96-7.05 (2H, m), 7.32 (2H, t, J=7.2 Hz), 7.69 (2H, d, J=7.8 Hz), 7.71 (1H, s).

Retention time=3.40 min, Mass (M+H)=633.15, Method=C.

To a solution of Compound 8 (36 mg, 0.057 mmol) in methylene chloride (360 μL) was added TFA (360 μL), and the reaction mixture was stirred at room temperature for 18 hours. After the raw material was observed to have disappeared, THF and a 2 mol/L solution of sodium hydroxide were added to the reaction mixture, which was then stirred at room temperature for 3 hours. After that, the reaction mixture was quenched with a saturated aqueous solution of sodium hydrogencarbonate and extracted with ethyl acetate, and the solvent was removed under reduced pressure. The obtained residue was purified by reverse-phase column chromatography to obtain Compound I-1-3 (2.2 mg, 0.00566 mmol, 10%).

Compound I-1-3; $^1$H-NMR (DMSO-D$_6$) δ: 3.40-3.47 (1H, m), 3.78 (2H, t, J=7.7 Hz), 4.12 (2H, dd, J=15.6, 8.8 Hz), 4.36 (1H, t, J=4.0 Hz), 4.78 (1H, t, J=4.6 Hz), 4.88-4.96 (1H, m), 5.33 (1H, dd, J=12.0, 6.8 Hz), 6.81-6.91 (1H, m), 7.22 (2H, t, J=7.5 Hz), 7.57-7.68 (1H, m), 7.58 (2H, d, J=8.5 Hz), 7.73-7.90 (1H, m).

Retention time=1.70 min, Mass (M+H)=389.10, Method=C.

EXAMPLE 4

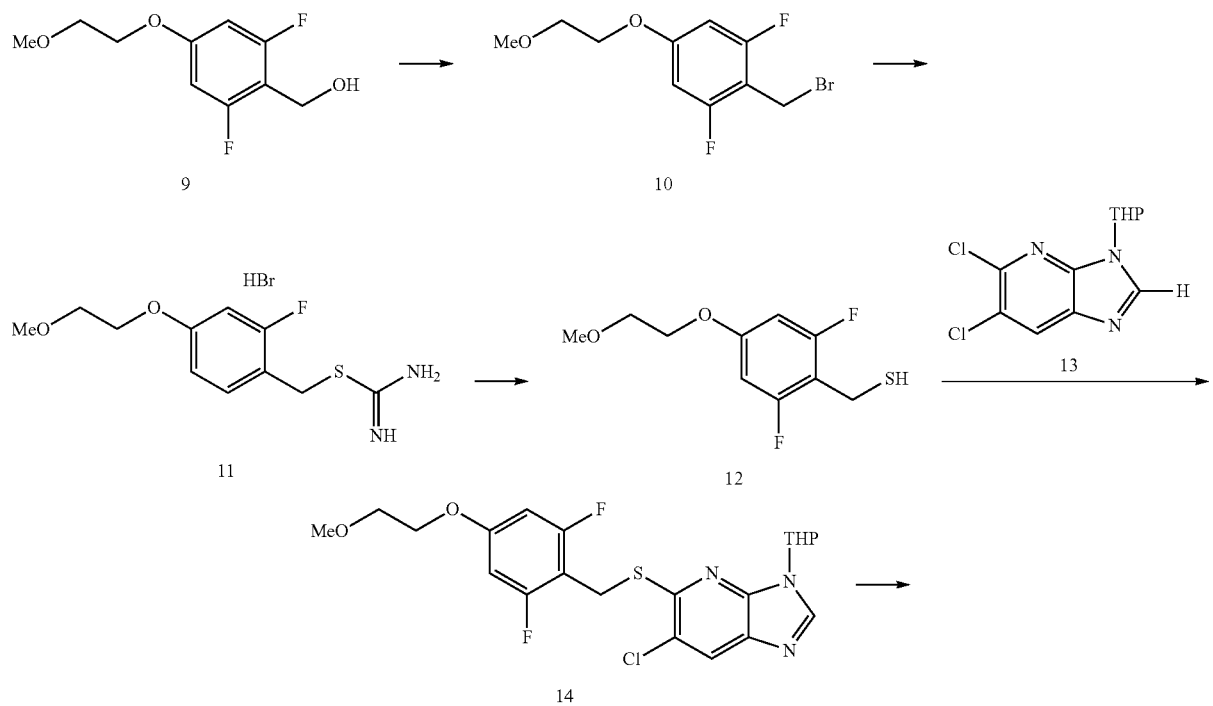

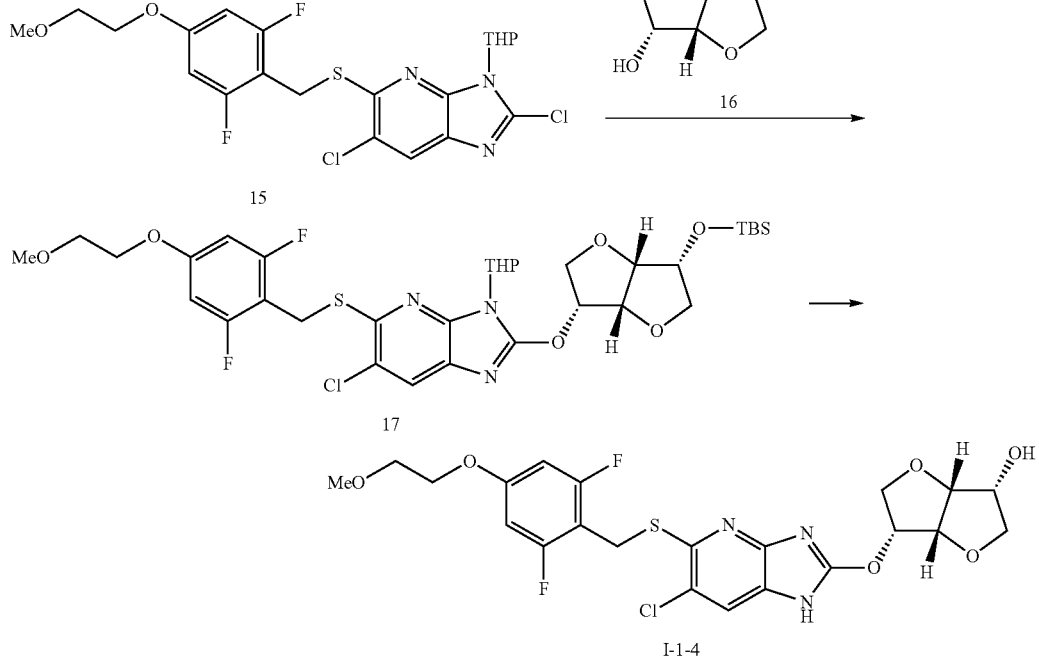

Compound 9 (203 mg, 0.928 mmol) was dissolved in dichloromethane (4 mL), to which were then added carbon tetrabromide (462 mg, 1.39 mmol) and triphenylphosphine (365 mg, 1.39 mmol) at room temperature, and the resulting mixture was stirred at room temperature for 1.5 hours. The reaction mixture was concentrated, and the obtained residue was purified by silica gel column chromatography to obtain Compound 10 (248 mg, 95.2%) as a colorless oily material.

Compound 10 (248 mg, 0.883 mmol) was dissolved in 1,4-dioxane (2.5 mL), to which was then added thiourea (74.0 mg, 0.972 mmol), and the resulting mixture was heated under reflux for 1 hour and 12 minutes. After that, a 2 mol/L aqueous solution of sodium hydroxide (0.530 mL, 1.06 mmol) was added to the reaction mixture, which was then heated under reflux for another 50 minutes. The reaction mixture was cooled to room temperature and diluted in water, followed by addition of potassium hydrogensulfate (241 mg, 1.77 mmol) and extraction with hexane. The extract was washed with water and concentrated, and the obtained residue was purified by silica gel column chromatography to obtain Compound 12 (193 mg, 93.0%) as a colorless oily material.

Compound 12; $^1$H-NMR (CDCl$_3$) δ: 1.95 (1H, t, J=8.0 Hz), 3.69-3.74 (4H, m), 4.07 (2H, t, J=4.0 Hz), 6.48 (2H, d, J=8.8 Hz).

Compound 12 (184 mg, 0.785 mmol) and Compound 13 (184 mg, 0.785 mmol) were dissolved in DMF (4 mL), to which was then added 60% sodium hydride (37.7 mg, 0.943 mmol), and the resulting mixture was stirred at room temperature for 2 hours. The reaction mixture was quenched with a saturated aqueous solution of ammonium chloride, and extracted with ethyl acetate. The extract was washed with water and concentrated, and the obtained residue was purified by silica gel column chromatography to obtain Compound 14 (247 mg, 78.7%) as a white powder.

Compound 14; $^1$H-NMR (CDCl$_3$) δ: 1.70-1.87 (3H, m), 2.05-2.18 (3H, m), 3.44 (3H, s), 3.73 (2H, t, J=4.5 Hz), 3.78-3.87 (1H, m), 4.07 (2H, t, J=4.5 Hz), 4.19-4.22 (1H, m), 4.46-4.57 (2H, m), 5.89 (1H, d, J=10.2 Hz), 6.49 (2H, d, J=9.3 Hz), 7.95 (1H, s), 8.17 (1H, s).

To a solution of Compound 14 (249 mg, 0.530 mmol) in THF (2.5 mL) was added hexachloroethane (144 mg, 0.610 mmol), and the solution was cooled to −45° C. To the cooled solution was added dropwise a 1 mol/L solution of hexamethyldisilazide in toluene (0.530 mL, 0.530 mmol), and at that temperature, the resulting mixture was stirred for 1.5 hours. The reaction mixture was quenched with a saturated aqueous solution of ammonium chloride, and extracted with ethyl acetate. The extract was washed with water and concentrated, and the obtained residue was purified by silica gel column chromatography to obtain Compound 15 (188 mg, 70.4%) as a white powder.

Compound 15; $^1$H-NMR (CDCl$_3$) δ: 1.63-1.96 (4H, in), 2.13-2.16 (1H, in), 3.00-3.06 (1H, m), 3.44 (3H, s), 3.73-3.79 (3H, m), 4.08 (2H, t, J=4.5 Hz), 4.17-4.25 (1H, m), 4.44-4.58 (2H, m), 5.83 (1H, t, J=5.5 Hz), 6.51 (2H, d, J=9.2 Hz), 7.83 (1H, s).

To a solution of Compound 15 (105 mg, 0.208 mmol) and Compound 16 (65.1 mg, 0.250 mmol) in THF (4 mL) was added potassium tert-butoxide (26.9 mg, 0.239 mmol), and the resulting mixture was stirred at room temperature for 6 hours. The reaction mixture was quenched with a saturated aqueous solution of ammonium chloride, and extracted with ethyl acetate. The extract was washed with water and concentrated, and the obtained residue was purified by silica gel column chromatography to obtain Compound 17 (188 mg, 70.4%) as a white powder.

Compound 17; $^1$H-NMR (CDCl$_3$) δ: 0.07-0.15 (6H, m), 0.84-0.97 (11H, m), 1.43-1.92 (9H, m), 2.04-2.14 (1H, m), 2.80-3.13 (1H, m), 3.44 (3H, s), 3.61-4.54 (16H, m), 4.90-

4.94 (1H, in), 5.30 (3H, s), 5.47-5.53 (1H, in), 5.62-5.76 (1H, in), 6.45-6.52 (2H, m), 7.63 (1H, s).

To a solution of Compound 17 (67.0 mg, 0.092 mmol) in 80% aqueous methanol (2 mL) was added pyridinium p-toluenesulfonate (23.1 mg, 0.092 mmol), and the mixture was heated under reflux for 5 hours. The reaction mixture was concentrated, diluted in water, and extracted with ethyl acetate. The extract was washed with water and concentrated, and the obtained residue was purified by silica gel column chromatography to obtain Compound I-1-4 (29.5 mg, 60.5%) as a white powder.

Compound I-1-4; $^1$H-NMR (CDCl$_3$) δ: 3.30-3.46 (4H, m), 3.64 (2H, s), 3.72-3.85 (1H, m), 3.85-3.96 (1H, m), 4.06-4.22 (4H, m), 4.33-4.37 (1H, m), 4.41 (2H, t, J=9.7 Hz), 4.80-4.88 (1H, m), 4.97-5.06 (1H, m), 5.46 (1H, tt, J=10.4, 3.7 Hz), 6.79-6.87 (2H, in), 7.79-7.90 (1H, in), 12.59-13.06 (1H, in).

EXAMPLE 5 p-toluenesulfonate (26.6 mg, 0.106 mmol), and the mixture was heated under reflux for 5 hours. The reaction mixture was concentrated, diluted in water, and extracted with ethyl acetate. The extract was washed with water and concentrated, and the obtained residue was purified by silica gel column chromatography to obtain Compound I-1-5 (45.6 mg, 76.7%) as a white powder.

Compound I-1-5; $^1$H-NMR (DMSO-D$_6$) δ: 3.27 (3H, s), 3.36-3.48 (1H, in), 3.59-3.66 (2H, m), 3.78 (1H, t, J=7.4 Hz), 3.95 (1H, dd, J=9.8, 5.4 Hz), 4.08-4.18 (4H, m), 4.36 (1H, t, J=4.7 Hz), 4.78-4.89 (3H, m), 5.03 (1H, d, J=6.7 Hz), 5.51 (1H, q, J=5.6 Hz), 6.80 (2H, t, J=10.5 Hz), 8.06-8.15 (1H, m), 13.41-13.56 (1H, m).

[Chemical formula 44]

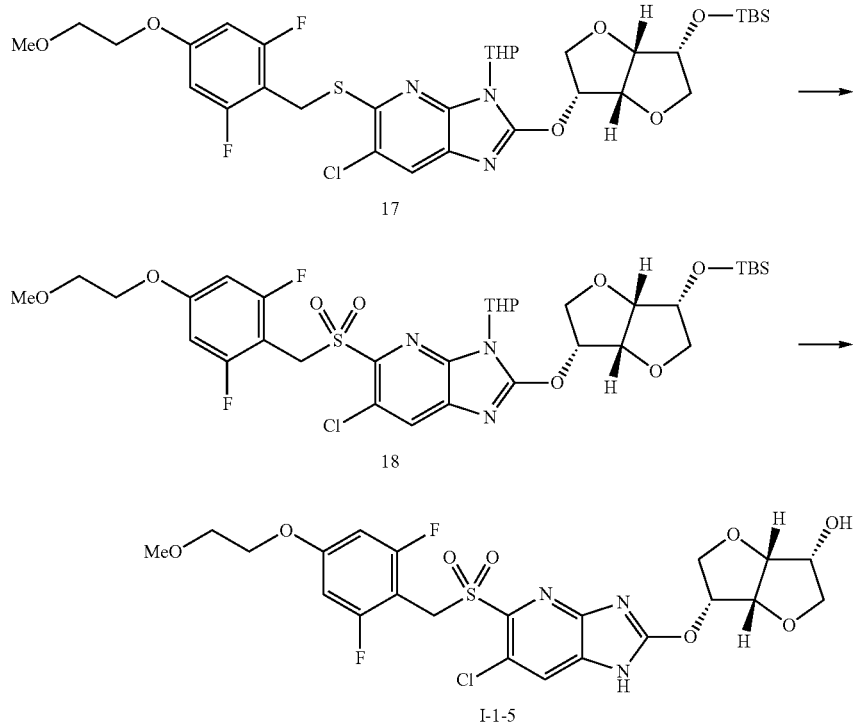

To a solution of Compound 17 (88.1 mg, 0.121 mmol) in dichloromethane (2 mL) was added 70% mCPBA (60.5 mg, 0.242 mmol), and the reaction mixture was stirred at room temperature for 20 hours. The reaction mixture was quenched with a 10% aqueous solution of sodium thiosulfate, and extracted with ethyl acetate. The extract was washed with saturated aqueous sodium bicarbonate and water and concentrated, and the obtained residue was purified by silica gel column chromatography to obtain Compound 18 (80.4 mg, 87.4%) as a white powder.

Compound 18; LC-MS:RT=2.82, M+H=760.20, Method C.

To a solution of Compound 18 (80.4 mg, 0.106 mmol) in 80% aqueous methanol (2.4 mL) was added pyridinium

EXAMPLE 6

[Chemical formula 45]

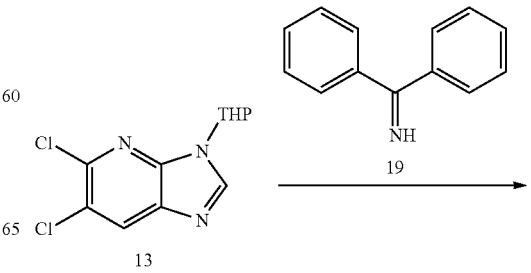

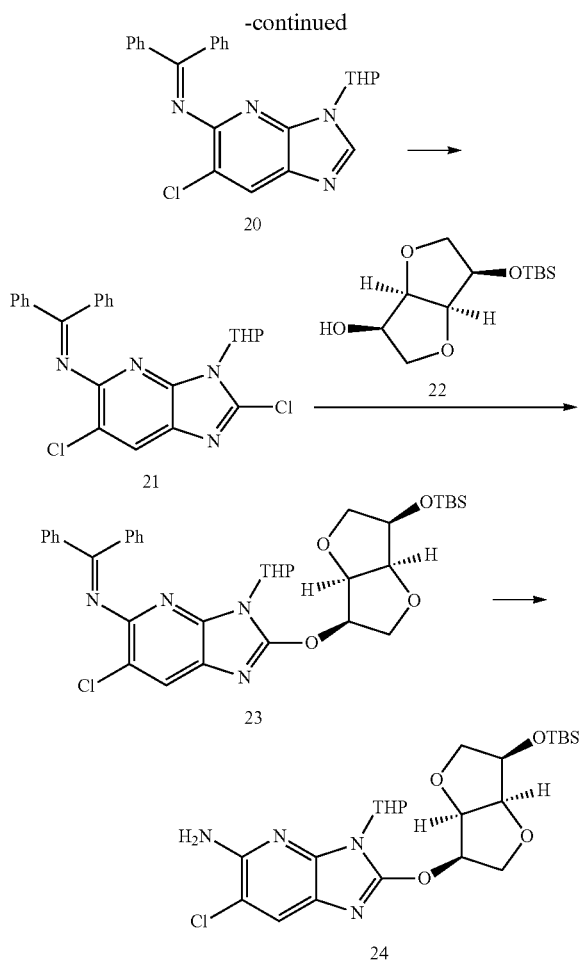

To degassed toluene (60 mL) were added tris(dibenzylideneacetone)dipalladium (168 mg, 0.184 mmol) and diphenylphosphinoferrocene (306 mg, 0.551 mmol) under a stream of nitrogen, and the resulting mixture was stirred at room temperature for 10 minutes. Subsequently, sodium t-butoxide (1.41 g, 14.7 mmol), Compound 13 (2.00 g, 7.35 mmol), and Compound 19 (1.48 mL, 8.82 mmol) were successively added to the reaction mixture, which was then stirred at 80° C. for 2 hours. The reaction mixture was cooled to room temperature, followed by addition of water (30 mL) and extraction with ethyl acetate. The extract, was washed with water, and then concentrated. The obtained residue was purified by silica gel column chromatography, and then crystallized from ethyl acetate (2 mL) and hexane (10 mL) to obtain Compound 20 (29.5 mg, 60.5%) as yellow crystals.

Compound 20; $^1$H-NMR (DMSO-D$_6$) δ: 1.61-1.66 (4H, m), 1.91 (1H, dd, J=12.3, 0.8 Hz), 2.03-2.13 (1H, m), 3.59-3.66 (1H, m), 3.96-4.01 (1H, m), 5.50 (1H, d, J=10.8 Hz), 7.19 (2H, d, J=15.8 Hz), 7.29 (3H, s), 7.53 (2H, t, J=6.7 Hz), 7.58-7.65 (1H, m), 7.71-7.80 (2H, m), 8.17 (1H, s), 8.45 (1H, s).

To a solution of Compound 20 (1.00 mg, 2.40 mmol) in THF (10 mL) was added hexachloroethane (596 mg, 2.52 mmol), and the solution was cooled to −50° C. To the cooled solution was added dropwise a 1 mol/L solution of hexamethyldisilazide in toluene (2.64 mL, 2.64 mmol) over 10 minutes, and at that temperature, the resulting mixture was stirred for 10 minutes. The reaction mixture was quenched with water, and then extracted with ethyl acetate. The extract was washed with water, filtered, and concentrated, and the obtained residue was purified by suspension in ethyl acetate (15 mL) and hexane (30 mL) to obtain Compound 21 (937 mg, 82.5%) as a white powder.

Compound 21; $^1$H-NMR (DMSO-D$_6$) δ: 1.46-1.67 (4H, m), 1.86-1.88 (1H, m), 2.52-2.55 (6H, m), 3.57-3.63 (1H, m), 3.98 (1H, d, J=11.3 Hz), 5.50 (1H, d, J=10.8 Hz), 7.16 (2H, s), 7.31 (3H, s), 7.54 (2H, t, J=7.0 Hz), 7.63 (1H, dt, J=10.0, 2.2 Hz), 7.77 (2H, d, J=7.0 Hz), 8.17 (1H, d, J=5.3 Hz).

To a solution of Compound 21 (200 mg, 0.443 mmol) and Compound 22 (150 mg, 0.576 mmol) in THF (4 mL) was added potassium tert-butoxide (64.6 mg, 0.576 mmol), and the resulting mixture was stirred at room temperature for 2 hours. Similarly, to a solution of Compound 21 (727 mg, 1.61 mmol) and Compound 22 (545 mg, 2.09 mmol) in THF (14.5 mL) was added potassium tert-butoxide (235 mg, 2.09 mmol), and the resulting mixture was stirred at room temperature for 40 minutes. These two reaction mixtures were combined, quenched with water, and extracted with ethyl acetate. The extract was washed with water, filtered, and concentrated, and the obtained residue was purified by suspension in ethyl acetate (2 mL) and hexane (4 mL) to obtain Compound 23 (714 mg, 51.5%) as white crystals. In addition, the mother liquid was concentrated, and the obtained residue was purified by silica gel column chromatography to obtain Compound 23 (650.8 mg, 46.9%) as a white powder.

Compound 23; $^1$H-NMR (DMSO-D$_6$) δ: 0.01 (3H, d, J=5.8 Hz), 0.03 (3H, s), 0.81 (9H, d, J=4.5 Hz), 0.99-1.85 (5H, m), 2.26-2.49 (1H, m), 3.11 (2H, d, J=5.0 Hz), 3.68-3.73 (1H, in), 3.85-3.99 (3H, in), 4.17-4.31 (2H, in), 4.71 (1H, q, J=5.5 Hz), 5.21-5.25 (1H, m), 5.31-5.34 (1H, m), 7.08 (2H, dd, J=2.5, 2.0 Hz), 7.25 (3H, d, J=0.5 Hz), 7.46 (2H, t, J=7.4 Hz), 7.55 (1H, dd, J=9.2, 5.1 Hz), 7.69 (2H, d, J=7.5 Hz), 7.80 (1H, s).

To a solution of Compound 23 (214 mg, 0.317 mmol) in methanol (8 mL) was added a 50% aqueous solution of hydroxylamine (41.9 mg, 0.635 mmol), and the mixture was stirred at room temperature for 1 hour. The reaction mixture was diluted in THF (4 mL) and methanol (1 mL), followed by heating under reflux for 6 hours. In order to further increase the reaction temperature, the reaction mixture was concentrated, followed by addition of ethanol (4 mL). The resulting mixture was heated at reflux for 1.5 hours. The reaction mixture was cooled to room temperature, and extracted with ethyl acetate. The extract was washed with water and concentrated, and the obtained residue was purified by silica gel column chromatography to obtain Compound 24 (127.2 mg, 78.4%) as a yellow powder.

Compound 24; LC-MS:RT=2.63, M+H=511.15 Method C.

EXAMPLE 7

[Chemical formula 46]

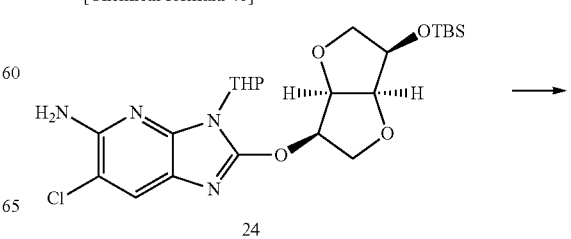

-continued

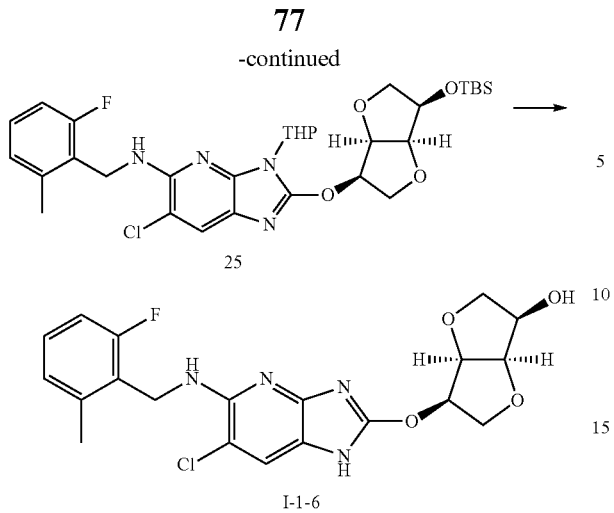

25

I-1-6

To a solution of Compound 24 (100 mg, 0.196 mmol) in DMF (1 mL) were added 2-(bromomethyl)-1-fluoro-3-methylbenzene (51.6 mg, 0.254 mmol) and cesium carbonate (96 mg, 0.293 mmol), and the reaction mixture was stirred at 80° C. for 6 hours. The reaction mixture was quenched with water, and then extracted with ethyl acetate. The solvent was removed under reduced pressure. The obtained residue was purified by silica gel column chromatography to obtain Compound 25 (68.1 mg, 0.108 mmol, 55%) as a white solid.

Compound 25; Retention time=3.18 min, Mass(M+H)=633.1, Method=C

To a solution of Compound 25 (68.1 mg, 0.108 mmol) in a mixture of methanol (1 mL) and water (0.2 mL) was added PPTS (54.1 mg, 0.215 mmol), and the reaction mixture was stirred at 80° C. for 5 hours. The reaction mixture was concentrated, and then purified by reverse-phase column chromatography to obtain Compound I-1-6 (36.7 mg, 0.084 mmol, 79%) as a white solid.

Compound I-1-6; Retention time=1.91 min, Mass(M+H)=434.95, Method=C

EXAMPLE 8

[Chemical formula 47]

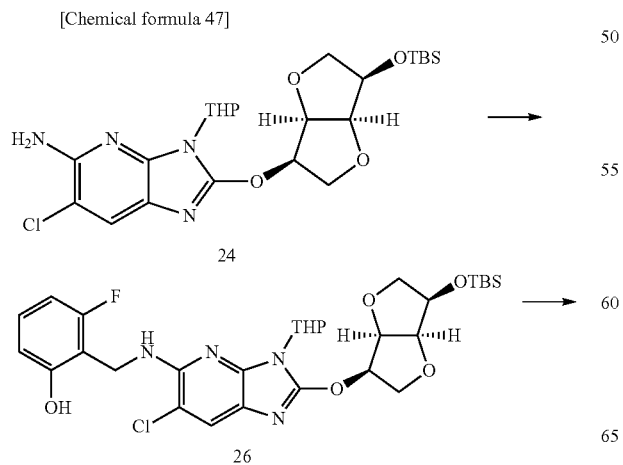

24

26

-continued

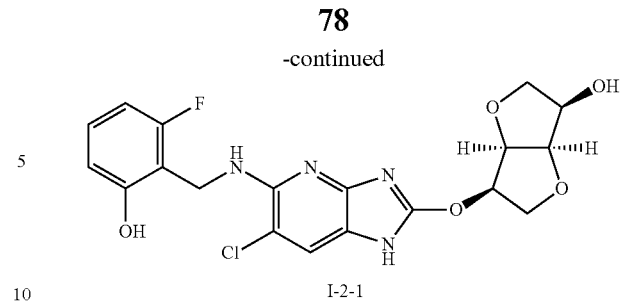

I-2-1

To a solution of Compound 24 (100 mg, 0.196 mmol) in methanol (2 mL) were added 2-fluoro-6-hydroxybenzaldehyde (32.9 mg, 0.254 mmol) and acetic acid (0.2 mL), and the reaction mixture was stirred at room temperature for 30 minutes. After that, 2-picoline-borane Complex (25.1 mg, 0.235 mmol) was added to the reaction mixture, which was then stirred for 2 hours. The reaction mixture was quenched with water, and extracted with ethyl acetate. The solvent was removed under reduced pressure. The obtained residue was purified by silica gel column chromatography to obtain a crude product (135.9 mg), containing Compound 26, which was used directly in the next reaction.

Compound 26; Retention time=2.96 min, Mass(M+H)=635.3, Method=C

To a solution of the crude product 26 (135.9 mg) in a mixture of methanol (1 mL) and water (0.2 mL) was added PPTS (108 mg, 0.428 mmol), and the reaction mixture was stirred at 80° C. for 5 hours. The reaction mixture was concentrated, and then purified by reverse-phase column chromatography to obtain Compound I-2-1 (56.6 mg, 0.130 mmol, 61%) as a white solid.

Compound I-2-E Retention time=1.59 min, Mass(M+H)=437.15, Method=C

EXAMPLE 9

[Chemical formula 18]

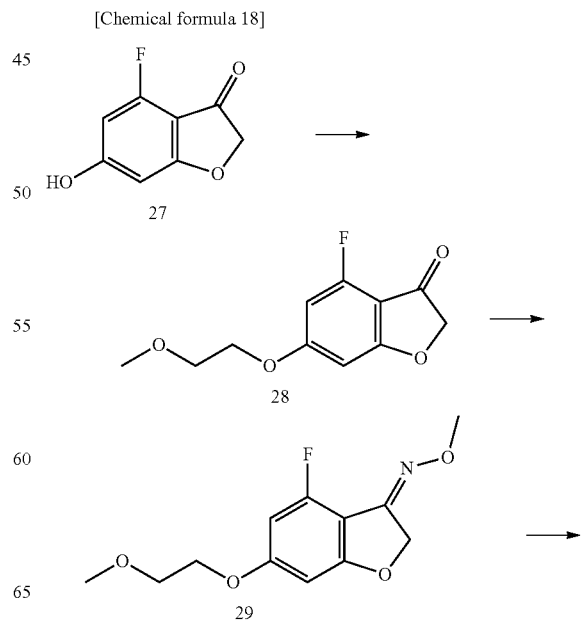

27

28

29

-continued

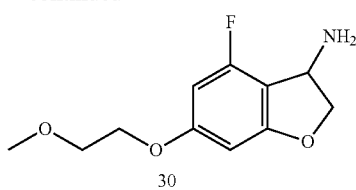

30

To a solution of Compound 27 (500 mg, 2.97 mmol) in DMF (5 mL) were added 1-bromo-2-methoxyethane (0.307 mL, 3.27 mmol) and potassium carbonate (534 mg, 3.87 mmol), and the reaction mixture was stirred at 80° C. for 3 hours. The reaction mixture was quenched with water, and extracted with ethyl acetate. The solvent was removed under reduced pressure. The obtained residue was purified by silica gel column chromatography to obtain Compound 28 (530 mg, 2.34 mmol, 79%) as a white solid.

Compound 28; Retention time=1.48 min, Mass(M+H)=226.9, Method=C

To a solution of Compound 28 (200 mg, 0.884 mmol) in ethanol (2 mL) were added O-methoxyhydroxylamine hydrochloride (148 mg, 1.77 mmol) and sodium acetate (145 mg, 1.77 mmol), and the reaction mixture was stirred overnight at 85° C. The reaction mixture was quenched with water, and extracted with ethyl acetate. The solvent was removed under reduced pressure. The obtained residue was filtered, washed with hexane, and then dried to obtain Compound 29 (221 mg, 0.867 mmol, 98%) as a white solid.

Compound 29; Retention time=1.87 min, Mass(M+H)=256.25, Method=C

To Compound 29 (171 mg, 0.672 mmol) was added BH₃ in THF (2.92 mL, 2.69 mmol, 0.92 M), and the reaction mixture was stirred at 50° C. for 7 hours. MeOH was added to the reaction mixture, which was then stirred for a while. After that, the reaction mixture was quenched with a 2 N aqueous solution of NaOH, and extracted with ethyl acetate. The solvent was removed under reduced pressure. The obtained residue was purified by silica gel column chromatography to obtain Compound 30 (55.4 mg, 0.244 mmol, 36%) as a colorless oil.

Compound 30; Retention time=0.85 min, Mass(M+H)=210.95, Method=C

[Chemical formula 49]

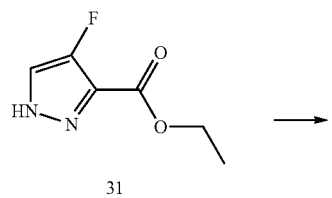

31

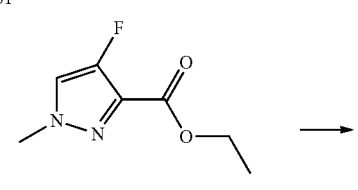

32

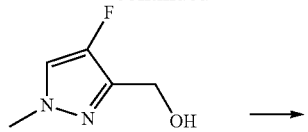

33

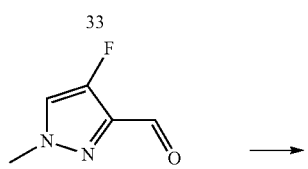

34

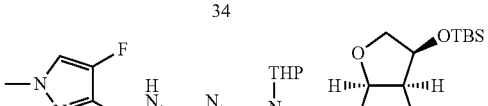

35

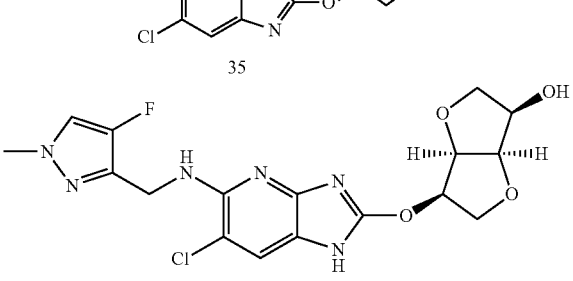

I-2-2

To a solution of Compound 31 (100 mg, 0.632 mmol) in DMF (1 mL) was added 60% NaH (32.9 mg, 0.882 mmol) at 0° C., and the reaction mixture was stirred for 10 minutes. After that, methyl iodide (0.047 mL, 0.759 mmol) was added at 0° C. to the reaction mixture, which was then stirred at room temperature for 1 hour. The reaction mixture was quenched with water, filtered through Celite, and then extracted with ethyl acetate. The solvent was removed under reduced pressure. The obtained residue was purified by silica gel column chromatography to obtain Compound 32 (27 mg, 0.157 mmol, 25%) as a white solid.

Compound 32; Retention time=1.32 min, Mass(M+H)=173.0, Method=C

To a solution of Compound 32 (27 mg, 0.157 mmol) in THF (1 mL) was added LAH (11.9 mg, 0.314 mmol) at 0° C., and the reaction mixture was stirred for 1 hour. The reaction mixture was quenched with water, filtered through Celite, and then extracted with ethyl acetate. The solvent was removed under reduced pressure to obtain Compound 33 (12.7 mg, 0.098 mmol, 62%) as a white solid.

Compound 33; Retention time=0.63 min, Mass(M+H)=131.0, Method=C

To a solution of Compound 33 (12.7 mg, 0.098 mmol) in THF (1 mL) was added manganese dioxide (85 mg, 0.976 mmol), and the reaction mixture was stirred at room temperature for 2 hours. The reaction mixture was filtered through Celite, and washed with ethyl acetate to obtain a crude product (8.4 mg), containing Compound 34, which was then used directly in the next reaction.

To a solution of Compound 24 (27.9 mg, 0.055 mmol) in methanol (1 mL) were added the crude product (8.4 mg) and acetic acid (0.1 mL), and the reaction mixture was stirred at room temperature for 30 minutes. After that, 2-picoline-borane complex (7.0 mg, 0.066 mmol) was added to the reaction mixture, which was then stirred overnight. The reaction mixture was quenched with water and extracted with ethyl acetate. The solvent was removed under reduced pressure to obtain a crude product (34 mg), containing Compound 35, which was then used directly in the next reaction.

To a solution of the crude product (34 mg) in a mixture of MeOH (1 mL) and water (0.1 mL) was added PPTS (27.5 mg, 0.109 mmol), and the reaction mixture was stirred at 80° C. for 4 hours. The reaction mixture was concentrated, and then purified by reverse-phase column chromatography to obtain Compound I-2-2 (1.7 mg, 0.004 mmol, 7%) as a colorless amorphous material.

Compound I-2-2; Retention time=1.36 min, Mass(M+H)=425.0, Method=C

The compounds shown below were synthesized in a similar way. The measurement results of NMR or LC/MS of the respective compounds are shown.

TABLE 1

| No. | Structure | NMR (δ) | retention time | Mass (M + H) | Method |
|---|---|---|---|---|---|
| I-1-7 | 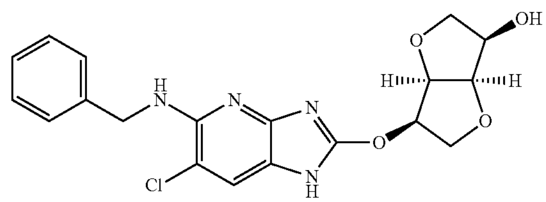 [SMILES: O[C@@H]1CO[C@H]2[C@@H]1OC[C@H]2Oc1nc2nc(NCc3ccccc3)c(Cl)cc2[nH]1] | 1H-NMR (DMSO-D6) δ: 3.73-3.81 (m, 2H), 4.07-4.13 (m, 2H), 4.33 (t, J = 4.6 Hz, 1H), 4.58 (d, J = 6.0 Hz, 2H), 4.75 (t, J = 4.6 Hz, 1H), 4.95 (d, J = 6.8 Hz, 1H), 5.28-5.31 (m, 1H), 7.18-7.19 (m, 1H), 7.27-7.28 (m, 4H), 7.62 (s, 1H). | 1.7 | 403.1 | C |
| I-1-8 | 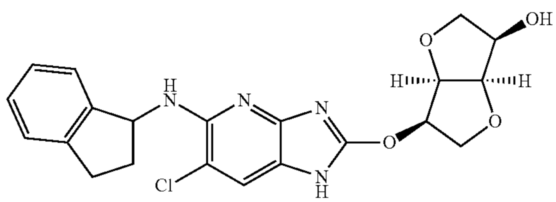 [SMILES: O[C@@H]1CO[C@H]2[C@@H]1OC[C@H]2Oc1nc2nc(NC3CCc4ccccc43)c(Cl)cc2[nH]1] | 1H-NMR (DMSO-D6) δ: 1.99-2.01 (m, 1H), 2.79-2.87 (m, 1H), 2.96-2.99 (m, 1H), 3.76-3.84 (m, 2H), 4.09-4.11 (m, 2H), 4.35 (s, 1H), 4.79 (s, 1H), 5.02 (d, J = 6.1 Hz, 1H), 5.34 (d, J = 5.3 Hz, 1H), 5.60-5.62 (m, 1H), 5.99 (s, 1H), 7.18-7.25 (m, 5H), 7.66 (s, 1H). | 1.93 | 429.2 | C |
| I-1-9 | 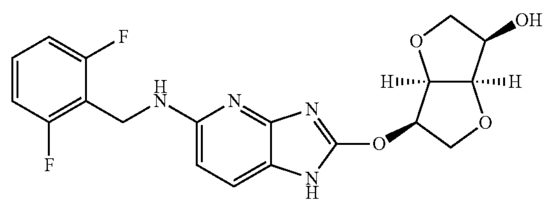 [SMILES: O[C@@H]1CO[C@H]2[C@@H]1OC[C@H]2Oc1nc2nc(NCc3c(F)cccc3F)ccc2[nH]1] | | 0.98 | 405.6 | B |
| I-1-10 | 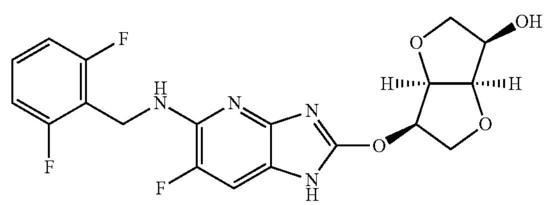 [SMILES: O[C@@H]1CO[C@H]2[C@@H]1OC[C@H]2Oc1nc2nc(NCc3c(F)cccc3F)c(F)cc2[nH]1] | | 1.58 | 423.2 | C |
| I-1-11 | 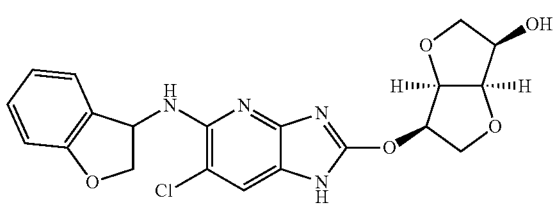 [SMILES: O[C@@H]1CO[C@H]2[C@@H]1OC[C@H]2Oc1nc2nc(NC3COc4ccccc43)c(Cl)cc2[nH]1] | 1H-NMR (DMSO-D6) δ: 3.42 (t, J = 8.5 Hz, 1H), 3.76-3.85 (m, 2H), 4.08-4.17 (m, 2H), 4.34-4.42 (m, 2H), 4.78-4.79 (m, 2H), 4.95 (d, J = 6.5 Hz, 1H), 5.35-5.36 (m, 1H), 5.77-5.78 (m, 1H), 6.10 (s, 1H), 6.83-6.68 (m, 2H), 7.20 (t, J = 7.8 Hz, 1H), 7.38 (d, J = 7.0 Hz, 1H), 7.66 (s, 1H). | 1.75 | 431.15 | C |

TABLE 2

| No. | Structure | NMR (δ) | retention time | Mass (M + H) | Method |
|---|---|---|---|---|---|
| I-1-12 | 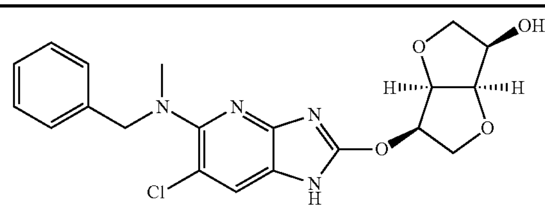 | 1H-NMR (DMSO-D6) δ: 3.76-3.78 (m, 1H), 3.84-3.87 (m, 1H), 4.08-4.17 (m, 2H), 4.34-4.36 (m, 3H), 4.50 (t, J = 5.0 Hz, 1H), 4.98 (d, J = 6.7 Hz, 1H), 5.39 (q, J = 5.9 Hz, 1H), 7.23-7.25 (m, 1H), 7.30-7.37 (m, 4H), 7.80 (s, 1H). | 1.86 | 417.2 | C |

TABLE 2-continued

| ID | Structure | NMR / Notes | Rt | MS | Method |
|---|---|---|---|---|---|
| I-1-13 | (structure) | 1H-NMR (CDCl3) δ: 2.74 (1H, s), 3.44 (3H, s), 3.71 (3H, s), 3.92-4.16 (4H, m), 4.27-4.41 (2H, m), 4.54-4.75 (3H, m), 4.85-5.14 (2H, m), 5.47-5.67 (1H, m), 6.38-6.79 (2H, m), 7.33-7.67 (1H, m), 8.67-9.16 (1H, m). | 1.80 | 513.1 | C |
| I-1-14 | (structure) | | 1.98 | 472.9 | C |
| I-1-15 | (structure) | | 1.57 | 499 | C |
| I-1-16 | (structure) | | 1.95 | 407 | C |

TABLE 3

| ID | Structure | Rt | MS | Method |
|---|---|---|---|---|
| I-1-17 | (structure) | 1.25 | 413 | C |
| I-1-18 | (structure) | 1.59 | 431 | A |

TABLE 3-continued
| | | | | | |
|---|---|---|---|---|---|
| I-1-19 | 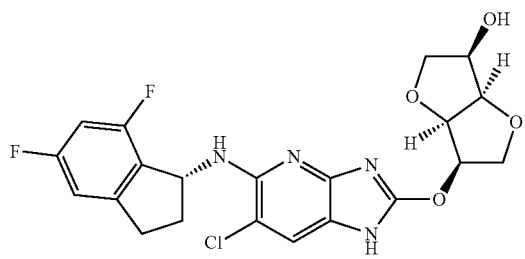 [SMILES: O[C@@H]1CO[C@H]2[C@@H]1OC[C@H]2Oc1nc2nc(N[C@@H]3CCc4cc(F)cc(F)c43)c(Cl)cc2[nH]1] | | 1.93 | 464.95 | C |
| I-1-20 | 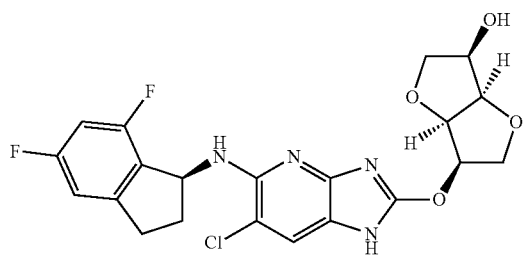 [SMILES: O[C@@H]1CO[C@H]2[C@@H]1OC[C@H]2Oc1nc2nc(N[C@H]3CCc4cc(F)cc(F)c43)c(Cl)cc2[nH]1] | | 1.96 | 464.95 | C |
| I-1-21 | 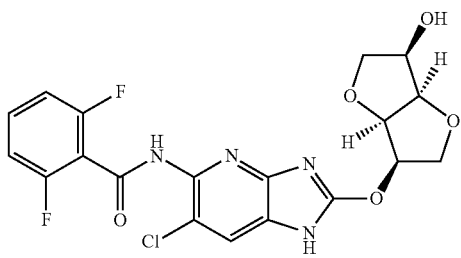 [SMILES: O=C(Nc1nc2nc(O[C@@H]3CO[C@H]4[C@@H]3OC[C@H]4O)[nH]c2cc1Cl)c1c(F)cccc1F] | | 1.31 | 452.95 | C |
TABLE 4
| | | | | | |
|---|---|---|---|---|---|
| I-1-22 | 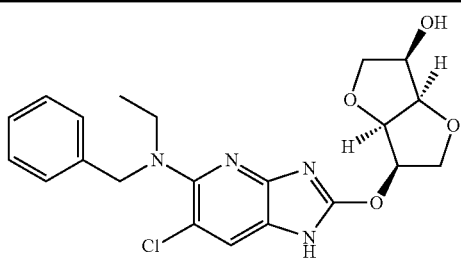 | | 1.95 | 431 | C |
| I-1-23 | 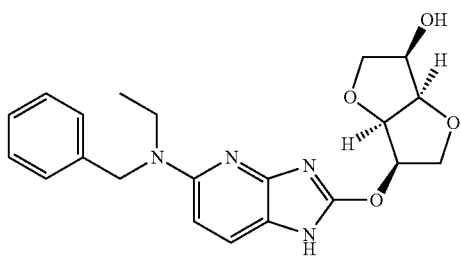 [SMILES: CCN(Cc1ccccc1)c1ccc2[nH]c(O[C@@H]3CO[C@H]4[C@@H]3OC[C@H]4O)nc2n1] | | 1.47 | 397.05 | C |
| I-1-24 | 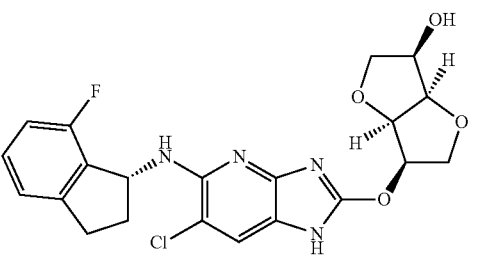 [SMILES: O[C@@H]1CO[C@H]2[C@@H]1OC[C@H]2Oc1nc2nc(N[C@@H]3CCc4cccc(F)c43)c(Cl)cc2[nH]1] | | 1.91 | 447 | C |

TABLE 4-continued
| | | | | |
|---|---|---|---|---|
| I-1-25 | 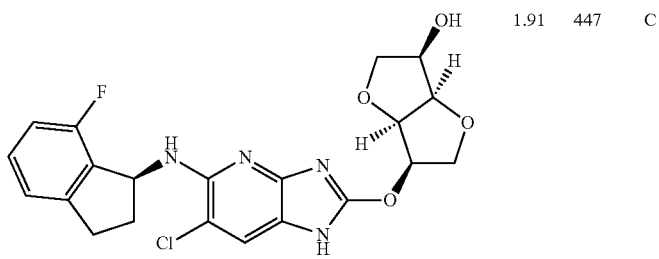 | 1.91 | 447 | C |
| I-1-26 | 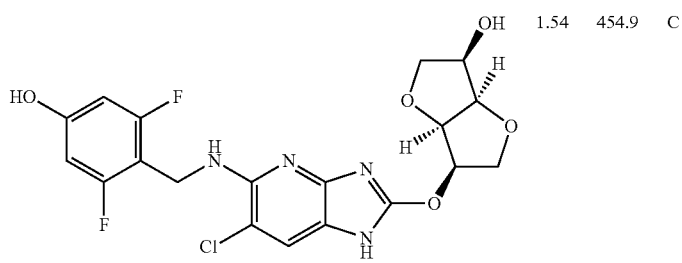 | 1.54 | 454.9 | C |
TABLE 5
| | | | | |
|---|---|---|---|---|
| I-1-27 | 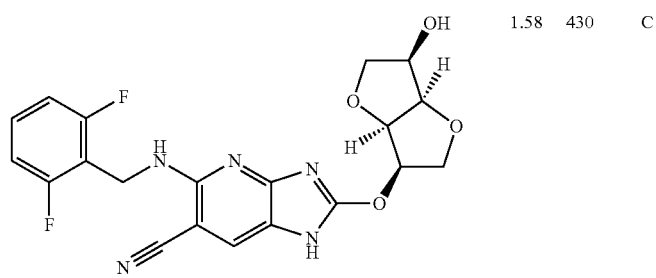 | 1.58 | 430 | C |
| I-1-28 | 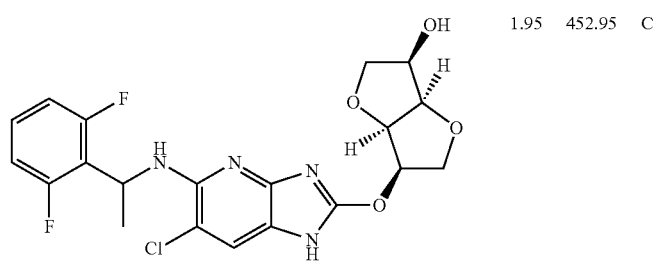 | 1.95 | 452.95 | C |
| I-1-29 | 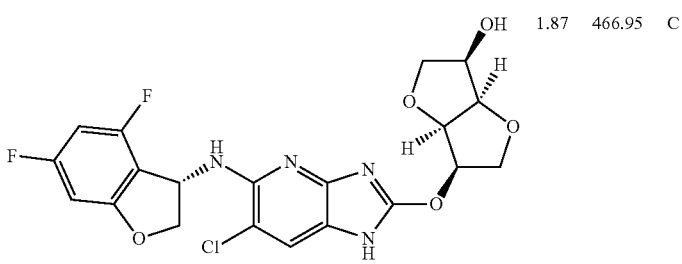 | 1.87 | 466.95 | C |

TABLE 5-continued
| | | | | |
|---|---|---|---|---|
| I-1-30 | 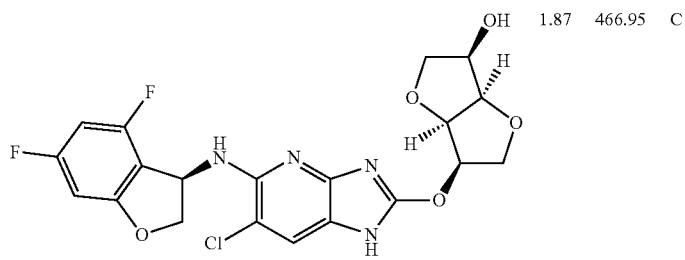 | 1.87 | 466.95 | C |
| I-1-31 | 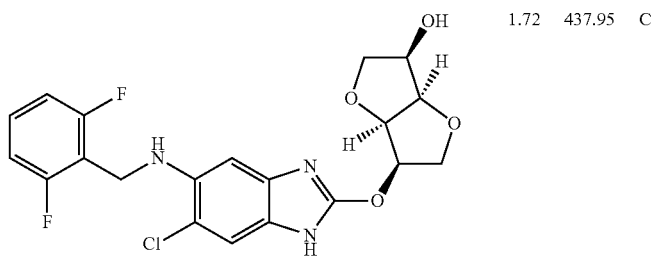 | 1.72 | 437.95 | C |
TABLE 6
| | | | | |
|---|---|---|---|---|
| I-1-32 | 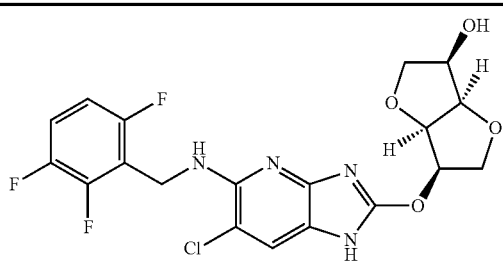 | 1.79 | 456.9 | C |
| I-1-33 | 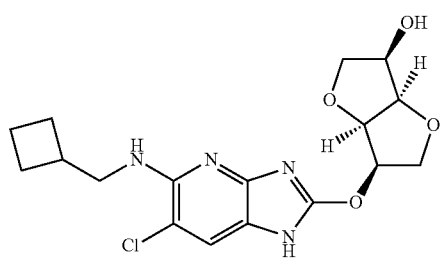 | 1.65 | 381.1 | B |
| I-1-34 | 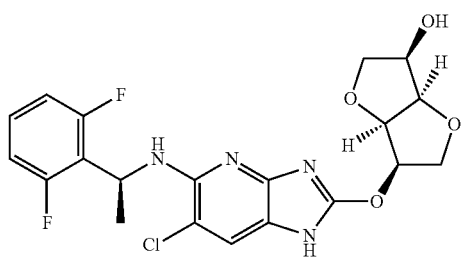 [SMILES: C[C@H](Nc1nc2nc(O[C@@H]3CO[C@H]4[C@@H]3OC[C@H]4O)[nH]c2cc1Cl)c1c(F)cccc1F] | 1.95 | 452.95 | C |
| I-1-35 | 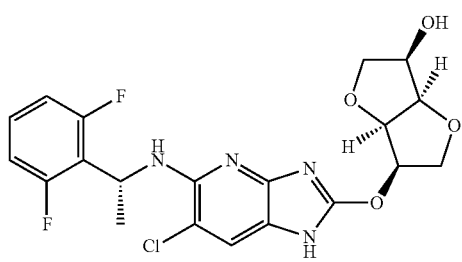 [SMILES: C[C@@H](Nc1nc2nc(O[C@@H]3CO[C@H]4[C@@H]3OC[C@H]4O)[nH]c2cc1Cl)c1c(F)cccc1F] | 1.95 | 452.95 | C |

TABLE 6-continued
| I-1-36 | 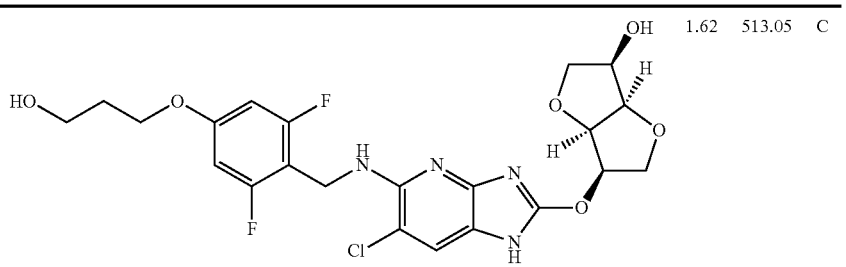 | 1.62 | 513.05 | C |
TABLE 7
| I-1-37 | 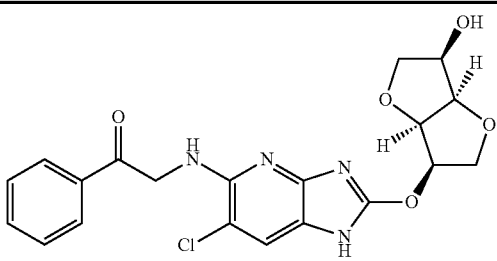 | 1.55 | 431.1 | B |
| I-1-38 | 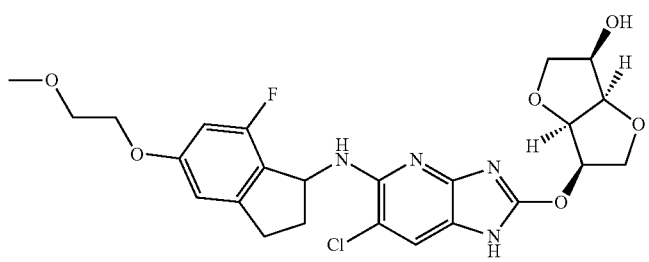 [SMILES: COCCOc1cc(F)c2c(c1)CCC2Nc1nc2nc(O[C@@H]3CO[C@H]4[C@@H]3OC[C@H]4O)[nH]c2cc1Cl] | 1.85 | 521 | C |
| I-1-39 | 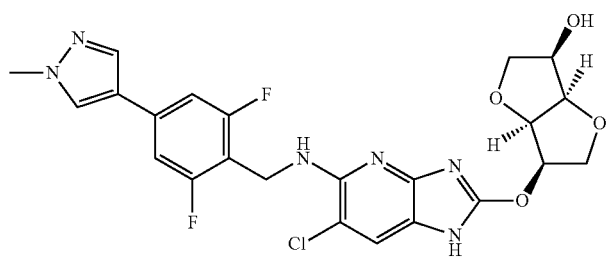 [SMILES: Cn1cc(-c2cc(F)c(CNc3nc4nc(O[C@@H]5CO[C@H]6[C@@H]5OC[C@H]6O)[nH]c4cc3Cl)c(F)c2)cn1] | 1.69 | 519 | C |
| I-1-40 | 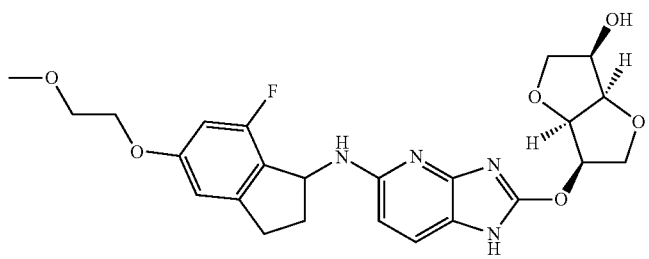 [SMILES: COCCOc1cc(F)c2c(c1)CCC2Nc1ccc2[nH]c(O[C@@H]3CO[C@H]4[C@@H]3OC[C@H]4O)nc2n1] | 1.32 | 487.05 | C |
| I-1-41 | 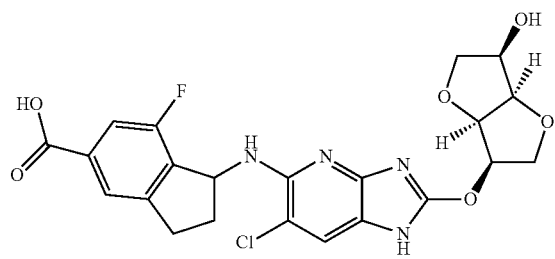 [SMILES: O=C(O)c1cc(F)c2c(c1)CCC2Nc1nc2nc(O[C@@H]3CO[C@H]4[C@@H]3OC[C@H]4O)[nH]c2cc1Cl] | 1.41 | 491.15 | C |

TABLE 8
| | | | | |
|---|---|---|---|---|
| I-1-42 | 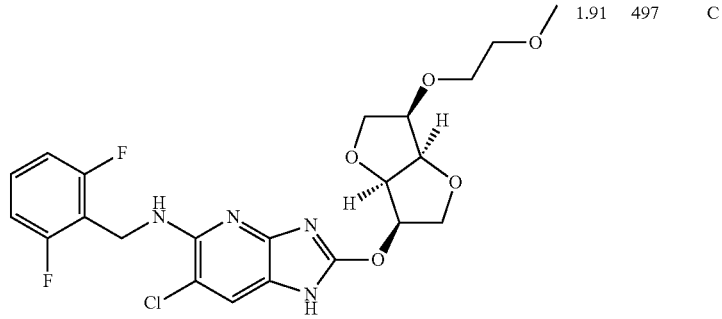 | 1.91 | 497 | C |
| I-1-43 | 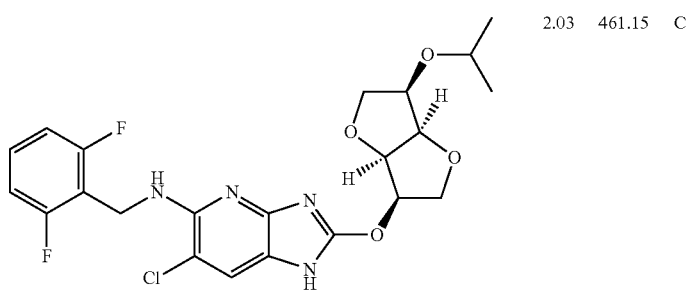 | 2.03 | 461.15 | C |
| I-1-44 | 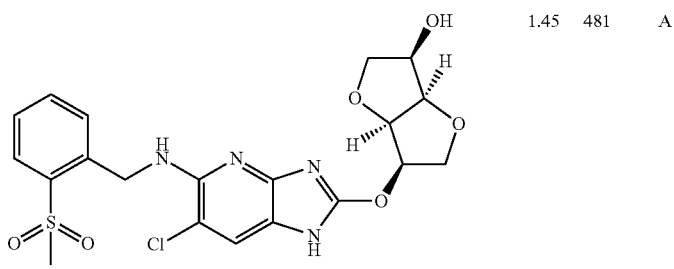 | 1.45 | 481 | A |
| I-1-45 | 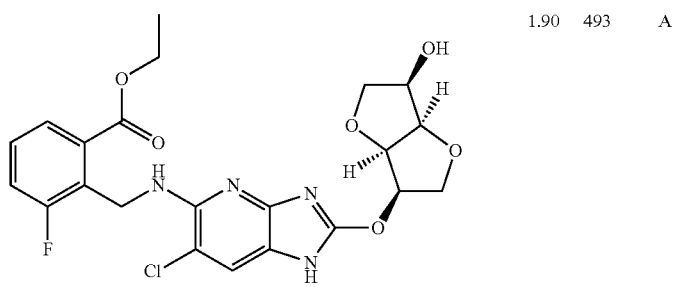 | 1.90 | 493 | A |
| I-1-46 | 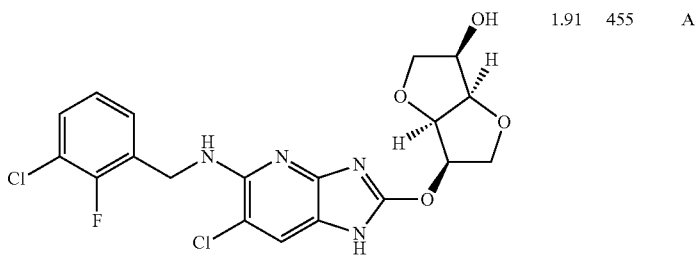 | 1.91 | 455 | A |

TABLE 9
| | | | | |
|---|---|---|---|---|
| I-1-47 | 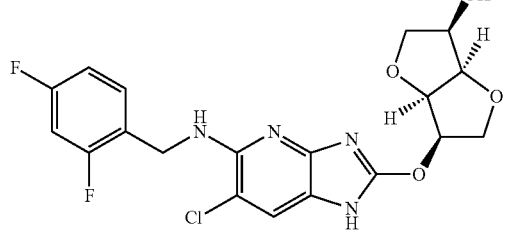 | 1.76 | 439 | A |
| I-1-48 | 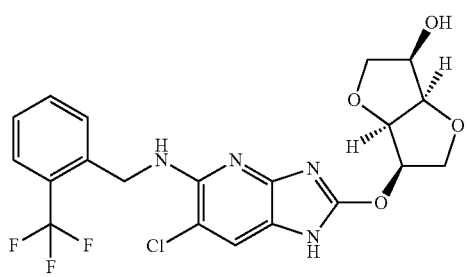 [SMILES: O[C@@H]1CO[C@H]2[C@@H]1OC[C@H]2Oc1nc2nc(NCc3ccccc3C(F)(F)F)c(Cl)cc2[nH]1] | 1.98 | 471 | A |
| I-1-49 | 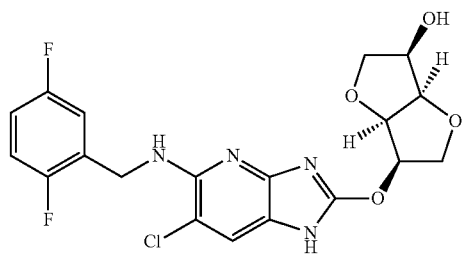 [SMILES: O[C@@H]1CO[C@H]2[C@@H]1OC[C@H]2Oc1nc2nc(NCc3cc(F)ccc3F)c(Cl)cc2[nH]1] | 1.75 | 439 | A |
| I-1-50 | 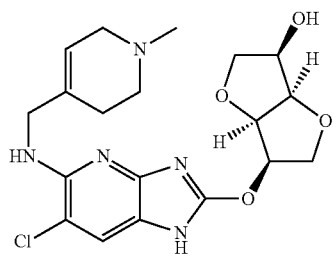 [SMILES: CN1CC=C(CNc2nc3nc(O[C@@H]4CO[C@H]5[C@@H]4OC[C@H]5O)[nH]c3cc2Cl)CC1] | 0.76 | 422 | A |
| I-1-51 | 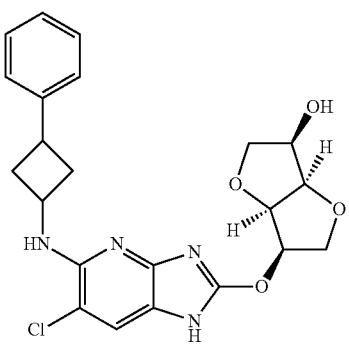 [SMILES: O[C@@H]1CO[C@H]2[C@@H]1OC[C@H]2Oc1nc2nc(NC3CC(c4ccccc4)C3)c(Cl)cc2[nH]1] | 2.04 | 443 | A |

TABLE 10

| | | | | |
|---|---|---|---|---|
| I-1-52 | [structure] | 1.59 | 409 | A |
| I-1-53 | [structure] | 0.75 | 404 | A |
| I-1-54 | [structure] | 0.74 | 404 | A |
| I-1-55 | [structure] | 0.74 | 404 | A |
| I-1-56 | [structure] | 1.49 | 367 | A |

TABLE 11

| | | | | |
|---|---|---|---|---|
| I-1-57 | [structure] | 2.09 | 427 | A |
| I-1-58 | [structure] | 1.46 | 367 | A |
| I-1-59 | [structure] | 2.03 | 409 | A |
| I-1-60 | [structure] | 1.13 | 407 | A |
| I-1-61 | [structure] | 1.16 | 472 | A |

TABLE 12

| | | | | |
|---|---|---|---|---|
| I-1-62 | [structure] | 2.29 | 471 | A |

TABLE 12-continued
I-1-63 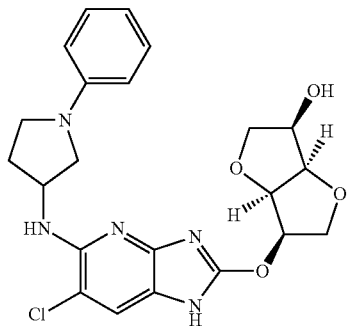 [SMILES: O[C@@H]1CO[C@H]2[C@@H]1OC[C@H]2Oc1nc2nc(NC3CCN(c4ccccc4)C3)c(Cl)cc2[nH]1] 1.94 458 A
I-1-64 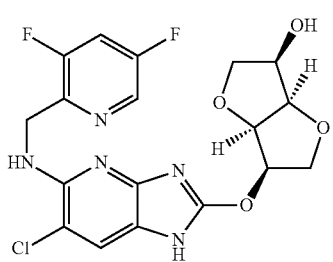 1.49 440 A
I-1-65 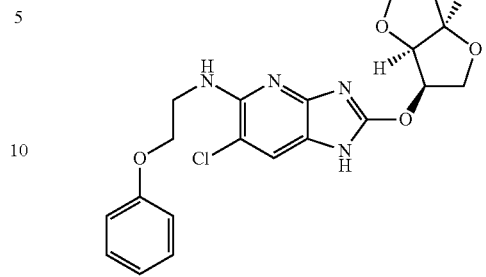 1.87 433 A
I-1-66 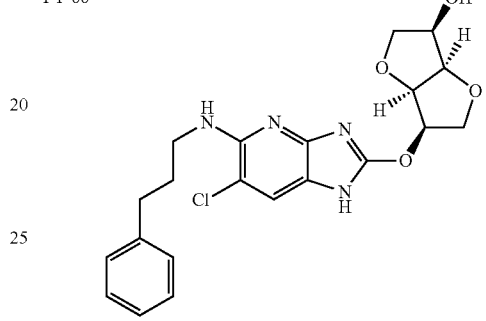 2.00 431 A
TABLE 13
I-1-67 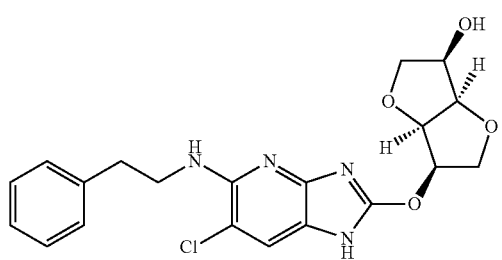 [SMILES: O[C@@H]1CO[C@H]2[C@@H]1OC[C@H]2Oc1nc2nc(NCCc3ccccc3)c(Cl)cc2[nH]1] 1.87 433 A
I-1-68 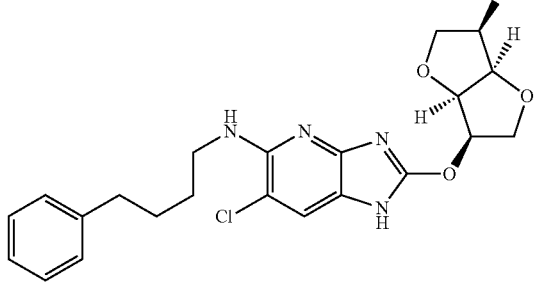 2.15 445 A
I-1-69 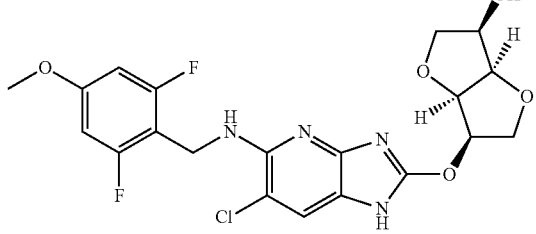 1.89 469 A TABLE 13-continued
| I-1-70 | 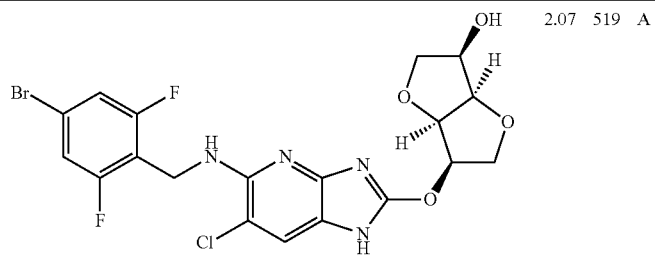 | 2.07 | 519 | A |
| I-1-71 | 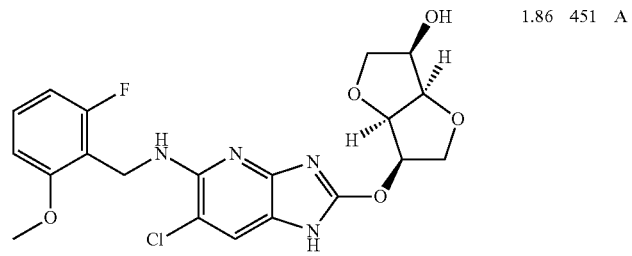 | 1.86 | 451 | A |
TABLE 14
| I-1-72 | 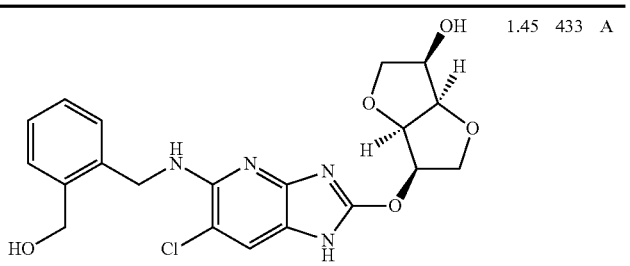 | 1.45 | 433 | A |
| I-1-73 | 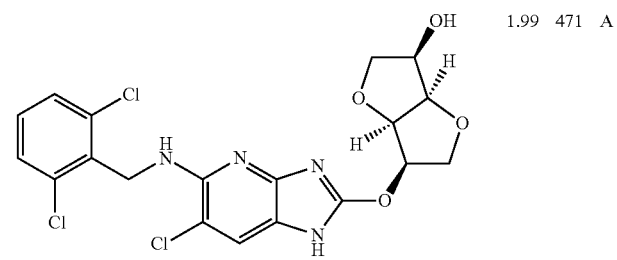 | 1.99 | 471 | A |
| I-1-74 | 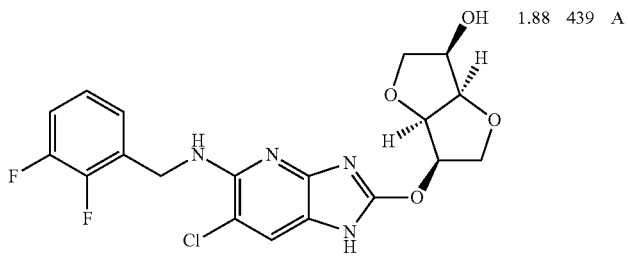 | 1.88 | 439 | A |
| I-1-75 | 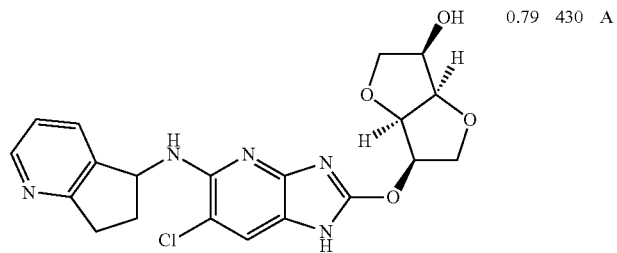 | 0.79 | 430 | A |

TABLE 14-continued
| I-1-76 | 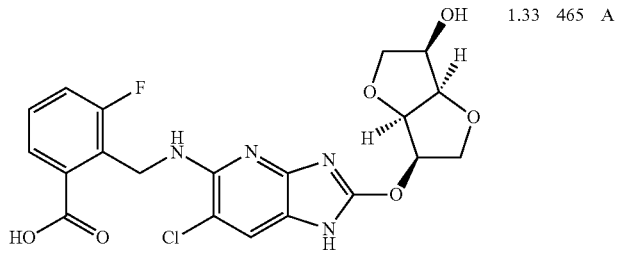 | 1.33 | 465 | A |
TABLE 15
| I-1-77 | 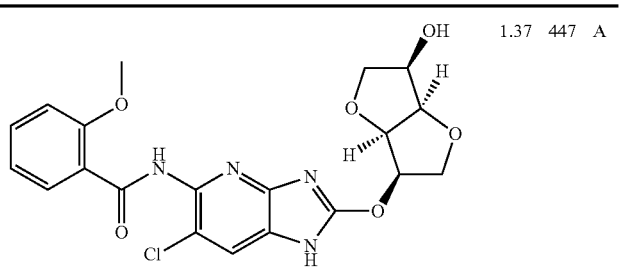 | 1.37 | 447 | A |
| I-1-78 | 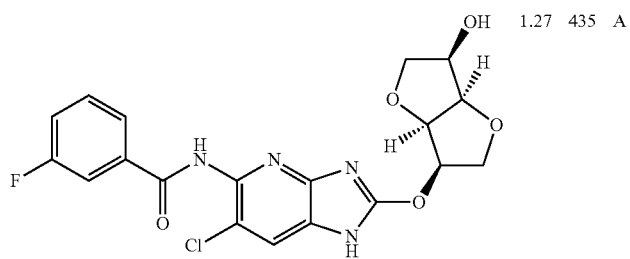 | 1.27 | 435 | A |
| I-1-79 | 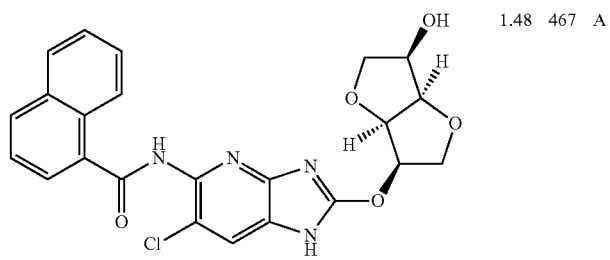 | 1.48 | 467 | A |
| I-1-80 | 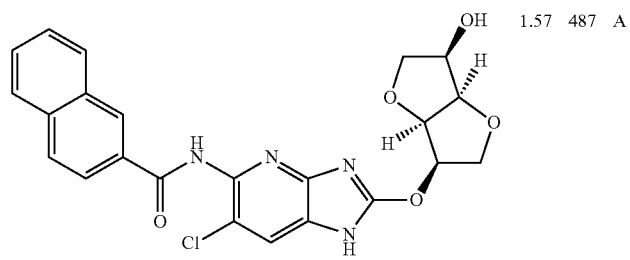 | 1.57 | 487 | A |

TABLE 15-continued
| I-1-81 | 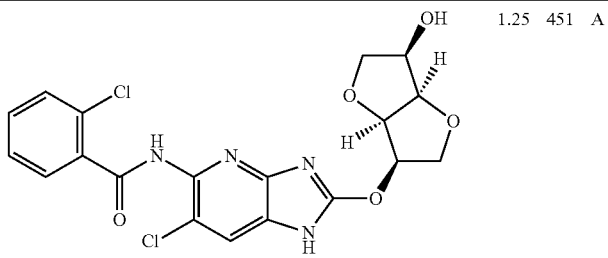 | 1.25 | 451 | A |
TABLE 16
| I-1-82 | 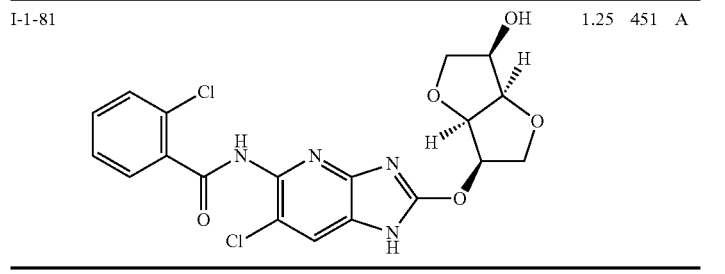 | 1.91 | 473 | A |
| I-1-83 | 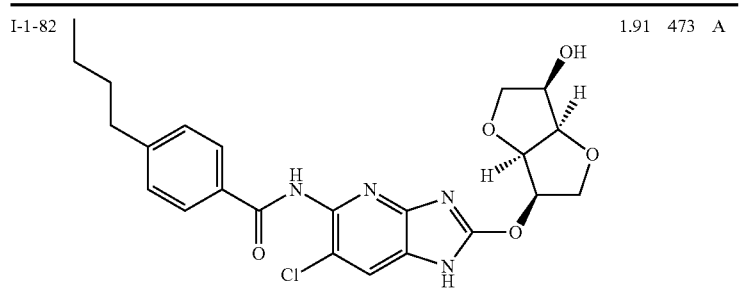 | 1.33 | 485 | A |
| I-1-84 | 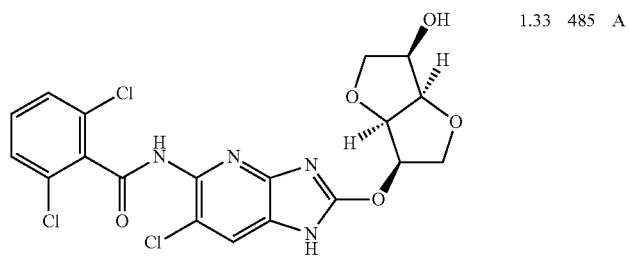 | 1.46 | 469 | A |
| I-1-85 | 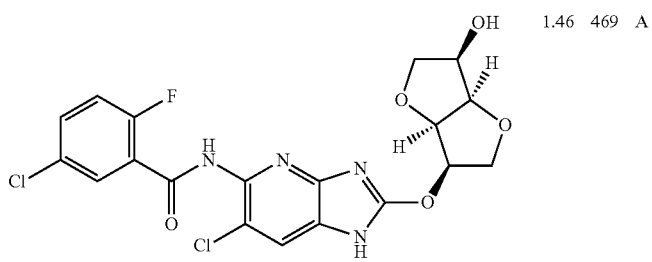 | 1.31 | 480 | A |

TABLE 16-continued
| I-1-86 | 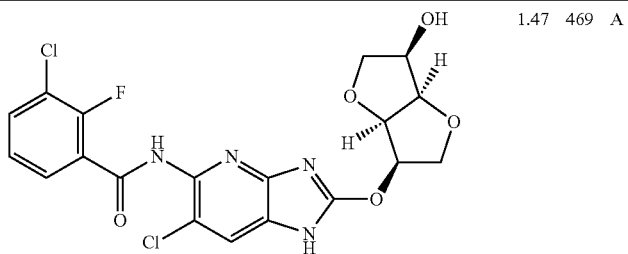 | 1.47 | 469 | A |
TABLE 17
| I-1-87 | 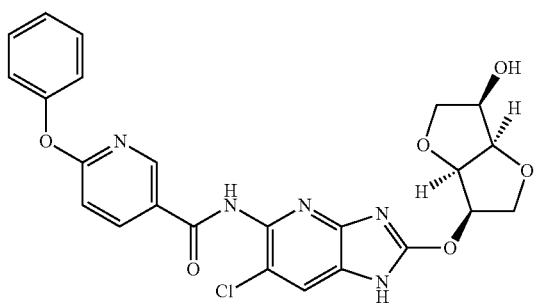 [SMILES: O=C(Nc1nc2nc(O[C@@H]3CO[C@H]4[C@@H]3OC[C@H]4O)[nH]c2cc1Cl)c1ccc(Oc2ccccc2)nc1] | 1.55 | 510 | A |
| I-1-88 | 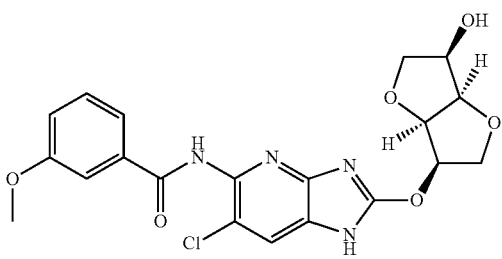 [SMILES: COc1cccc(C(=O)Nc2nc3nc(O[C@@H]4CO[C@H]5[C@@H]4OC[C@H]5O)[nH]c3cc2Cl)c1] | 1.27 | 447 | A |
| I-1-89 | 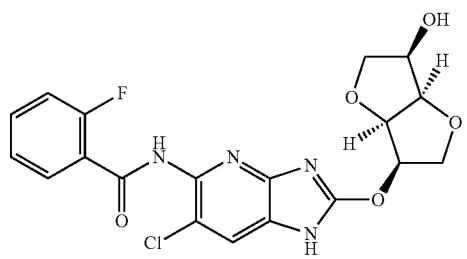 [SMILES: O=C(Nc1nc2nc(O[C@@H]3CO[C@H]4[C@@H]3OC[C@H]4O)[nH]c2cc1Cl)c1ccccc1F] | 1.25 | 435 | A |
| I-1-90 | 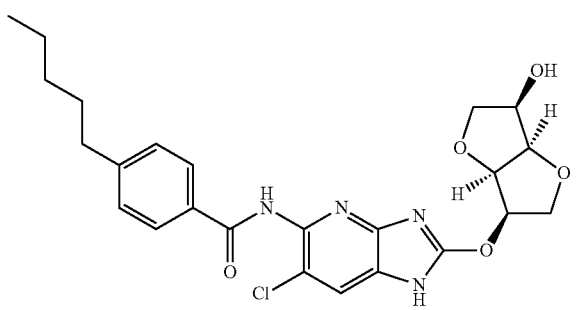 [SMILES: CCCCCc1ccc(C(=O)Nc2nc3nc(O[C@@H]4CO[C@H]5[C@@H]4OC[C@H]5O)[nH]c3cc2Cl)cc1] | 2.09 | 487 | A |

TABLE 17-continued
| I-1-91 | 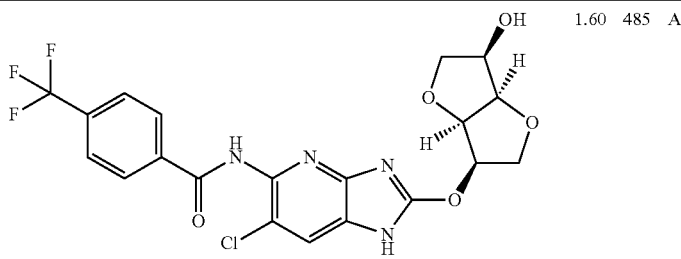 | 1.60 | 485 | A |
TABLE 18
| I-1-92 | 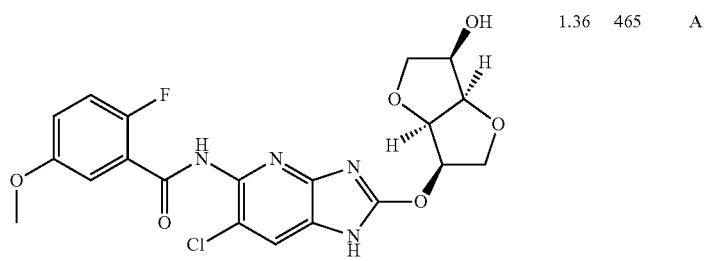 | 1.36 | 465 | A |
| I-1-93 | 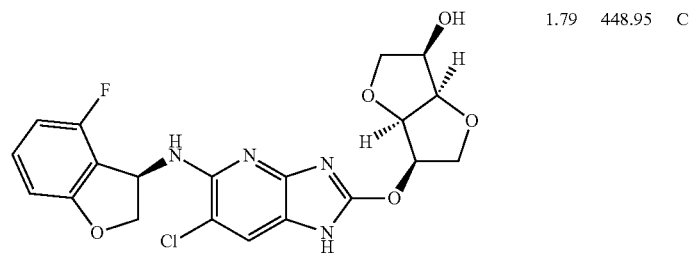 | 1.79 | 448.95 | C |
| I-1-94 | 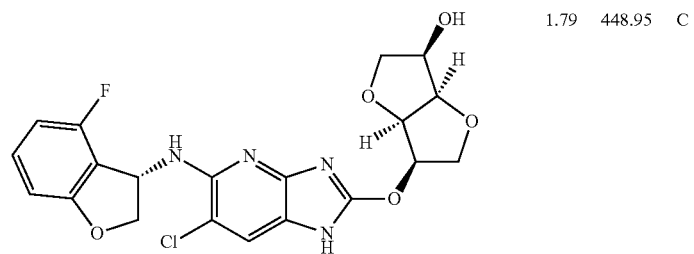 | 1.79 | 448.95 | C |
| I-1-95 | 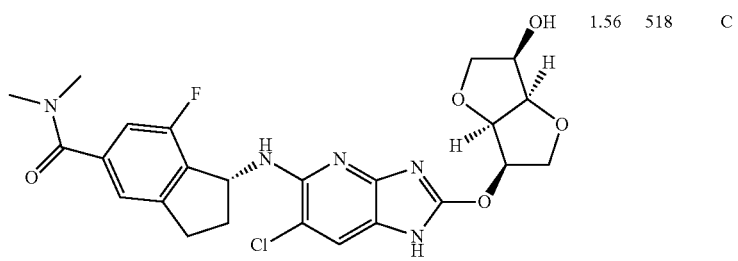 | 1.56 | 518 | C |

TABLE 18-continued
| I-1-96 | 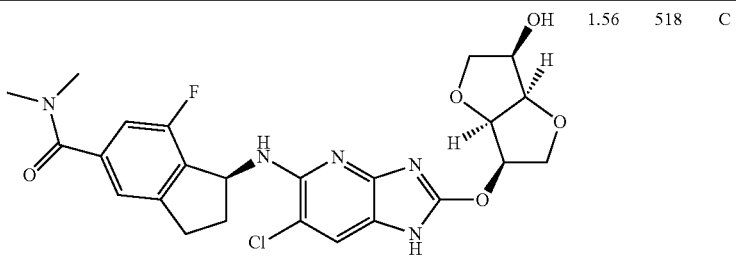 | 1.56 | 518 | C |
TABLE 19
| I-1-97 | 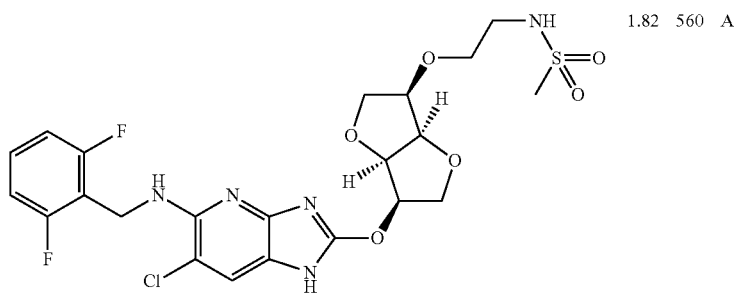 | 1.82 | 560 | A |
| I-1-98 | 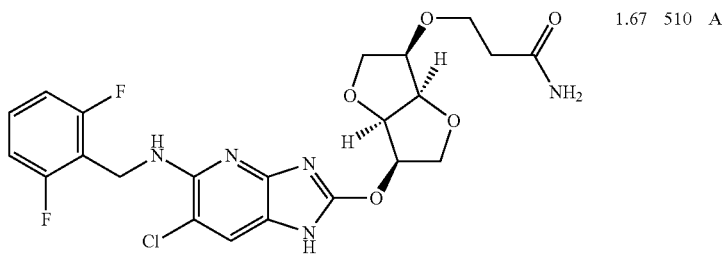 | 1.67 | 510 | A |
| I-1-99 | 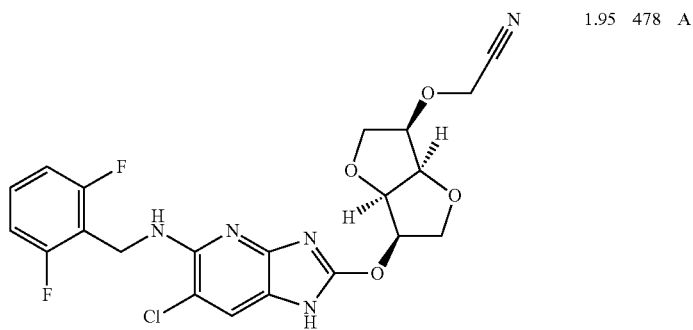 | 1.95 | 478 | A |
| I-1-100 | 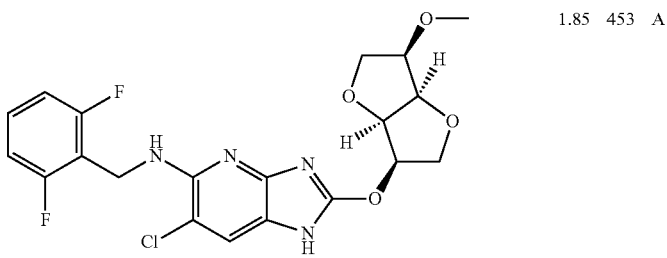 | 1.85 | 453 | A |

TABLE 20
| I-1-101 | 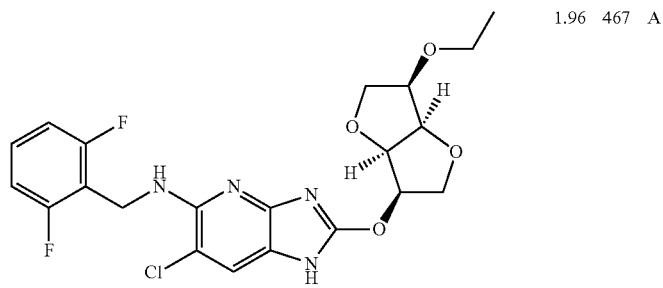 | 1.96 | 467 | A |
| I-1-102 | 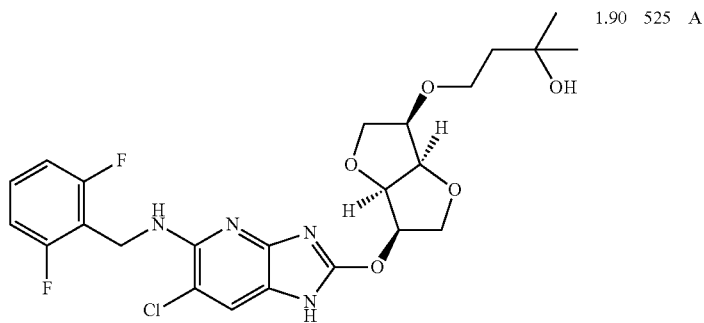 | 1.90 | 525 | A |
| I-1-103 | 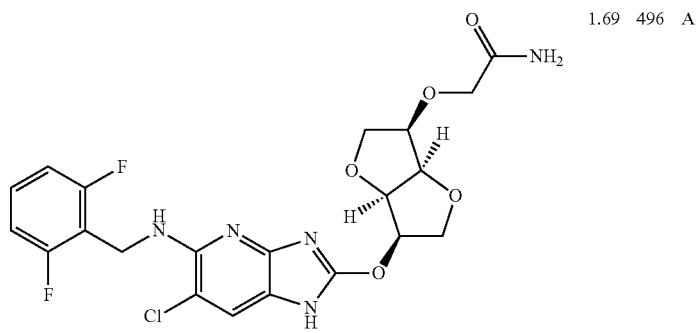 | 1.69 | 496 | A |
| I-1-104 | 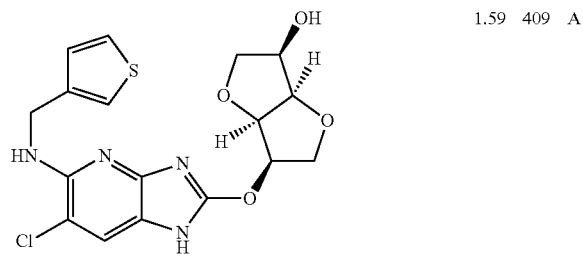 | 1.59 | 409 | A |
| I-1-105 | 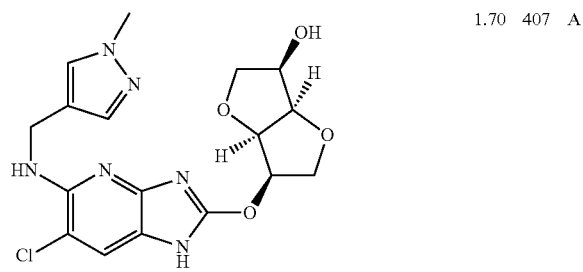 | 1.70 | 407 | A |

TABLE 21
| I-1-106 | 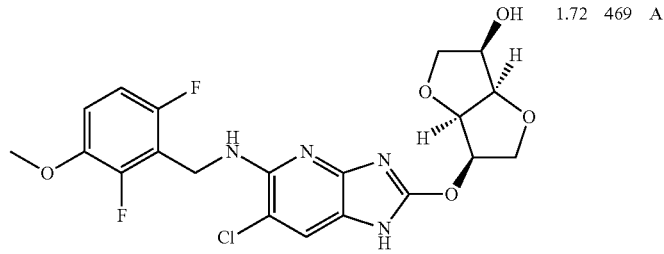 | 1.72 | 469 | A |
| I-1-107 | 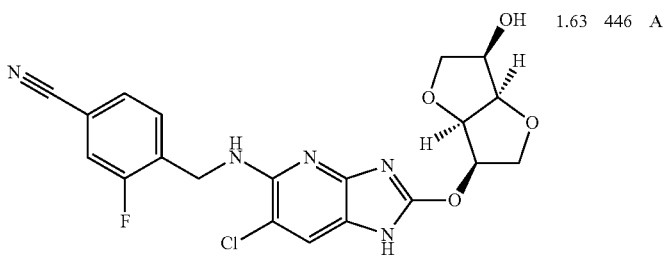 | 1.63 | 446 | A |
| I-1-108 | 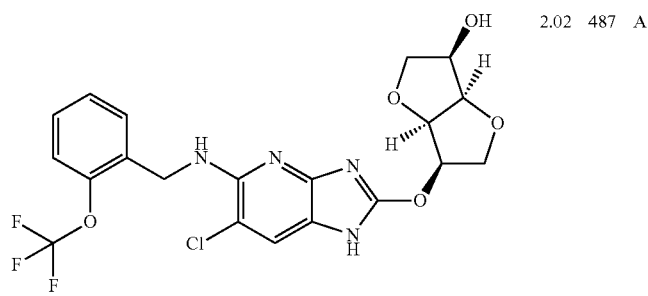 | 2.02 | 487 | A |
| I-1-109 | 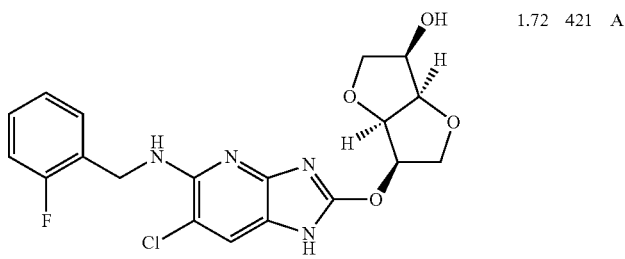 | 1.72 | 421 | A |
| I-1-110 | 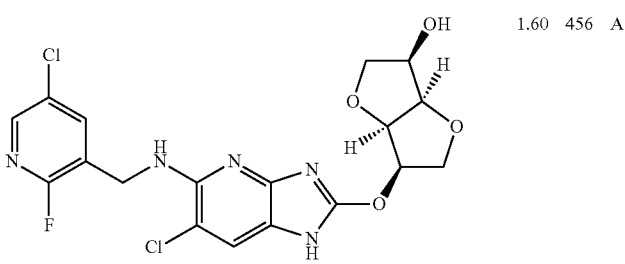 | 1.60 | 456 | A |

TABLE 22
| | | | | | |
|---|---|---|---|---|---|
| I-1-111 | 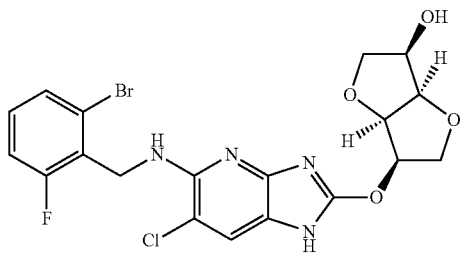 [SMILES: O[C@@H]1CO[C@H]2[C@@H]1OC[C@H]2Oc1nc2nc(NCc3c(F)cccc3Br)c(Cl)cc2[nH]1] | | 1.92 | 501 | A |
| I-1-112 | 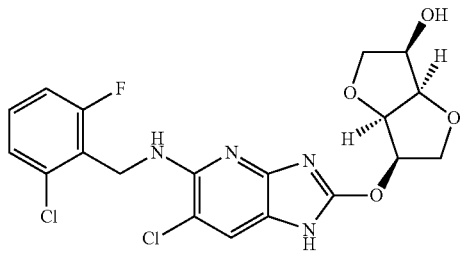 [SMILES: O[C@@H]1CO[C@H]2[C@@H]1OC[C@H]2Oc1nc2nc(NCc3c(F)cccc3Cl)c(Cl)cc2[nH]1] | | 1.87 | 455 | A |
| I-1-113 | 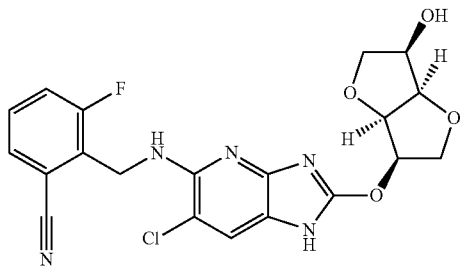 [SMILES: N#Cc1cccc(F)c1CNc1nc2nc(O[C@@H]3CO[C@H]4[C@@H]3OC[C@H]4O)[nH]c2cc1Cl] | | 1.58 | 446 | A |
| I-1-114 | 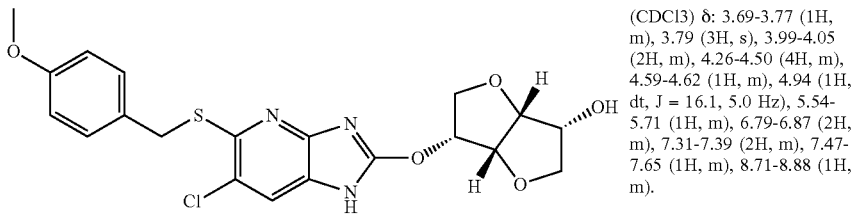 | (CDCl3) δ: 3.69-3.77 (1H, m), 3.79 (3H, s), 3.99-4.05 (2H, m), 4.26-4.50 (4H, m), 4.59-4.62 (1H, m), 4.94 (1H, dt, J = 16.1, 5.0 Hz), 5.54-5.71 (1H, m), 6.79-6.87 (2H, m), 7.31-7.39 (2H, m), 7.47-7.65 (1H, m), 8.71-8.88 (1H, m). | 1.94 | 450.05 | C |
| I-1-115 | 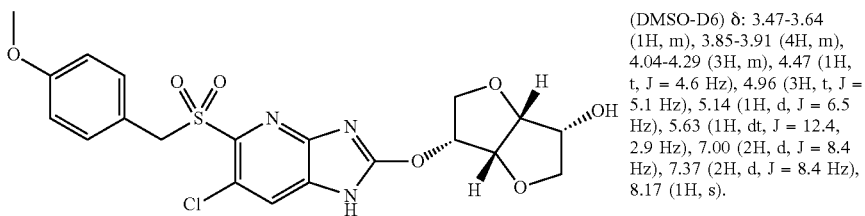 | (DMSO-D6) δ: 3.47-3.64 (1H, m), 3.85-3.91 (4H, m), 4.04-4.29 (3H, m), 4.47 (1H, t, J = 4.6 Hz), 4.96 (3H, t, J = 5.1 Hz), 5.14 (1H, d, J = 6.5 Hz), 5.63 (1H, dt, J = 12.4, 2.9 Hz), 7.00 (2H, d, J = 8.4 Hz), 7.37 (2H, d, J = 8.4 Hz), 8.17 (1H, s). | 1.50 | 462.05 | C |
TABLE 23
| | | | | | |
|---|---|---|---|---|---|
| I-1-116 | 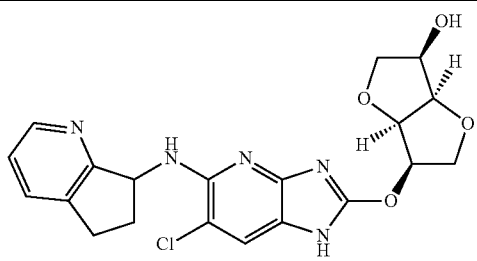 | | 1.09 | 430 | C |

TABLE 23-continued
| I-1-117 | 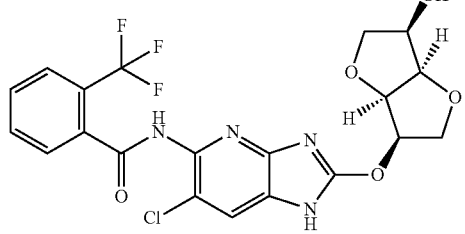 | 1.35 | 485 | A |
| I-1-118 | 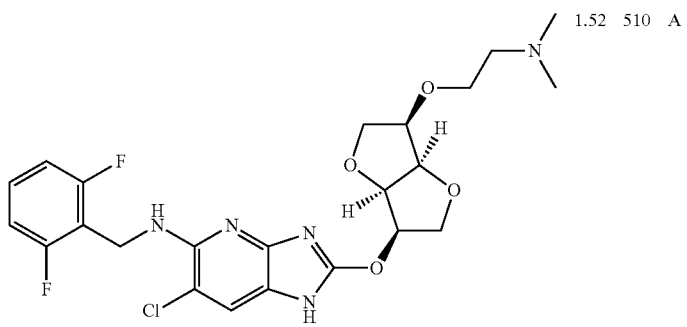 | 1.52 | 510 | A |
| I-1-119 | 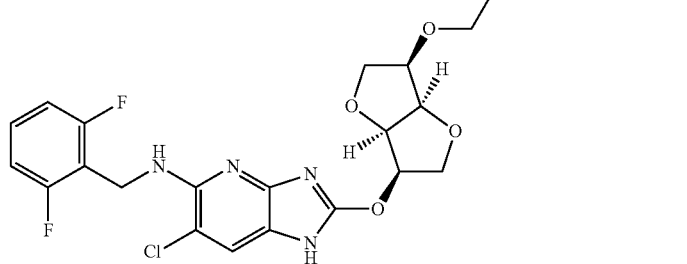 | 1.70 | 483 | A |
TABLE 24
| I-1-120 | 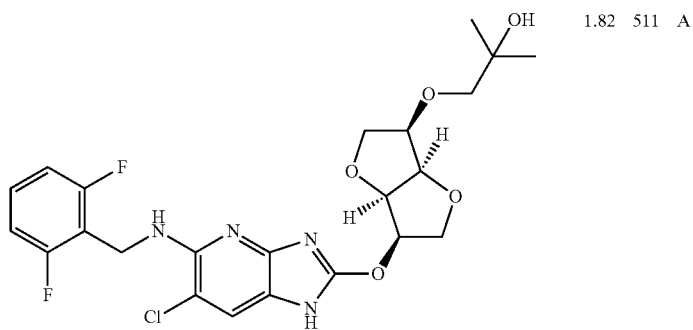 | 1.82 | 511 | A |
| I-1-121 | 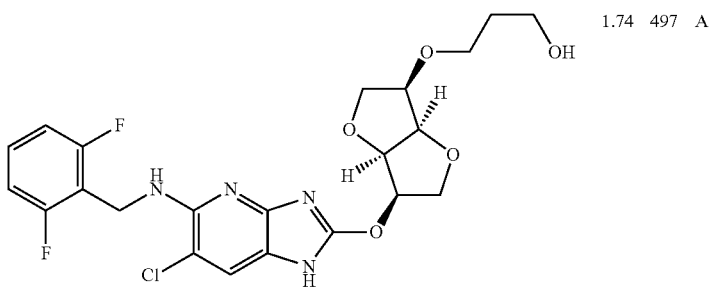 | 1.74 | 497 | A |

TABLE 24-continued
| I-1-122 | 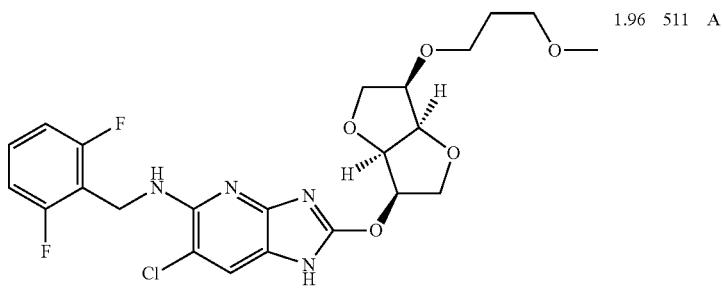 | | 1.96 | 511 | A |
|---|---|---|---|---|---|
| I-1-123 | 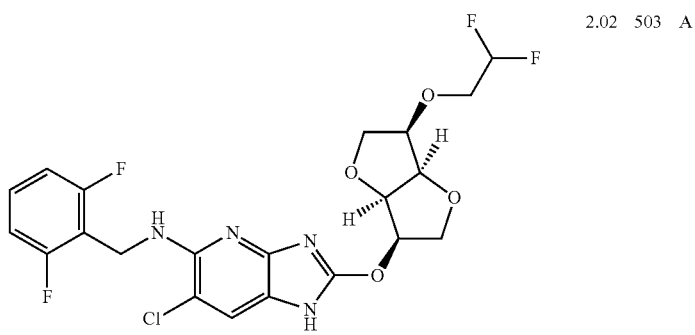 | | 2.02 | 503 | A |
| I-1-124 | 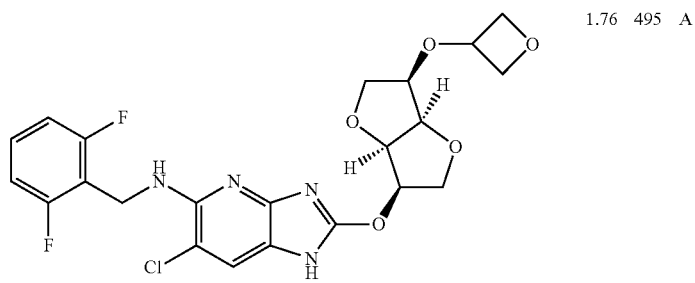 | | 1.76 | 495 | A |
TABLE 25
| I-1-125 | 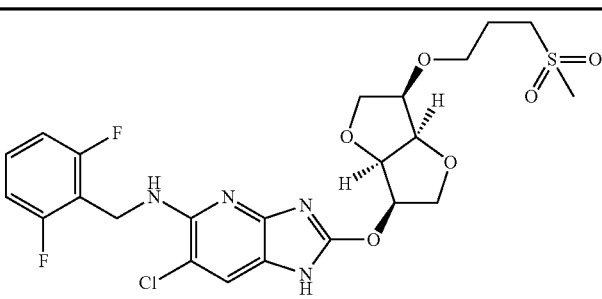 | | 1.83 | 559 | A |
|---|---|---|---|---|---|
| I-1-126 | 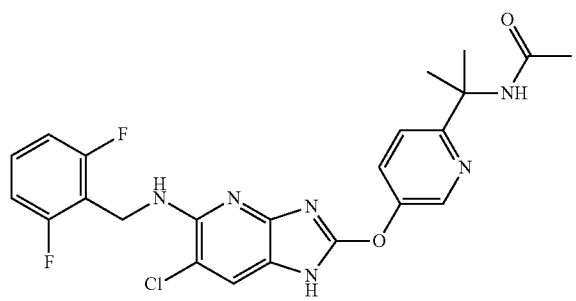 [SMILES: CC(=O)NC(C)(C)c1ccc(Oc2nc3nc(NCc4c(F)cccc4F)c(Cl)cc3[nH]2)cn1] | 1H-NMR (DMSO-D6) δ: 1.56 (s, 6H), 1.85 (s, 3H), 4.65 (d, J = 5.4 Hz, 2H), 6.23 (bs, 1H), 7.06 (t, J = 7.8 Hz, 2H), 7.32-7.40 (m, 1H), 7.42 (d, J = 8.8 Hz, 1H), 7.69 (s, 1H), 7.74-7.77 (m, 1H), 8.17 (s, 1H), 8.50 (s, 1H), 12.7 (bs, 1H) | 1.95 | 487 | C |

TABLE 25-continued
| ID | Structure | NMR | | | |
|---|---|---|---|---|---|
| I-1-127 | 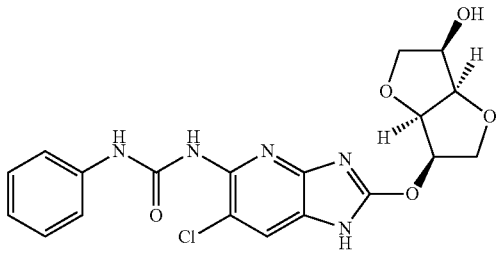 [SMILES: O=C(Nc1ccccc1)Nc1nc2nc(O[C@@H]3CO[C@H]4[C@@H]3OC[C@H]4O)[nH]c2cc1Cl] | | 1.52 | 431.95 | C |
| I-1-128 | 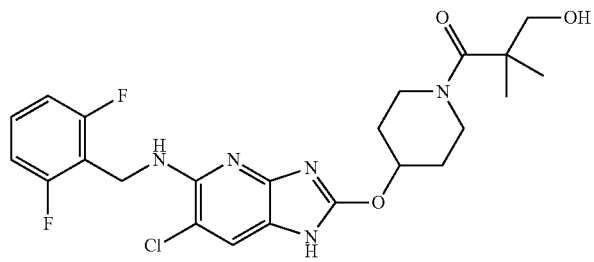 [SMILES: CC(C)(CO)C(=O)N1CCC(Oc2nc3nc(NCc4c(F)cccc4F)c(Cl)cc3[nH]2)CC1] | 1H-NMR (DMSO-D6) δ: 1.17 (s, 6H), 1.60-1.67 (m, 2H), 2.05-2.08 (m, 2H), 3.29-3.34 (m, 2H), 3.43 (s, 2H), 3.87-3.97 (m, 2H), 4.63 (d, J = 5.4 Hz, 2H), 5.15 (bs, 1H), 6.10 (bs, 1H), 7.02-7.12 (m, 2H), 7.32-7.39 (m, 1H), 7.63 (bs, 1H), 12.19 (bs, 1H) | 2.00 | 494.05 | C |
| I-1-129 | 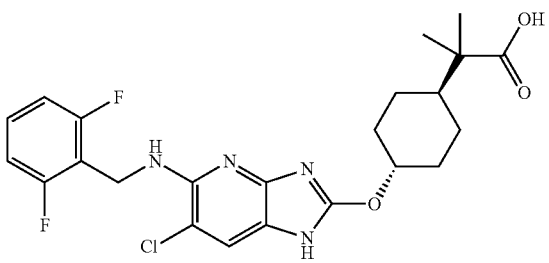 [SMILES: CC(C)(C(=O)O)[C@H]1CC[C@H](Oc2nc3nc(NCc4c(F)cccc4F)c(Cl)cc3[nH]2)CC1] | | 2.23 | 479.05 | C |
TABLE 26
| ID | Structure | NMR | | | |
|---|---|---|---|---|---|
| I-1-130 | 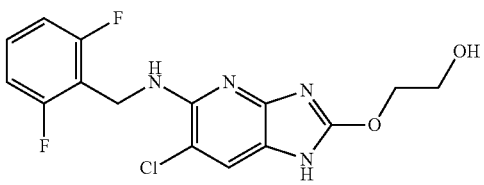 [SMILES: OCCOc1nc2nc(NCc3c(F)cccc3F)c(Cl)cc2[nH]1] | 1H-NMR (DMSO-D6) δ: 3.73 (t, J = 4.9 Hz, 2H), 4.39 (t, J = 4.8 Hz, 2H), 4.63 (d, J = 5.5 Hz, 2H), 6.05 (bs, 1H), 7.03-7.09 (m, 2H), 7.32-7.40 (m, 1H), 7.60 (s, 1H) | 1.73 | 354.95 | C |
| I-1-131<br>I-2-239 | 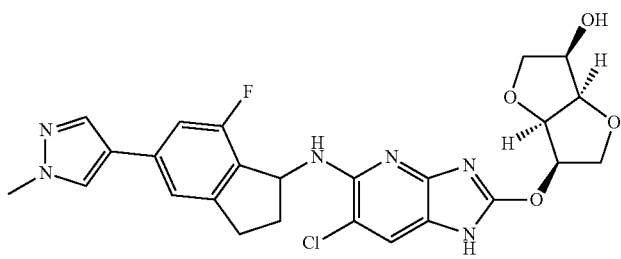 [SMILES: Cn1cc(-c2cc(F)c3c(c2)CCC3Nc2nc3nc(O[C@@H]4CO[C@H]5[C@@H]4OC[C@H]5O)[nH]c3cc2Cl)cn1] | | 1.74<br>1.63 | 527.05<br>527.25 | C<br>B |
| I-1-132 | 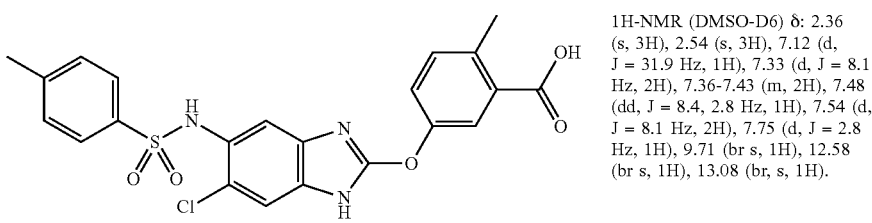 | 1H-NMR (DMSO-D6) δ: 2.36 (s, 3H), 2.54 (s, 3H), 7.12 (d, J = 31.9 Hz, 1H), 7.33 (d, J = 8.1 Hz, 2H), 7.36-7.43 (m, 2H), 7.48 (dd, J = 8.4, 2.8 Hz, 1H), 7.54 (d, J = 8.1 Hz, 2H), 7.75 (d, J = 2.8 Hz, 1H), 9.71 (br s, 1H), 12.58 (br s, 1H), 13.08 (br, s, 1H). | | | |

TABLE 26-continued
| | | |
|---|---|---|
| I-1-133 | 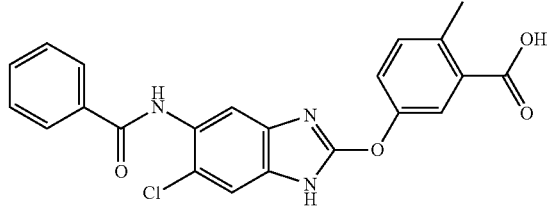 [SMILES: Cc1ccc(Oc2nc3cc(NC(=O)c4ccccc4)c(Cl)cc3[nH]2)cc1C(=O)O] | 1H-NMR (DMSO-D6) δ: 2.55 (s, 3H), 7.41 (d, J = 8.6 Hz, 1H), 7.48-7.65 (m, 6H), 7.79 (d, J = 2.5 Hz, 1H), 8.01 (d, J = 7.6 Hz, 2H), 9.99 (d, J = 10.1 Hz, 1H), 12.63 (s, 1H), 13.08 (s, 1H). |
| I-1-134 | 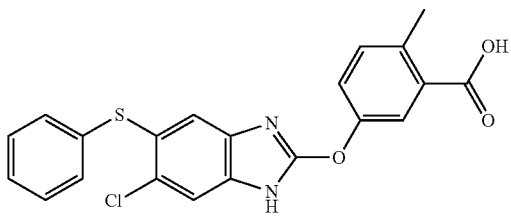 [SMILES: Cc1ccc(Oc2nc3cc(Sc4ccccc4)c(Cl)cc3[nH]2)cc1C(=O)O] | 1H-NMR (DMSO-D6) δ: 2.54 (s, 3H), 7.13-7.44 (m, 7H), 7.49 (dd, J = 8.4, 2.8 Hz, 1H), 7.61 (s, 1H), 7.77 (d, J = 2.8 Hz, 1H), 12.68 (s, 1H), 13.09 (s, 1H). |
| I-1-135 | 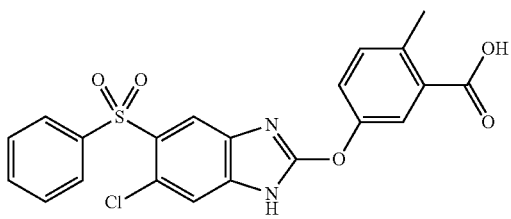 [SMILES: Cc1ccc(Oc2nc3cc(S(=O)(=O)c4ccccc4)c(Cl)cc3[nH]2)cc1C(=O)O] | 1H-NMR (DMSO-D6) δ: 2.55 (s, 3H), 7.43 (d, J = 8.6 Hz, 1H), 7.53 (dd, J = 8.4, 2.8 Hz, 1H), 7.60 (t, J = 7.6 Hz, 3H), 7.69 (dd, J = 7.4, 7.4 Hz, 1H), 7.81 (d, J = 2.8 Hz, 1H), 7.86-7.92 (m, 2H), 8.26 (s, 1H), 13.18 (s, 2H). |
TABLE 27
| No. | Structure | retention time | Mass (M + H) | Method |
|---|---|---|---|---|
| I-2-3 | 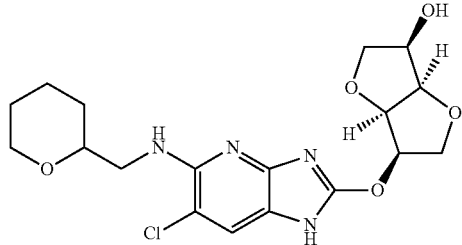 [SMILES: O[C@@H]1CO[C@H]2[C@@H]1OC[C@H]2Oc1nc2nc(NCC3CCCCO3)c(Cl)cc2[nH]1] | 1.59 | 411 | C |
| I-2-4 | 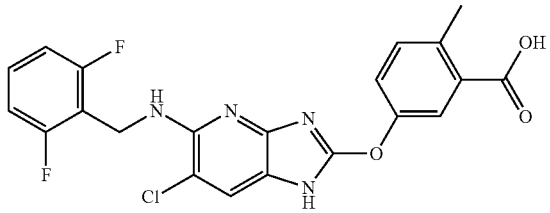 [SMILES: Cc1ccc(Oc2nc3nc(NCc4c(F)cccc4F)c(Cl)cc3[nH]2)cc1C(=O)O] | 2.14 | 445 | A |
| I-2-5 | 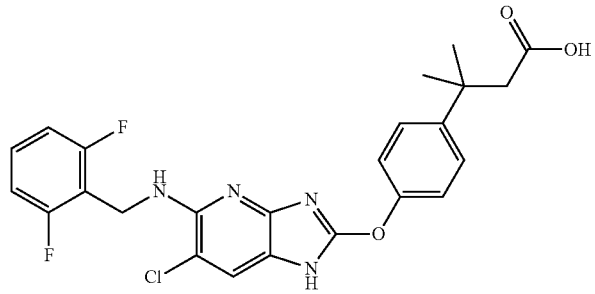 [SMILES: CC(C)(CC(=O)O)c1ccc(Oc2nc3nc(NCc4c(F)cccc4F)c(Cl)cc3[nH]2)cc1] | 1.59 | 187 | A |

TABLE 27-continued

| No. | Structure | retention time | Mass (M + H) | Method |
|---|---|---|---|---|
| I-2-6 | 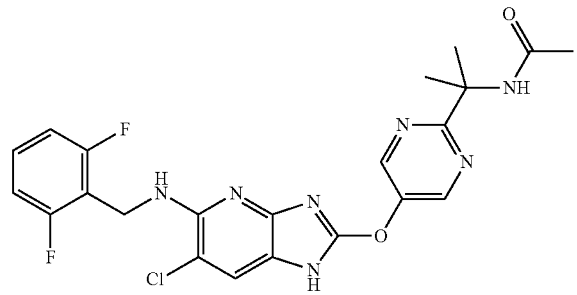 [SMILES: CC(=O)NC(C)(C)c1ncc(Oc2nc3nc(NCc4c(F)cccc4F)c(Cl)cc3[nH]2)cn1] | 1.77 | 488 | A |

TABLE 28

| No. | Structure | retention time | Mass (M + H) | Method |
|---|---|---|---|---|
| I-2-7 | 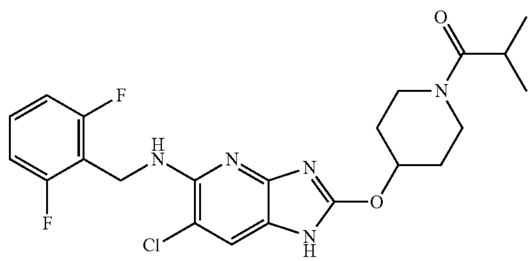 [SMILES: CC(C)C(=O)N1CCC(Oc2nc3nc(NCc4c(F)cccc4F)c(Cl)cc3[nH]2)CC1] | 2.11 | 464 | A |
| I-2-8 | 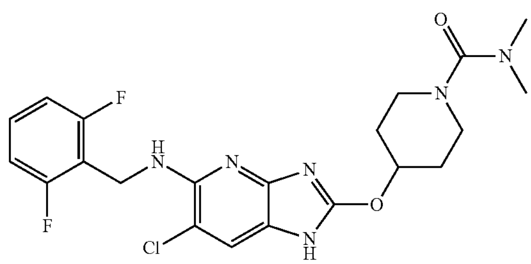 [SMILES: CN(C)C(=O)N1CCC(Oc2nc3nc(NCc4c(F)cccc4F)c(Cl)cc3[nH]2)CC1] | 2.02 | 465 | A |
| I-2-9 | 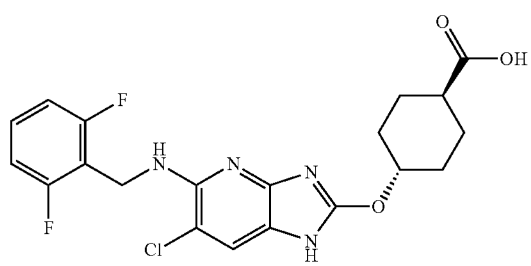 [SMILES: O=C(O)[C@H]1CC[C@H](Oc2nc3nc(NCc4c(F)cccc4F)c(Cl)cc3[nH]2)CC1] | 1.45 | 437 | A |
| I-2-10 | 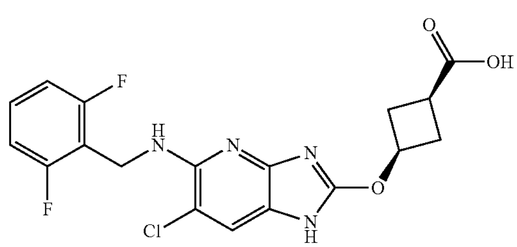 [SMILES: O=C(O)[C@H]1C[C@@H](Oc2nc3nc(NCc4c(F)cccc4F)c(Cl)cc3[nH]2)C1] | 1.37 | 409 | A |

TABLE 28-continued
| | | | | |
|---|---|---|---|---|
| I-2-11 | 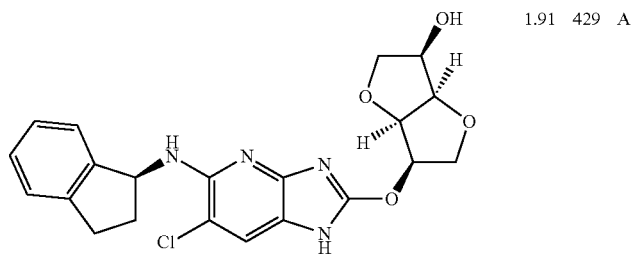 | 1.91 | 429 | A |
TABLE 29
| | | | | |
|---|---|---|---|---|
| I-2-12 | 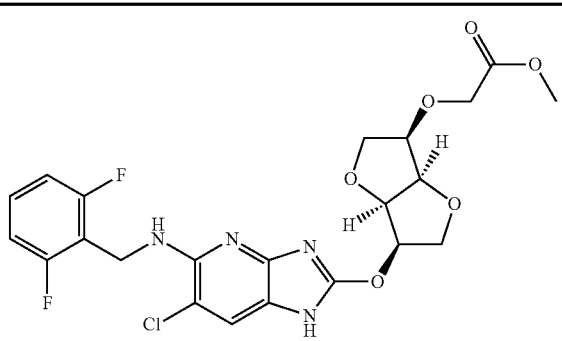 | 1.92 | 511 | A |
| I-2-13 | 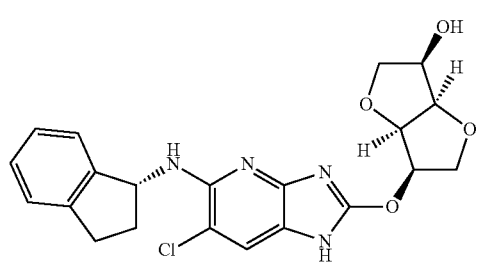 | 1.92 | 429 | A |
| I-2-14 | 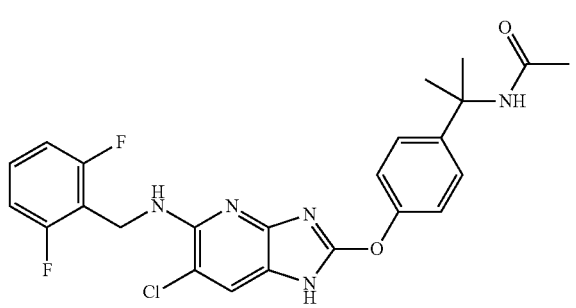 [SMILES: CC(=O)NC(C)(C)c1ccc(Oc2nc3nc(NCc4c(F)cccc4F)c(Cl)cc3[nH]2)cc1] | 2.08 | 486 | A |
| I-2-15 | 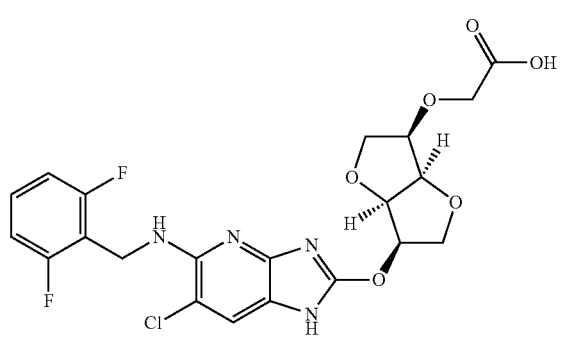 [SMILES: O=C(O)CO[C@@H]1CO[C@H]2[C@@H]1OC[C@H]2Oc1nc2nc(NCc3c(F)cccc3F)c(Cl)cc2[nH]1] | 1.78 | 496.9 | C |

TABLE 29-continued
| I-2-16 | 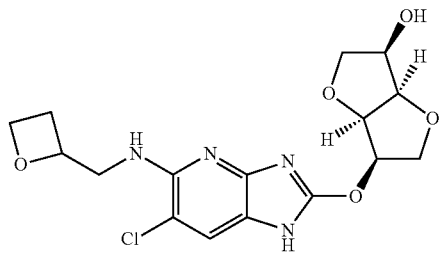 [SMILES: O[C@@H]1CO[C@H]2[C@@H]1OC[C@H]2Oc1nc2nc(NCC3CCO3)c(Cl)cc2[nH]1] | 1.23 | 382.95 | C |
TABLE 30
| I-2-17 | 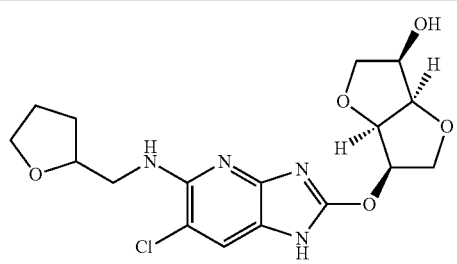 [SMILES: O[C@@H]1CO[C@H]2[C@@H]1OC[C@H]2Oc1nc2nc(NCC3CCCO3)c(Cl)cc2[nH]1] | 1.41 | 396.95 | C |
| I-2-18 | 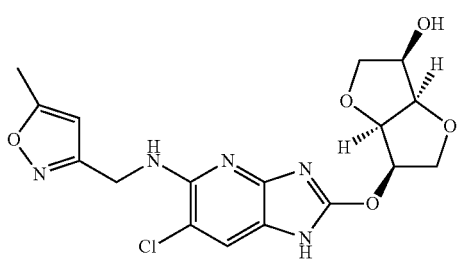 [SMILES: Cc1cc(CNc2nc3nc(O[C@@H]4CO[C@H]5[C@@H]4OC[C@H]5O)[nH]c3cc2Cl)no1] | 1.40 | 408.9 | C |
| I-2-19 | 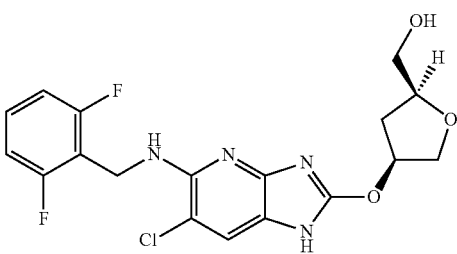 [SMILES: OC[C@@H]1C[C@H](Oc2nc3nc(NCc4c(F)cccc4F)c(Cl)cc3[nH]2)CO1] | 1.79 | 410.95 | C |
| I-2-20 | 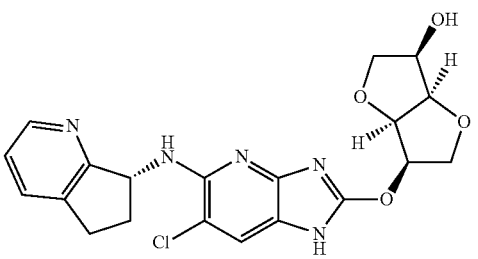 [SMILES: O[C@@H]1CO[C@H]2[C@@H]1OC[C@H]2Oc1nc2nc(N[C@@H]3CCc4cccnc43)c(Cl)cc2[nH]1] | 1.08 | 429.95 | C |

TABLE 30-continued
| | | | | |
|---|---|---|---|---|
| I-2-21 | 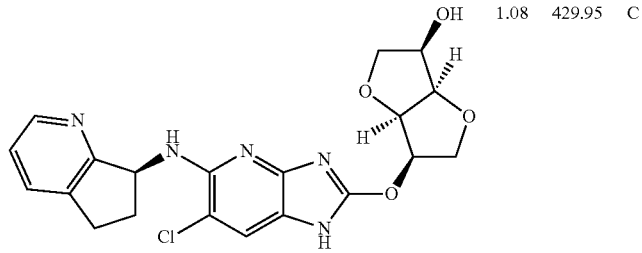 | 1.08 | 429.95 | C |
TABLE 31
| | | | | |
|---|---|---|---|---|
| I-2-22 | 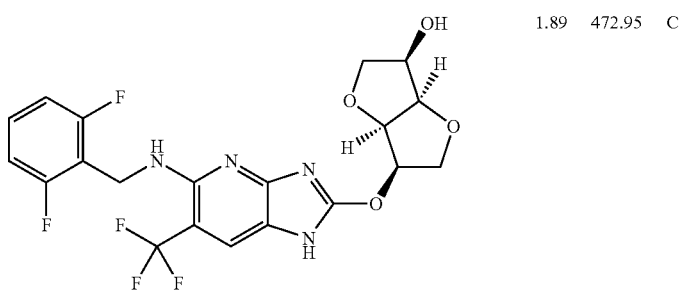 | 1.89 | 472.95 | C |
| I-2-23 | 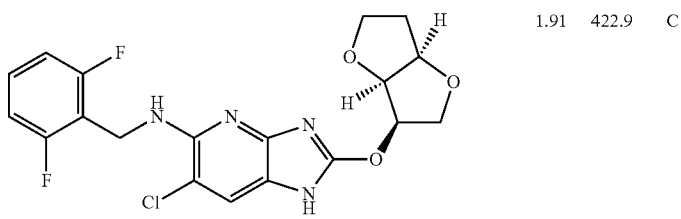 | 1.91 | 422.9 | C |
| I-2-24 | 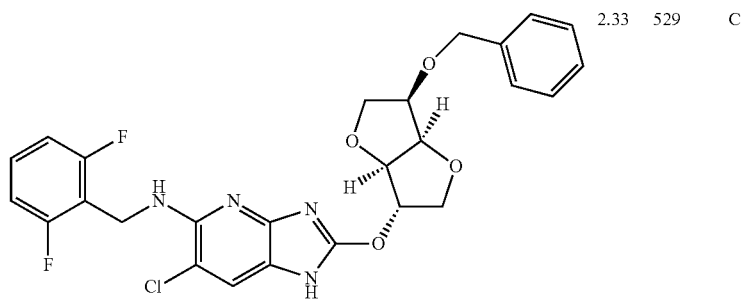 | 2.33 | 529 | C |
| I-2-25 | 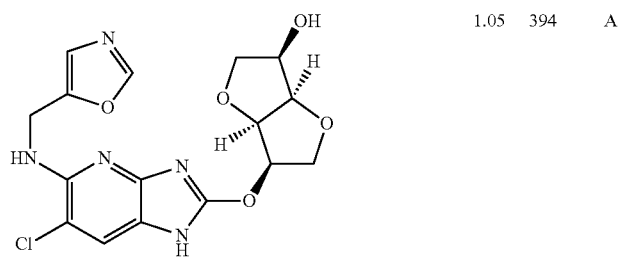 | 1.05 | 394 | A |

TABLE 31-continued
I-2-26 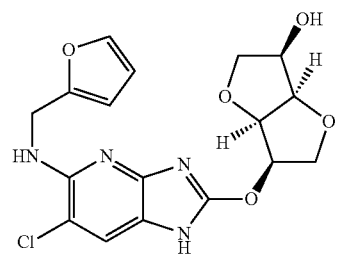 [SMILES: O[C@@H]1CO[C@H]2[C@@H]1OC[C@H]2Oc1nc2nc(NCc3ccco3)c(Cl)cc2[nH]1] 1.46 393 A
| TABLE 32 | | | | | TABLE 32-continued | | | |
|---|---|---|---|---|---|---|---|---|
| I-2-27 | 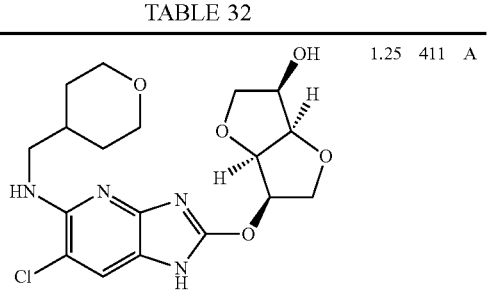 | 1.25 | 411 | A | I-2-30 | 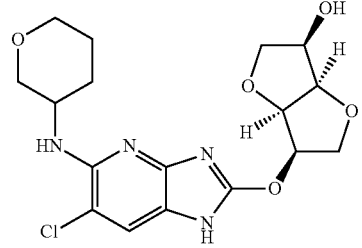 [SMILES: O[C@@H]1CO[C@H]2[C@@H]1OC[C@H]2Oc1nc2nc(NC3CCCOC3)c(Cl)cc2[nH]1] | 1.31 397 | A |
| I-2-28 | 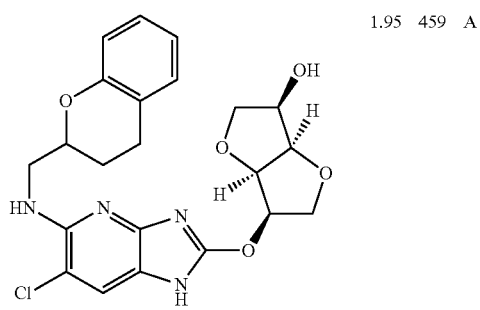 | 1.95 | 459 | A | | | | |
| I-2-29 | 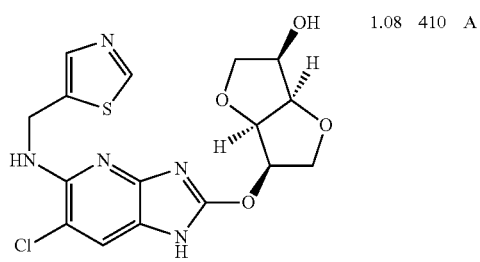 | 1.08 | 410 | A | I-2-31 | 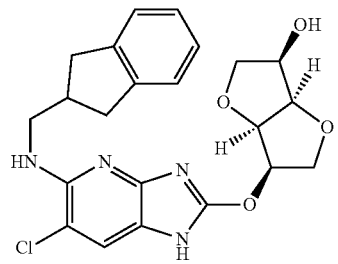 [SMILES: O[C@@H]1CO[C@H]2[C@@H]1OC[C@H]2Oc1nc2nc(NCC3Cc4ccccc4C3)c(Cl)cc2[nH]1] | 2.00 443 | A |
TABLE 33
I-2-32 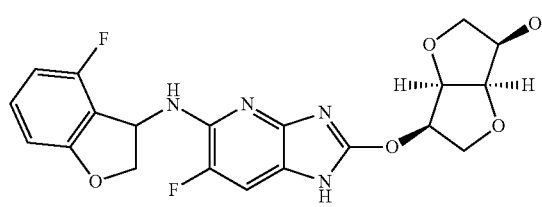 1.62 433 C TABLE 33-continued
| I-2-33 | 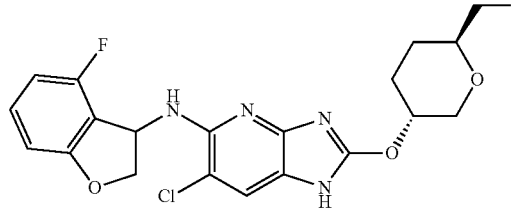 | 1.89 | 434.95 | C |
| I-2-34 | 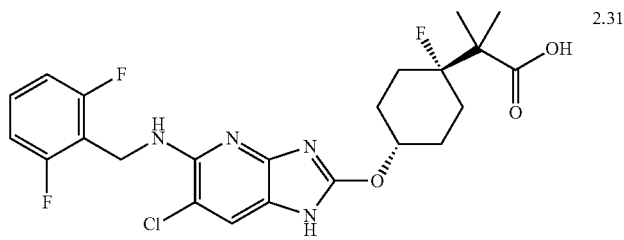 | 2.31 | 497 | A |
| I-2-35 | 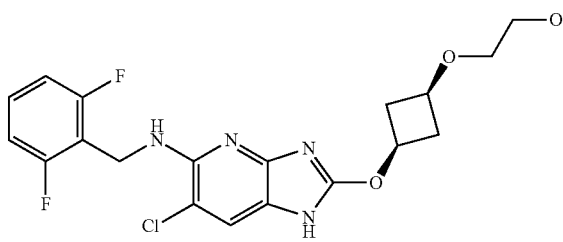 | 1.84 | 425 | A |
| I-2-36 | 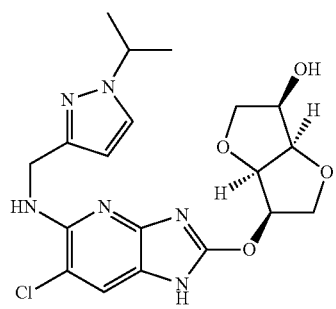 | 1.42 | 435 | A |
TABLE 34
| I-2-37 | 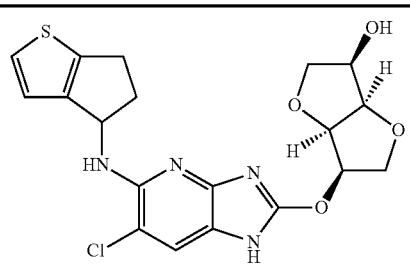 | 1.91 | 435 | A | I-2-39 | 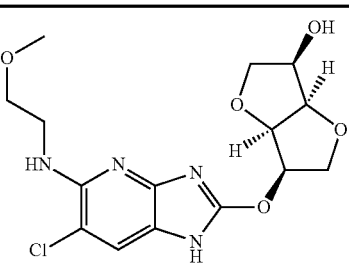 | 1.13 | 371 | A |
| I-2-38 | 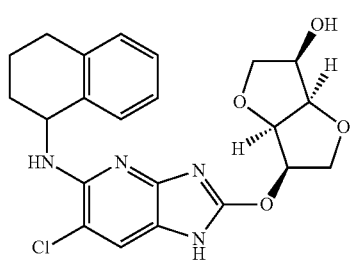 [SMILES: O[C@@H]1CO[C@H]2[C@@H]1OC[C@H]2Oc1nc2nc(NC3CCCc4ccccc43)c(Cl)cc2[nH]1] | 2.11 | 443 | A | I-2-40 | 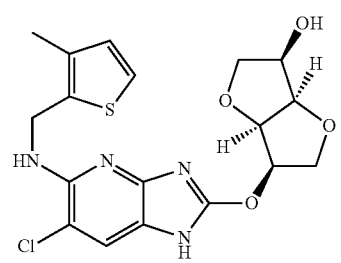 [SMILES: Cc1ccsc1CNc1nc2nc(O[C@@H]3CO[C@H]4[C@@H]3OC[C@H]4O)[nH]c2cc1Cl] | 1.76 | 423 | A |

TABLE 34-continued
| | | | | |
|---|---|---|---|---|
| I-2-41 | 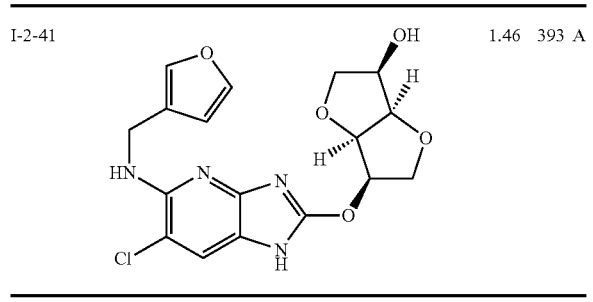 | 1.46 | 393 | A |
TABLE 35
| | | | | |
|---|---|---|---|---|
| I-2-42 | 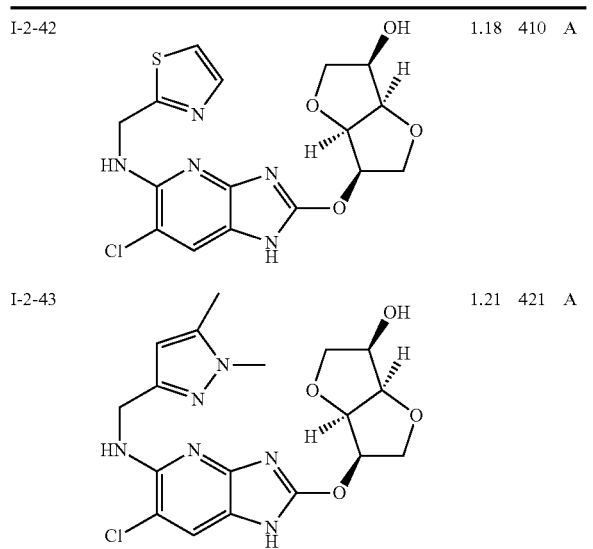 | 1.18 | 410 | A |
| I-2-43 | | 1.21 | 421 | A |
| I-2-44 | | 1.13 | 413 | A |
| I-2-45 | 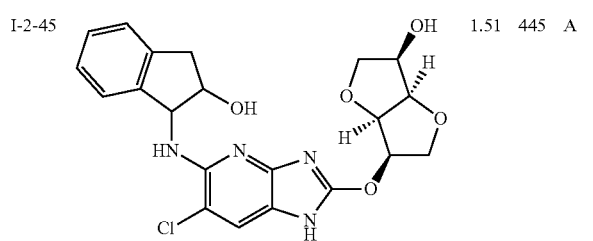 | 1.51 | 445 | A |
| I-2-46 | 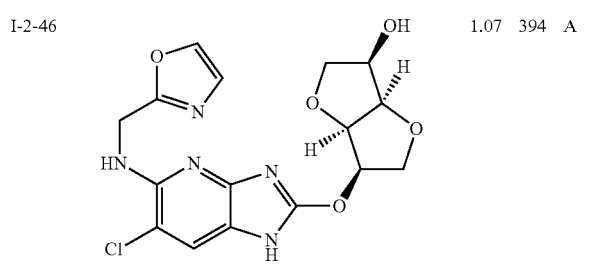 | 1.07 | 394 | A |
TABLE 36
| | | | | |
|---|---|---|---|---|
| I-2-47 | 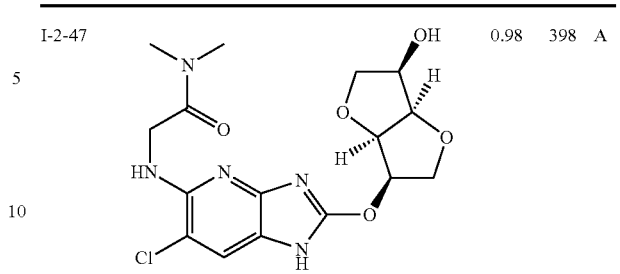 | 0.98 | 398 | A |
| I-2-48 | 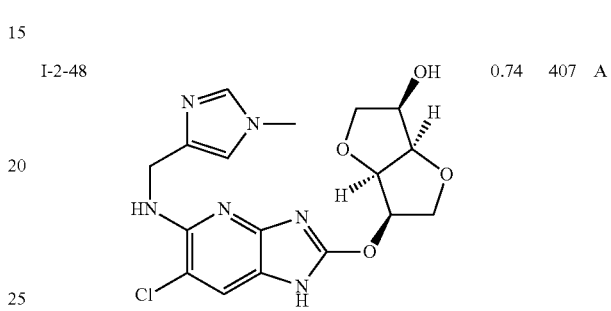 | 0.74 | 407 | A |
| I-2-49 | 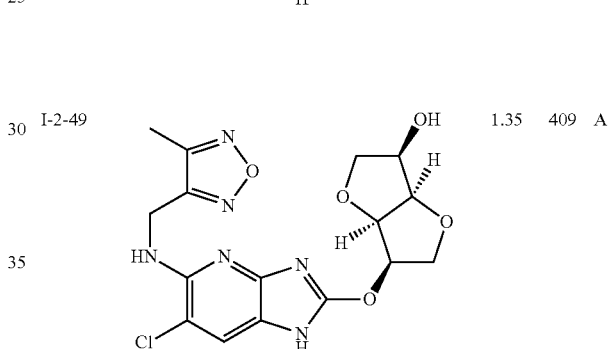 | 1.35 | 409 | A |
| I-2-50 | 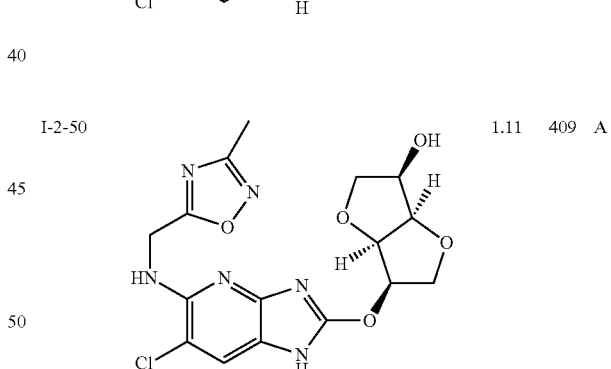 | 1.11 | 409 | A |
| I-2-51 | 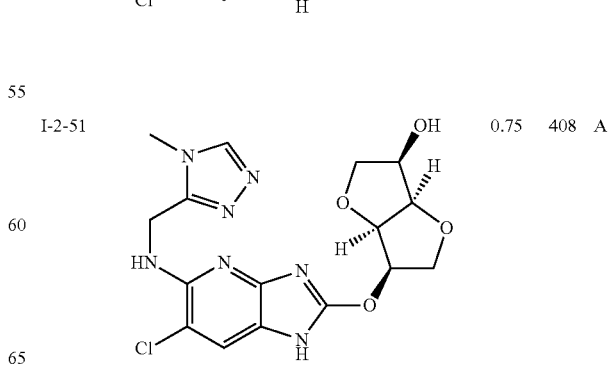 | 0.75 | 408 | A |

TABLE 37
| | | | | |
|---|---|---|---|---|
| I-2-52 | 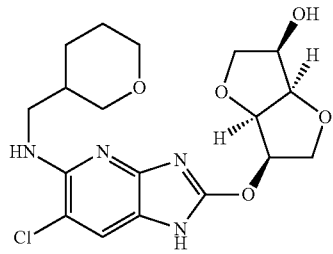 | 1.33 | 411 | A |
| I-2-53 | 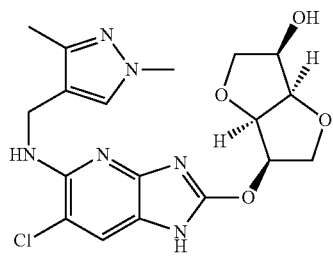 [SMILES: Cc1nn(C)cc1CNc1nc2nc(O[C@@H]3CO[C@H]4[C@@H]3OC[C@H]4O)[nH]c2cc1Cl] | 1.12 | 421 | A |
| I-2-54 | 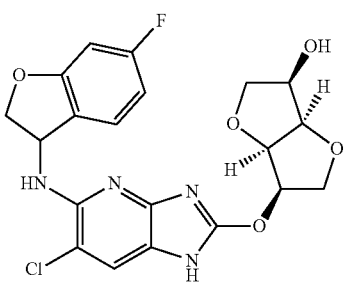 [SMILES: O[C@@H]1CO[C@H]2[C@@H]1OC[C@H]2Oc1nc2nc(NC3COc4cc(F)ccc43)c(Cl)cc2[nH]1] | 1.85 | 449 | A |
| I-2-55 | 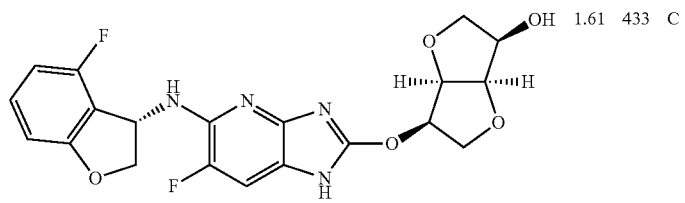 | 1.61 | 433 | C |
| I-2-56 | 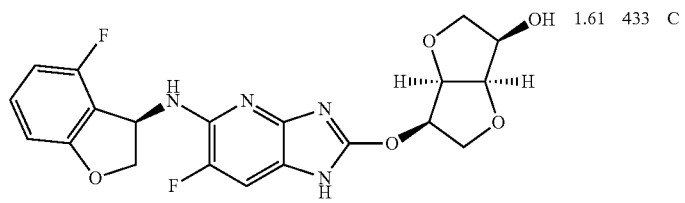 | 1.61 | 433 | C |
TABLE 38
| | | | | |
|---|---|---|---|---|
| I-2-57 | 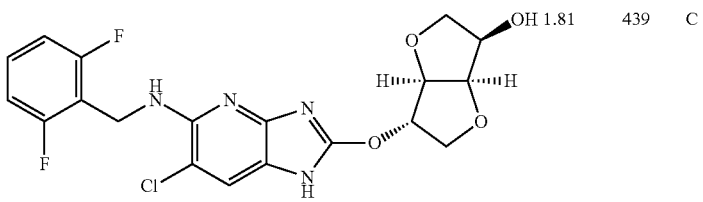 | 1.81 | 439 | C |

TABLE 38-continued
| | | | | |
|---|---|---|---|---|
| I-2-58 | 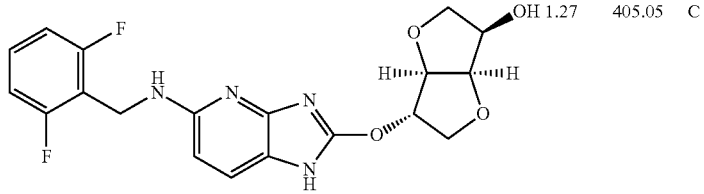 | 1.27 | 405.05 | C |
| I-2-59 | 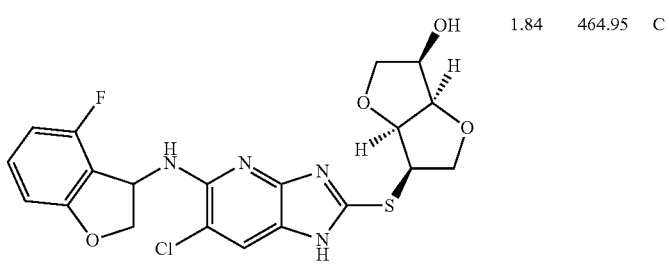 | 1.84 | 464.95 | C |
| I-2-60 | 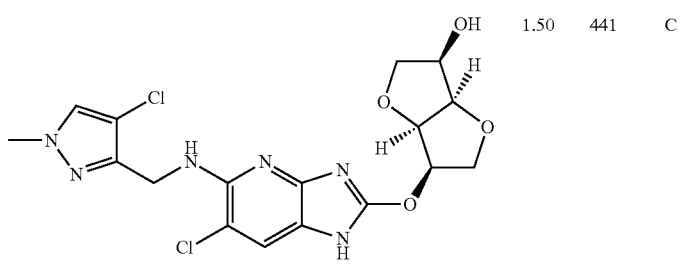 | 1.50 | 441 | C |
| I-2-61 | 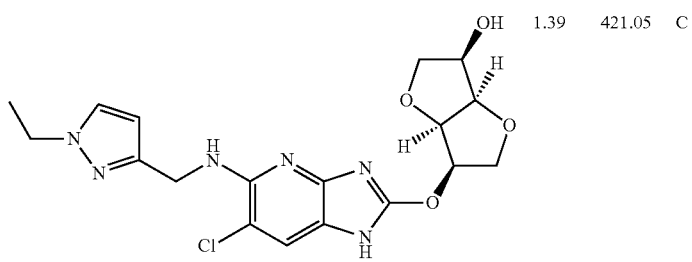 | 1.39 | 421.05 | C |
TABLE 39
| | | | | |
|---|---|---|---|---|
| I-2-62 | 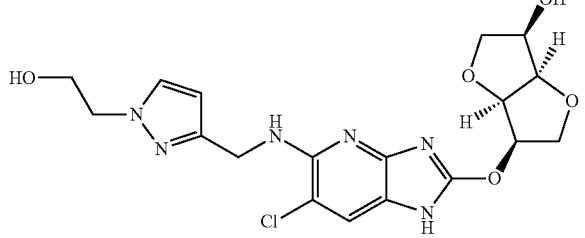 | 0.98 | 437 | A |
| I-2-63 | 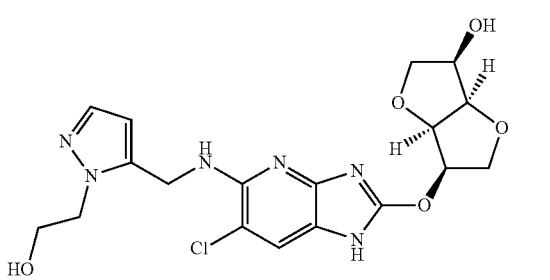 [SMILES: OCCn1nccc1CNc1nc2nc(O[C@@H]3CO[C@H]4[C@@H]3OC[C@H]4O)[nH]c2cc1Cl] | 1.01 | 437 | A |

TABLE 39-continued
| | | | | |
|---|---|---|---|---|
| I-2-64 | 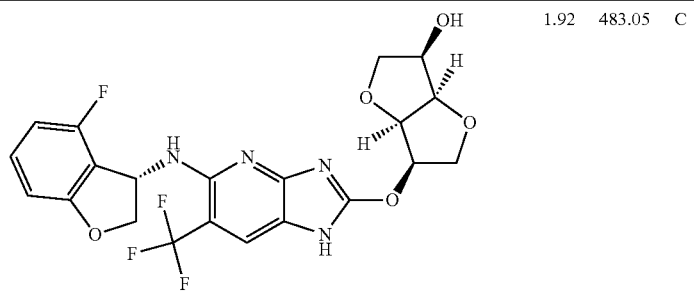 | 1.92 | 483.05 | C |
| I-2-65 | 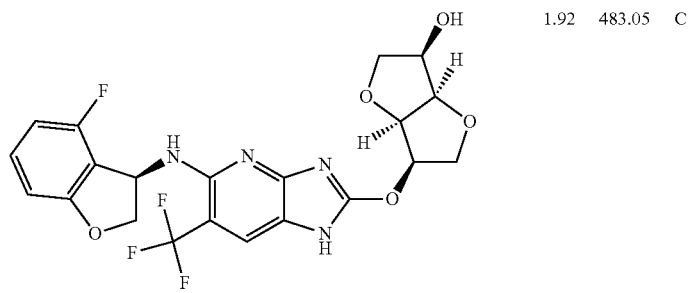 | 1.92 | 483.05 | C |
| I-2-66 | 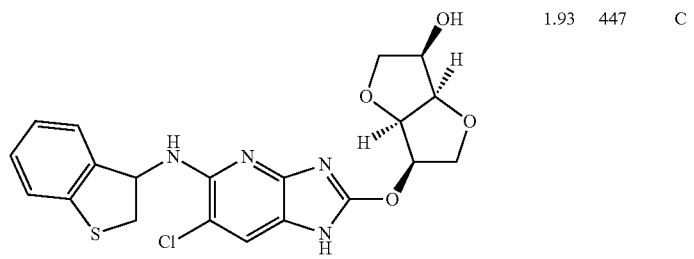 | 1.93 | 447 | C |
TABLE 40
| | | | | |
|---|---|---|---|---|
| I-2-67 | 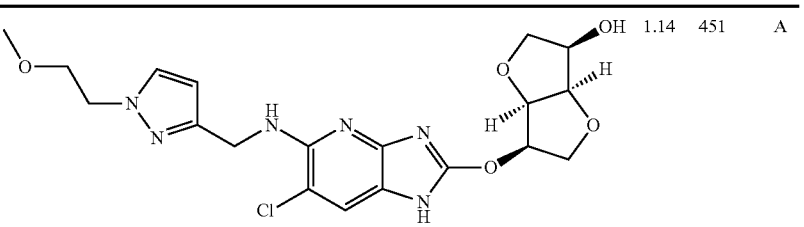 | 1.14 | 451 | A |
| I-2-68 | 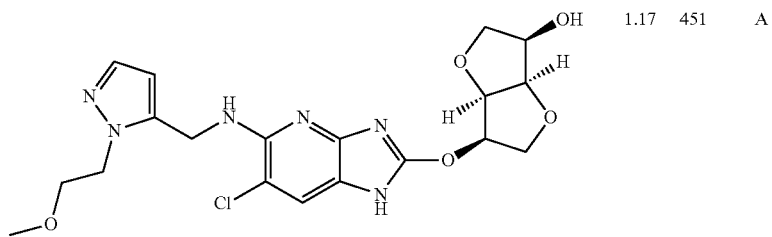 | 1.17 | 451 | A |
| I-2-69 | 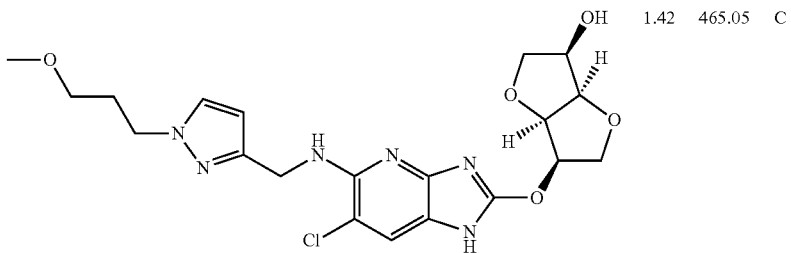 | 1.42 | 465.05 | C |

TABLE 40-continued
| | | | | |
|---|---|---|---|---|
| I-2-70 | 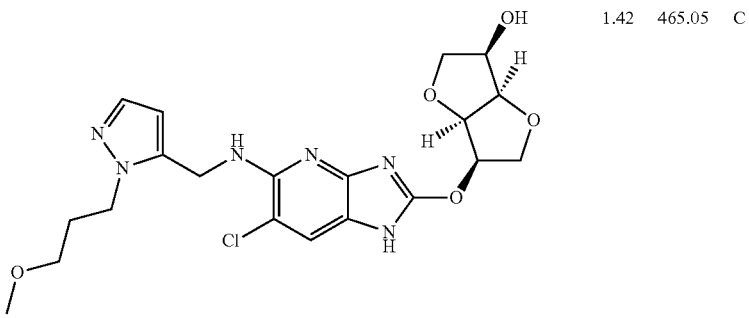 | 1.42 | 465.05 | C |
| I-2-71 | 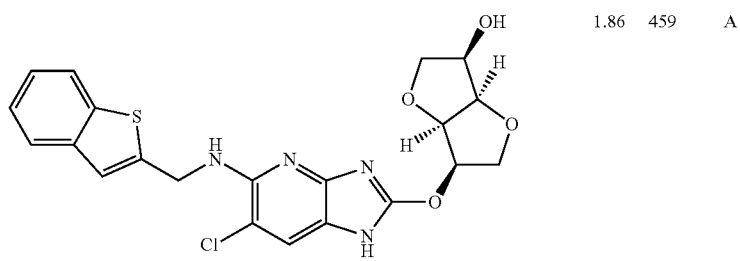 | 1.86 | 459 | A |
TABLE 41
| | | | | |
|---|---|---|---|---|
| I-2-72 | 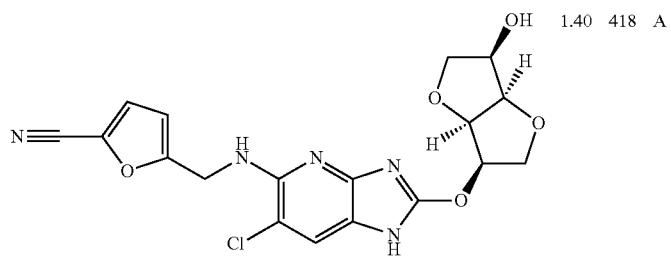 | 1.40 | 418 | A |
| I-2-73 | 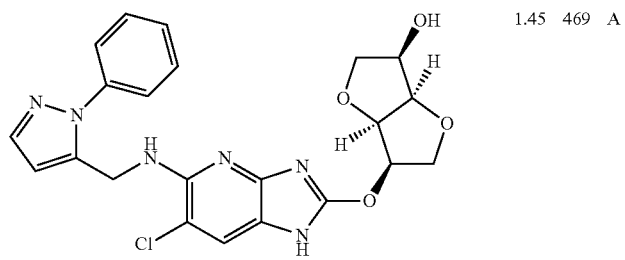 | 1.45 | 469 | A |
| I-2-74 | 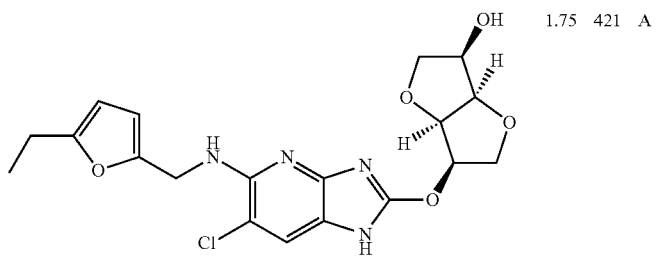 | 1.75 | 421 | A |

TABLE 41-continued
| I-2-75 | 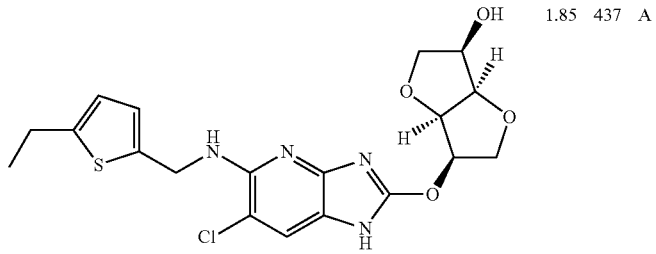 | 1.85 | 437 | A |
| I-2-76 | 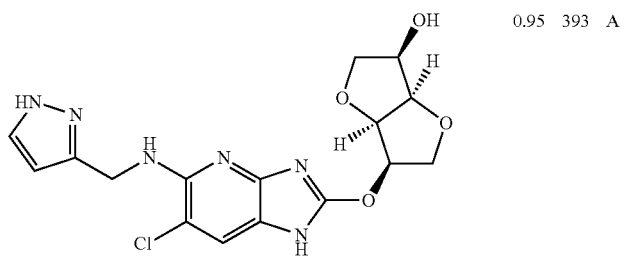 | 0.95 | 393 | A |
TABLE 42
| I-2-77 | 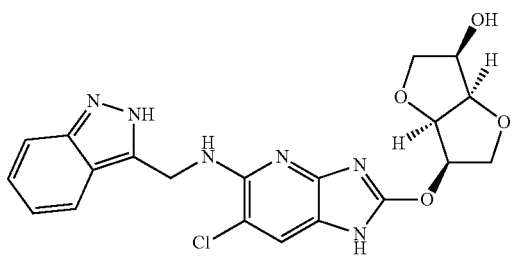 [SMILES: O[C@@H]1CO[C@H]2[C@@H]1OC[C@H]2Oc1nc2nc(NCc3[nH]nc4ccccc34)c(Cl)cc2[nH]1] | 1.34 | 443 | A |
| I-2-78 | 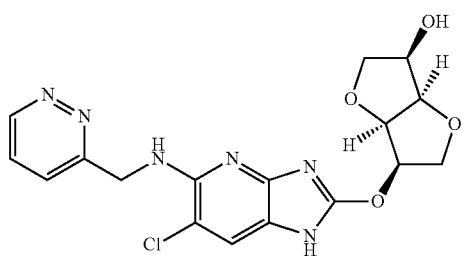 [SMILES: O[C@@H]1CO[C@H]2[C@@H]1OC[C@H]2Oc1nc2nc(NCc3cccnn3)c(Cl)cc2[nH]1] | 0.86 | 405 | A |
| I-2-79 | 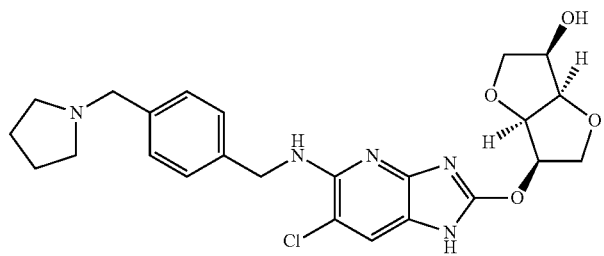 [SMILES: O[C@@H]1CO[C@H]2[C@@H]1OC[C@H]2Oc1nc2nc(NCc3ccc(CN4CCCC4)cc3)c(Cl)cc2[nH]1] | 0.96 | 486 | A |

TABLE 42-continued
I-2-80 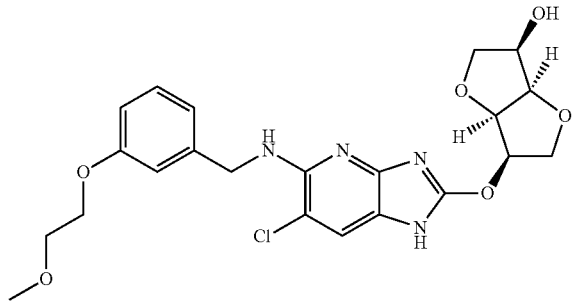 [SMILES: COCCOc1cccc(CNc2nc3nc(O[C@@H]4CO[C@H]5[C@@H]4OC[C@H]5O)[nH]c3cc2Cl)c1] 1.56 477 A
I-2-81 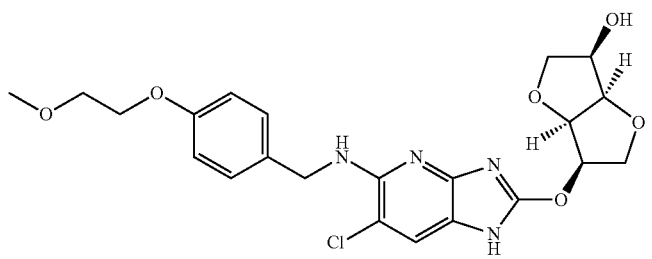 [SMILES: COCCOc1ccc(CNc2nc3nc(O[C@@H]4CO[C@H]5[C@@H]4OC[C@H]5O)[nH]c3cc2Cl)cc1] 1.53 477 A
TABLE 43
I-2-82 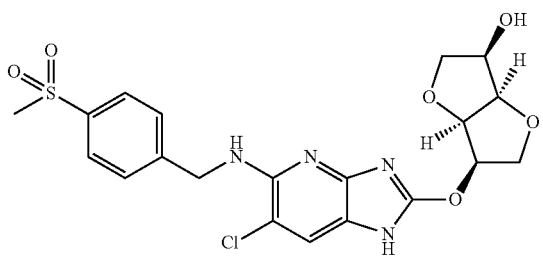 [SMILES: CS(=O)(=O)c1ccc(CNc2nc3nc(O[C@@H]4CO[C@H]5[C@@H]4OC[C@H]5O)[nH]c3cc2Cl)cc1] 1.27 481 A
I-2-83 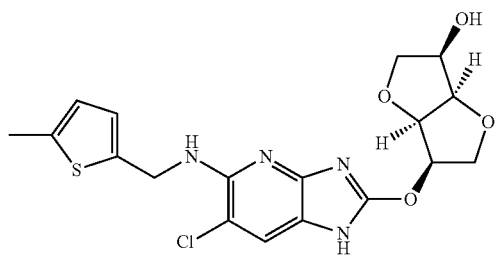 [SMILES: Cc1ccc(CNc2nc3nc(O[C@@H]4CO[C@H]5[C@@H]4OC[C@H]5O)[nH]c3cc2Cl)s1] 1.70 423 A
I-2-84 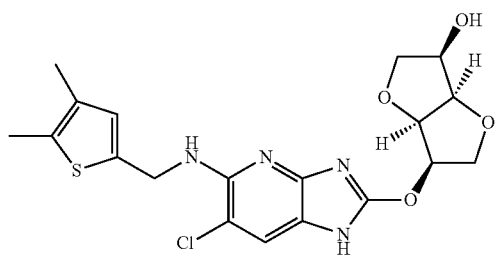 [SMILES: Cc1cc(CNc2nc3nc(O[C@@H]4CO[C@H]5[C@@H]4OC[C@H]5O)[nH]c3cc2Cl)sc1C] 1.84 437 A TABLE 43-continued
| | | | | |
|---|---|---|---|---|
| I-2-85 | 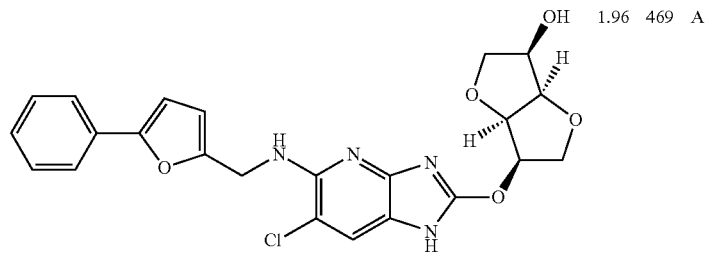 | 1.96 | 469 | A |
| I-2-86 | 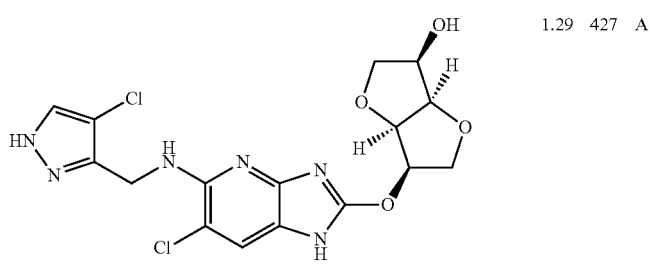 | 1.29 | 427 | A |
TABLE 44
| | | | | |
|---|---|---|---|---|
| I-2-87 | 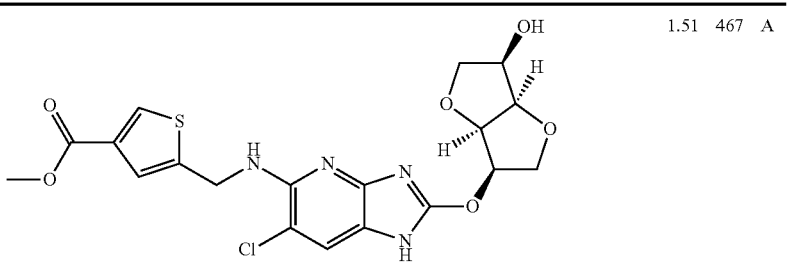 | 1.51 | 467 | A |
| I-2-88 | 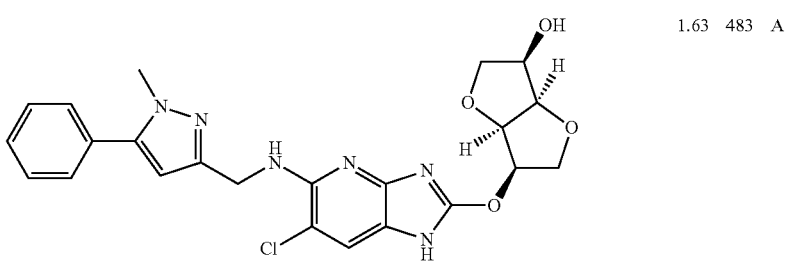 | 1.63 | 483 | A |
| I-2-89 | 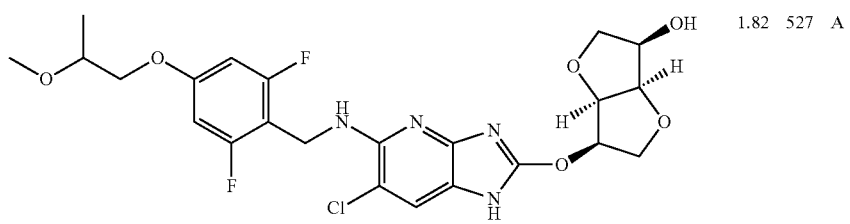 | 1.82 | 527 | A |
| I-2-90 | 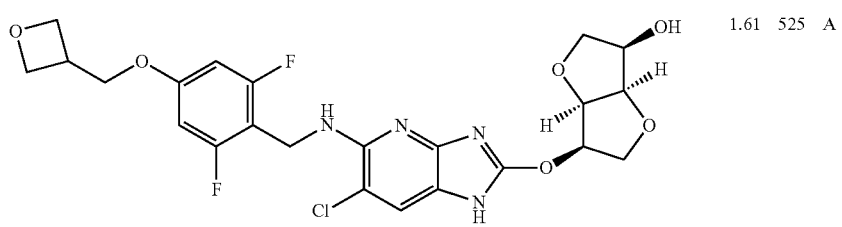 | 1.61 | 525 | A |

TABLE 44-continued
| I-2-91 | 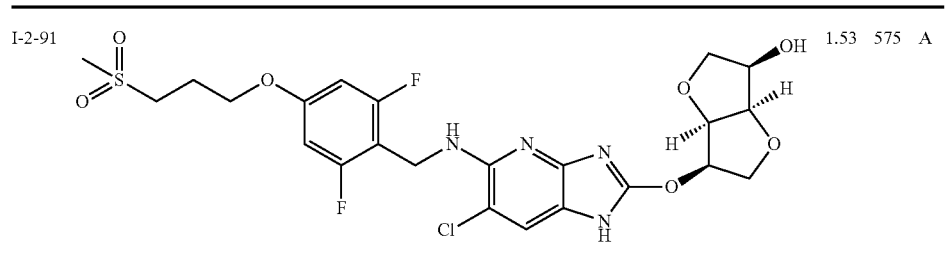 | 1.53 | 575 | A |
TABLE 45
| I-2-92 | 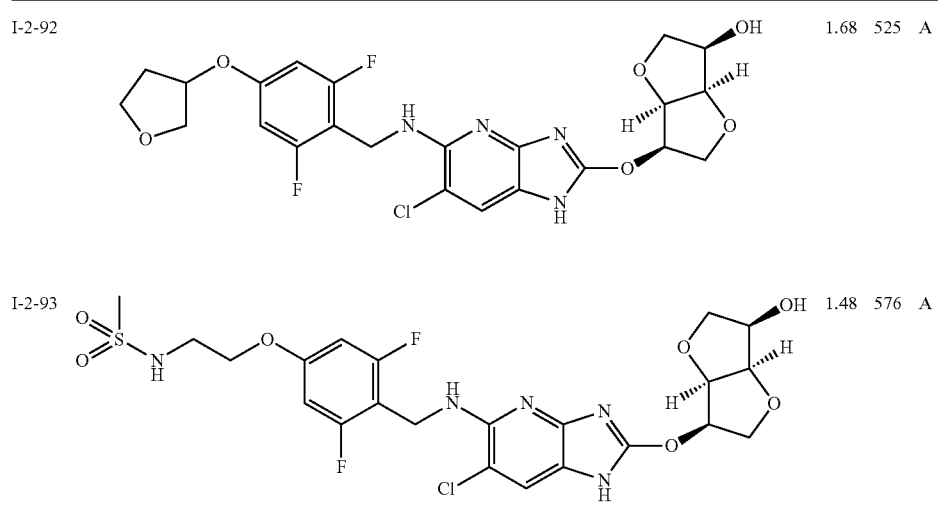 | 1.68 | 525 | A |
| I-2-93 | | 1.48 | 576 | A |
| I-2-94 | 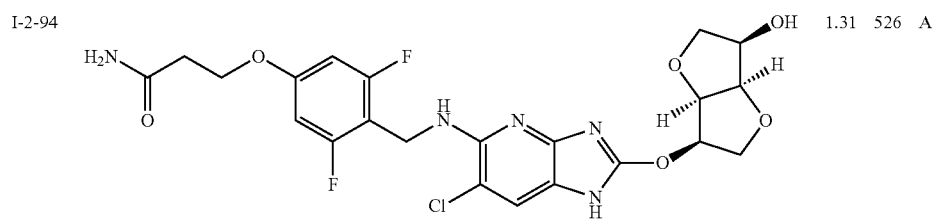 | 1.31 | 526 | A |
| I-2-95 | 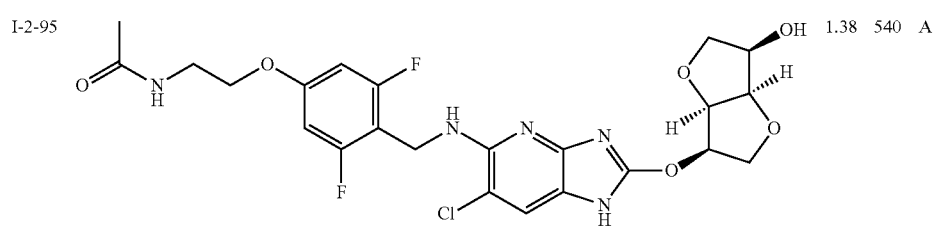 | 1.38 | 540 | A |
| I-2-96 | 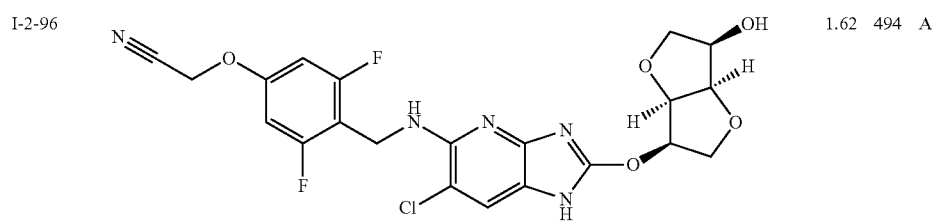 | 1.62 | 494 | A |

TABLE 46
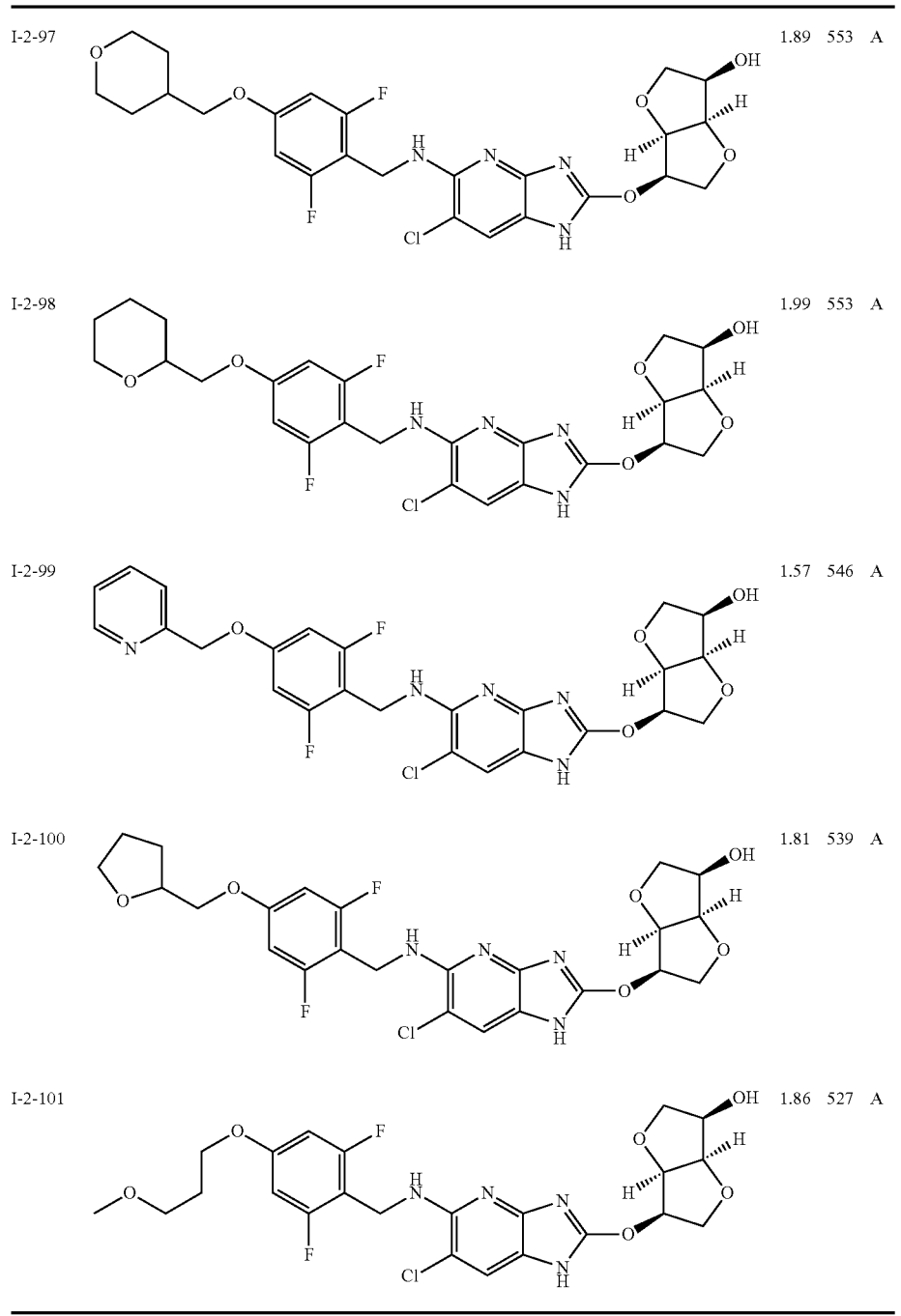
TABLE 47
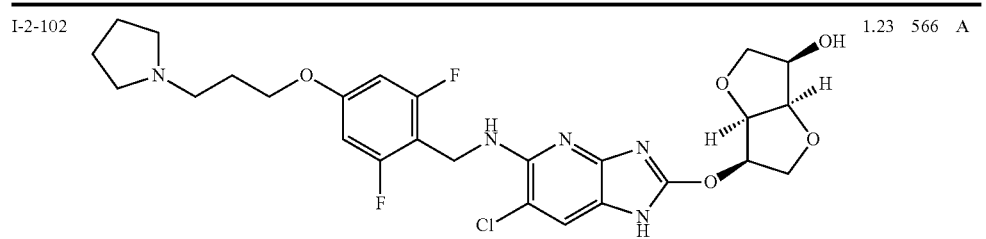

TABLE 47-continued
| I-2-103 | 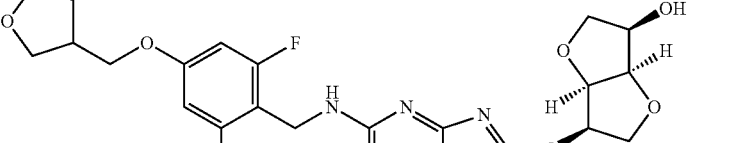 | 1.73 | 536 | A |
| I-2-104 | | 1.60 | 511 | A |
| I-2-105 | | 1.15 | 552 | A |
| I-2-106 | | 1.42 | 555 | A |
TABLE 48
| I-2-107 | 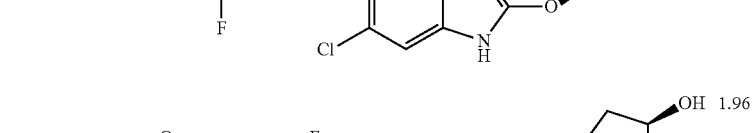 | 1.78 | 539 | A |
| I-2-108 | | 1.96 | 541 | A |

TABLE 48-continued

| ID | Structure | | | |
|---|---|---|---|---|
| I-2-109 | (structure) | 1.64 | 527 | A |
| I-2-110 | (structure) | 1.28 | 512 | A |
| I-2-111 | (structure) | 1.63 | 525 | A |

TABLE 49

| ID | Structure | | | |
|---|---|---|---|---|
| I-2-112 | (structure) | 1.71 | 552 | A |
| I-2-113 | (structure) | 1.37 | 538 | A |
| I-2-114 | (structure) | 1.61 | 536 | A |

TABLE 49-continued

| | | | | |
|---|---|---|---|---|
| I-2-115 | | 1.62 | 549 | A |
| I-2-116 | | 0.90 | 437 | A |

TABLE 50

| | | | | |
|---|---|---|---|---|
| I-2-117 | | 1.14 | 451 | A |
| I-2-118 | | 1.18 | 465 | A |
| I-2-119 | | 1.16 | 554 | A |
| I-2-120 | | 1.69 | 483.05 | C |

TABLE 50-continued
| | | | | |
|---|---|---|---|---|
| I-2-121 | 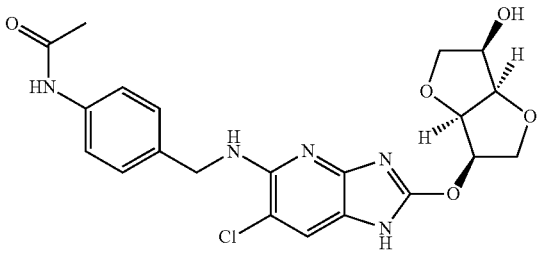 [SMILES: CC(=O)Nc1ccc(CNc2nc3nc(O[C@@H]4CO[C@H]5[C@@H]4OC[C@H]5O)[nH]c3cc2Cl)cc1] | 1.19 | 460 | A |
TABLE 51
| | | | | |
|---|---|---|---|---|
| I-2-122 | 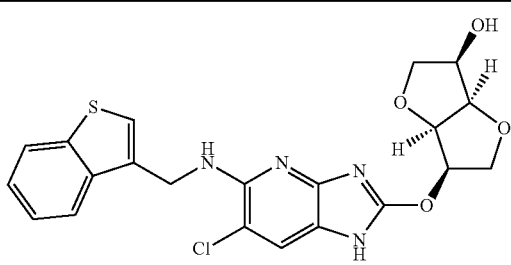 | 1.88 | 459 | A |
| I-2-123 | 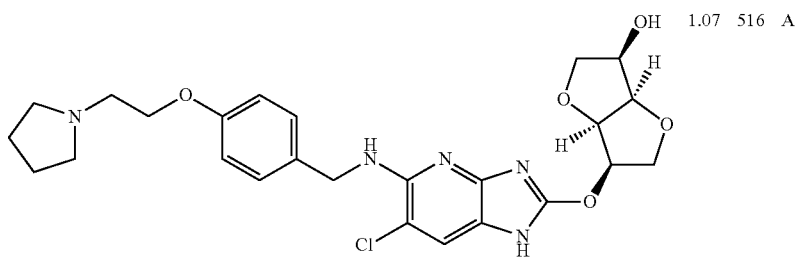 | 1.07 | 516 | A |
| I-2-124 | 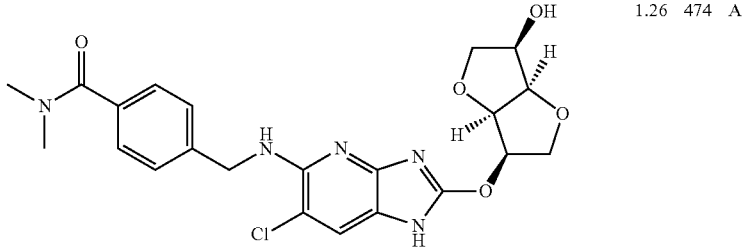 | 1.26 | 474 | A |
| I-2-125 | 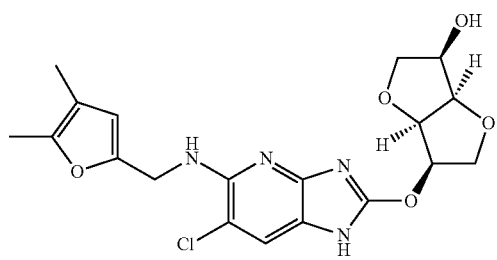 | 0.80 | 421 | A |

TABLE 51-continued
| I-2-126 | 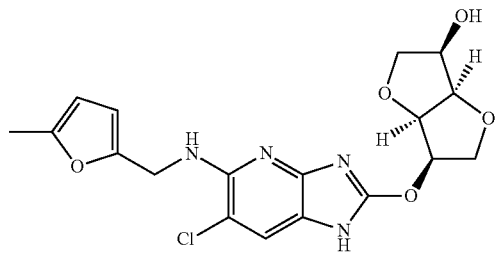 | 1.57 | 407 | A |
TABLE 52
| I-2-127 | 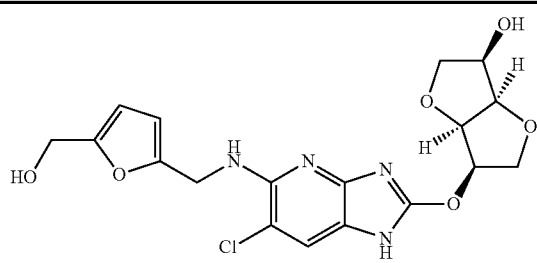 | 1.09 | 423 | A |
| I-2-128 | 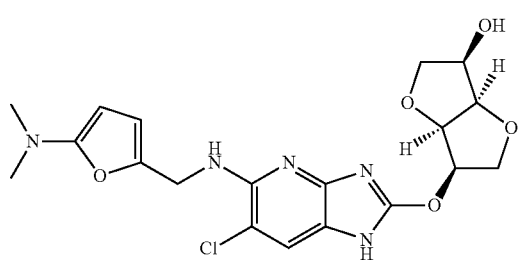 [SMILES: CN(C)c1ccc(CNc2nc3nc(O[C@@H]4CO[C@H]5[C@@H]4OC[C@H]5O)[nH]c3cc2Cl)o1] | 0.87 | 434 | A |
| I-2-129 | 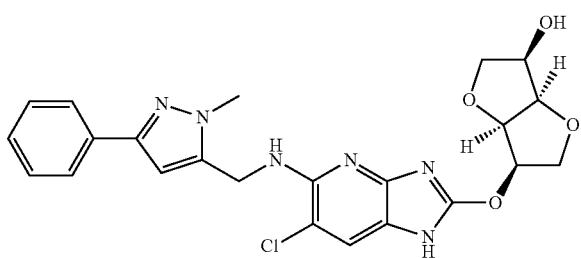 [SMILES: Cn1nc(-c2ccccc2)cc1CNc1nc2nc(O[C@@H]3CO[C@H]4[C@@H]3OC[C@H]4O)[nH]c2cc1Cl] | 1.59 | 483 | A |
| I-2-130 | 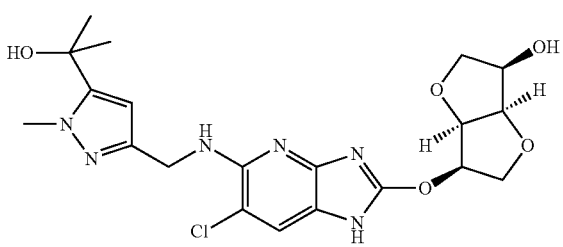 [SMILES: Cn1nc(CNc2nc3nc(O[C@@H]4CO[C@H]5[C@@H]4OC[C@H]5O)[nH]c3cc2Cl)cc1C(C)(C)O] | 1.33 | 465 | A |
| I-2-131 | 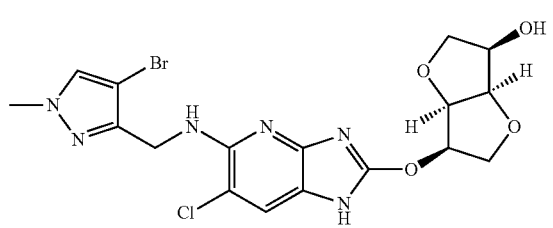 | 1.39 | 485 | A |

TABLE 53
| I-2-132 | 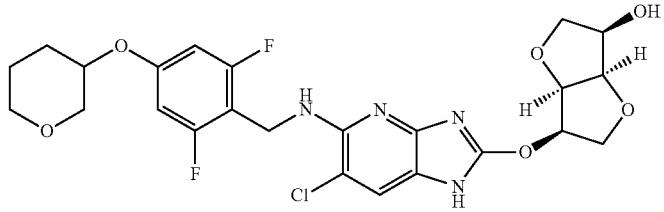 [SMILES: O[C@@H]1CO[C@H]2[C@@H]1OC[C@H]2Oc1nc2nc(NCc3c(F)cc(OC4CCCOC4)cc3F)c(Cl)cc2[nH]1] | 1.81 | 539 | A |
| I-2-133 | 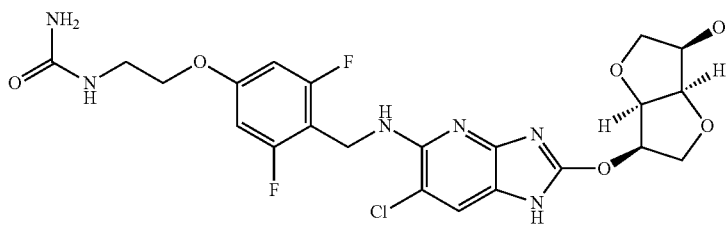 | 1.84 | 539 | A |
| I-2-134 | 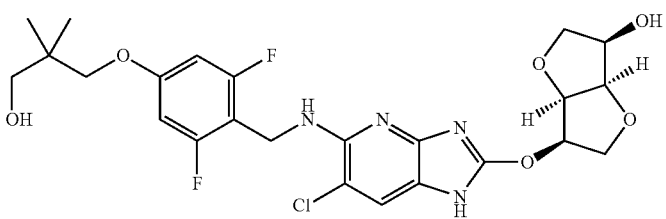 [SMILES: CC(C)(CO)COc1cc(F)c(CNc2nc3nc(O[C@@H]4CO[C@H]5[C@@H]4OC[C@H]5O)[nH]c3cc2Cl)c(F)c1] | 1.82 | 541 | A |
| I-2-135 | 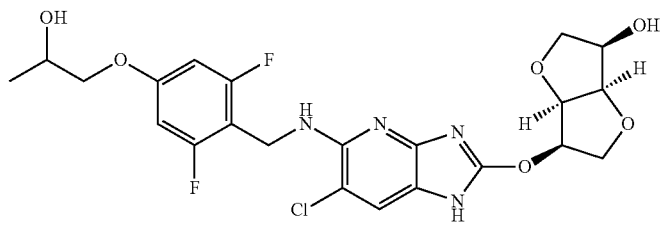 [SMILES: CC(O)COc1cc(F)c(CNc2nc3nc(O[C@@H]4CO[C@H]5[C@@H]4OC[C@H]5O)[nH]c3cc2Cl)c(F)c1] | 1.50 | 513 | A |
| I-2-136 | 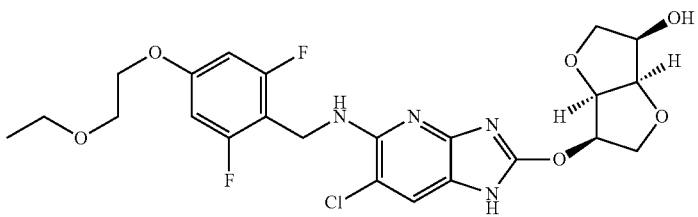 | 1.84 | 527 | A |
TABLE 54
| I-2-137 | 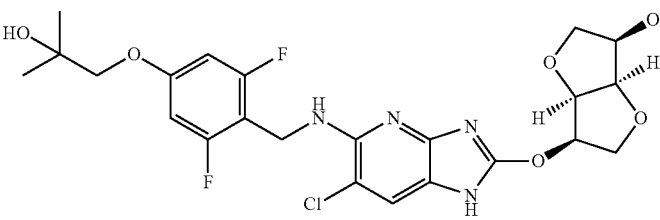 | 1.56 | 527 | A |

TABLE 54-continued
| | | | | |
|---|---|---|---|---|
| I-2-138 | 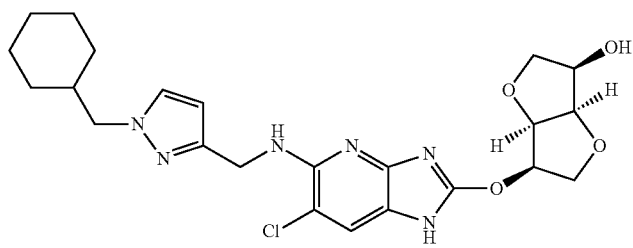 [SMILES: O[C@@H]1CO[C@H]2[C@@H]1OC[C@H]2Oc1nc2nc(NCc3ccn(CC4CCCCC4)n3)c(Cl)cc2[nH]1] | 1.96 | 489.1 | C |
| I-2-139 | 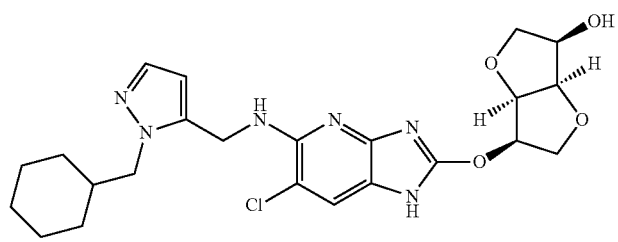 | 1.87 | 489.1 | C |
| I-2-140 | 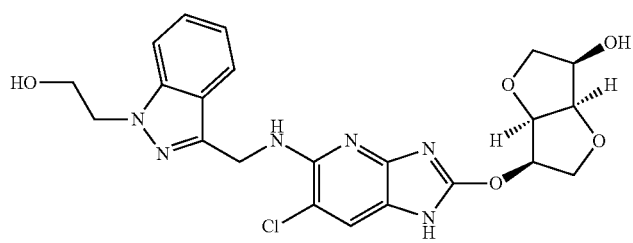 [SMILES: OCCn1nc(CNc2nc3nc(O[C@@H]4CO[C@H]5[C@@H]4OC[C@H]5O)[nH]c3cc2Cl)c2ccccc21] | 1.44 | 487 | C |
| I-2-141 | 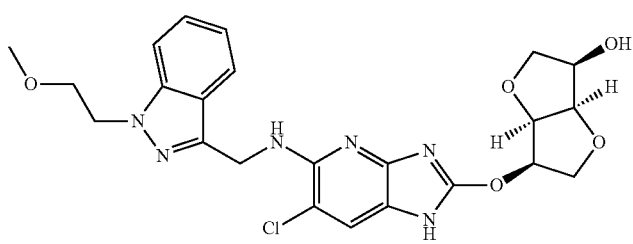 [SMILES: COCCn1nc(CNc2nc3nc(O[C@@H]4CO[C@H]5[C@@H]4OC[C@H]5O)[nH]c3cc2Cl)c2ccccc21] | 1.67 | 501.1 | C |
TABLE 55
| | | | | |
|---|---|---|---|---|
| I-2-142 | 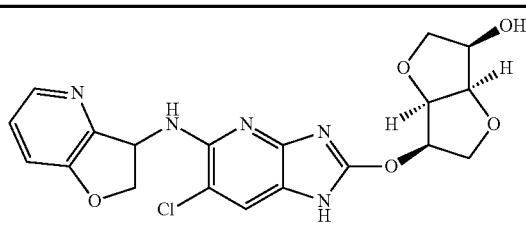 | 1.31 | 432 | C |
| I-2-143 | 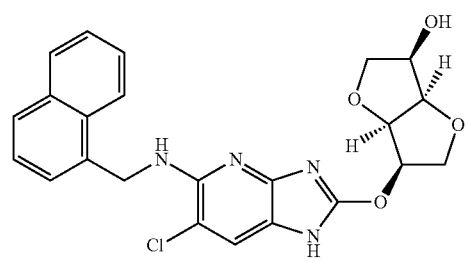 [SMILES: O[C@@H]1CO[C@H]2[C@@H]1OC[C@H]2Oc1nc2nc(NCc3cccc4ccccc34)c(Cl)cc2[nH]1] | 1.98 | 453 | C |

TABLE 55-continued
| I-2-144 | 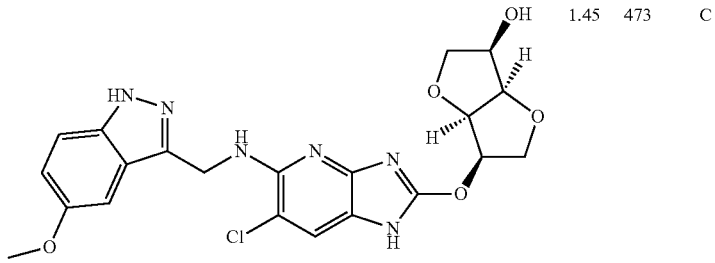 | 1.45 | 473 | C |
| I-2-145 | 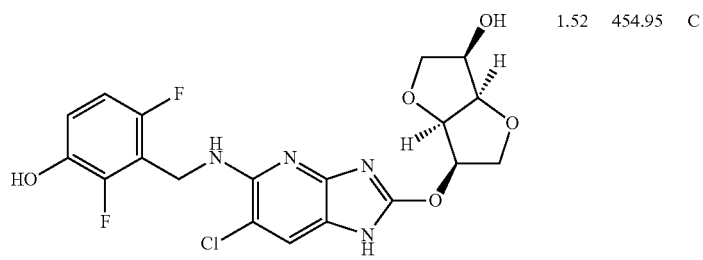 | 1.52 | 454.95 | C |
| I-2-146 | 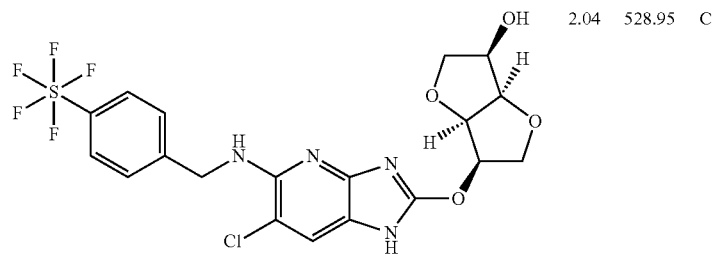 | 2.04 | 528.95 | C |
TABLE 56
| I-2-147 | 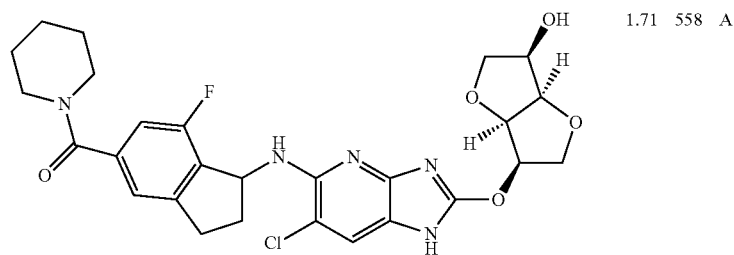 | 1.71 | 558 | A |
| I-2-148 | 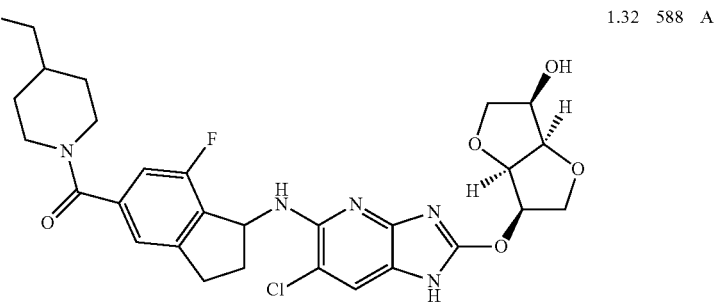 | 1.32 | 588 | A |

TABLE 56-continued
| | | | | |
|---|---|---|---|---|
| I-2-149 | 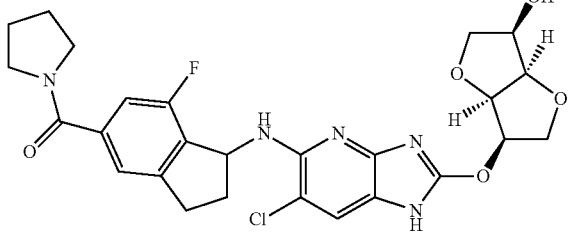 | 1.55 | 544 | A |
| I-2-150 | 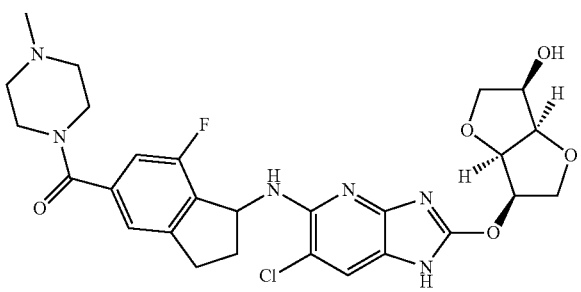 [SMILES: CN1CCN(C(=O)c2cc(F)c3c(c2)CCC3Nc2nc3nc(O[C@@H]4CO[C@H]5[C@@H]4OC[C@H]5O)[nH]c3cc2Cl)CC1] | 1.03 | 573 | A |
| I-2-151 | 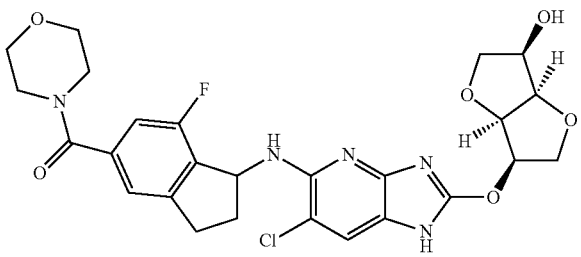 [SMILES: O=C(c1cc(F)c2c(c1)CCC2Nc1nc2nc(O[C@@H]3CO[C@H]4[C@@H]3OC[C@H]4O)[nH]c2cc1Cl)N1CCOCC1] | 1.40 | 560 | A |
TABLE 57
| | | | | |
|---|---|---|---|---|
| I-2-152 | 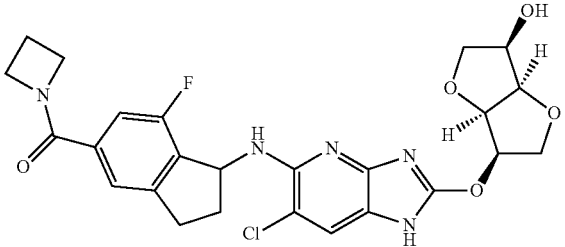 [SMILES: O=C(c1cc(F)c2c(c1)CCC2Nc1nc2nc(O[C@@H]3CO[C@H]4[C@@H]3OC[C@H]4O)[nH]c2cc1Cl)N1CCC1] | 1.44 | 530 | A |
| I-2-153 | 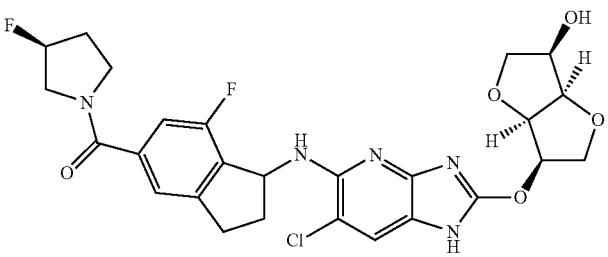 [SMILES: O=C(c1cc(F)c2c(c1)CCC2Nc1nc2nc(O[C@@H]3CO[C@H]4[C@@H]3OC[C@H]4O)[nH]c2cc1Cl)N1CC[C@H](F)C1] | 1.49 | 562 | A |

TABLE 57-continued
| I-2-154 | 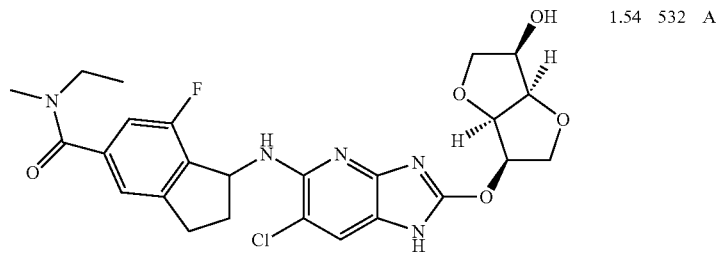 | 1.54 | 532 | A |
| I-2-155 | 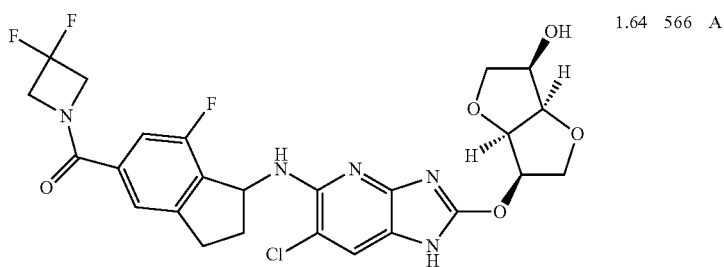 | 1.64 | 566 | A |
| I-2-156 | 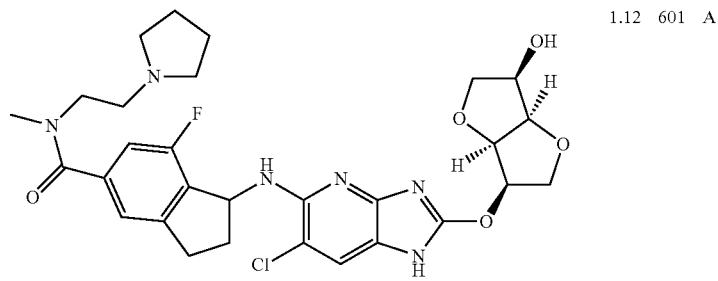 | 1.12 | 601 | A |
TABLE 58
| I-2-157 | 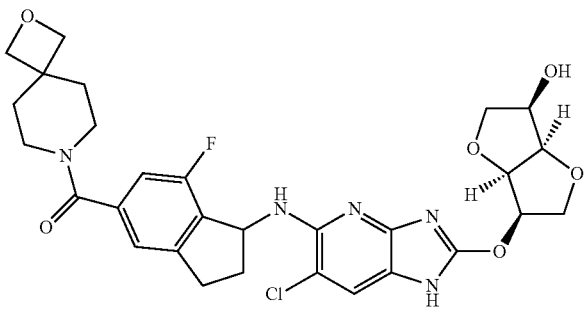 [SMILES: O=C(c1cc(F)c2c(c1)CCC2Nc1nc2nc(O[C@@H]3CO[C@H]4[C@@H]3OC[C@H]4O)[nH]c2cc1Cl)N1CCC2(CC1)COC2] | 1.42 | 600 | A |
| I-2-158 | 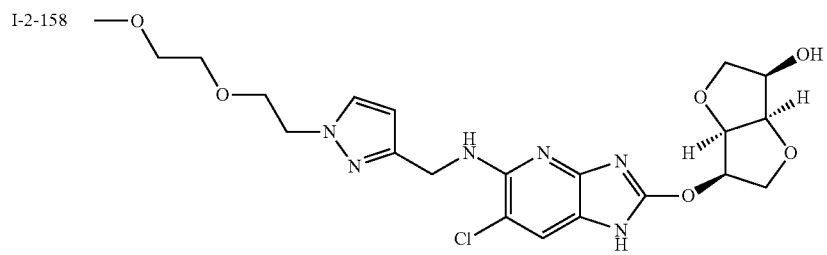 | 1.16 | 495 | A |

TABLE 58-continued

| ID | Structure | | | |
|---|---|---|---|---|
| I-2-159 | (structure) | 1.40 | 447 | A |
| I-2-160 | (structure) | 1.41 | 491 | A |
| I-2-161 | (structure) | 1.59 | 461 | A |

TABLE 59

| ID | Structure | | | |
|---|---|---|---|---|
| I-2-162 | (structure) | 1.25 | 477 | A |
| I-2-163 | (structure) | 1.19 | 495 | C |
| I-2-164 | (structure) | 1.43 | 491 | C |

TABLE 59-continued

| | | | | |
|---|---|---|---|---|
| I-2-165 | | 1.64 | 457 | C |
| I-2-166 | | 1.19 | 474 | A |

TABLE 60

| | | | | |
|---|---|---|---|---|
| I-2-167 | | 1.31 | 479 | A |
| I-2-168 | | 1.71 | 405 | C |
| I-2-169 | | 1.38 | 421 | C |
| I-2-170 | | 1.47 | 530 | C |

TABLE 60-continued
| | | | | |
|---|---|---|---|---|
| I-2-171 | 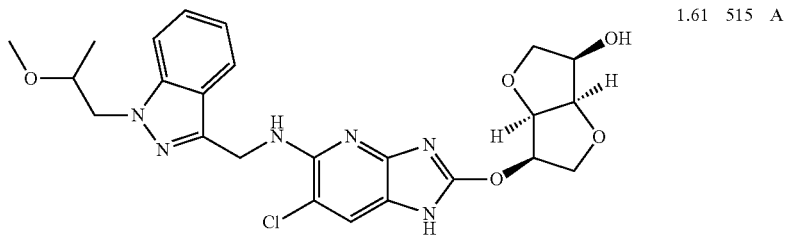 | 1.61 | 515 | A |
TABLE 61
| | | | | |
|---|---|---|---|---|
| I-2-172 | 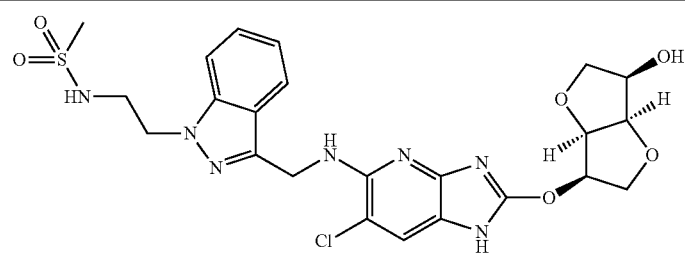 | 1.36 | 564 | A |
| I-2-173 | 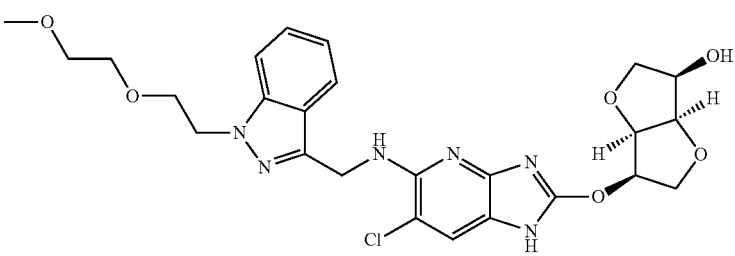 [SMILES: COCCOCCn1nc(CNc2nc3nc(O[C@@H]4CO[C@H]5[C@@H]4OC[C@H]5O)[nH]c3cc2Cl)c2ccccc21] | 1.51 | 545 | A |
| I-2-174 | 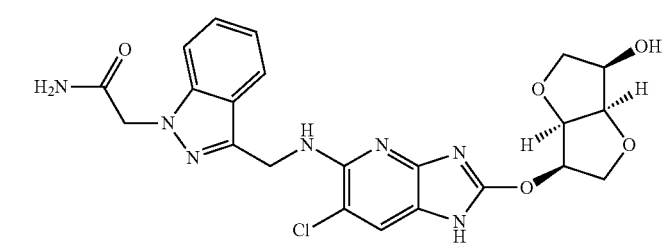 [SMILES: NC(=O)Cn1nc(CNc2nc3nc(O[C@@H]4CO[C@H]5[C@@H]4OC[C@H]5O)[nH]c3cc2Cl)c2ccccc21] | 1.19 | 500 | A |
| I-2-175 | 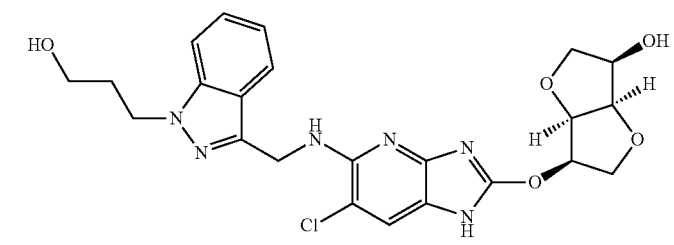 [SMILES: OCCCn1nc(CNc2nc3nc(O[C@@H]4CO[C@H]5[C@@H]4OC[C@H]5O)[nH]c3cc2Cl)c2ccccc21] | 1.35 | 501 | A |
| I-2-176 | 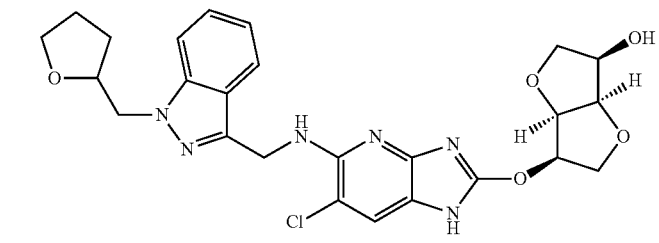 [SMILES: O[C@@H]1CO[C@H]2[C@@H]1OC[C@H]2Oc1nc2nc(NCc3nn(CC4CCCO4)c4ccccc34)c(Cl)cc2[nH]1] | 1.62 | 527 | A |

TABLE 62
| | | | | |
|---|---|---|---|---|
| I-2-177 | 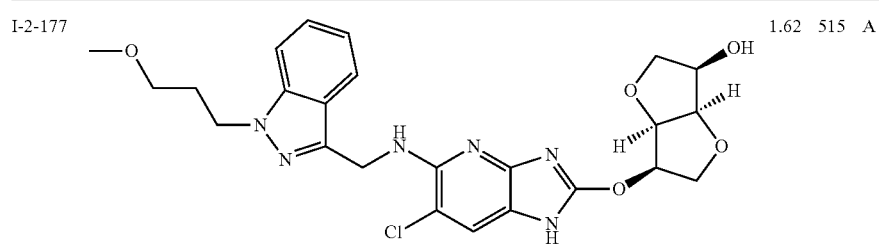 | 1.62 | 515 | A |
| I-2-178 | 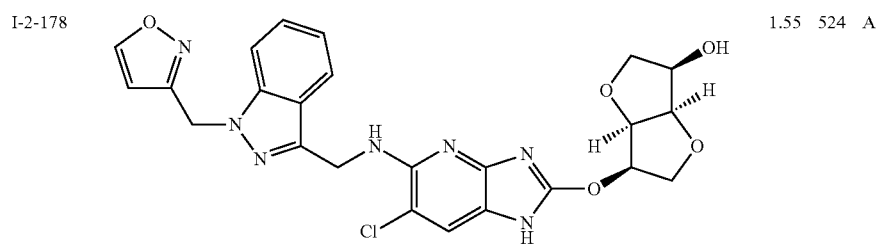 | 1.55 | 524 | A |
| I-2-179 | 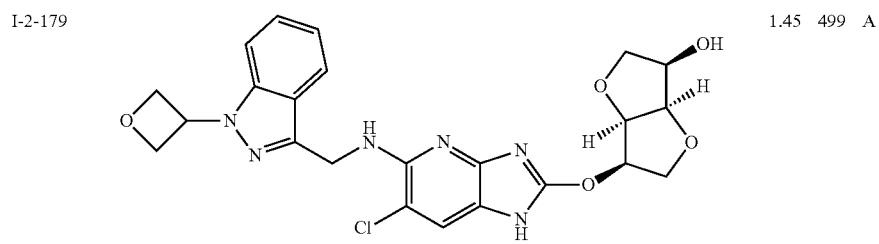 | 1.45 | 499 | A |
| I-2-180 | 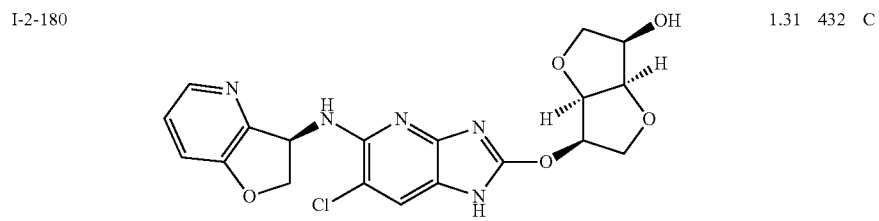 | 1.31 | 432 | C |
| I-2-181 | 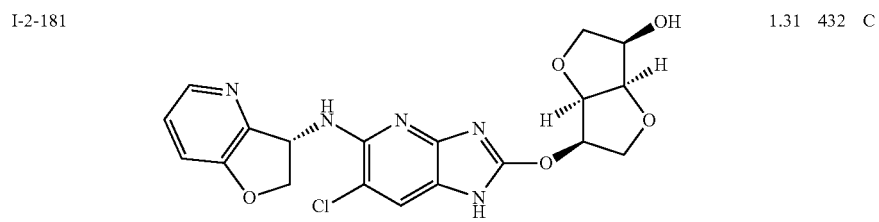 | 1.31 | 432 | C |
TABLE 63
| | | | | |
|---|---|---|---|---|
| I-2-182 | 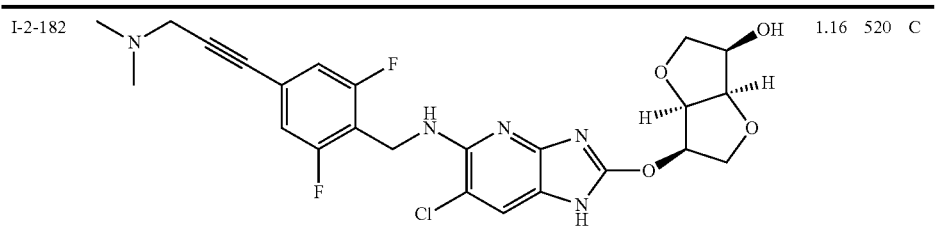 | 1.16 | 520 | C |

TABLE 63-continued

| ID | Structure | | | |
|---|---|---|---|---|
| I-2-183 | (structure) | 1.70 | 521 | C |
| I-2-184 | (structure) | 1.84 | 507 | C |
| I-2-185 | (structure) | 1.77 | 523 | C |
| I-2-186 | (structure) | 1.22 | 566 | A |

TABLE 64

| ID | Structure | | | |
|---|---|---|---|---|
| I-2-187 | (structure) | 1.25 | 582 | A |
| I-2-188 | (structure) | 1.52 | 566 | A |

TABLE 64-continued

| ID | Structure | | | |
|---|---|---|---|---|
| I-2-189 | (structure) | 2.06 | 509 | A |
| I-2-190 | (structure) | 1.58 | 580 | A |
| I-2-191 | (structure) | 1.19 | 566 | A |

TABLE 65

| ID | Structure | | | |
|---|---|---|---|---|
| I-2-192 | (structure) | 1.17 | 552 | A |
| I-2-193 | (structure) | 1.17 | 540 | A |
| I-2-194 | (structure) | 2.34 | 523 | A |
| I-2-195 | (structure) | 1.67 | 557 | A |

TABLE 65-continued
| I-2-196 | 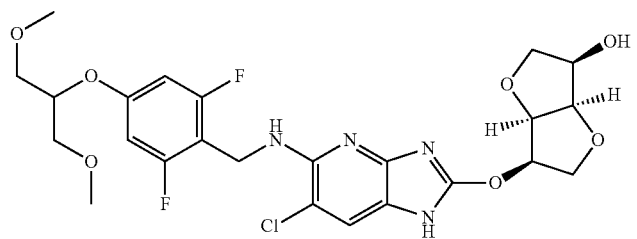 [SMILES: COCC(COC)Oc1cc(F)c(CNc2nc3nc(O[C@@H]4CO[C@H]5[C@@H]4OC[C@H]5O)[nH]c3cc2Cl)c(F)c1] | 1.76 | 557 | A |
TABLE 66
| I-2-197 | 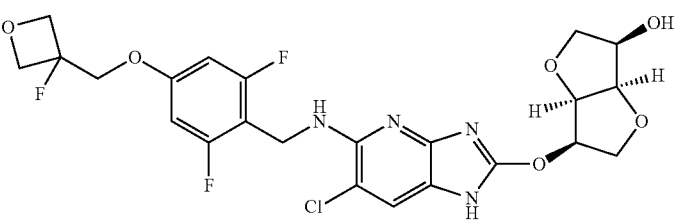 [SMILES: O[C@@H]1CO[C@H]2[C@@H]1OC[C@H]2Oc1nc2nc(NCc3c(F)cc(OCC4(F)COC4)cc3F)c(Cl)cc2[nH]1] | 1.70 | 543 | A |
| I-2-198 | 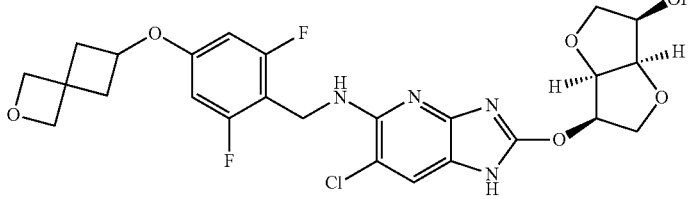 | 1.75 | 551 | A |
| I-2-199 | 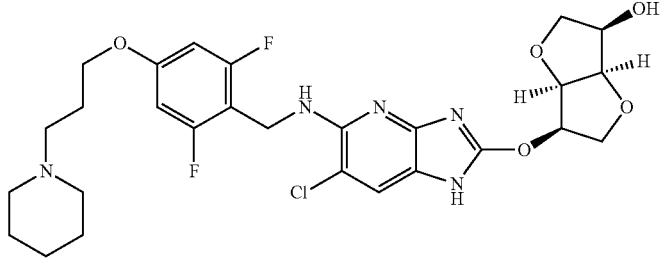 [SMILES: O[C@@H]1CO[C@H]2[C@@H]1OC[C@H]2Oc1nc2nc(NCc3c(F)cc(OCCCN4CCCCC4)cc3F)c(Cl)cc2[nH]1] | 1.26 | 580 | A |
| I-2-200 | 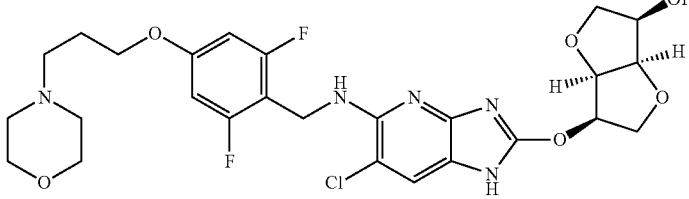 | 1.16 | 582 | A |
| I-2-201 | 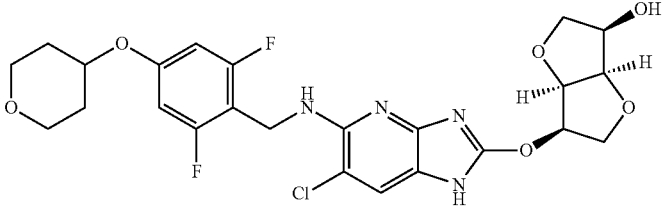 [SMILES: O[C@@H]1CO[C@H]2[C@@H]1OC[C@H]2Oc1nc2nc(NCc3c(F)cc(OC4CCOCC4)cc3F)c(Cl)cc2[nH]1] | 1.77 | 539 | A |

TABLE 67

| | | | |
|---|---|---|---|
| I-2-202 | | 2.38 | 652 A |
| I-2-203 | | 2.07 | 567 A |
| I-2-204 | | 1.76 | 539 A |
| I-2-205 | | 2.11 | 610 A |
| I-2-206 | | 1.71 | 533 A |

TABLE 68

| | | | |
|---|---|---|---|
| I-2-207 | | 1.13 | 534 A |

TABLE 68-continued
| | | | | |
|---|---|---|---|---|
| I-2-208 | 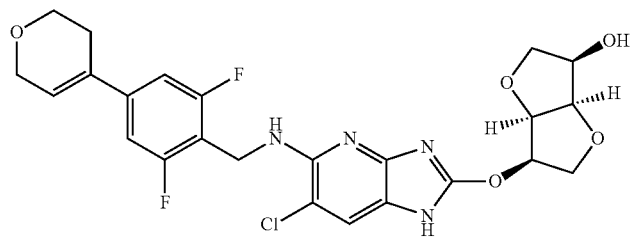 [SMILES: O[C@@H]1CO[C@H]2[C@@H]1OC[C@H]2Oc1nc2nc(NCc3c(F)cc(C4=CCOCC4)cc3F)c(Cl)cc2[nH]1] | 1.79 | 521 | A |
| I-2-209 | 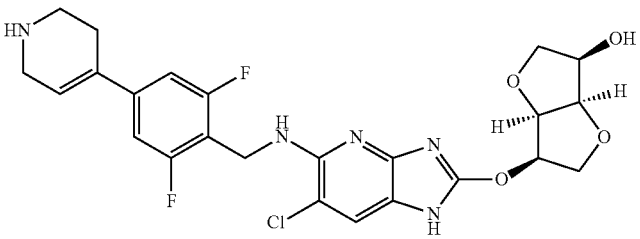 [SMILES: O[C@@H]1CO[C@H]2[C@@H]1OC[C@H]2Oc1nc2nc(NCc3c(F)cc(C4=CCNCC4)cc3F)c(Cl)cc2[nH]1] | 1.12 | 520 | A |
| I-2-210 | 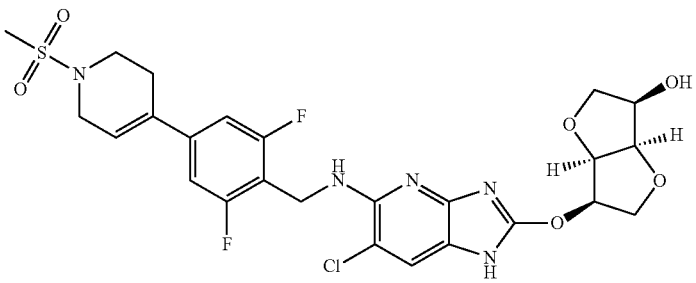 [SMILES: CS(=O)(=O)N1CC=C(c2cc(F)c(CNc3nc4nc(O[C@@H]5CO[C@H]6[C@@H]5OC[C@H]6O)[nH]c4cc3Cl)c(F)c2)CC1] | 1.71 | 598 | A |
| I-2-211 | 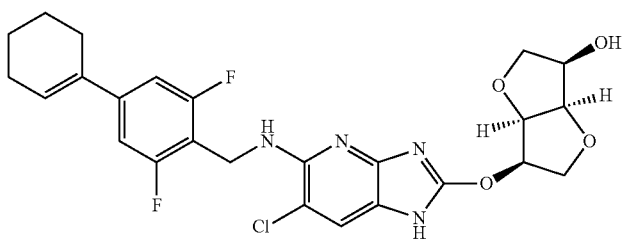 [SMILES: O[C@@H]1CO[C@H]2[C@@H]1OC[C@H]2Oc1nc2nc(NCc3c(F)cc(C4=CCCCC4)cc3F)c(Cl)cc2[nH]1] | 2.45 | 519 | A |
TABLE 69
| | | | | |
|---|---|---|---|---|
| I-2-212 | 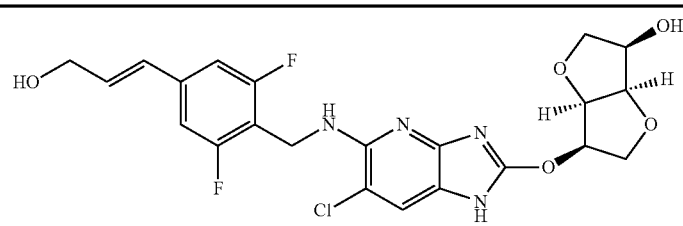 | 1.48 | 495 | A |
| I-2-213 | 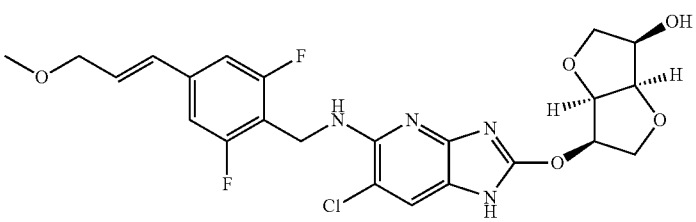 [SMILES: COC/C=C/c1cc(F)c(CNc2nc3nc(O[C@@H]4CO[C@H]5[C@@H]4OC[C@H]5O)[nH]c3cc2Cl)c(F)c1] | 1.83 | 509 | A |

TABLE 69-continued

| ID | Structure | | | |
|---|---|---|---|---|
| I-2-214 | (structure) | 1.41 | 546 | A |
| I-2-215 | (structure) | 1.76 | 588 | A |
| I-2-216 | (structure) | 1.13 | 534 | A |

TABLE 70

| ID | Structure | | | |
|---|---|---|---|---|
| I-2-217 | (structure) | 1.44 | 546 | A |
| I-2-218 | (structure) | 1.50 | 513 | C |
| I-2-219 | (structure) | 1.85 | 521 | C |

TABLE 70-continued

| ID | Structure | | | |
|---|---|---|---|---|
| I-2-220 | (structure) | 1.85 | 521 | C |
| I-2-221 | (structure) | 2.46 | 509.1 | C |

TABLE 71

| ID | Structure | | | |
|---|---|---|---|---|
| I-2-222 | (structure) | 1.25 | 524 | C |
| I-2-223 | (structure) | 2.00 | 535.05 | C |
| I-2-224 | (structure) | 1.06 | 568 | A |
| I-2-225 | (structure) | 1.17 | 552 | A |

TABLE 71-continued
| | | | | |
|---|---|---|---|---|
| I-2-226 | 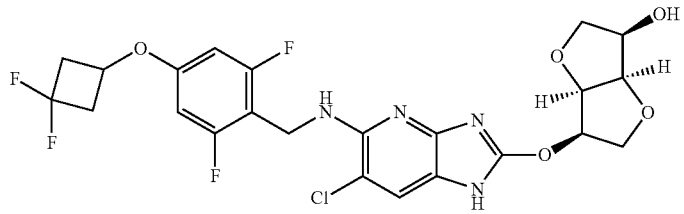 [SMILES: O[C@@H]1CO[C@H]2[C@@H]1OC[C@H]2Oc1nc2nc(NCc3c(F)cc(OC4CC(F)(F)C4)cc3F)c(Cl)cc2[nH]1] | 2.04 | 545 | A |
TABLE 72
| | | | | |
|---|---|---|---|---|
| I-2-227 | 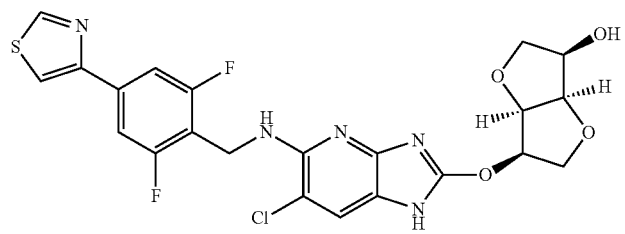 [SMILES: O[C@@H]1CO[C@H]2[C@@H]1OC[C@H]2Oc1nc2nc(NCc3c(F)cc(-c4cscn4)cc3F)c(Cl)cc2[nH]1] | 1.75 | 522 | A |
| I-2-228 | 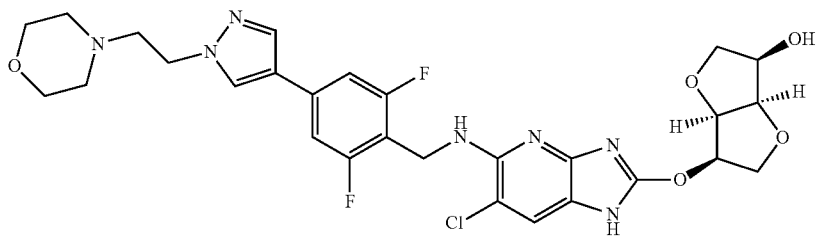 [SMILES: O[C@@H]1CO[C@H]2[C@@H]1OC[C@H]2Oc1nc2nc(NCc3c(F)cc(-c4cnn(CCN5CCOCC5)c4)cc3F)c(Cl)cc2[nH]1] | 1.22 | 618 | A |
| I-2-229 | 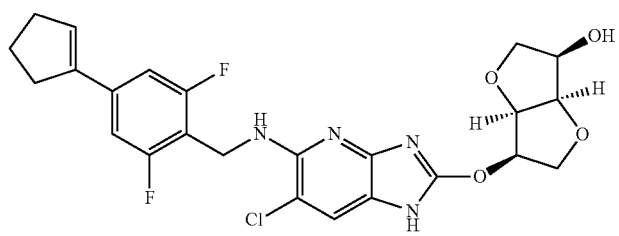 [SMILES: O[C@@H]1CO[C@H]2[C@@H]1OC[C@H]2Oc1nc2nc(NCc3c(F)cc(C4=CCCC4)cc3F)c(Cl)cc2[nH]1] | 2.32 | 505 | A |
| I-2-230 | 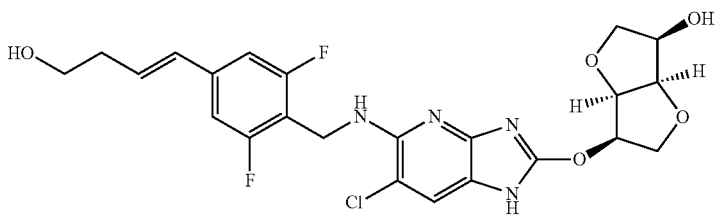 [SMILES: OCC/C=C/c1cc(F)c(CNc2nc3nc(O[C@@H]4CO[C@H]5[C@@H]4OC[C@H]5O)[nH]c3cc2Cl)c(F)c1] | 1.57 | 509 | A |
| I-2-231 | 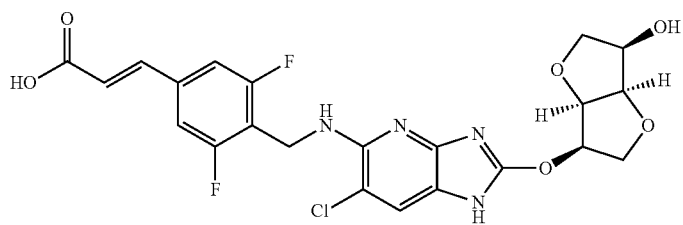 [SMILES: O=C(O)/C=C/c1cc(F)c(CNc2nc3nc(O[C@@H]4CO[C@H]5[C@@H]4OC[C@H]5O)[nH]c3cc2Cl)c(F)c1] | 1.59 | 509 | C |

TABLE 73

| ID | Structure | RT | MS | Method |
|---|---|---|---|---|
| I-2-232 | 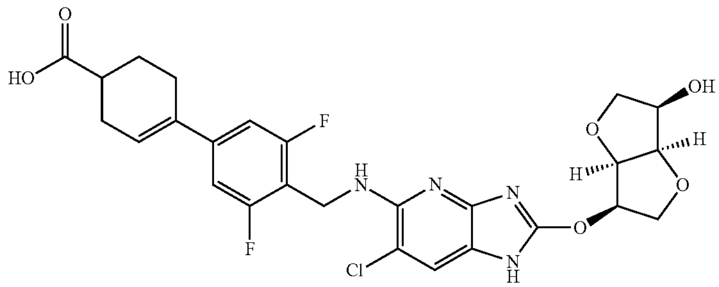 [SMILES: O=C(O)C1CC=C(c2cc(F)c(CNc3nc4nc(O[C@@H]5CO[C@H]6[C@@H]5OC[C@H]6O)[nH]c4cc3Cl)c(F)c2)CC1] | 1.80 | 563.05 | C |
| I-2-233 | 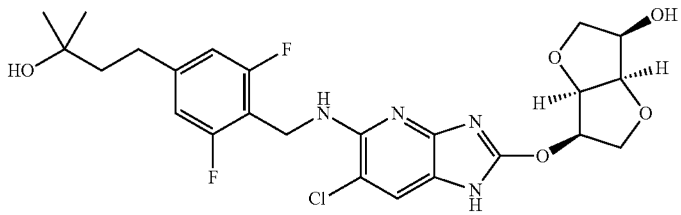 [SMILES: CC(C)(O)CCc1cc(F)c(CNc2nc3nc(O[C@@H]4CO[C@H]5[C@@H]4OC[C@H]5O)[nH]c3cc2Cl)c(F)c1] | 1.80 | 525.05 | C |
| I-2-234 | 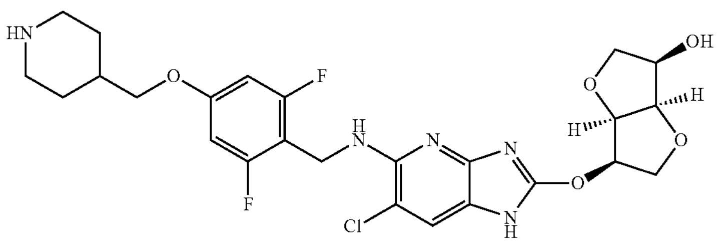 [SMILES: O[C@@H]1CO[C@H]2[C@@H]1OC[C@H]2Oc1nc2nc(NCc3c(F)cc(OCC4CCNCC4)cc3F)c(Cl)cc2[nH]1] | 1.30 | 552.05 | C |
| I-2-235 | 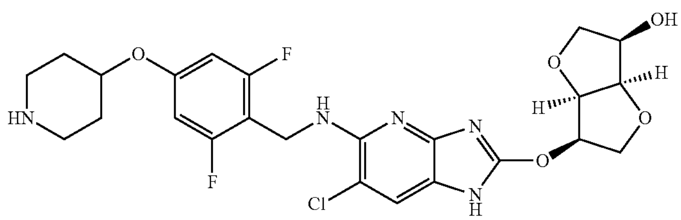 [SMILES: O[C@@H]1CO[C@H]2[C@@H]1OC[C@H]2Oc1nc2nc(NCc3c(F)cc(OC4CCNCC4)cc3F)c(Cl)cc2[nH]1] | 1.25 | 538 | C |
| I-2-236 | 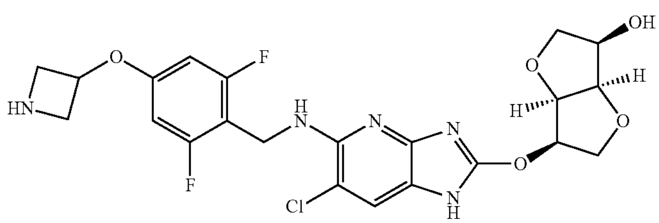 [SMILES: O[C@@H]1CO[C@H]2[C@@H]1OC[C@H]2Oc1nc2nc(NCc3c(F)cc(OC4CNC4)cc3F)c(Cl)cc2[nH]1] | 1.18 | 510 | C |

TABLE 74

| ID | Structure | RT | MS | Method |
|---|---|---|---|---|
| I-2-237 | 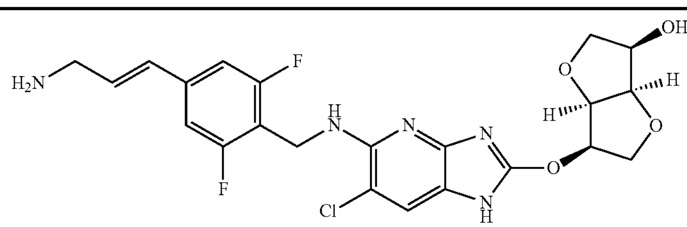 | 1.21 | 494 | C |

TABLE 74-continued

| I-2-238 | [structure] | 2.00 | 517 | C |
| I-2-240 | [structure] | 2.00 | 479 | C |
| I-2-241 | [structure] | 1.00 | 538 | C |

TABLE 75

| I-2-242 | [structure] | 1.46 | 580 | C |
| I-2-243 | [structure] | 0.97 | 496 | C |
| I-2-244 | [structure] | 2.05 | 435.9 | A |

TABLE 76

| No. | Structure | retention time | Mass (M + H) | Method |
|---|---|---|---|---|
| I-3-1 | 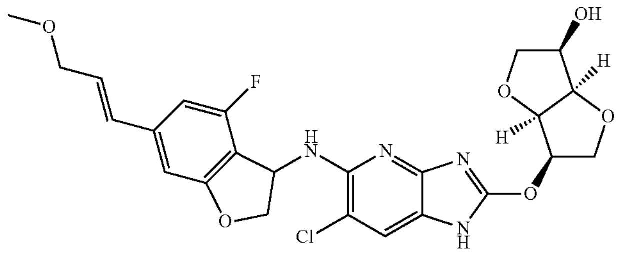 [SMILES: COC/C=C/c1cc(F)c2c(c1)OCC2Nc1nc2nc(O[C@@H]3CO[C@H]4[C@@H]3OC[C@H]4O)[nH]c2cc1Cl] | 1.79 | 519 | B |
| I-3-2 | 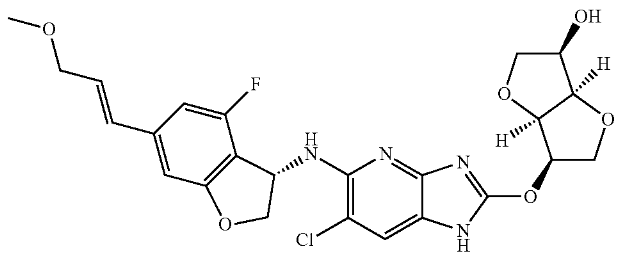 [SMILES: COC/C=C/c1cc(F)c2c(c1)OC[C@H]2Nc1nc2nc(O[C@@H]3CO[C@H]4[C@@H]3OC[C@H]4O)[nH]c2cc1Cl] | 1.79 | 519 | B |
| I-3-3 | 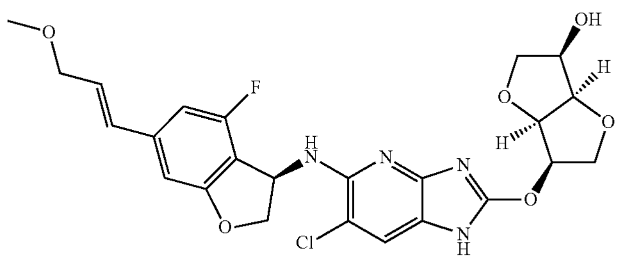 [SMILES: COC/C=C/c1cc(F)c2c(c1)OC[C@@H]2Nc1nc2nc(O[C@@H]3CO[C@H]4[C@@H]3OC[C@H]4O)[nH]c2cc1Cl] | 1.79 | 519 | B |

As compounds of the present invention, the compounds shown below can be also synthesized in accordance with the above Examples.

[Chemical formula 50]

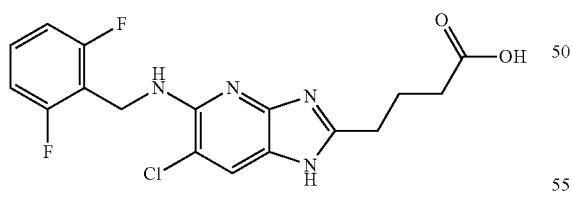

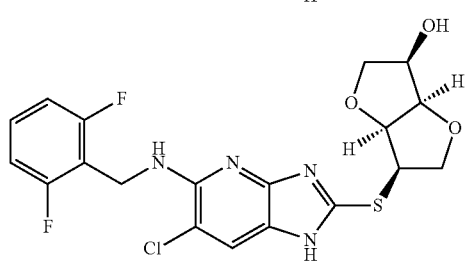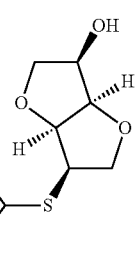

-continued

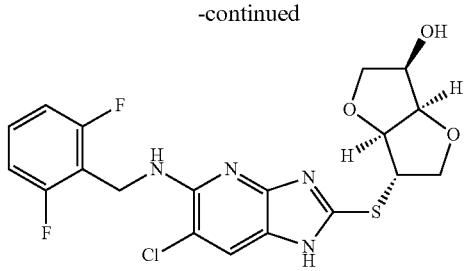

Evaluation Method of an Activator for AMP-Activated Protein Kinase (AMPK)

Test Example 1

To a buffer solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis(2-aminoethyl ether)-N,N,N',N'-tetraacetic acid (EGTA), 5 mM disodium 6-glycerophosphate and 2 mM dithiothreitol, a human AMPK α1β1γ1 enzyme (manufactured by Carna Biosciences, Inc.) was added in an amount to give a conversion rate of approximately 10% by reaction for 2 hours, and a compound dissolved in DMSO was added thereto so as to have a 1% DMSO concentration. The obtained liquid was left to stand for 10 minutes.

To the liquid, a substrate solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis (2-aminoethyl ether)-N,N,N',N'-tetraacetic acid (EGTA), 5 mM disodium β-glycerophosphate, 2 mM dithiothreitol, 0.4 mM ATP and 3 μM FL-Peptide 7 (manufactured by Caliper Life Sciences, Inc.) was added in equal amount (10 μl in total). The obtained liquid was allowed to react at 25° C. for 2 hours, and 10 μl of 20 mM EDTA was then added thereto to stop the reaction.

To detect phosphorylated fluorescent substrates, the reaction liquid was applied to a measuring device, LabChip EZ Reader II manufactured by Caliper Life Science, Inc., for detecting fluorescence by using differences in mobility due to differences in charge. The setting conditions for the device were pressure, −1.5 PSI; upstream voltage, −2250 V; downstream voltage, −400 V; post sample buffer sip time, 40 seconds; final delay, 120 seconds; and peak order, Product First.

A conversion rate was calculated from the peak heights of the resulting substrate and product. The conversion rate when not containing a compound was used as a control, and a concentration dependent curve was made by plotting the rate of increase in activity to the control at each concentration of a compound. The compound concentration showing 150% relative to the control (100%) was used as the EC 150 value, and the maximum rate of increase in activity within the measurement range was used as Emax.

Preparation Method of Human AMPK α2β2γ1

The full length cDNAs of human AMPK β2 (NM_005399.3) and human AMPK α2 (NM_006252.3) were inserted into the MCS1 and MCS2 of the pETDuet-1 vector to prepare a human AMPK β2 and human AMPK α2 (6× His tag at the 5' terminus) expressing plasmid. The plasmid was cotransfected with an expression plasmid, in which the full length cDNA of human AMPK γ1 (NM_002733.3) had been inserted into pET28b(+), into BL21 CodonPlus (DE3)-RIL to obtain an expression strain. The expression strain was cultured in TB medium, followed by induction with 0.5 mM IPTG, and cultured at 25° C. for 3 hours and then harvested. After ultrasonication, supernatant was collected and applied to Histrap FF column (GE) and RESOUECE Q column (GE) to prepare 12.5 mg of purified sample containing three types of subunit from 1.8 L of broth.

Preparation Method of Human CaMKK2 Used to Impart Activity to AMPK

An expression vector, in which the full length cDNA of human CAMKK β (NM_172226.1) had been inserted into pGEX-6P-3, was transfected into BL21 Star (DE3). The expression strain was cultured in TB medium, followed by induction with 0.5 mM IPTG, and cultured at 25° C. for 3 hours and then harvested. After ultrasonication, supernatant was collected and applied to GSTrap FF column (GE) to prepare 14 mg of GST-fused CAMKK β from 720 ml of broth.

Evaluation Method of an Activator for AMP-Activated Protein Kinase (AMPK)

Test Example 2

Human AMPK α2β2γ1 prepared in *Escherichia coli* was not phosphorylated and did not exhibit activity. Thus, phosphorylation treatment was carried out as pretreatment.

Human AMPK α2β2γ1 in an amount to give a conversion rate of approximately 10% by reaction for 2 hours, and CaMKK2 in an amount capable of sufficiently imparting activity to AMPK for one hour were mixed in a buffer solution consisting of a 50 mM HEPES-NaOH buffer solution (pH 7.0), 100 mM NaCl, 5 mM magnesium chloride, 0.1% bovine serum albumin, 0.2 mM sodium orthovanadate (V), 1 mM ethylene glycol-bis(2-aminoethyl ether)-N,N,N', N'-tetraacetic acid (EGTA), 5 mM disodium β-glycerophosphate, 1 mM dithiothreitol and 0.2 mM ATP, and the obtained liquid was left to stand at 25° C. for 1 to 1.5 hours to sufficiently phosphorylate AMPK.

After that, to the enzyme liquid, which had been subjected to phosphorylation treatment, a compound dissolved in DMSO was added so as to have a 1% DMSO concentration. The obtained liquid was left to stand for 10 minutes.

To the liquid, a substrate solution consisting of a 50 mM HEPES-NaOH buffer solution (pH 7.0), 100 mM NaCl, 10 mM magnesium chloride, 0.1% bovine serum albumin, 0.2 mM sodium orthovanadate(V), 1 mM ethylene glycol-bis (2-aminoethyl ether)-N,N,N',N'-tetraacetic acid (EGTA), 5 mM disodium β-glycerophosphate, 2 mM dithiothreitol, 0.4 mM ATP and 3 μM FL-Peptide 7 (manufactured by Caliper Life Sciences, Inc.) was added in equal amount (10 μl in total). The obtained liquid was allowed to react at 25° C. for 2 hours, and 10 μl of 20 mM EDTA was then added thereto to stop the reaction.

To detect phosphorylated fluorescent substrates, the reaction liquid was applied to a measuring device, LabChip EZ Reader II manufactured by Caliper Life Science, Inc., for detecting fluorescence by using differences in mobility due to differences in charge. The setting conditions for the device were pressure, −1.5 PSI; upstream voltage, −2250 V; downstream voltage, −400 V; post sample buffer sip time, 40 seconds; final delay, 120 seconds; and peak order, Product First.

A conversion rate was calculated from the peak heights of the resulting substrate and product. The conversion rate when not containing a compound was used as a control, and a concentration dependent curve was made by plotting the rate of increase in activity to the control at each concentration of a compound. The compound concentration showing 150% relative to the control (100%) was used as the EC 150 value, and the maximum rate of increase in activity within the measurement range was used as Emax.

The results of Test Example 2 are shown below.
Compound (I-1-1): EC150=29 nM, Emax=484%
Compound (I-1-4): EC150=40 nM, Emax=766%
Compound (I-1-6): EC150=21 nM, Emax=496%
Compound (I-1-8): EC150=67 nM, Emax=617%
Compound (I-1-10): EC150=740 nM, Emax=406%
Compound (I-1-11): EC150=170 nM, Emax=512%
Compound (I-1-13): EC150=17 nM, Emax=838%
Compound (I-1-14): EC150=42 nM, Emax=750%
Compound (I-1-15): EC150=5.8 nM, Emax=894%
Compound (I-1-36): EC150=16 nM, Emax=475%
Compound (I-1-38): EC150=1.2 nM, Emax=568%
Compound (I-1-39): EC150=26 nM, Emax=506%
Compound (I-1-52): EC150=100 nM, Emax=407%
Compound (I-1-80): EC150=880 nM, Emax=397%
Compound (I-1-109): EC150=48 nM, Emax=499%
Compound (I-1-116): EC150=94 nM, Emax=450%
Compound (I-1-119): EC150=84 nM, Emax=432%
Compound (I-1-126): EC150=170 nM, Emax=332%
Compound (I-2-1): EC150=30 nM, Emax=588%
Compound (I-2-19): EC150=74 nM, Emax=506%
Compound (I-2-22): EC150=130 nM, Emax=480%

Compound (I-2-62): EC150=94 nM, Emax=388%
Compound (I-2-75): EC150=26 nM, Emax=542%
Compound (I-2-91): EC150=5.4 nM, Emax=532%
Compound (I-2-93): EC150=9.9 nM, Emax=602%
Compound (I-2-119): EC150=13 nM, Emax=581%
Compound (I-2-147): EC150=4.5 nM, Emax=532%
Compound (I-2-153): EC150=5.2 nM, Emax=546%
Compound (I-2-185): EC150=6 nM, Emax=569%
Compound (I-2-188): EC150=15 nM, Emax=603%
Compound (I-2-192): EC150=7.6 nM, Emax=568%
Compound (I-2-209): EC150=22 nM, Emax=558%
Compound (I-2-217): EC150=47 nM, Emax=637%
Compound (I-2-220): EC150=1.1 nM, Emax=669%
Compound (I-2-222): EC150=16 nM, Emax=532%
Compound (I-2-223): EC1 50=2.8 nM, Emax=649%
Compound (I-2-228): EC150=8.5 nM, Emax=528%
Compound (I-2-233): EC150=9.3 nM, Emax=507%
Compound (I-2-238): EC150=4.1 nM, Emax=553%
Compound (I-2-239): EC150=5.6 nM, Emax=535%
Compound (I-2-244): EC150=92 nM, Emax=517%

The compounds of the present invention have an excellent activating effect on an AMPK α1 trimer and/or an AMPK α2 trimer.

Usefulness as a medicament can be examined by the following tests, etc. CYP3A4 fluorescent MBI test The CYP3A4 fluorescent MBT test is a test of investigating enhancement of CYP3A4 inhibition of a compound by a metabolism reaction, and the test was performed using, as CYP3A4 enzyme expressed in *Escherichia coli* and employing, as an index, a reaction in which 7-benzyloxytrifluoromethylcoumarin (7-BFC) is debenzylated by the CYP3A4 enzyme to produce a metabolite, 7-hydroxytrifluoromethylcoumarin (HFC) emitting fluorescent light.

The reaction conditions were as follows: substrate, 5.6 μmol/L 7-BFC; pre-reaction time, 0 or 30 minutes; reaction time, 15 minutes; reaction temperature, 25° C. (room temperature); CYP3A4 content (enzyme expressed in *Escherichia coli*), at pre-reaction 62.5 pmol/mL, at reaction 6.25 μmol/mL (at 10-fold dilution); test drug concentration, 0.625, 1.25, 2.5, 5, 10, 20 μmol/L (six points).

An enzyme in a K-Pi buffer (pH 7.4) and a test drug solution as a pre-reaction solution were added to a 96-well plate at the composition of the pre-reaction, a part of it was transferred to another 96-well plate so that it was 1/10 diluted with a substrate and a K-Pi buffer, NADPH as a coenzyme was added to initiate a reaction as an index (without pre-reaction) and, after a predetermined time of a reaction, acetonitrile/0.5 mol/L Tris (trishydroxyaminomethane)=4/1 was added to stop the reaction. In addition, NADPH was added to a remaining pre-reaction solution to initiate a pre-reaction (with pre-reaction) and, after a pre-determined time of a pre-reaction, a part was transferred to another plate so that it was 1/10 diluted with a substrate and a K-Pi buffer to initiate a reaction as an index. After a predetermined time of a reaction, acetonitrile/0.5 mol/L Tris (trishydroxyaminomethane)=4/1 was added to stop the reaction. For the plate on which each index reaction had been performed, a fluorescent value of 7-HFC which is a metabolite was measured with a fluorescent, plate reader. (Ex=420 nm, Em=535 nm).

Addition of only DMSO being a solvent dissolving a drug to a reaction system was adopted as a control (100%), remaining activity (%) was calculated at each concentration of a test drug added as the solution and $IC_{50}$ was calculated by reverse presumption by a logistic model using a concentration and an inhibition rate. When a difference between $IC_{50}$ values is 5 μM or more, this was defined as (+) and, when the difference is 3 μM or less, this was defined as (−).

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenadine hydroxylation (CYP3A4) as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 μmol/L ethoxyresorufin (CYP1A2), 100 μmol/L tolbutamide (CYP2C9), 50 μmol/L S-mephenytoin (CYP2C19), 5 μmol/L dextromethorphan (CYP2D6), 1 μmol/L terfenadine (CYP3A4); reaction time, 15 minutes; reaction temperature, 3TC; enzyme, pooled human hepatic microsome 0.2 mg protein/mL; test drug concentration, 1, 5, 10, 20 μmol/L (four points).

Each five kinds of substrates, human hepatic microsome, or a test drug in 50 mM Hepes buffer as a reaction solution was added to a 96-well plate at the composition as described above, NADPH, as a coenzyme was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the centrifuge supernatant was quantified by a fluorescent multilabel counter and tolbutamide hydroxide (CYP2C9 metabolite), mephenytoin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and $IC_{50}$ was calculated by reverse presumption by a logistic model using a concentration and an inhibition rate.

FAT Test

Each 20 μL of freeze-stored *Salmonella typhimurium* (strains TA98 and TA100) was inoculated in 10 mL of liquid nutrient medium (2.5% Oxoid nutrient broth No. 2), and the cultures were preincubated at 37° C. under shaking for 10 hours. 9 mL of TA98 culture was centrifuged (2000×g, 10 minutes) to remove medium, and the bacteria was suspended in 9 mL of Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4.7H_2O$: 0.1 g/L), and the suspension was added to 110 mL of Exposure medium (Micro F buffer containing Biotin: 8 μg/mL, histidine: 0.2 μg/mL, glucose: 8 mg/mL). 3.16 mL of TA100 culture was added to 120 mL of Exposure medium to prepare the test bacterial solution. 588 μL of the test bacterial solution (or mixed solution of 498 μL of the test bacterial solution and 90 μL of the S9 mix in the case with metabolic activation conditions) was mixed with each 12 μL of the following solution: DMSO solution of the test substance (eight dose levels from maximum dose 50 mg/mL at 2-fold ratio); DMSO as negative control; 50 μg/mL of 4-nitroquinoline-1-oxide DMSO solution as positive control for strain TA98 without metabolic activation conditions; 0.25 μg/mL of 2-(2-furyl)-3-(5-nitro-2-furyl)acrylamide DMSO solution as positive control for strain TA100 without metabolic activation conditions; 40 μg/mL of 2-aminoanthracene DMSO solution as positive control for strain TA98 with metabolic activation conditions; or 20 μg/mL of 2-aminoanthracene DMSO solution as positive control for strain TA100 with metabolic activation conditions. 12 μL, of the solution and 588 μL of the test bacterial solution (a mixed solution of 498 μL of the test bacterial solution and 90 μL of S9 mix with metabolic activation conditions) were mixed and incubated at 37° C. under shaking for 90 minutes. 460 µL of the bacterial solution exposed to the test substance was mixed with 2300 µL of Indicator medium (Micro F buffer containing biotin: 8 µg/mL, histidine: 0.2 µg/mL, glucose: 8 mg/mL, Bromo Cresol Purple: 37.5 µg/mL), each 50 µL was dispensed into 48 wells per dose in the microwell plates, and was subjected to stationary cultivation at 37° C. for 3 days. A well containing the bacteria, which has obtained the ability of proliferation by mutation in the gene coding amino acid (histidine) synthetase, turns the color from purple to yellow due to pH change. Thus, the number of the yellow wells among the 48 total wells per dose was counted to evaluate the mutagenicity by comparing with the negative control group.

Solubility Test

The solubility of a compound was determined under a condition in which 1% DMSO was added. 10 mM compound solution was prepared using DMSO, and then 6 µL of the compound solution was added to 594 µL of artificial intestinal juice in pH 6.8 (to 250 mL of a 0.2 mol/L potassium dihydrogen phosphate reagent solution were added 118 mL of a 0.2 mol/L NaOH reagent solution and water to provide a final volume of 1000 mL). After standing at 25° C. for 16 hours, the mixed solution was filtrated with suction. The filtrate was diluted twice with methanol/water (1/1), and then a concentration in the filtration was measured with HPLC or LC/MS/MS by the absolute calibration method.

Metabolic Stability Test

Using commercially available pooled human hepatic microsomes, an test compound was reacted for a constant time, a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 µL of the reaction solution was added to 100 µL of a methanol/acetonitrile=1/1 (v/v), and the mixture was mixed and centrifuged at 3000 rpm for 15 minutes. The test compound in the centrifuge supernatant was quantified by LC/MS/MS, and a remaining amount of the test compound after the reaction was calculated, letting a compound amount at 0 minute reaction time to be 100%. Hydrolysis reaction was performed in the absence of NADPH and glucuronidation reaction was performed in the presence of 5 mM UDP-glucuronic acid in place of NADPH, followed by similar operations.

hERG Test

For the purpose of assessing risk of an electrocardiogram QT interval prolongation, effects on delayed rectifier K+ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000A, Axon Instruments Inc.), $I_{Kr}$ induced by depolarization pulse stimulation at +40 mV for 2 seconds and, further, repolarization pulse stimulation at −50 mV for 2 seconds was recorded. After the generated current was stabilized, extracellular solution (NaCl: 135 mmol/L, KCl: 5.4 mmol/L, $NaH_2PO_4$: 0.3 mmol/L, $CaCl_2.2H_2O$: 1.8 mmol/L, $MgCl_2.6H_2O$: 1 mmol/L, glucose: 10 mmol/L, HEPES (4-(2-hydroxyethyl)-1-piperazine ethanesulfonic acid): 10 mmol/L, pH=7.4) in which the test compound had been dissolved at an objective concentration was applied to the cell under the room temperature condition for 10 minutes. From the recording $I_{Kr}$, an absolute value of the tail peak current was measured based on the current value at the resting membrane potential using an analysis software (DataXpress ver.1, Molecular Devices Corporation). Further, the % inhibition relative to the tail peak current before application of the test substance was calculated, and compared with the vehicle-applied group (0.1% dimethyl sulfoxide solution) to assess influence of the test substance on $I_{Kr}$.

Powder Solubility Test

Appropriate amounts of the test substances were put into appropriate containers. To the respective containers were added 200 µL of JP-1 fluid (sodium chloride 2.0 g, hydrochloric acid 7.0 mL and water to reach 1000 mL), 200 µL of JP-2 fluid (phosphate buffer (pH 6.8) 500 mL and water 500 mL), and 200 µL of 20 mmol/L TCA (sodium taurocholate)/JP-2 fluid (TCA 1.08 g and water to reach 100 mL). In the case that the test compound was dissolved after the addition of the test fluid, the bulk powder was added as appropriate. The containers were sealed, and shaken for 1 hour at 37° C. The mixtures were filtered, and 100 µL of methanol was added to each of the filtrate (100 µL) so that the filtrates were two-fold diluted. The dilution ratio was changed if necessary. After confirmation of no bubbles and precipitates, the containers were sealed and shaken. Quantification was performed by HPLC with an absolute calibration method.

BA Test

Materials and Methods for Studies on Oral Absorption (1) Animals: mice or rats
(2) Animal husbandry: Mice and rats had free access to solid food and sterilized bottled tap water.
(3) Setting of Dose and group compositions: orally or intravenously administered at a predetermined dose; Group compositions were as shown below (Dose depends on the compound)
  Oral: 1 to 30 mg/kg (n=2 to 3)
  Intravenous: 0.5 to 10 mg/kg (n=2 to 3)
(4) Preparation for dosing formulation: for oral administration, in a solution or a suspension state; for intravenous administration, in a solubilized state
(5) Dosing procedure: In oral administration study, the test substance was forcibly administered to the stomach of rats by using a gavage tube. In intravenous administration study, the test substance was administered to rats via tail vein using a syringe with a needle.
(6) Evaluation items: Blood was collected at each time point, and plasma concentration of the test substance was determined by LC/MS/MS.
(7) Data analysis: Regarding the transition of the plasma concentration, area under the plasma concentration-time curve (AUC) was calculated by means of WinNonlin® program, respectively. Bioavailability (BA) was calculated by using AUC values of the oral administration group and intravenous administration group.

Formulation Examples are shown below.

Formulation Example 1

Tablets

The compound of the present invention, lactose and calcium stearate are mixed. The mixture is crushed, granulated and dried to give a suitable size of granules. Next, calcium stearate is added to the granules, and the mixture is compressed and molded to give tablets.

Formulation Example 2

Capsules

The compound of the present invention, lactose and calcium stearate are mixed uniformly to obtain powder medicines in the form of powders or fine granules. The powder medicines are filled into capsule containers to give capsules.

Formulation Example 3

Granules

The compound of the present invention, lactose and calcium stearate are mixed uniformly and the mixture is compressed and molded. Then, it is crushed, granulated and sieved to give suitable sizes of granules.

Formulation Example 4

Orally Disintegrating Tablets

The compound of the present invention and crystalline cellulose are mixed and granulated, then tableted to give orally disintegrating tablets.

Formulation Example 5

Dry Syrups

The compound of the present invention and lactose are mixed, crushed, granulated and sieved to give suitable sizes of dry syrups.

Formulation Example 6

Injections

The compound of the present invention and phosphate buffer are mixed to give injection.

Formulation Example 7

Infusions

The compound of the present invention and phosphate buffer are mixed to give injection.

Formulation Example 8

Inhalations

The compound of the present invention and lactose are mixed and crushed finely to give inhalations.

Formulation Example 9

Ointments

The compound of the present invention and petrolatum are mixed to give ointments.

Formulation Example 10

Patches

The compound of the present invention and base such as adhesive plaster or the like are mixed to give patches.

INDUSTRIAL APPLICABILITY

As is apparent from the above test examples, the compounds of the present invention show an AMPK activating effect. Therefore, the compounds of the present invention are very useful as a therapeutic agent for type I diabetes, type II diabetes, hyperglycemia, metabolic syndrome, obesity, hypercholesterolemia and hypertension.

The invention claimed is:
1. A compound of formula (I), or a pharmaceutically acceptable salt thereof,
wherein
L is $NR^2R^3$;
$R^2$ is hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl;
$R^3$ is substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted acyl, substituted or unsubstituted carbamoyl, substituted or unsubstituted alkylsulfonyl, substituted or unsubstituted alkenylsulfonyl, substituted or unsubstituted alkynylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, or substituted or unsubstituted sulfamoyl;
Y is substituted or unsubstituted heterocyclyl;
Z is $\mu N=$;
$R^1$ is hydrogen;
$R^4$ is hydrogen, halogen, cyano, or substituted or unsubstituted alkyl;
$R^5$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino; and the heterocyclyl is a 5- to 10-membered non-aromatic heterocyclic group and may have a bond at any substitutable position of a ring having at least one of a nitrogen atom, an oxygen atom, and a sulfur atom in the ring, or a ring fused with a cycloalkane, a benzene ring and/or a ring having at least one of a nitrogen atom, an oxygen atom and a sulfur atom in the ring.

2. The compound according to claim 1 or pharmaceutically acceptable salt thereof, wherein Y is substituted or unsubstituted heterocyclyl and the substituted or unsubstituted heterocyclyl is

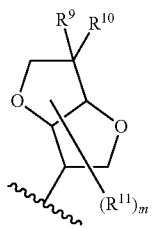

where $R^9$ and $R^{10}$ are each independently hydrogen, halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino: $R^{11}$ is each independently halogen, hydroxy, cyano, nitro, carboxy, substituted or unsubstituted alkyl, substituted or unsubstituted alkenyl, substituted or unsubstituted alkynyl, substituted or unsubstituted alkyloxy, substituted or unsubstituted alkylthio, substituted or unsubstituted alkylsulfonyl, substituted or unsubstituted acyl, substituted or unsubstituted carbamoyl, substituted or unsubstituted sulfamoyl, or substituted or unsubstituted amino; and m is an integer from 0 to 6.

3. The compound according to claim 1 or pharmaceutically acceptable salt thereof, wherein $R^2$ is hydrogen or substituted or unsubstituted alkyl.

4. The compound according to claim 1 or pharmaceutically acceptable salt thereof, wherein $R^3$ is substituted or unsubstituted alkyl, substituted or unsubstituted cycloalkenyl, or substituted or unsubstituted heterocyclyl.

5. The compound according to claim 4 or pharmaceutically acceptable salt thereof, wherein $R^3$ is substituted alkyl, wherein the substituent of substituted alkyl is one or more substituent(s) selected from substituted or unsubstituted aryl, substituted or unsubstituted heteroaryl, substituted or unsubstituted cycloalkyl, substituted or unsubstituted cycloalkenyl, and/or substituted or unsubstituted heterocyclyl.

6. The compound according to claim 4 or pharmaceutically acceptable salt thereof, wherein $R^3$ is substituted or unsubstituted cycloalkenyl, or substituted or unsubstituted heterocyclyl.

7. The compound according to claim 1 or pharmaceutically acceptable salt thereof, wherein $R^5$ is hydrogen.

8. The compound according to claim 1 or pharmaceutically acceptable salt thereof, wherein $R^4$ is halogen.

9. A pharmaceutical composition comprising the compound of claim 1 or pharmaceutically acceptable salt thereof.

10. A compound selected from the group consisting of

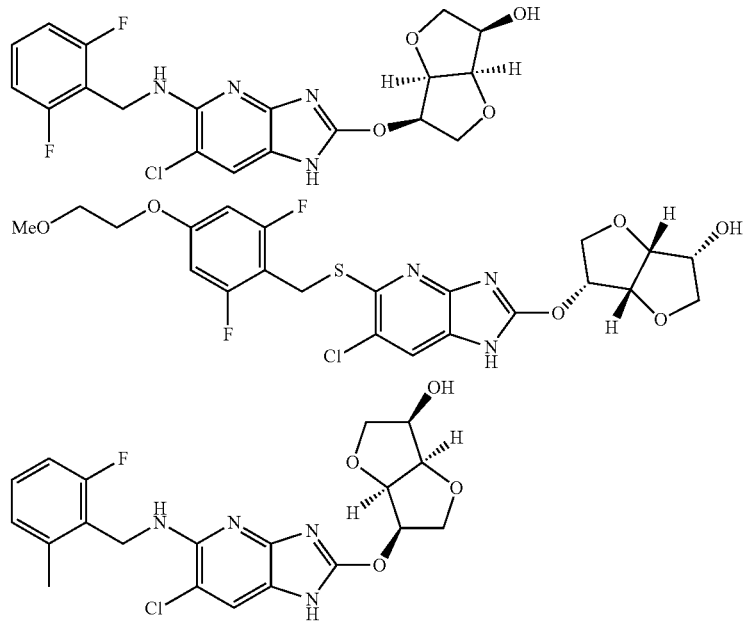

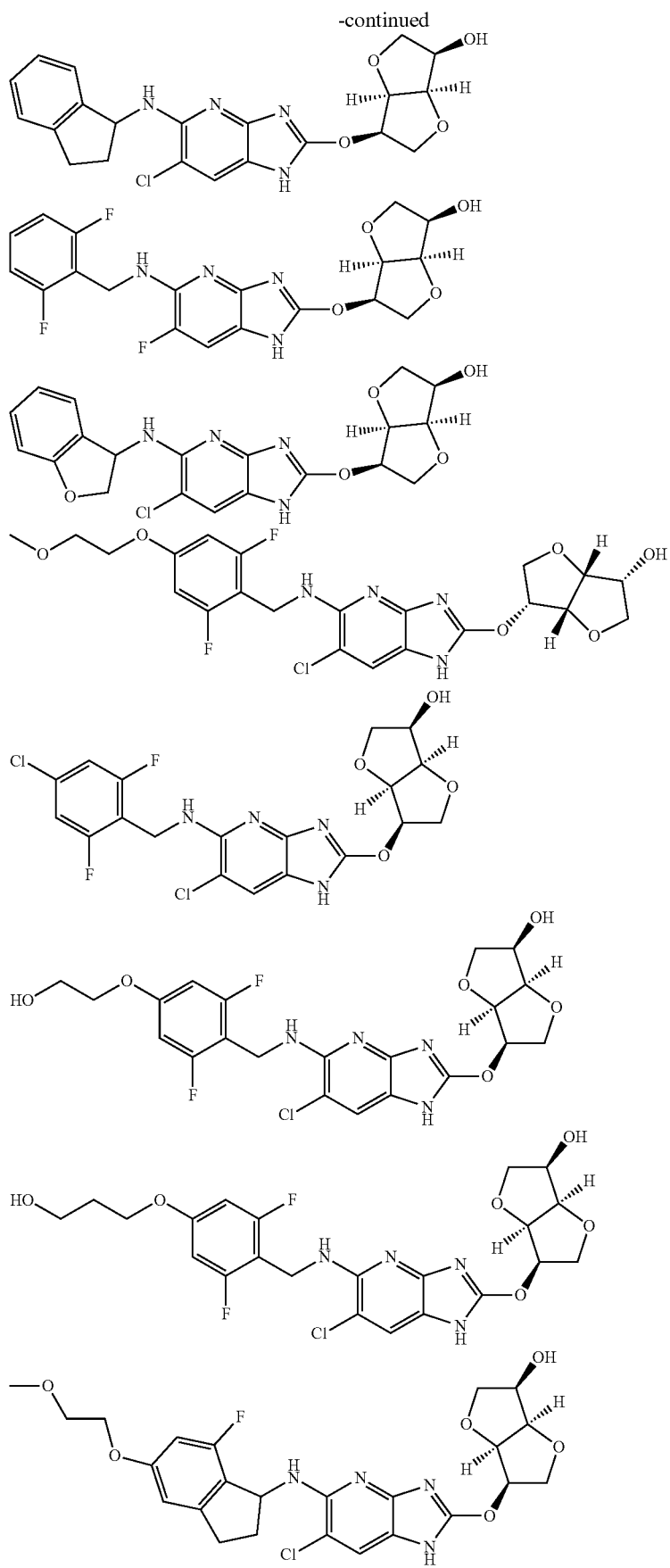

-continued
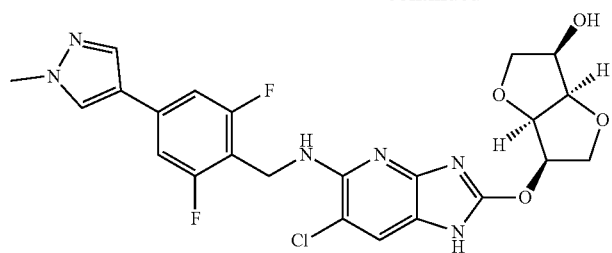
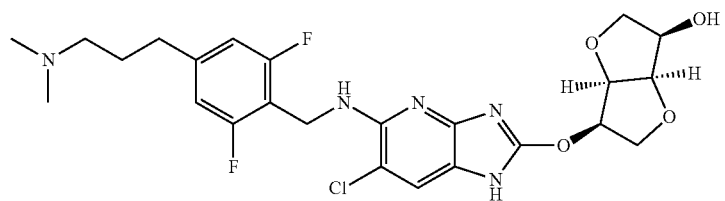
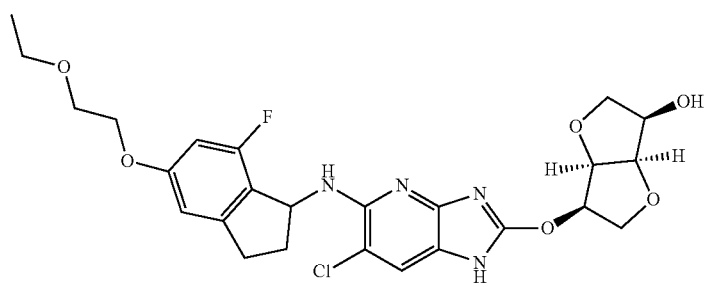
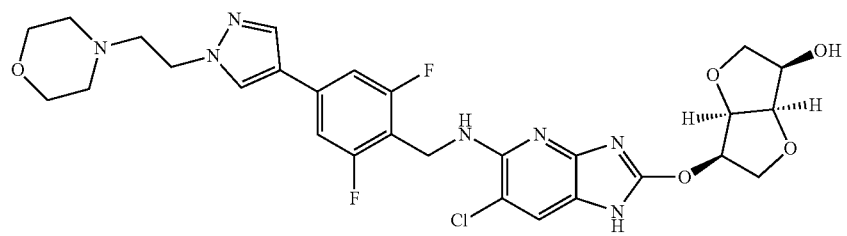
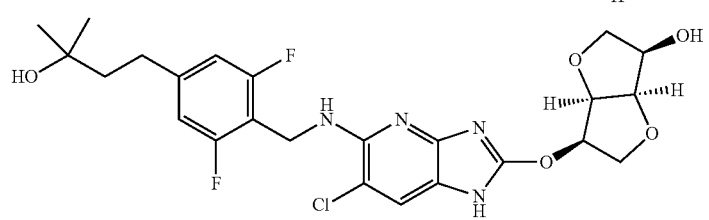
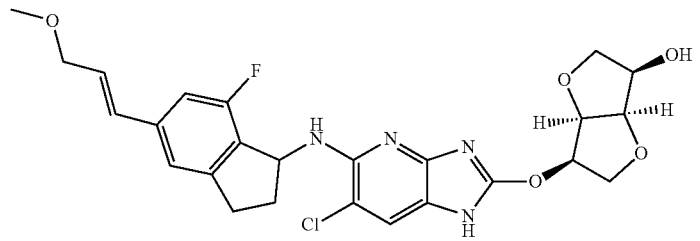
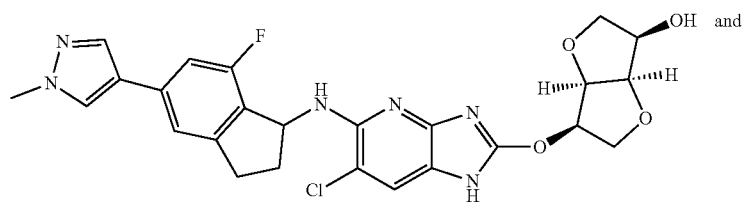 and

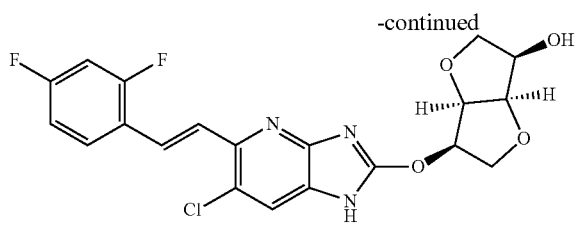

or a pharmaceutically acceptable salt thereof.

11. A compound of formula (IIIa) or (IIIb),

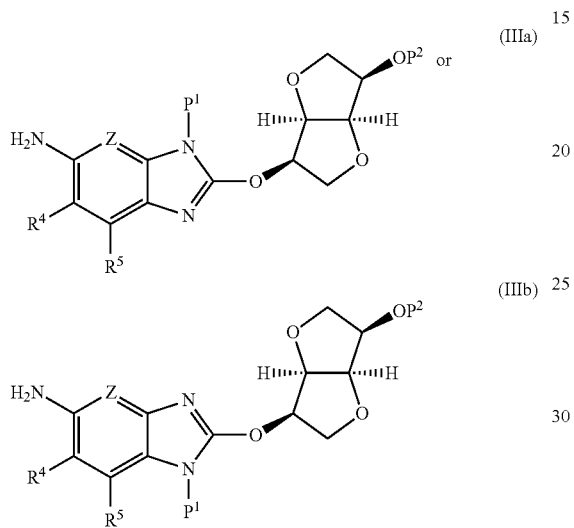

or a pharmaceutically acceptable salt thereof,
wherein
Z is —N=;
$P^1$ and $P^2$ are each independently benzyl, para-methoxybenzyl, acetyl, benzoyl, trimethylsilylethoxymethyl, tetrahydropyranyl, tert-butyldimethylsilyl, or tert-butyldiphenylsilyl;
$R^4$ is hydrogen, halogen, cyano, or substituted or unsubstituted alkyl; and
$R^5$ is hydrogen, halogen, hydroxy, cyano, nitro, carboxy, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted alkyloxy, substituted or unsubstituted aryloxy, substituted or unsubstituted heteroaryloxy, substituted or unsubstituted cycloalkyloxy, substituted or unsubstituted cycloalkenyloxy, substituted or unsubstituted heterocyclyloxy, substituted or unsubstituted alkylthio, substituted or unsubstituted arylthio, substituted or unsubstituted heteroarylthio, substituted or unsubstituted cycloalkylthio, substituted or unsubstituted cycloalkenylthio, substituted or unsubstituted heterocyclylthio, substituted or unsubstituted alkylsulfonyl, substituted or unsubstituted arylsulfonyl, substituted or unsubstituted heteroarylsulfonyl, substituted or unsubstituted cycloalkylsulfonyl, substituted or unsubstituted cycloalkenylsulfonyl, substituted or unsubstituted heterocyclylsulfonyl, substituted or unsubstituted acyl, substituted or unsubstituted carbamoyl, substituted or unsubstituted sulfamoyl, or substituted or unsubstituted amino.

12. The compound according to claim 2 or pharmaceutically acceptable salt thereof, wherein $R^5$ is hydrogen.

13. The compound according to claim 3 or pharmaceutically acceptable salt thereof, wherein $R^5$ is hydrogen.

14. The compound according to claim 4 or pharmaceutically acceptable salt thereof, wherein $R^5$ is hydrogen.

15. The compound according to claim 5 or pharmaceutically acceptable salt thereof, wherein $R^5$ is hydrogen.

16. The compound according to claim 6 or pharmaceutically acceptable salt thereof, wherein $R^5$ is hydrogen.

17. A method for treating diabetes, comprising:
administering the compound of claim 1 or pharmaceutically acceptable salt thereof to a patient in need thereof.

18. A method for treating diabetes, comprising:
administering the compound of claim 2 or pharmaceutically acceptable salt thereof to a patient in need thereof.

19. A method for treating diabetes, comprising:
administering the compound of claim 3 or pharmaceutically acceptable salt thereof to a patient in need thereof.

20. A method for treating diabetes, comprising:
administering the compound of claim 4 or pharmaceutically acceptable salt thereof to a patient in need thereof.

21. A method for treating diabetes, comprising:
administering the compound of claim 5 or pharmaceutically acceptable salt thereof to a patient in need thereof.

22. A method for treating diabetes, comprising:
administering the compound of claim 6 or pharmaceutically acceptable salt thereof to a patient in need thereof.

23. A method for treating diabetes, comprising:
administering the compound of claim 7 or pharmaceutically acceptable salt thereof to a patient in need thereof.

* * * * *